(12) United States Patent
Langenfeld et al.

(10) Patent No.: US 10,052,761 B2
(45) Date of Patent: Aug. 21, 2018

(54) ROBOTIC SURGERY SYSTEM, METHOD, AND APPARATUS

(71) Applicant: DEKA Products Limited Partnership, Manchester, NH (US)

(72) Inventors: Christopher C. Langenfeld, Nashua, NH (US); Michael J. Slate, Merrimack, NH (US); Prashant Bhat, Bedford, NH (US); Dirk A. van der Merwe, Canterbury, NH (US); David D. B. Cannan, Manchester, NH (US); Keith D. Violette, Sandown, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 15/212,143

(22) Filed: Jul. 15, 2016

(65) Prior Publication Data

US 2017/0014998 A1 Jan. 19, 2017

Related U.S. Application Data

(60) Provisional application No. 62/193,959, filed on Jul. 17, 2015.

(51) Int. Cl.
*G05B 19/04* (2006.01)
*G05B 19/08* (2006.01)
(Continued)

(52) U.S. Cl.
CPC ............ *B25J 9/1638* (2013.01); *A61B 34/30* (2016.02); *A61B 34/73* (2016.02); *A61B 46/10* (2016.02);
(Continued)

(58) Field of Classification Search
CPC ........ A61B 2090/034; A61B 2090/064; A61B 34/30; A61B 46/10; B25J 9/06;
(Continued)

(56) References Cited

U.S. PATENT DOCUMENTS

| 5,807,377 A | 9/1998 | Madhani et al. |
| 5,964,676 A | 12/1999 | Rennerfelt |

(Continued)

FOREIGN PATENT DOCUMENTS

| AU | 2007254247 B2 | 9/2013 |
| CA | 2652548 C | 9/2016 |

(Continued)

OTHER PUBLICATIONS

International application No. PCT/US2016/042666, Invitation to Pay Additional Fees dated Oct. 12, 2016 (7 pages).
(Continued)

*Primary Examiner* — Harry Y Oh
(74) *Attorney, Agent, or Firm* — Kathleen Chapman

(57) ABSTRACT

A surgical system which may be configured to be a minimally invasive and/or computer assisted surgical system. Operation of the system may be controlled by transmission of a force from a first section to a second section of the system. The first section and the second section may be separated by a partition or a barrier. The first section may be a non-sterile section and the second section may be a sterile section of the surgical system.

20 Claims, 121 Drawing Sheets

(51) Int. Cl.
*B25J 9/16* (2006.01)
*A61B 34/30* (2016.01)
*A61B 34/00* (2016.01)
*A61B 46/10* (2016.01)
*B25J 9/12* (2006.01)
*B25J 9/06* (2006.01)
*B25J 9/10* (2006.01)
*F16H 25/20* (2006.01)
*F16C 1/16* (2006.01)
*A61B 17/00* (2006.01)
*A61B 90/00* (2016.01)

(52) U.S. Cl.
CPC ............... *B25J 9/06* (2013.01); *B25J 9/104* (2013.01); *B25J 9/126* (2013.01); *B25J 9/161* (2013.01); *B25J 9/1635* (2013.01); *A61B 2017/00477* (2013.01); *A61B 2090/034* (2016.02); *A61B 2090/064* (2016.02); *F16C 1/16* (2013.01); *F16H 25/20* (2013.01); *Y10S 901/02* (2013.01); *Y10S 901/19* (2013.01); *Y10S 901/21* (2013.01); *Y10S 901/23* (2013.01); *Y10S 901/28* (2013.01)

(58) Field of Classification Search
CPC ... B25J 9/104; B25J 9/126; B25J 9/161; B25J 9/1635; B25J 9/1638; F16H 25/20; Y10S 901/02; Y10S 901/19; Y10S 901/23; Y10S 901/28
USPC .......................................................... 700/254
See application file for complete search history.

(56) References Cited

U.S. PATENT DOCUMENTS

| | | | |
|---|---|---|---|
| 6,436,107 B1* | 8/2002 | Wang | A61B 1/00149 318/568.11 |
| 6,699,177 B1* | 3/2004 | Wang | A61B 34/75 414/2 |
| 6,939,297 B2 | 9/2005 | Gannoe et al. | |
| 7,727,244 B2* | 6/2010 | Orban, III | A61B 34/71 128/849 |
| 7,833,156 B2 | 11/2010 | Williams et al. | |
| 8,206,406 B2 | 6/2012 | Orban, III | |
| 8,246,617 B2 | 8/2012 | Welt et al. | |
| 8,496,647 B2 | 7/2013 | Blumenkranz et al. | |
| 8,518,024 B2 | 8/2013 | Williams et al. | |
| 8,602,031 B2* | 12/2013 | Reis | A61B 19/081 128/852 |
| 8,919,348 B2 | 12/2014 | Williams et al. | |
| 9,320,568 B2 | 5/2016 | Orban, III et al. | |
| 9,333,040 B2 | 5/2016 | Shellenberger et al. | |
| 9,345,545 B2 | 5/2016 | Shellenberger et al. | |
| 9,360,934 B2 | 6/2016 | Morales et al. | |
| 9,486,288 B2 | 11/2016 | Devengenzo et al. | |
| 9,603,672 B2 | 3/2017 | Shellenberger et al. | |
| 9,730,719 B2 | 8/2017 | Brisson et al. | |
| 2002/0077532 A1 | 6/2002 | Gannoe et al. | |
| 2003/0083648 A1* | 5/2003 | Wang | A61B 17/11 606/1 |
| 2003/0125716 A1* | 7/2003 | Wang | A61B 17/11 606/1 |
| 2007/0203517 A1 | 8/2007 | Williams et al. | |
| 2008/0140088 A1* | 6/2008 | Orban, III | A61B 19/2203 606/130 |
| 2009/0024142 A1* | 1/2009 | Ruiz Morales | B25J 9/041 606/130 |
| 2009/0157076 A1 | 6/2009 | Athas et al. | |
| 2009/0227843 A1 | 9/2009 | Smith et al. | |
| 2010/0204713 A1* | 8/2010 | Ruiz Morales | B25J 9/041 606/130 |
| 2010/0298636 A1 | 11/2010 | Castro et al. | |
| 2010/0298839 A1 | 11/2010 | Castro | |
| 2011/0060183 A1 | 3/2011 | Castro et al. | |
| 2011/0066173 A1 | 3/2011 | Williams et al. | |
| 2011/0092963 A1 | 4/2011 | Castro | |
| 2011/0112371 A1 | 5/2011 | Smith et al. | |
| 2011/0184231 A1 | 7/2011 | Page et al. | |
| 2011/0196418 A1 | 8/2011 | Castro | |
| 2011/0230723 A1 | 9/2011 | Castro et al. | |
| 2011/0251599 A1 | 10/2011 | Shellenberger et al. | |
| 2012/0265214 A1 | 10/2012 | Bender et al. | |
| 2013/0041372 A1 | 2/2013 | Welt et al. | |
| 2013/0172713 A1 | 7/2013 | Kirschenman | |
| 2013/0172906 A1 | 7/2013 | Olson et al. | |
| 2013/0184676 A1 | 7/2013 | Kamenn et al. | |
| 2013/0281924 A1 | 10/2013 | Shellenberger | |
| 2014/0221749 A1 | 8/2014 | Grant et al. | |
| 2014/0222020 A1 | 8/2014 | Bender et al. | |
| 2014/0276667 A1 | 9/2014 | Shellenberger et al. | |
| 2014/0314538 A1 | 10/2014 | Carter et al. | |
| 2015/0066050 A1* | 3/2015 | Jardine | A61B 34/30 606/130 |
| 2015/0088158 A1 | 3/2015 | Shellenberger et al. | |
| 2015/0088159 A1 | 3/2015 | Shellenberger et al. | |
| 2015/0105629 A1 | 4/2015 | Williams et al. | |
| 2015/0173840 A1* | 6/2015 | Lohmeier | A61B 19/2203 606/130 |
| 2015/0238267 A1* | 8/2015 | Devengenzo | A61B 1/00149 606/130 |

FOREIGN PATENT DOCUMENTS

| | | |
|---|---|---|
| EP | 2023793 B1 | 11/2015 |
| JP | 2012-518478 | 8/2012 |
| JP | 5256194 B2 | 8/2013 |
| JP | 5730873 B2 | 4/2015 |
| JP | 6202759 B2 | 9/2017 |
| WO | WO 2007/136683 A2 | 11/2007 |
| WO | WO 2009/035650 A2 | 3/2009 |
| WO | WO 2009/035663 A2 | 3/2009 |
| WO | WO 2010/096580 A1 | 8/2010 |
| WO | WO 2011/014711 A1 | 2/2011 |
| WO | WO 2011/130457 A1 | 10/2011 |
| WO | WO 2013/116869 A1 | 8/2013 |
| WO | 2016090459 A1 | 6/2016 |

OTHER PUBLICATIONS

Written Opinion of the International Search Report, dated Jan. 26, 2017, PCT/US2016/042666, filed Jul. 15, 2016, entitled Robotic Surgery System, Method, and Apparatus.

* cited by examiner

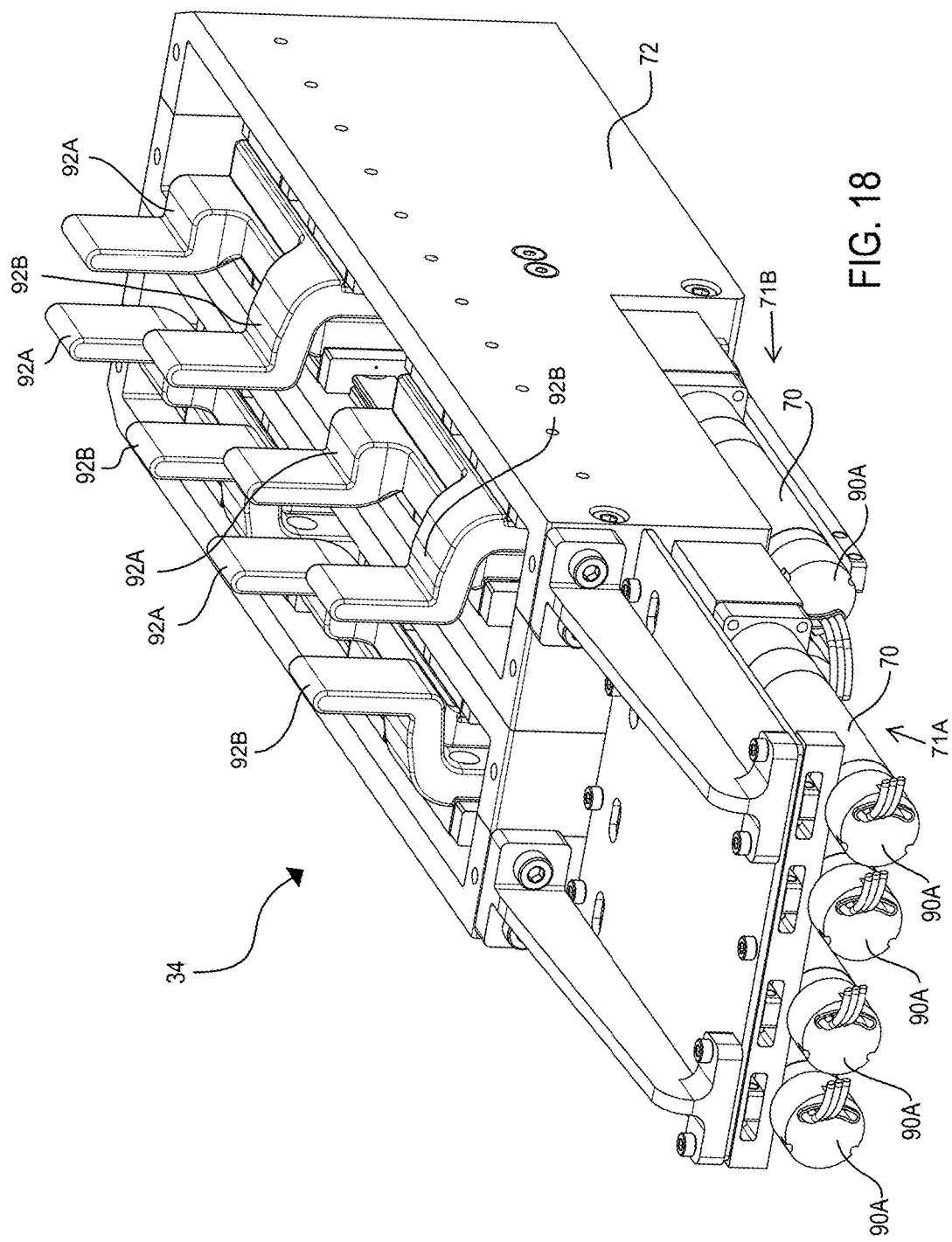

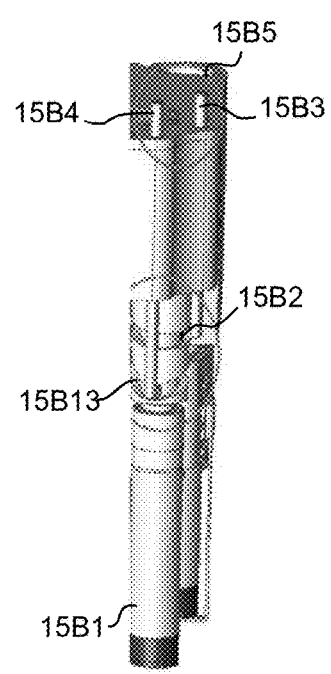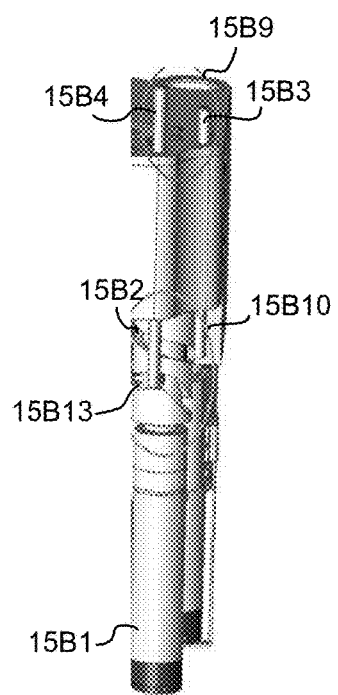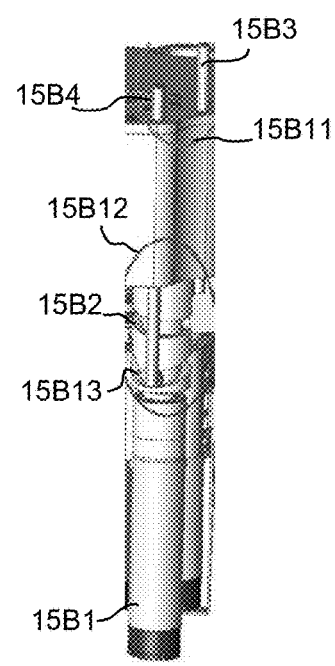
FIG. 40A-1       FIG. 40A-2       FIG. 40A-3

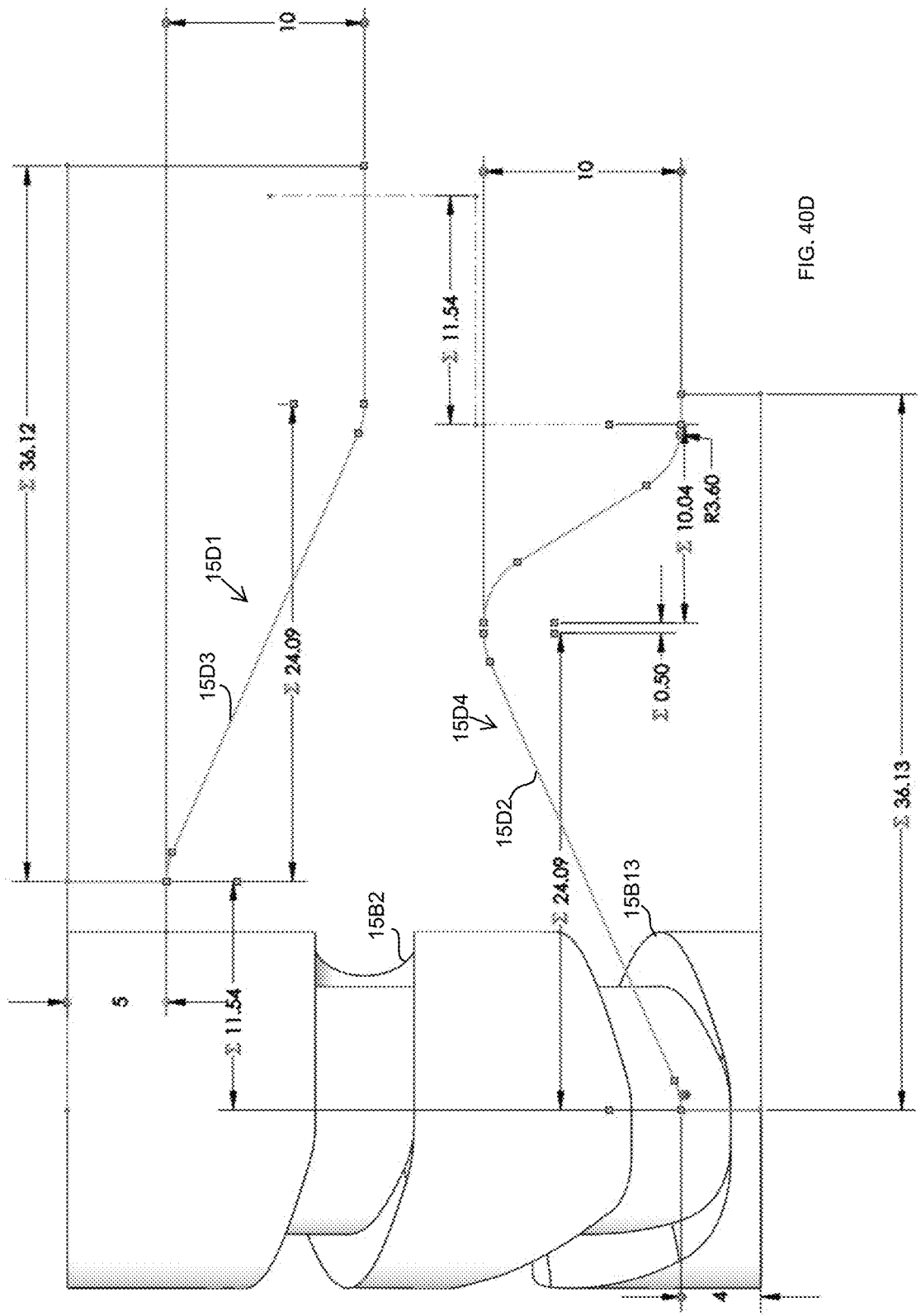

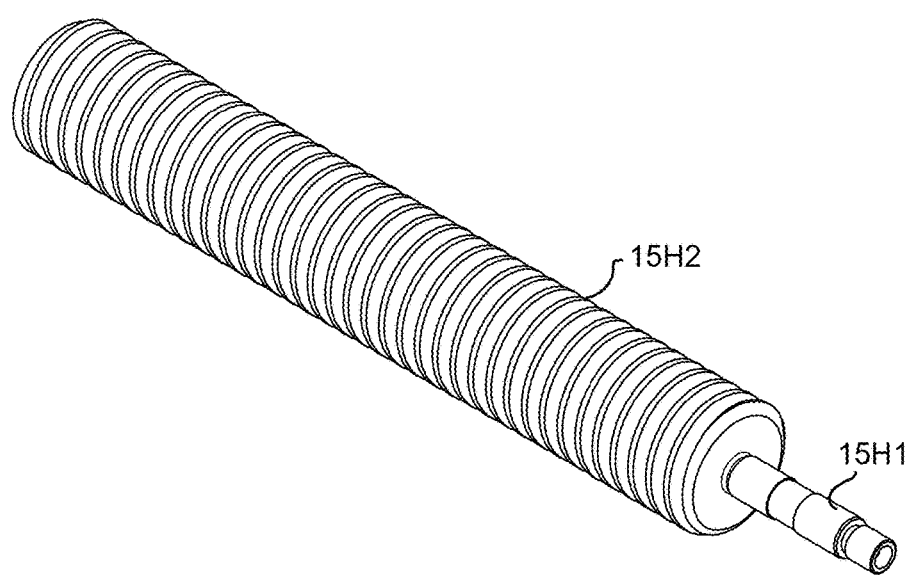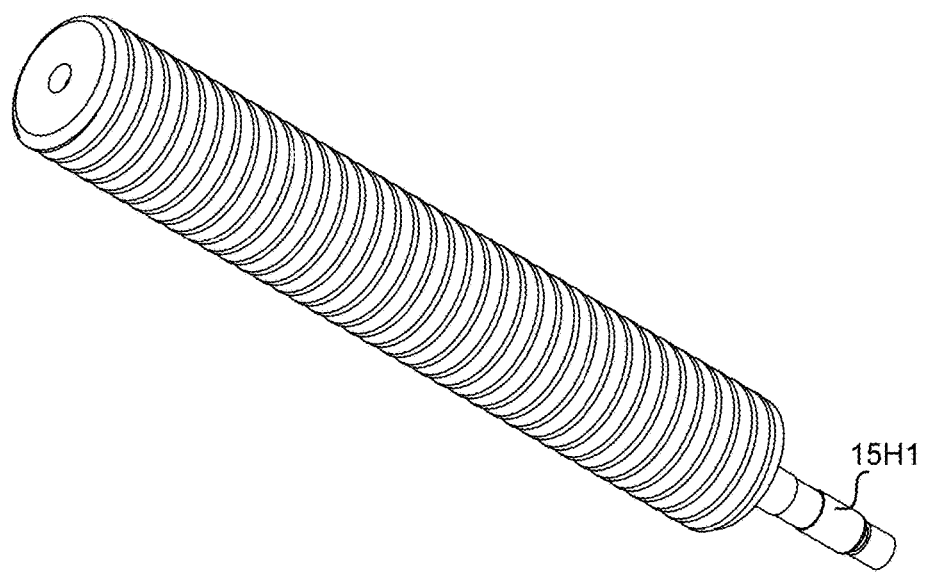
FIG. 40H

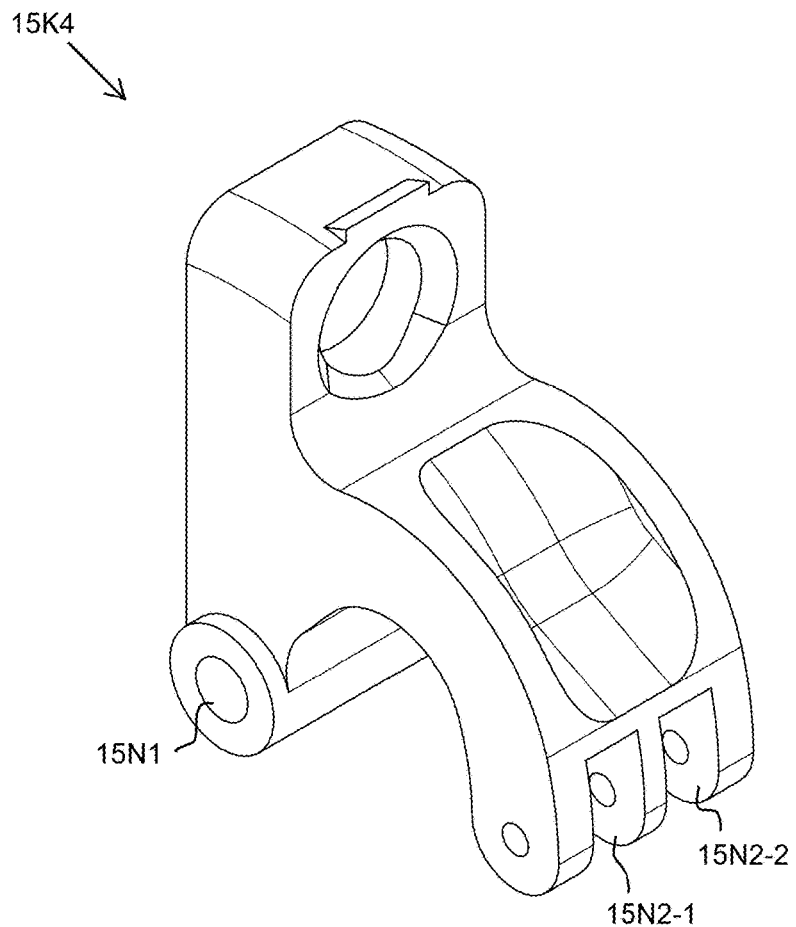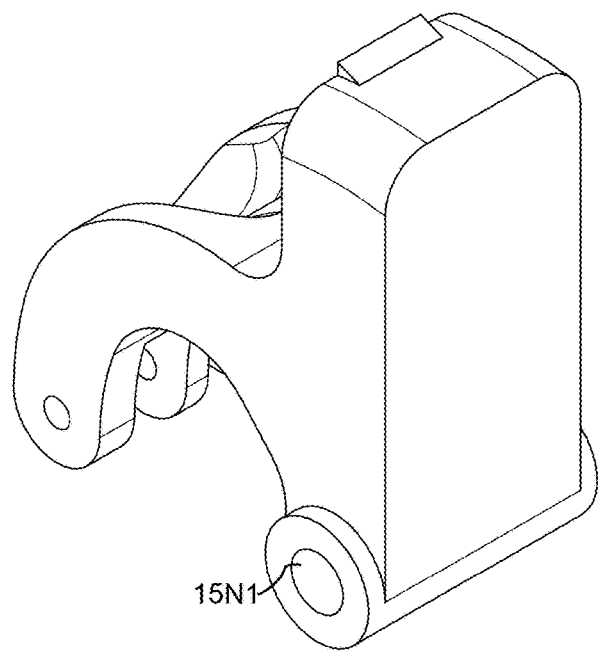
FIG. 40N

15K9
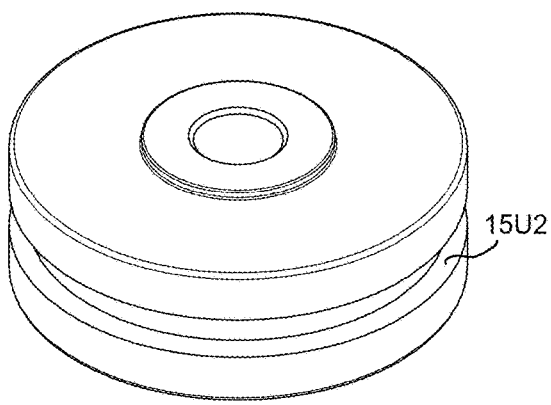
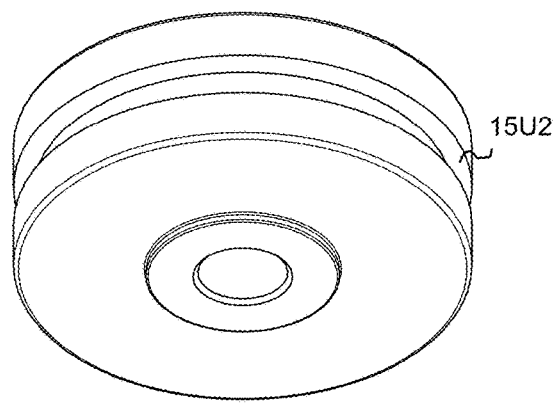
FIG. 40P

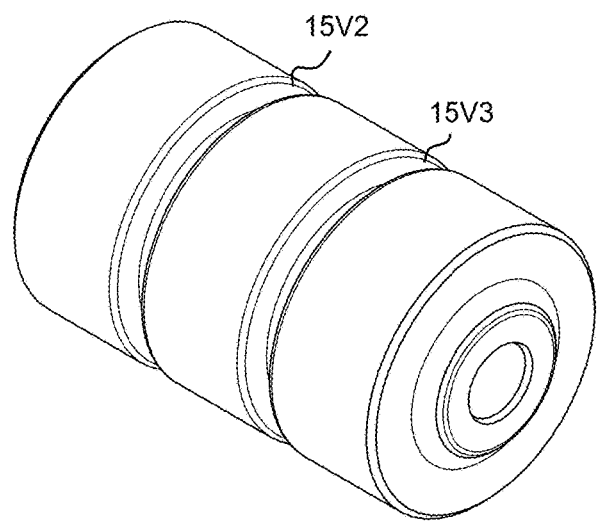
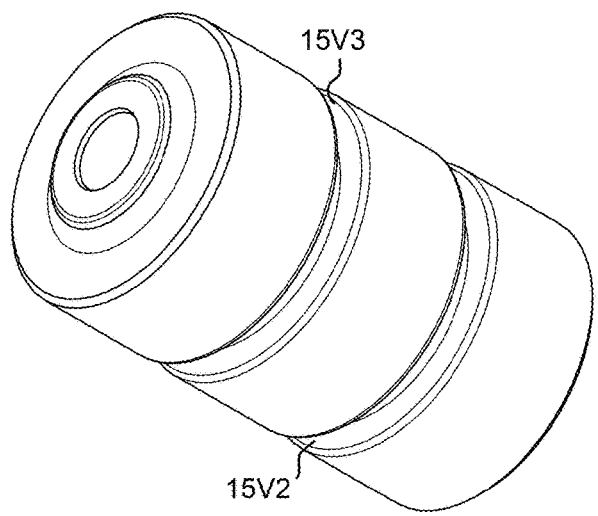
FIG. 40Q

15R1
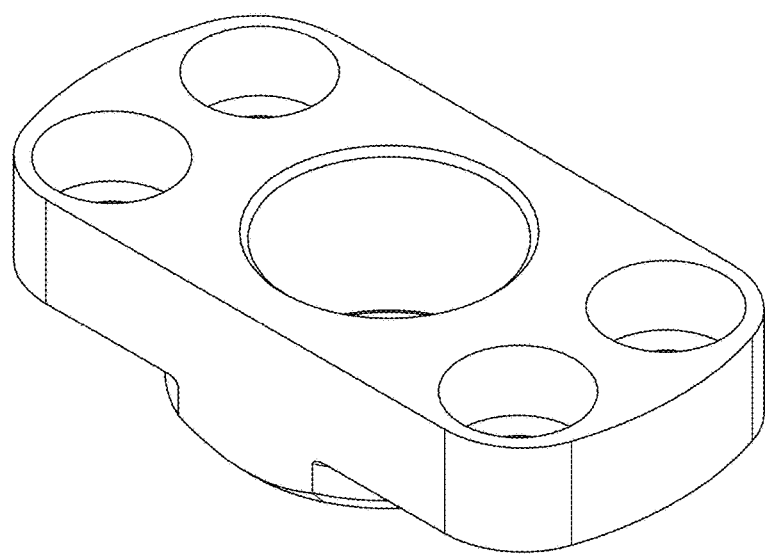
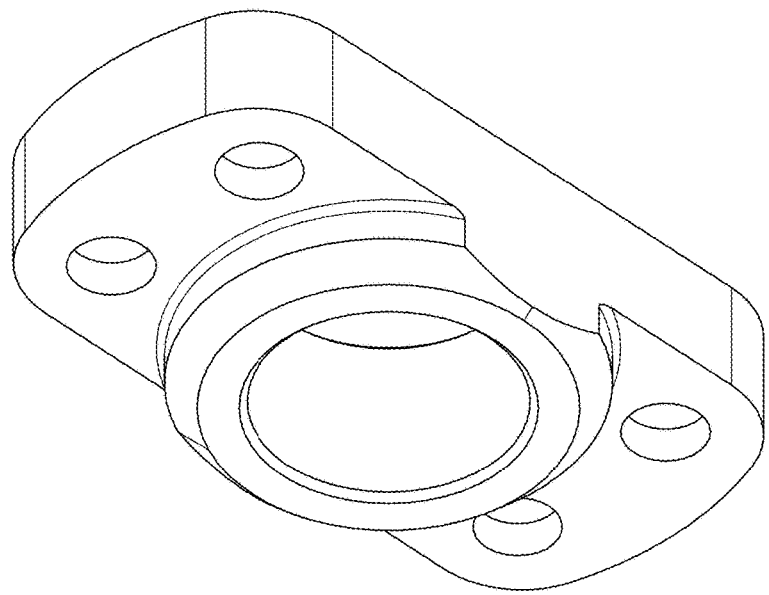
FIG. 40R

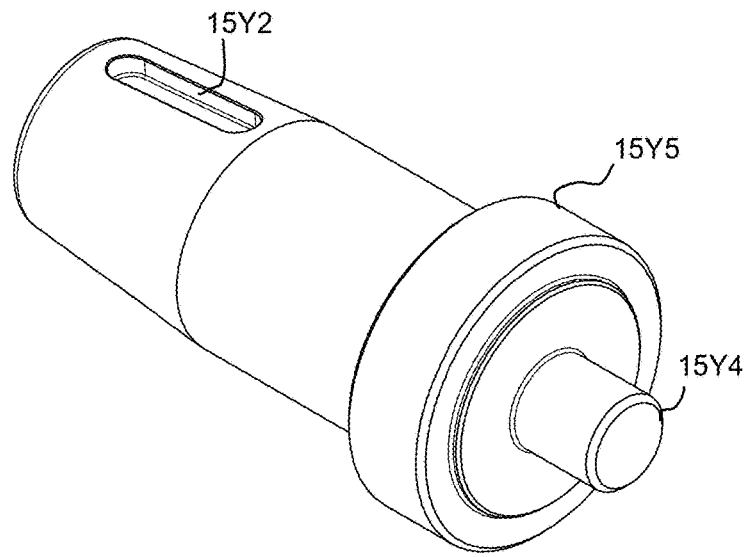
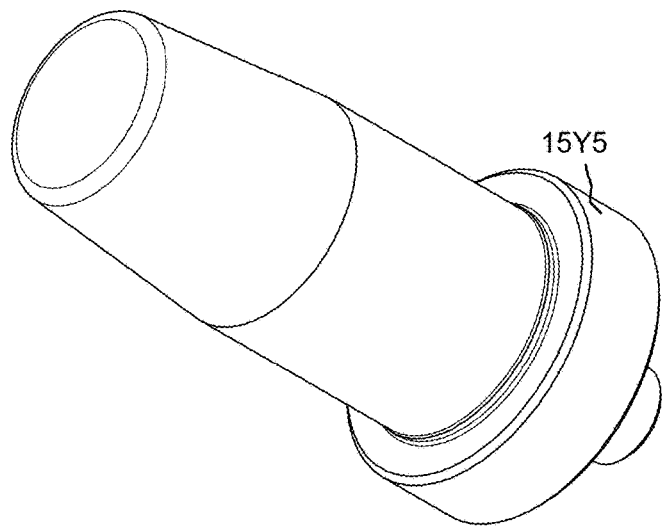
FIG. 40S

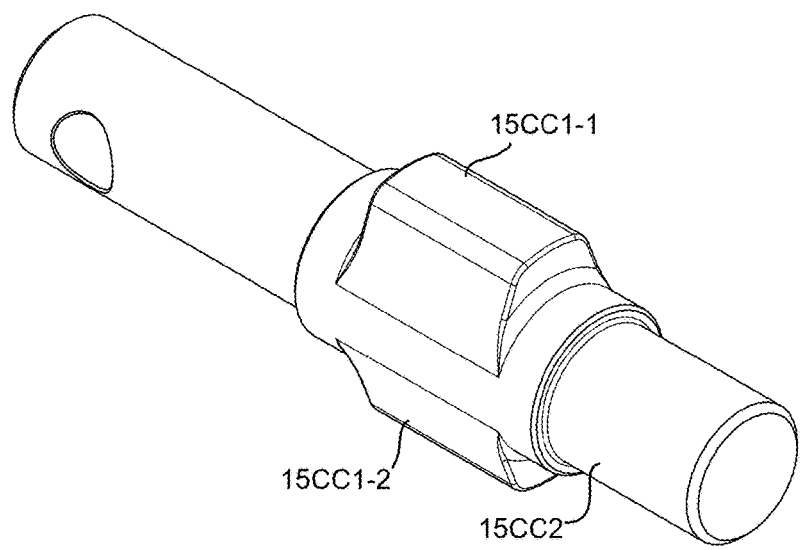
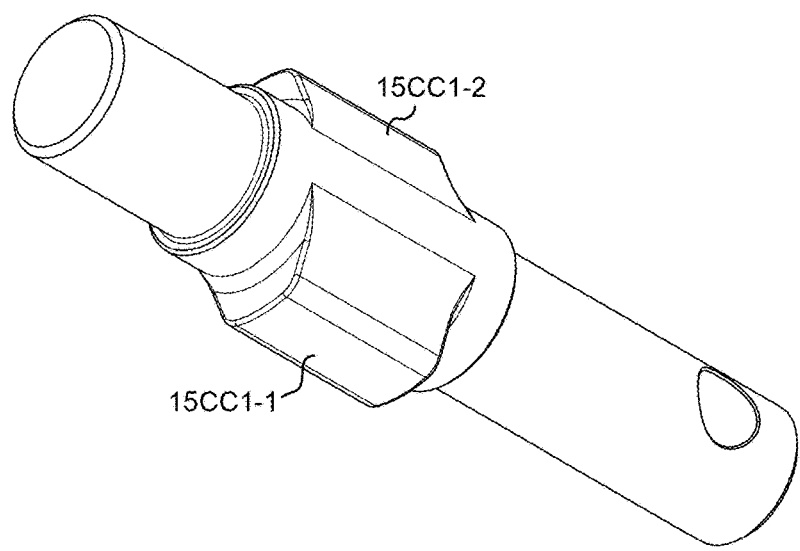
FIG. 40CC

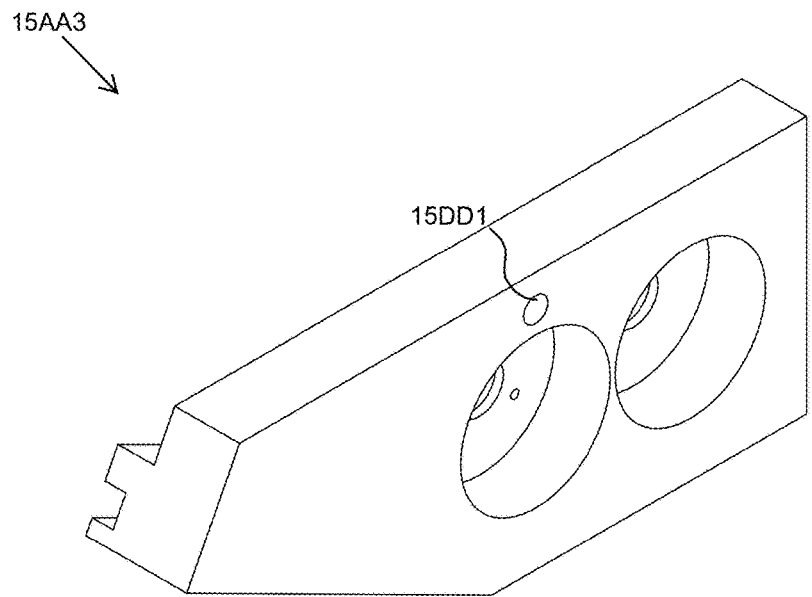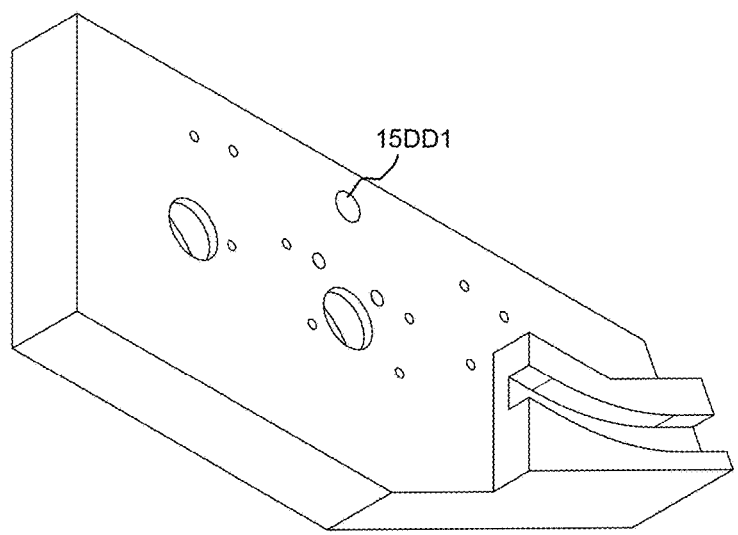
FIG. 40DD

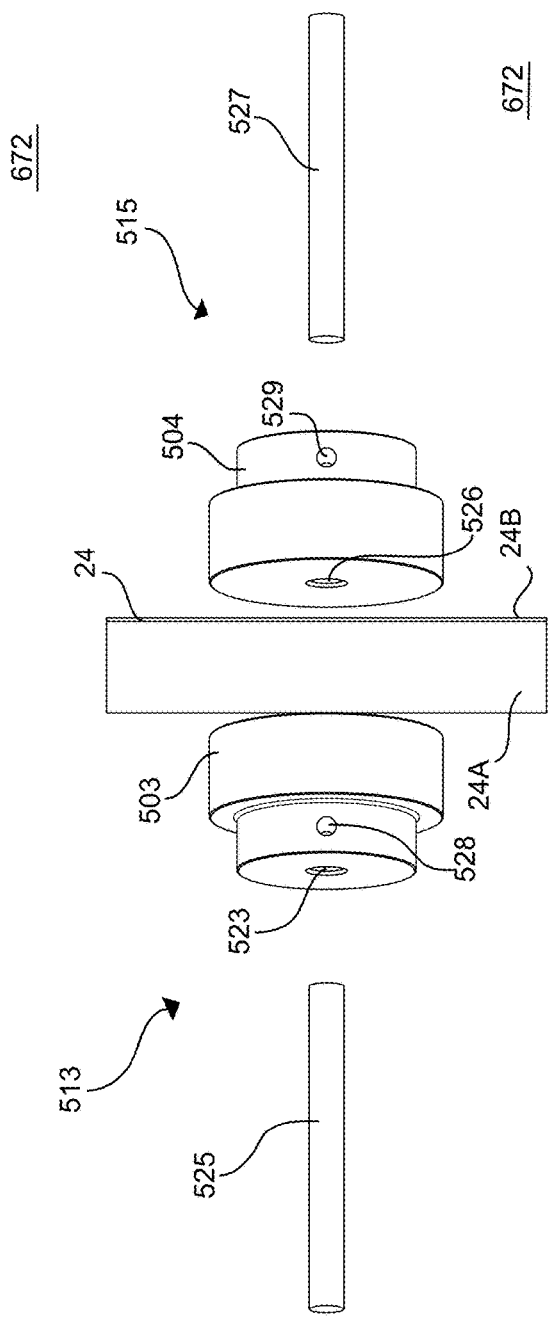
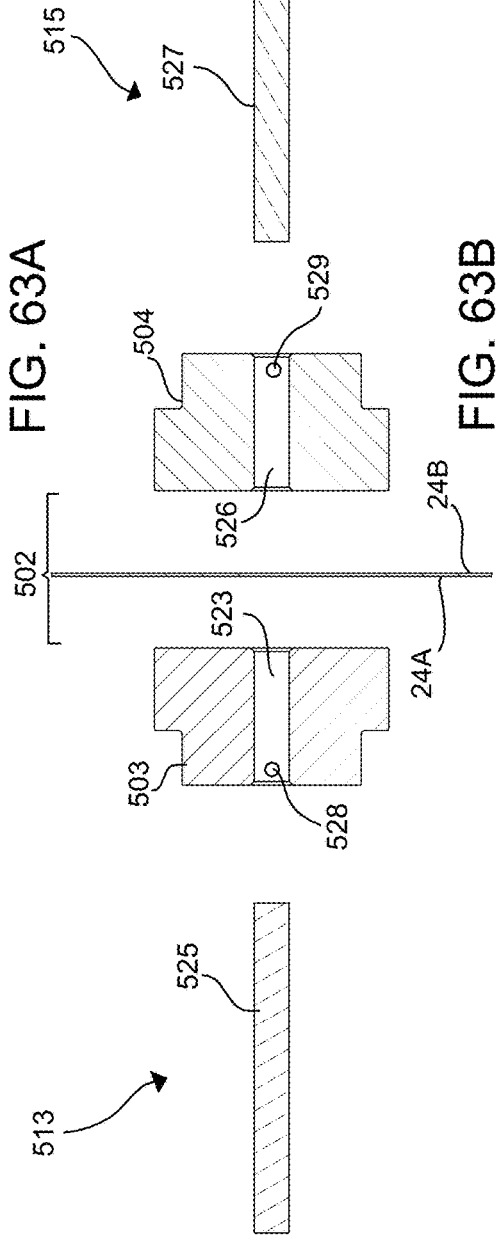
FIG. 63A
FIG. 63B

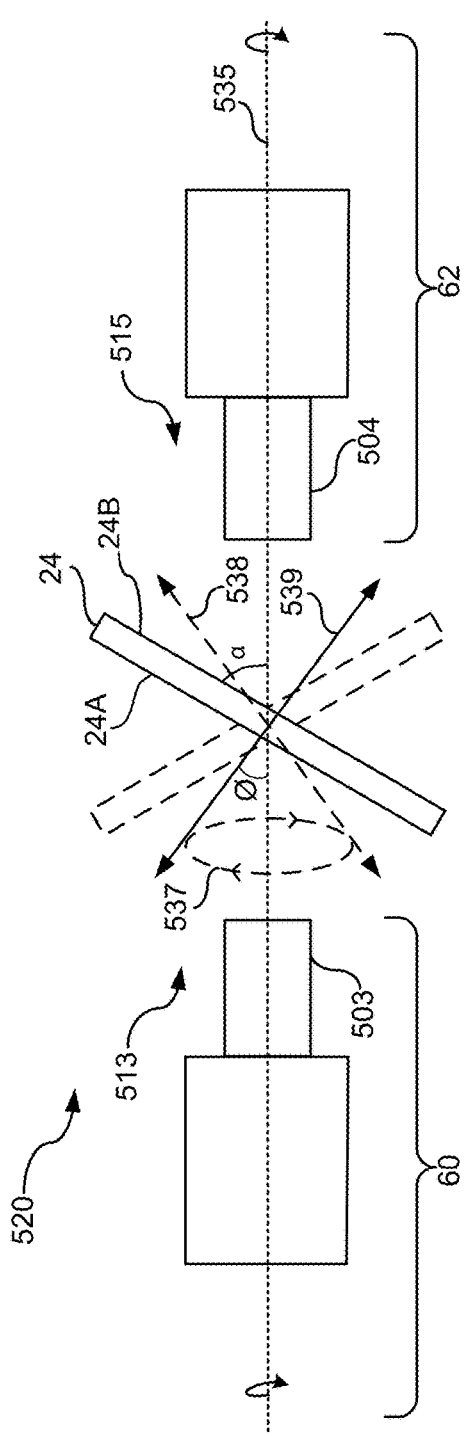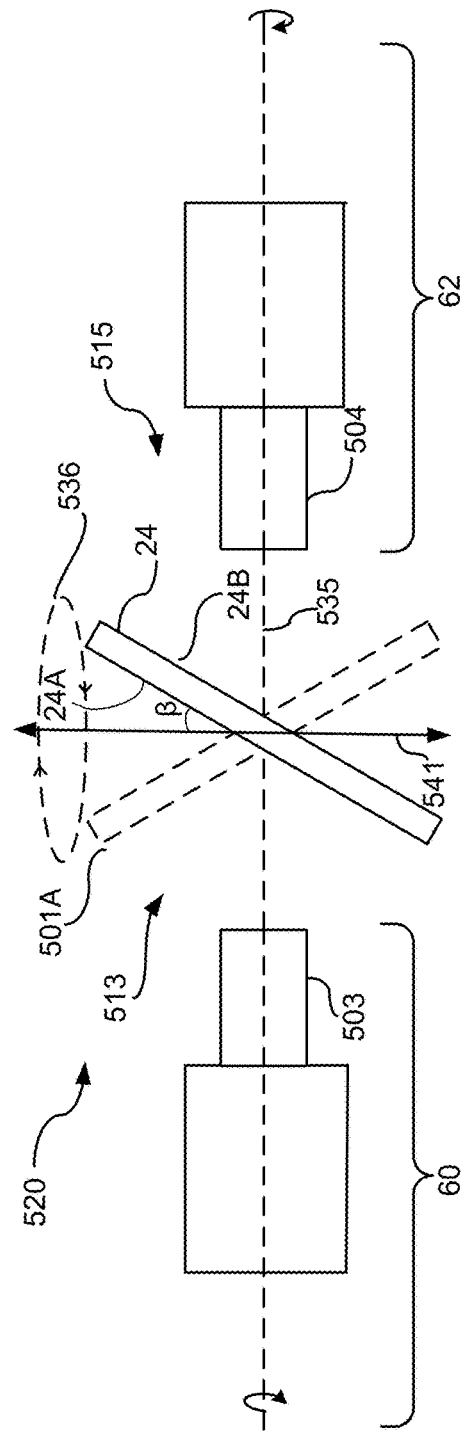

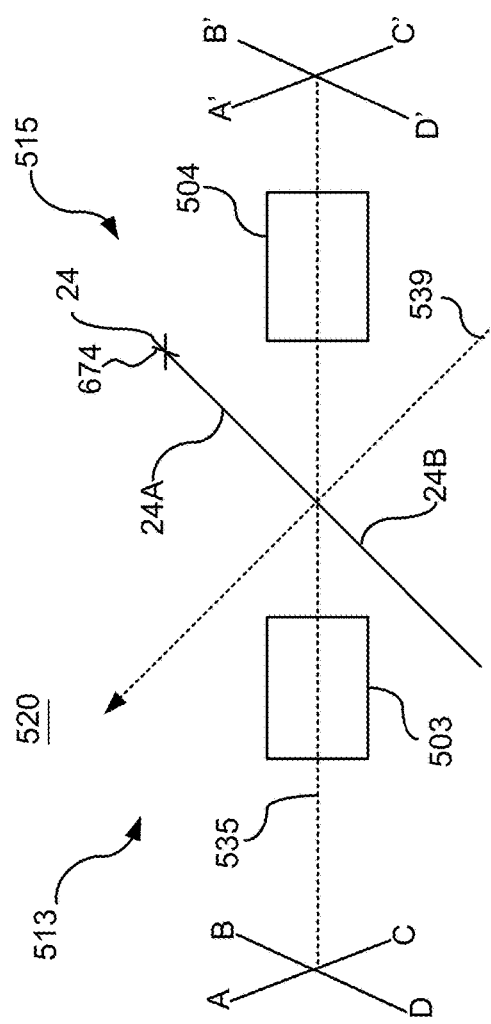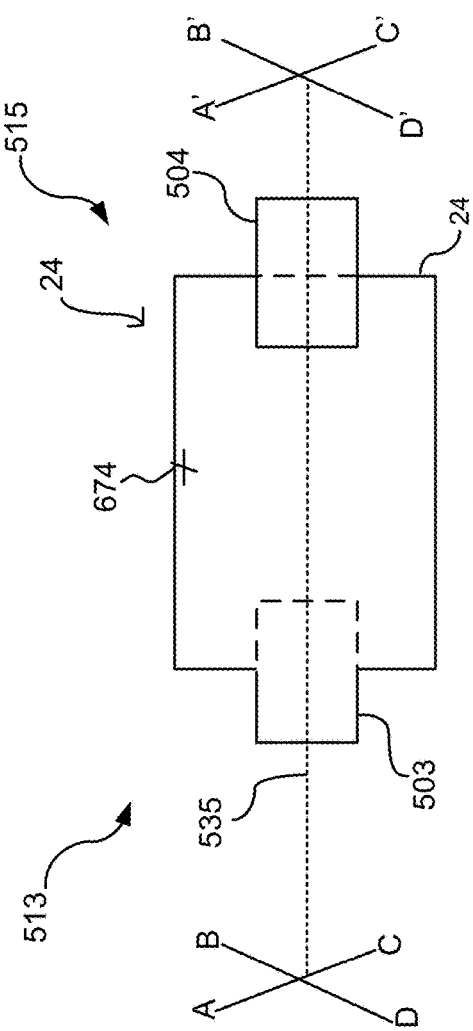

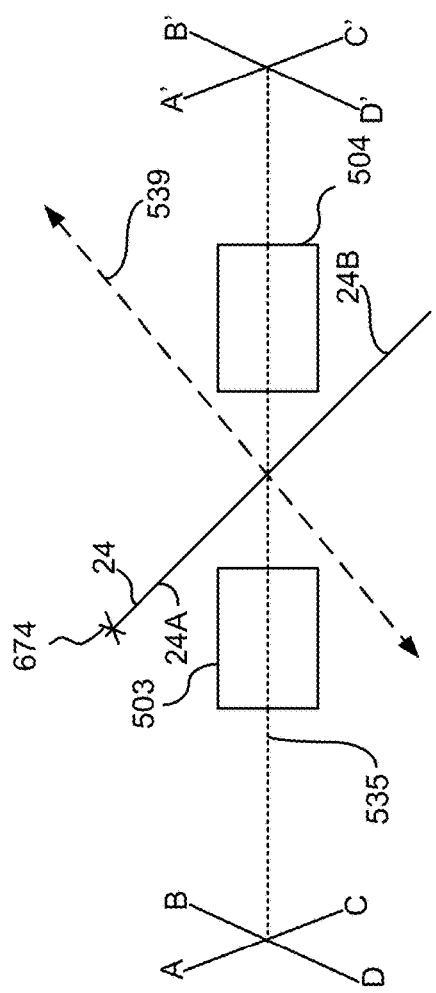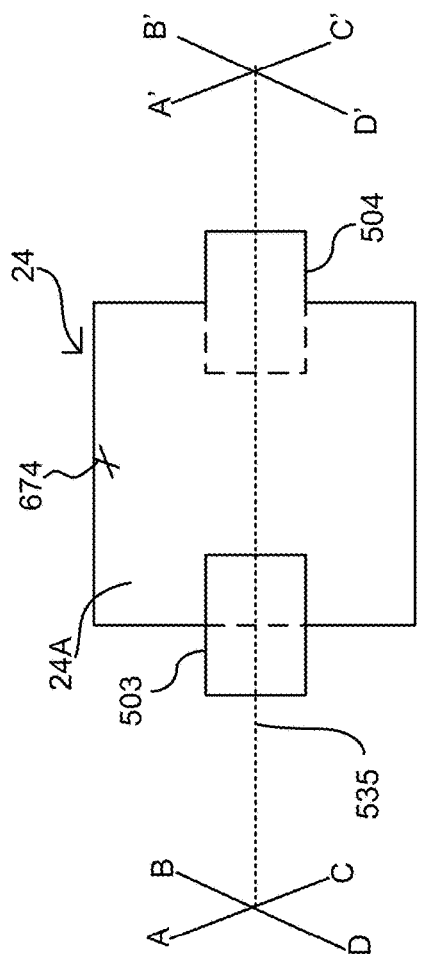

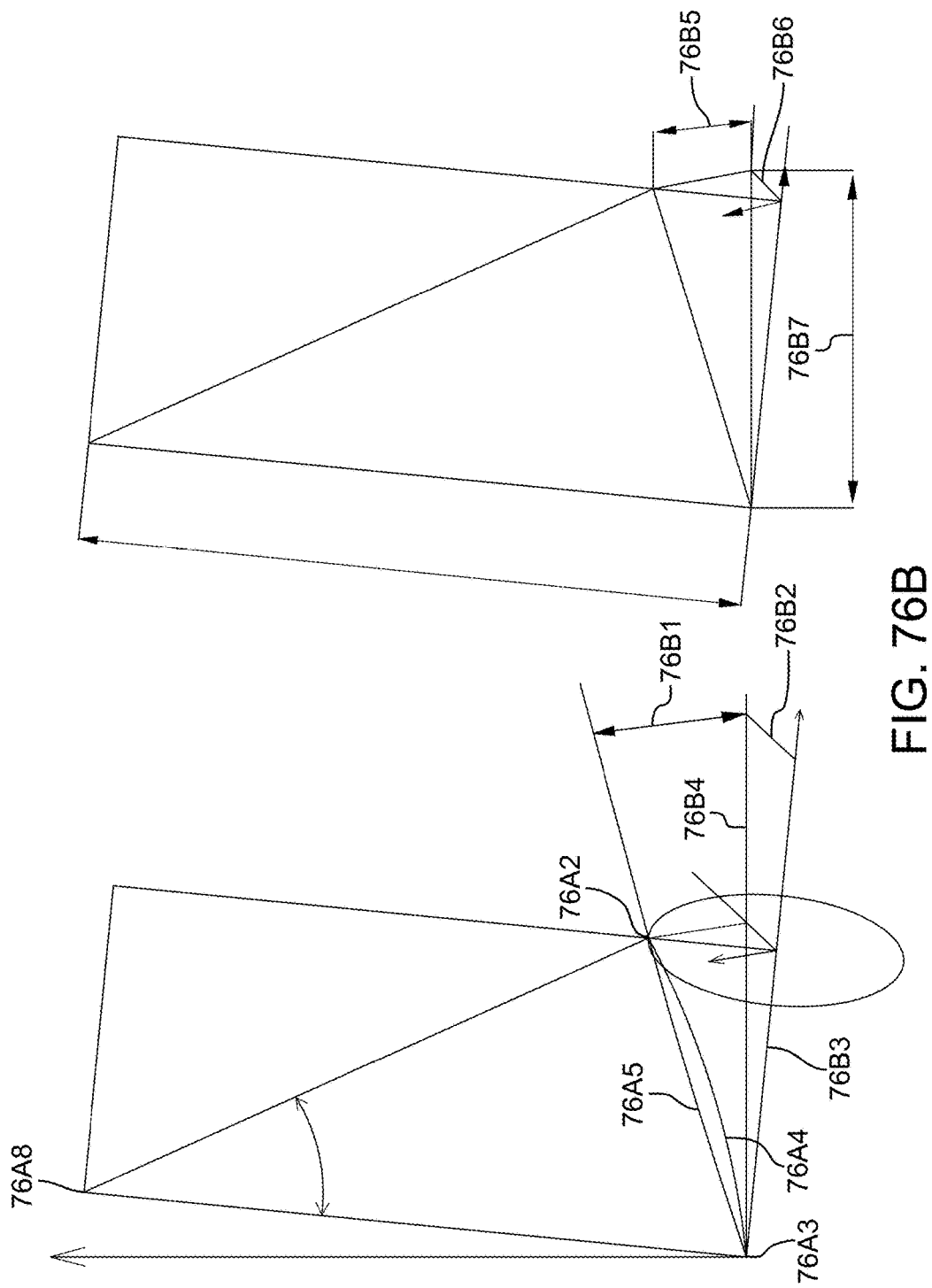

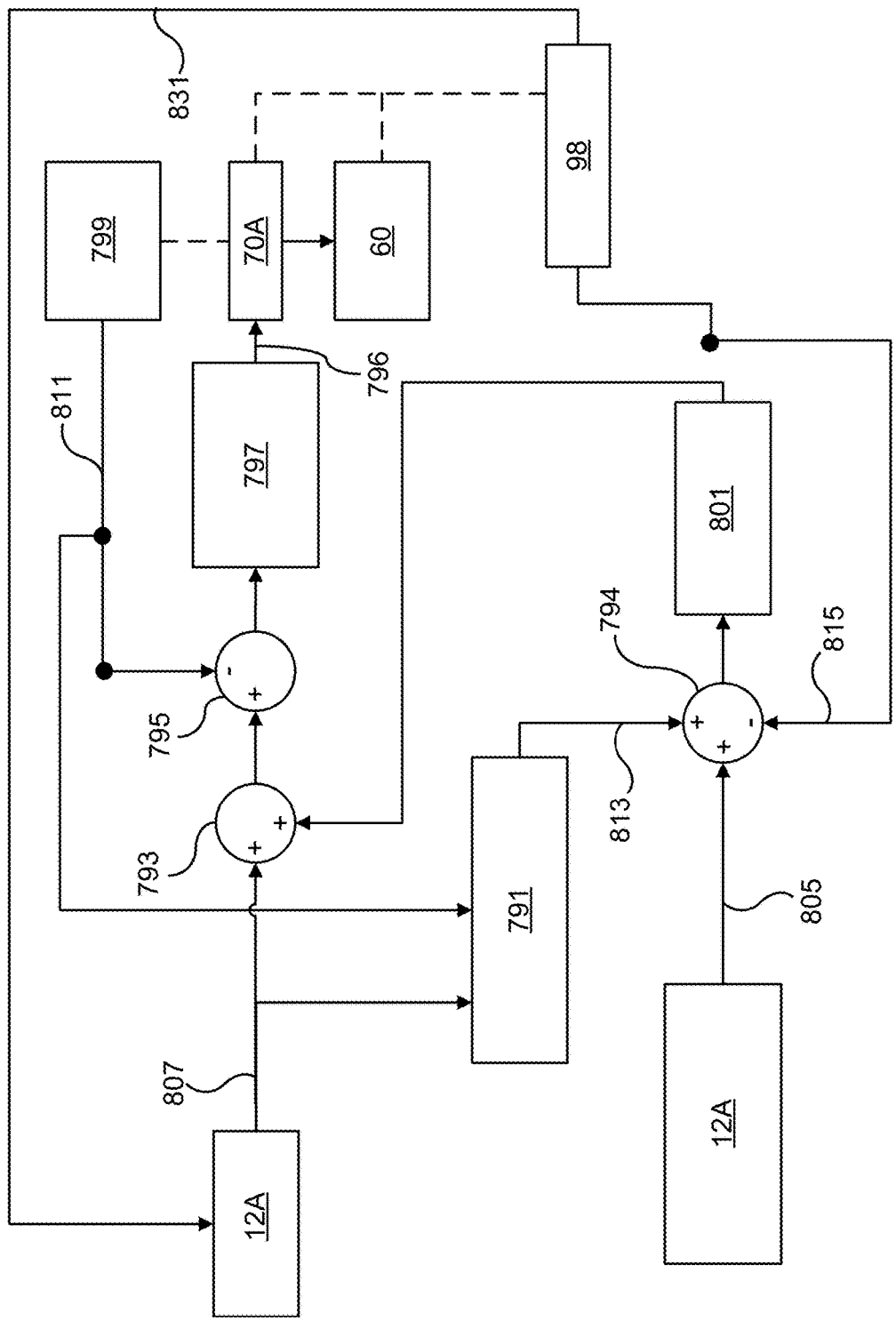

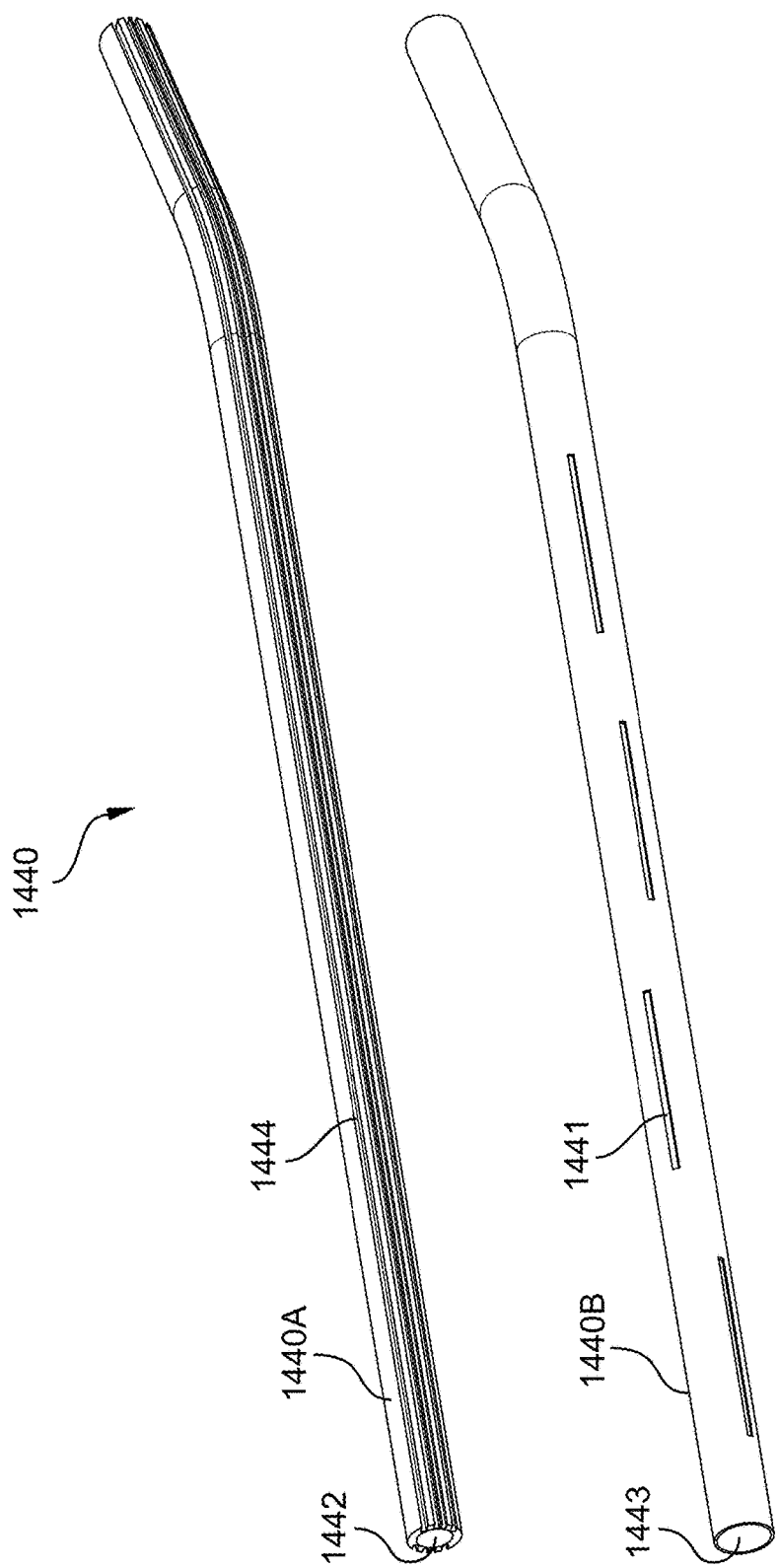

ROBOTIC SURGERY SYSTEM, METHOD, AND APPARATUS

CROSS-REFERENCE TO RELATED APPLICATIONS

The present application claims priority to U.S. Provisional Patent Application Ser. No. 62/193,959, filed Jul. 17, 2015, and entitled Robotic Surgery System, Method, and Apparatus, which is incorporated by reference herein in its entirety.

BACKGROUND

The present teachings relate to surgery. More specifically, the present teachings relate to an apparatus and method for providing minimally invasive surgery and robotic surgery.

The present teachings relate to performing surgical procedures. More specifically, the present teachings relate to an apparatus and method for performing minimally invasive surgical procedures. In recent times, minimally invasive surgical procedures have gained popularity and are widely chosen over conventional surgery methods. An acclaimed benefit is apparent decrease in post-surgery recovery time and significantly less scarring.

Typically, minimally invasive surgical procedures are computer-assisted procedures involving one or more minute incisions at the surgical site followed by insertion of flexible housing tubes holding instruments used for performing the surgical procedure. The surgical instruments are remotely controlled by medical personnel or a surgeon via a user interface portal. As a result, there need not be physical contact between the instruments performing the surgery and the supervising surgeon or medical personnel during the surgery. A goal of automated surgical procedures is to maintain the flexibility and freedom associated with manual surgical procedures and further refine such procedures beyond what would be feasible for a human surgeon.

Contamination of the surgical site or the surgical instruments used can cause severe consequences with respect to the desired course of the surgical procedure and/or the patient's health. Hygiene can be maintained by medical personnel during a manual surgical procedure by use of surgical gloves, mask and regular sterilization of surgical instruments during the operation. This may, however, present a challenge in a minimally invasive surgical procedure. In order to perform the computerized surgical procedure, an instrument driving force is passed from a non-sterile side to a sterile side while keeping the two sides isolated.

SUMMARY

In accordance with the present teachings, aspects of the current disclosure relate to a surgical system which may be configured to be a minimally invasive and/or computer assisted surgical system. The surgical system may require an occasional or continuous intervention from medical personnel. The requirement and extent of such intervention may vary depending on various factors, such as, for example, but not limited to, nature of the surgical procedure, anatomical site for performing such procedure, duration of the procedure, and extent of automating the surgical instrument. In some configurations, the system may be divided into two sections. Operation of the system may be controlled by transmission of a force from a first section to a second section of the system. The first section and the second section may be separated by a partition or a barrier. The first section may be a non-sterile section and the second section may be a sterile section of the surgical system.

A robotic surgery apparatus of some configurations of the present teachings can include, but is not limited to including, a drive component including at least one motor and an associated drive element for each of the at least one motor. The associated drive element can have a drive screw, a nut which can translationally displace about a longitudinal axis of the drive screw in response to drive screw rotation about the longitudinal axis, and a projection oriented transverse to the longitudinal axis. The robotic surgery apparatus can also include a manipulator including at least one driven element having a receiving feature which can engage the projection. The driven element can translationally displace with the projection when the projection is engaged in the receiving feature. The robotic surgery apparatus can still further include a continuous barrier separating the manipulator and the drive component. At least a portion of the barrier can cover the projection so that the projection engages the receiving feature through the barrier. The robotic surgery apparatus can also include at least one actuator having a first end coupled to the driven element and a second end coupled to an articulated shaft.

Optionally, the projection can be an integrally formed part of the nut, the nut can include a receiving structure into which the projection may be coupled, possibly removably coupled, and the driven element can translationally displace along an axis parallel to the longitudinal axis. The robotic surgery apparatus can optionally include one or more linear bearing along which the nut displaces. Also optionally, at least a portion of the barrier can move with the projection and driven element, the barrier can include a pocketed region including at least one pocket, and the at least one pocket can be surrounded by a variable region including at least one pleat. The manipulator can optionally include only mechanical components. The motor can optionally be configured to displace a piston in a master hydraulic cylinder, and the associated drive element can be coupled to a slave piston in a slave hydraulic cylinder for the master hydraulic cylinder.

A load sensor for measuring a load of the present teachings can include, but is not limited to including, a mechanical component having a compliant body which can deform in proportion to a magnitude of the load. The compliant body can include at least one stop projection which can extend from a first portion of the complaint body toward a second portion of the compliant body leaving a gap between the first and second portions when the magnitude of the load is in a first range. The at least one stop projection can contact the second portion when the magnitude of the load is in a second range. The load sensor can further include a projection attached to the compliant body. The projection can displace in response to deformation of the compliant body. The load sensor can also include an electrical component that can be physically separate from the mechanical component. The electrical component can include at least one sensor which can monitor displacement of the projection.

The projection can optionally include a magnet. The electrical component can optionally include at least one Hall effect sensor which can produce a Hall voltage based on the position of the magnet. The projection can optionally include a fiducial reference marking, and the electrical component can optionally include an optical sensor which can monitor the location of the fiducial reference marking. The electrical component can optionally include a potentiometer whose wiper can displace in response to displacement of the projection. The projection can optionally include a first end attached to the compliant body and a second end distal to the complaint body. The displacement of a point on the second end can be equal to the length of the projection multiplied radian angle of projection with respect to an unloaded position of the projection. The load sensor can optionally be constructed of aluminum. The first range can optionally be between 0 and 50 pounds. The compliant body can optionally be an S beam, and can include a number of cutouts and channels. The cutouts and channels can optionally create a parallelogram frame in the compliant body. The compliant body can optionally include a void extending through the complaint body from a first side of the complaint body to a second side of the compliant body.

In another configuration of the present teachings, a load sensor for measuring a load can include, but is not limited to including, a mechanical component including a compliant body that can deform in proportion to a magnitude of the load. The load sensor can also include an insert extending through the compliant body. The insert can have an insert first face spaced from a compliant body first face by a first gap. The first face can be a part of a first end of the compliant body. The load sensor can still further include an adjustable spacer on the insert. The adjustable spacer can have an adjustable insert face spaced from a compliant body second face by a second gap. The compliant body second face can be disposed opposite the complaint body first face. The load sensor can also include a projection attached to the compliant body. The projection can displace in response to deformation of the compliant body. The load sensor can also include an electrical component physically separate from the mechanical component. The electrical component can include at least one sensor which can monitor displacement of the projection.

The insert can optionally be a threaded insert. The adjustable spacer can optionally be a nut. The projection can optionally include a bend which can divide the projection into a pre-bend portion and a post-bend portion. The pre-bend portion can optionally be attached to the complaint body, and the post-bend portion can optionally have a face that is substantially perpendicular to the complaint body first face.

A sterile component for a robotic surgery system of the present teachings can include, but is not limited to including, a manipulated component having a first proximal portion with a proximal end and an articulated distal portion with a distal end. The articulated distal portion can include at least one articulation about which the articulated distal portion may be bent. The sterile component can also include at least one displaceable actuator having a first actuator end and a second actuator end. The first actuator end can be anchor to the distal articulated portion. Each displaceable actuator can have a constrained portion including the first actuator end which can be located in a guide of the manipulated component and a second portion including the second actuator end which can be disposed outside of the guide. The sterile component can also include a surgical tool disposed at the distal end of the manipulated component, and a manipulator that can include at least one driven element. The driven element can include an anchor point to which the second actuator end can be anchored. The driven element can be translationally displaceable along at least one bearing surface in the manipulator. The driven element can have a receiving feature which can be dimensioned to engage a portion of a drive element through a barrier.

The at least one articulation can optionally include a living hinge. The at least one articulation can optionally include a kinematic pair of bodies. The kinematic pair of bodies can optionally include a ball and socket joint. At least a portion of the proximal portion of the manipulated component can optionally be housed within the manipulator. The at least one displaceable actuator can optionally be a pull wire. Each of the displaceable actuators can optionally exit the guide at a cutout in the manipulated component. The driven element can optionally include a rail projection which can extend into the cutout and can ride along the cutout as the driven element is displaced. The driven element can optionally include a channel in which a majority of the second actuator portion is located. The driven element can optionally be a block like structure. The manipulator can optionally include a housing having at least one slot. Each slot can optionally be aligned with one receiving feature of one of the at least one driven elements. The sterile component can optionally include only mechanical components. The manipulator can optionally include comprises at least one rotary driven element configured to interact with a rotary drive element through a barrier. The manipulator can optionally include a rotary driven element including a magnet. The manipulator can optionally include a rotary driven element having a multi-pocketed structure. The manipulator can optionally include a rotary drive element having a shaft rotating about a first axis. The shaft attached to a barrier interfacing element can optionally have a face with an irregular surface oriented at an acute angle to the first axis.

An apparatus for transmission of force in a surgical system of the present teachings can include, but is not limited to including, a barrier positioned between a non-sterile section and a sterile section of the surgical system. The barrier can include a first surface facing the non-sterile section and an opposing second surface facing the sterile section. The apparatus can also include at least one drive element located in the non-sterile section of the surgical system. The drive element can generate and transmit a pre-determined force, and can include one or more barrier interfacing members that are in communication with the first surface of the barrier in the non-sterile section. The apparatus can further include at least one driven element located in the sterile section of the surgical system. The driven element can include one or more co-operating barrier interfacing members in communication with the opposing second face of the barrier in the sterile section. The driven element can receive the pre-determined force from the drive element in the non-sterile section across the barrier. The barrier can maintain integrity during the transmission of the pre-determined force. The pre-determined force can optionally be linear or rotational. The at least one drive element and the one or more first barrier interfacing member can optionally be disposed in a first housing in the non-sterile section, and the at least one driven element and the one or more co-operating barrier interfacing members can optionally be disposed in a second housing in the sterile section. The barrier can optionally be continuous, and/or can be composed of one or more layers, and can optionally be in a contact-free communication with the one or more barrier interfacing members in the non-sterile section. The one or more barrier interfacing member and the co-operating one or more barrier interfacing member can optionally form a magnetic coupling that can achieve the contact-free communication across the barrier for transmission of the pre-determined force.

An apparatus for transmission of torque in a surgical system of the present teachings can include, but is not limited to including, a barrier positioned between a non-sterile section and a sterile section of the surgical system. The barrier can include a first face and an opposing second face. The apparatus can also include at least one drive element disposed in the non-sterile section of the surgical system. The drive element can generate and transmit torque along a reference axis that is transverse to an axis that is parallel to the first surface and the second opposing surface. The reference axis can originate in the non-sterile section and terminate in the sterile section. The drive element can include one or more barrier interfacing members in communication with the first face of the barrier. The apparatus can also include at least one driven element disposed in the sterile section. The driven element can include one or more cooperating barrier interfacing members in communication with the barrier on the opposing second surface of the barrier. The driven element can receive the pre-determined torque from the drive element along the reference axis. The apparatus can also include at least one bridging element tailored in the barrier. The bridging element can link the drive element and the driven element, and can include a first set of accessible parts on the non-sterile section and a second set of accessible parts on the sterile section. The first set of accessible parts and the second set of accessible parts can mate with the one or more barrier interfacing members in the non-sterile section and the one or more co-operating barrier interfacing members in the sterile section, respectively.

BRIEF DESCRIPTION OF THE DRAWINGS

These and other aspects will become more apparent from the following detailed description of the various configurations of the present disclosure with reference to the drawings wherein:

FIG. 18 is a schematic diagram of a drive component including motors or motor assemblies;

FIGS. 40A-1, 40A-2, and 40A-3 are pictorial representations of actuator pins reacting to double cam rotation of the present teachings;

FIG. 40D is a graphical representation of the tracks of the double cams of FIG. 40C when in operation;

FIG. 40H is a schematic diagram of the ball screw of the present teachings;

FIG. 40L-1 is a schematic diagram of the cable drive actuator module of the present teachings;

FIG. 40L-2 is a schematic diagram of an explosion of the cable drive actuator module of FIG. 40L-1;

FIG. 40N is a schematic diagram of the swing arm of the present teachings;

FIG. 40P is a schematic diagram of the swing arm pulley of the present teachings;

FIG. 40Q is a schematic diagram of the pulley of the present teachings;

FIG. 40R is a schematic diagram of the pulley drive shaft bearing of the present teachings;

FIG. 40S is a schematic diagram of the pulley box drive shaft of the present teachings;

FIGS. 40AA and 40BB are a schematic diagrams of a second configuration of the tensioning assembly of the present teachings including a cam;

FIG. 40CC is a schematic diagram of the tension relief cam of the present teachings;

FIG. 40DD is a schematic diagram of another configuration of the capstan housing of the present teachings;

FIG. 63A is an exploded perspective view of a torque transmitting arrangement of the present teachings;

FIG. 63B is a cross section of the view of FIG. 63A;

FIG. 64A is a representational view of an example torque transmission arrangement of the present teachings;

FIG. 64B is a pictorial representation of nutation described with respect to possible axes;

FIGS. 64C-64F are pictorial representations of the displacement of a barrier as a drive element and a driven element rotate about a reference axis;

FIG. 68 is a pictorial representation of the gear train of the rotational element of the present teachings;

FIG. 69 is a schematic diagram of a manipulator seated on an interface plate of the present teachings;

FIG. 70 is a schematic diagram of a manipulator positioned for docking onto an interface plate of the present teachings;

FIG. 71 is a pictorial representation of an articulated part of the manipulated component of the present teachings;

FIG. 72 is a pictorial representation of the bend plane of the present teachings;

FIG. 73 is a pictorial representation of an initial position of articulated segments of the present teachings;

FIG. 74 is a pictorial representation of articulation of articulated segments of the present teachings;

FIG. 75 is a plan view of actuator relationships of the present teachings;

FIG. 76 is a flowchart of a method for controlling the operation of an articulated segment;

Figure 76:
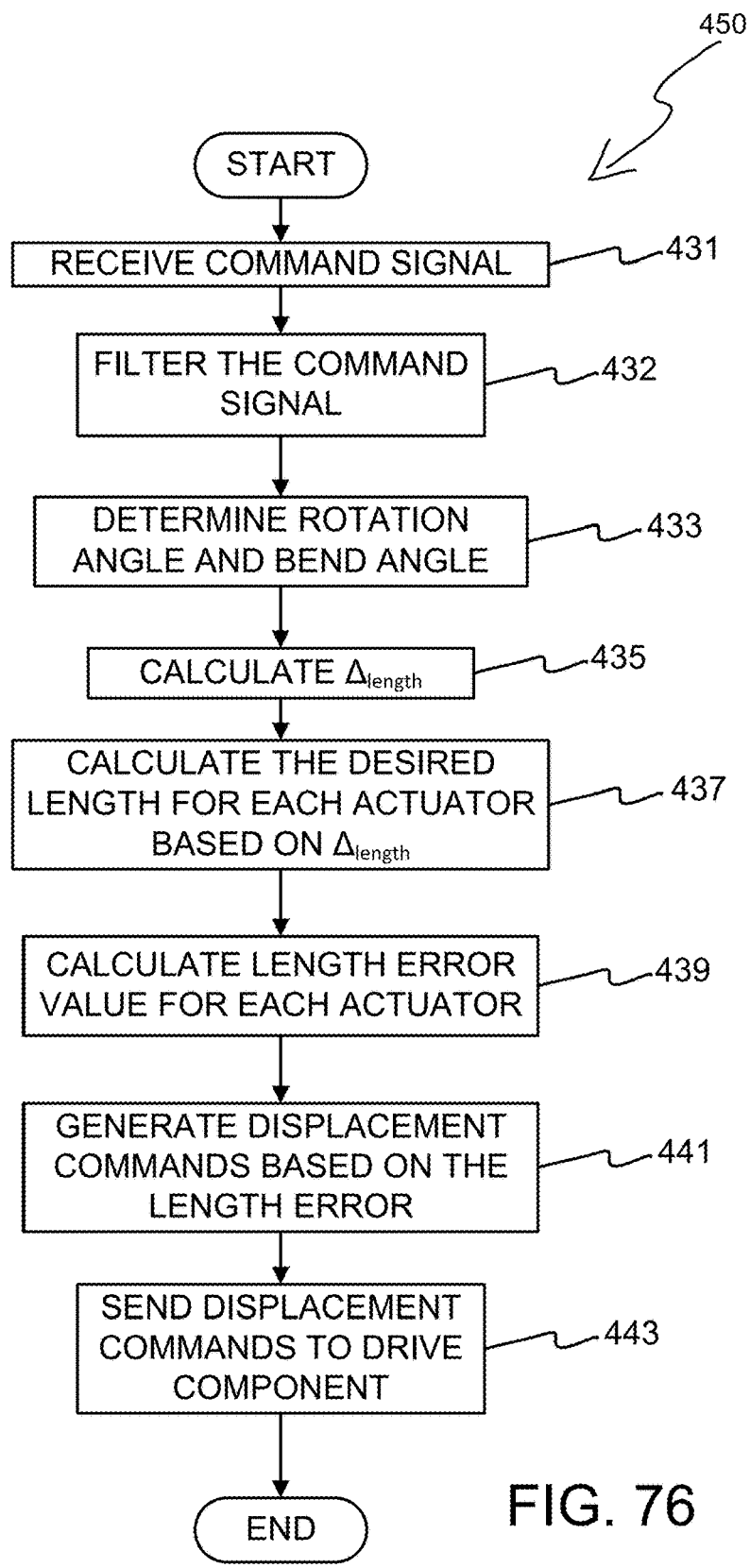
Figure 76A:
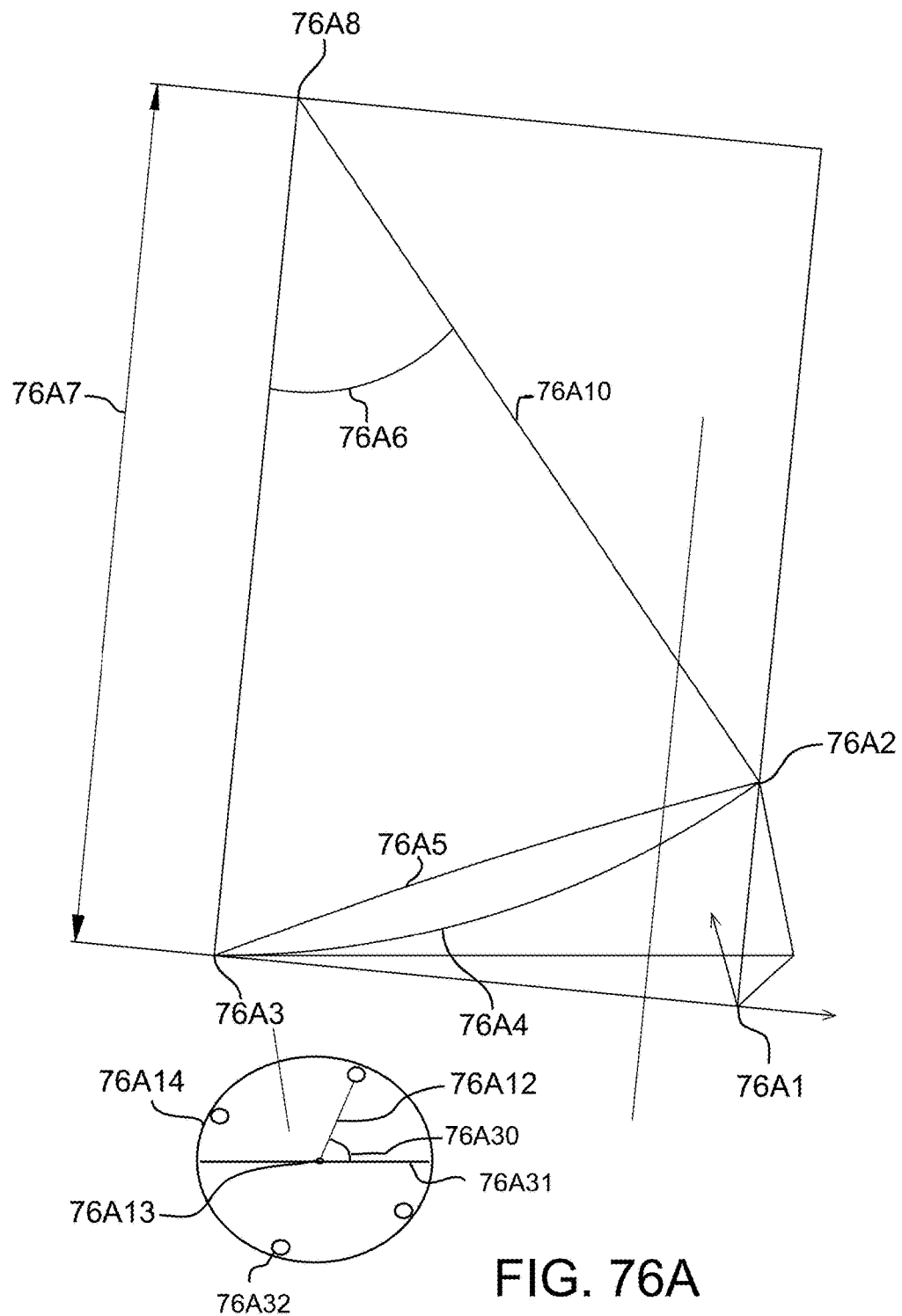
Figure 76C:
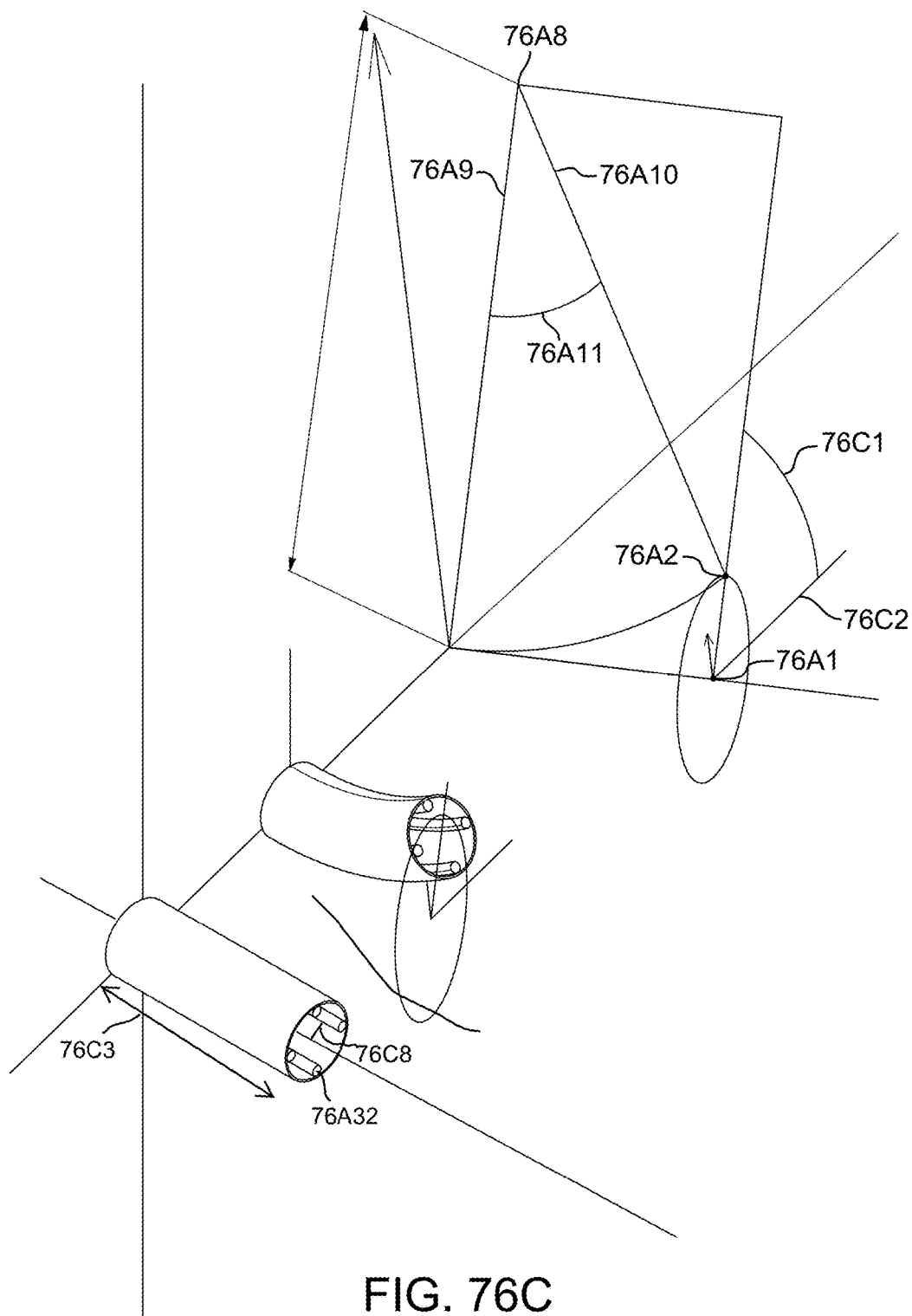
Figure 77:
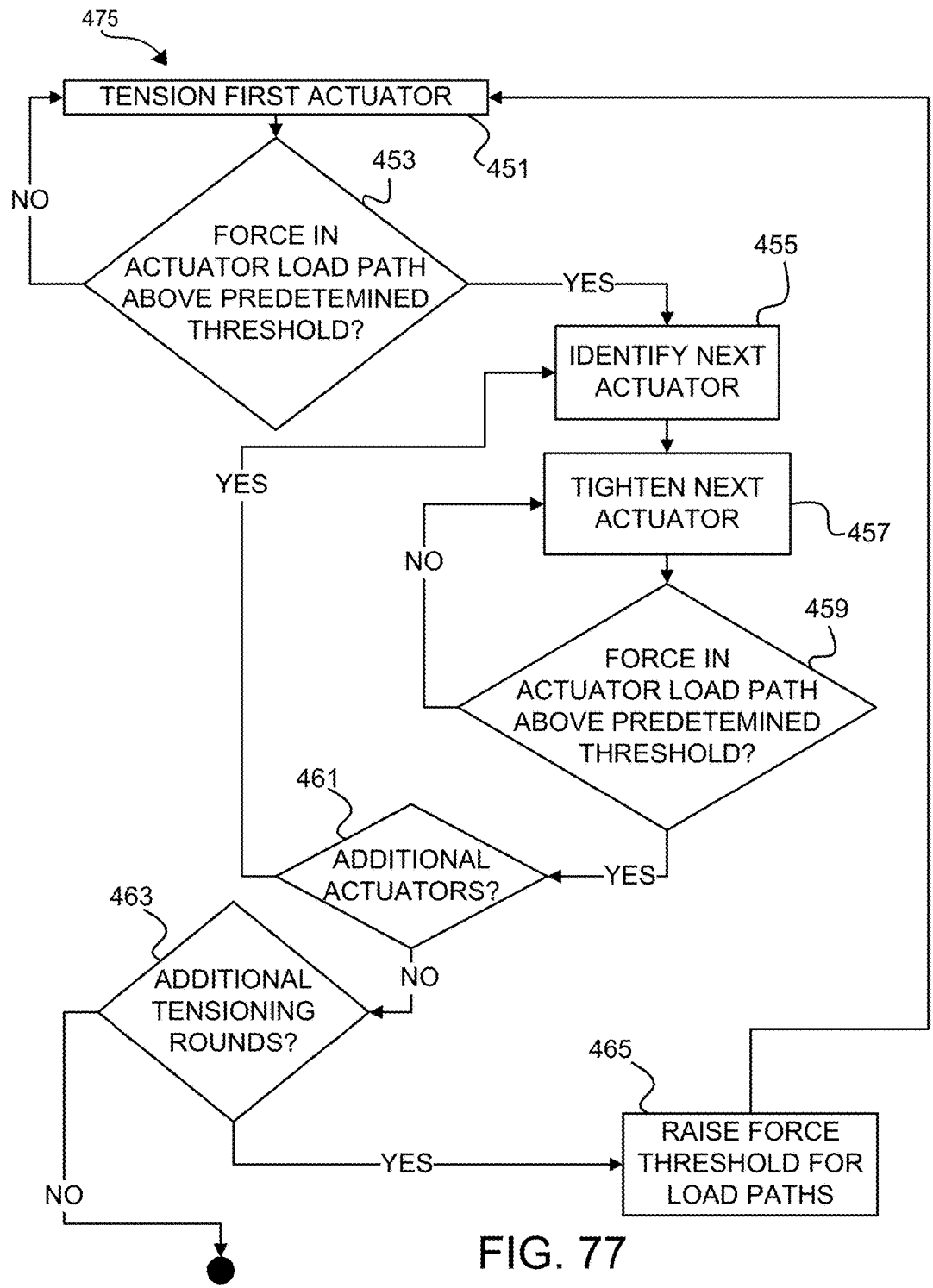
Figure 78:
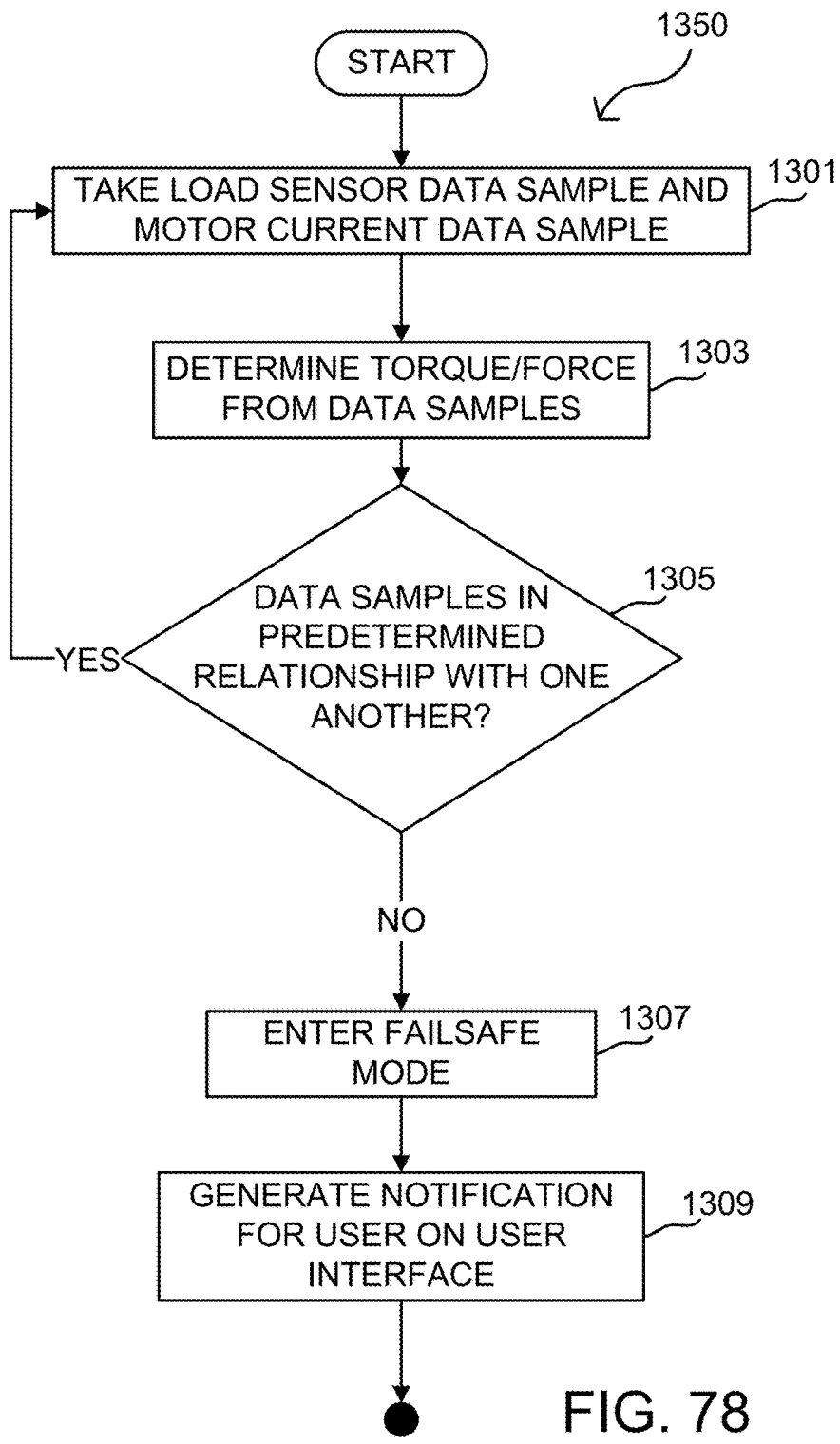
Figure 79A:
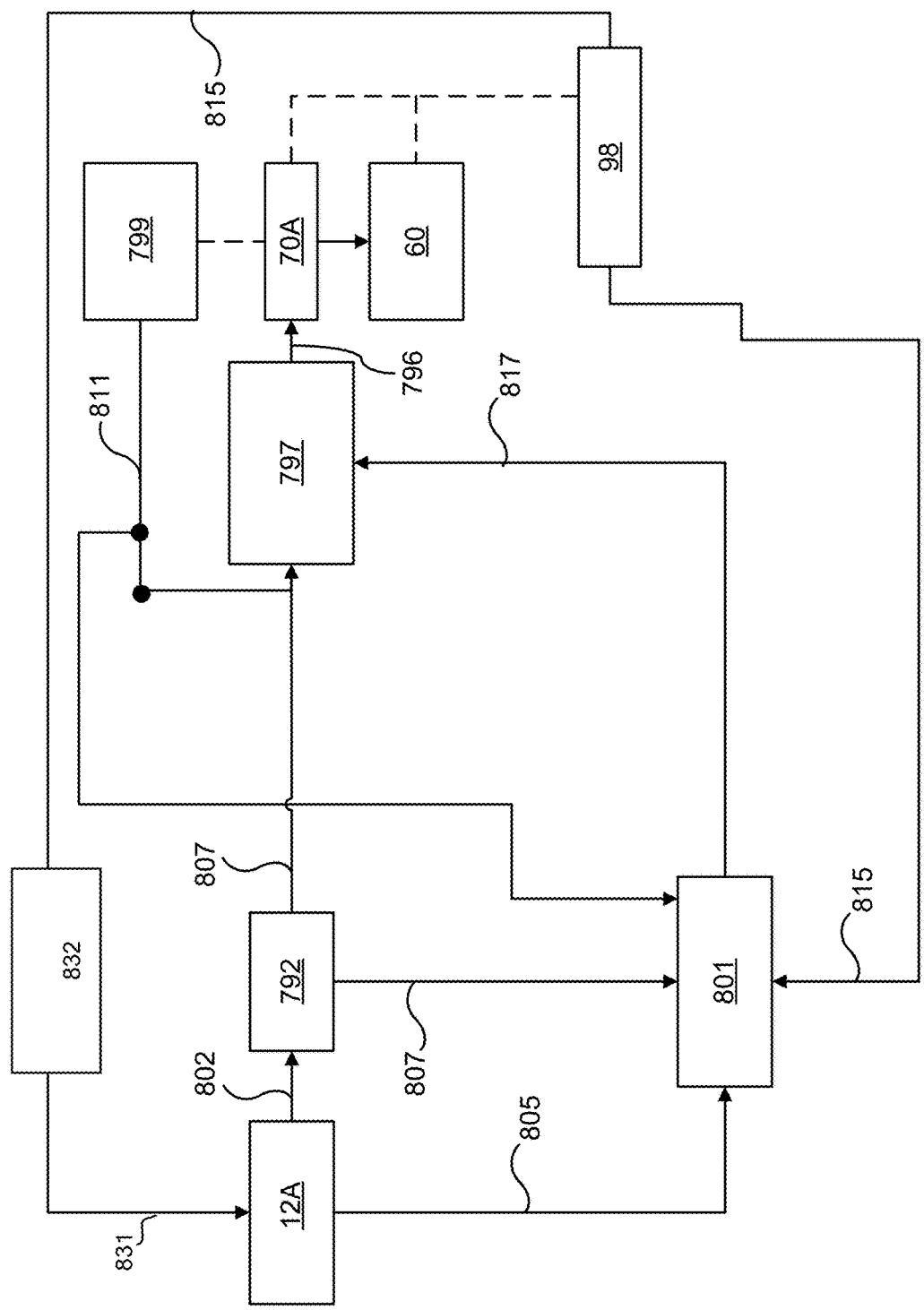
Figure 79C:
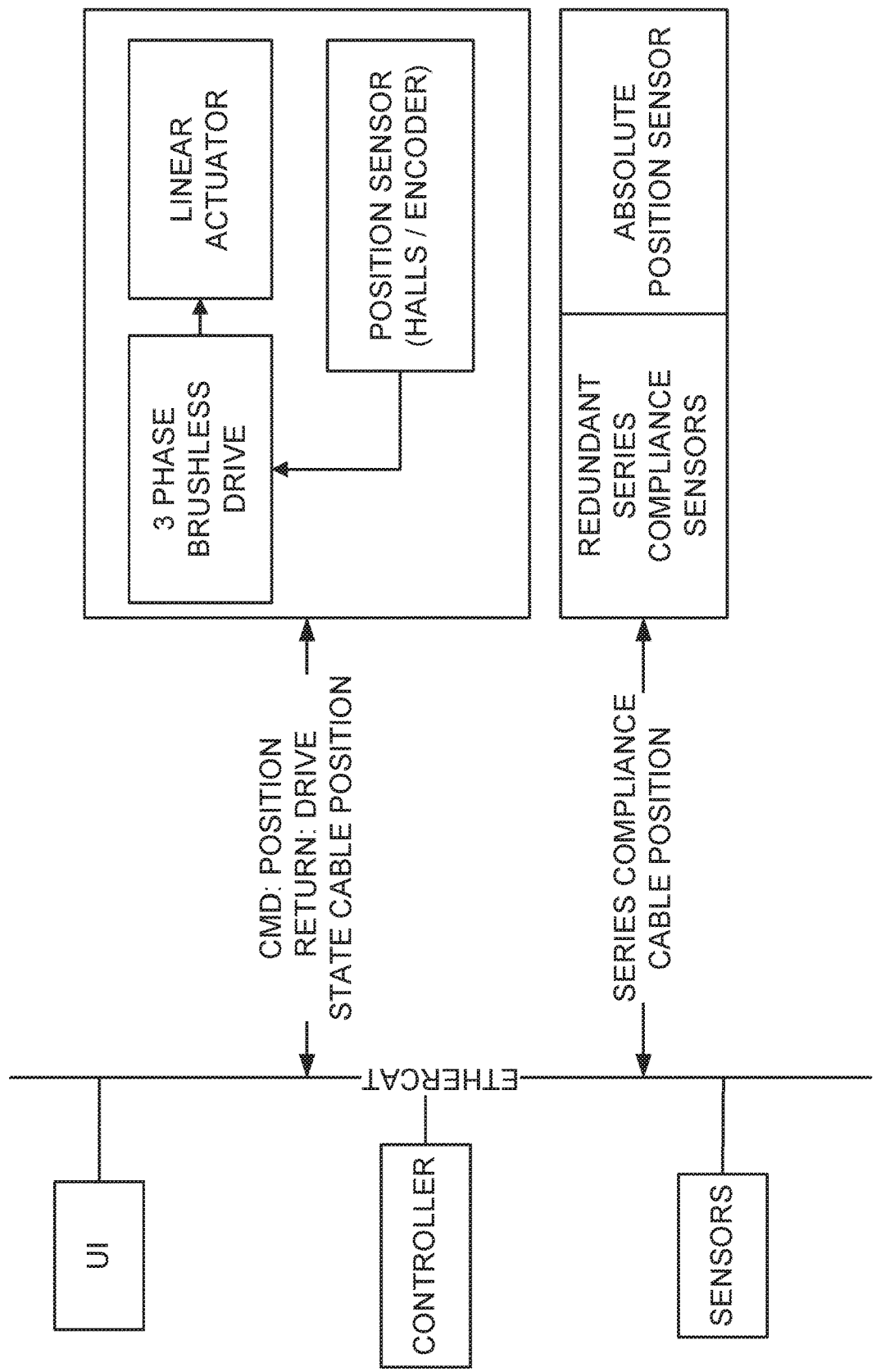
Figure 80B:
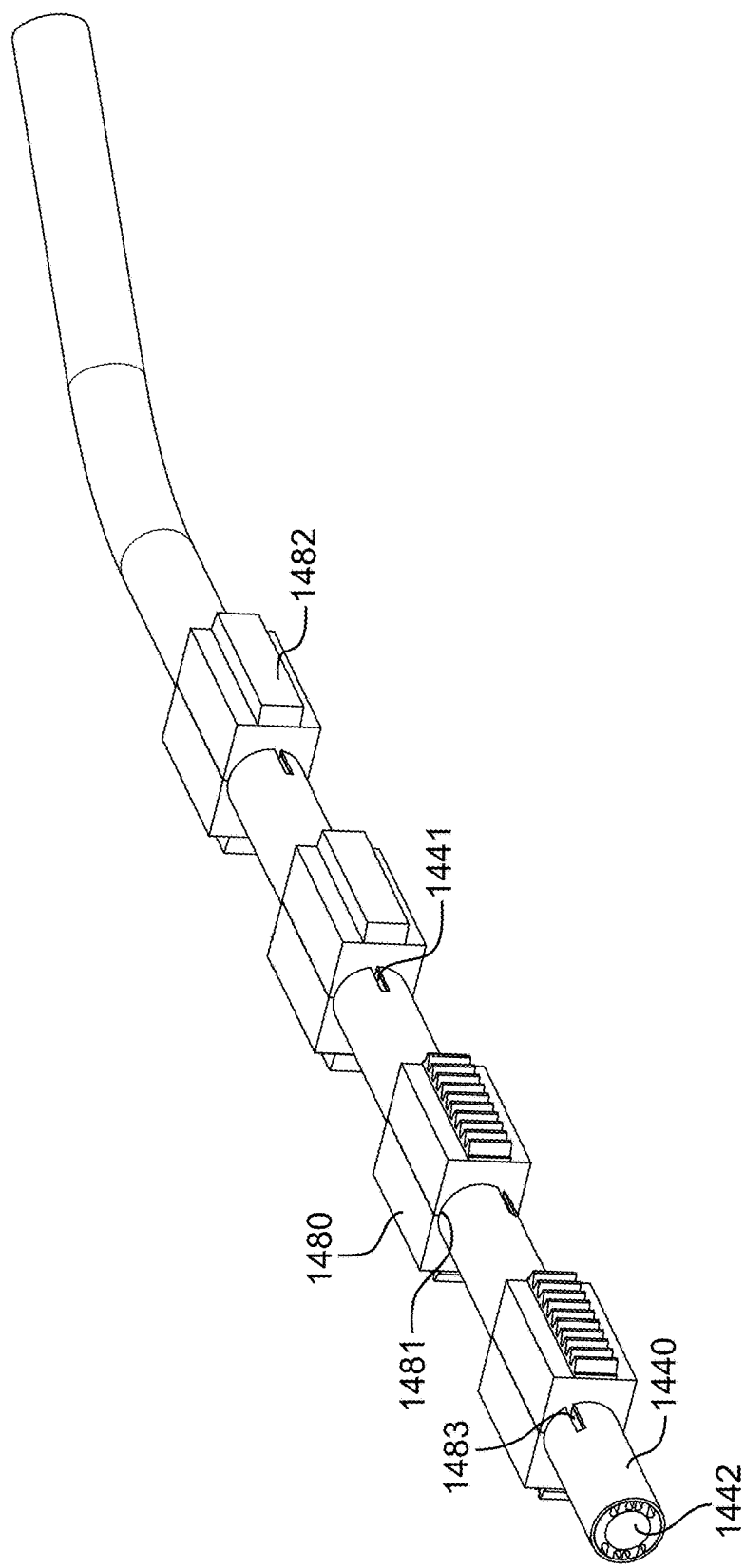
Figure 81A:
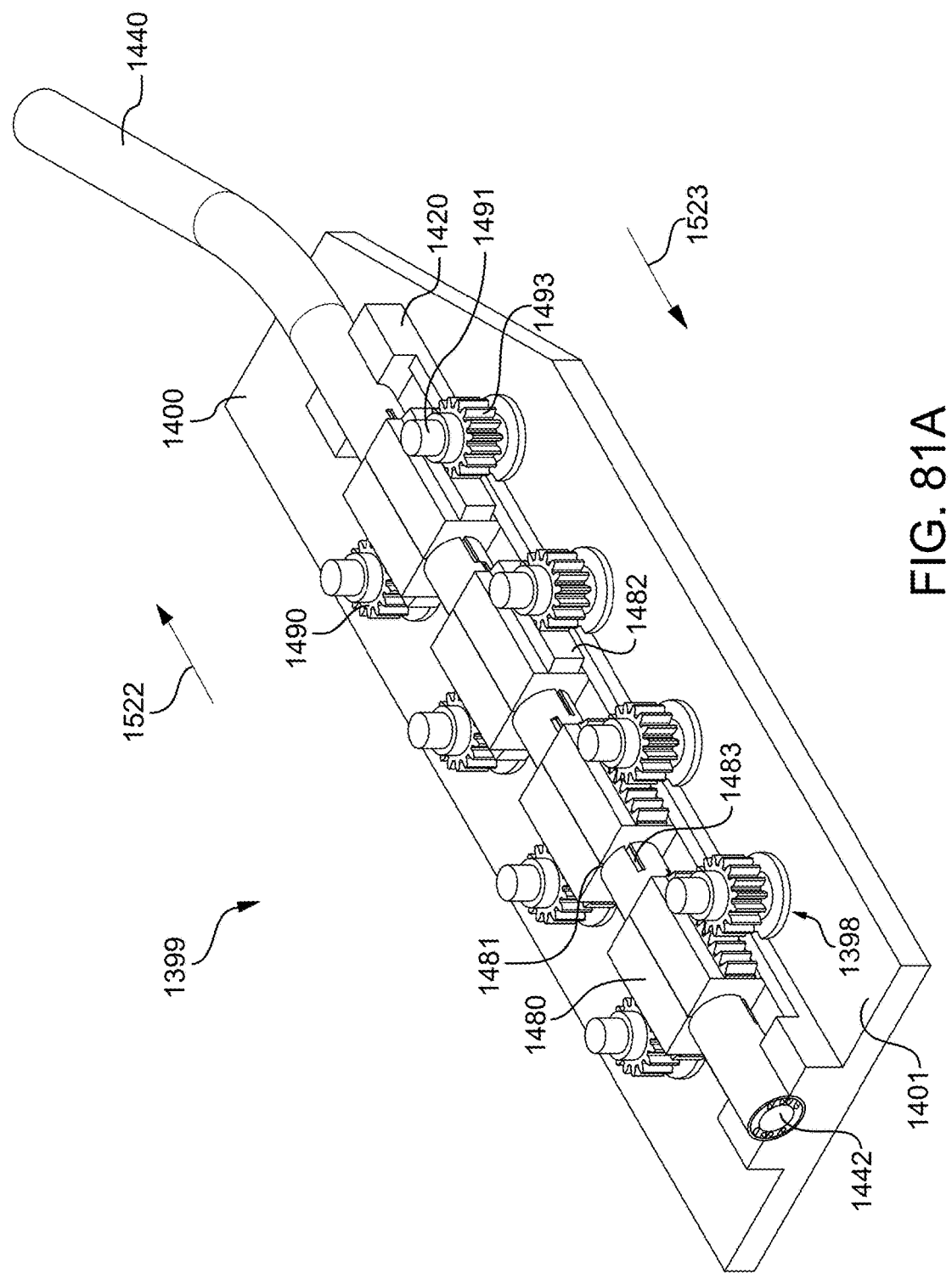
Figure 81B:
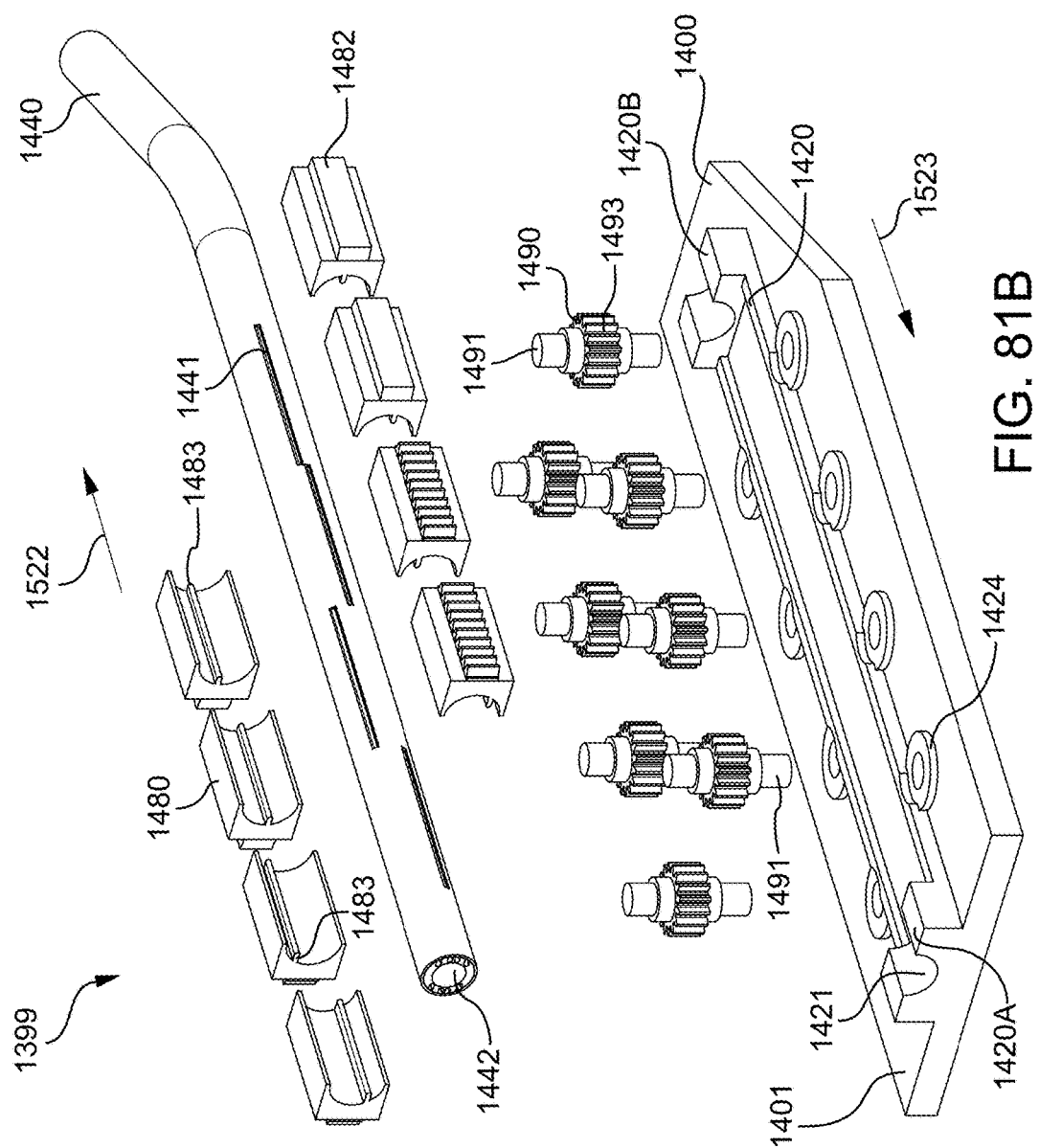
Figure 81C:
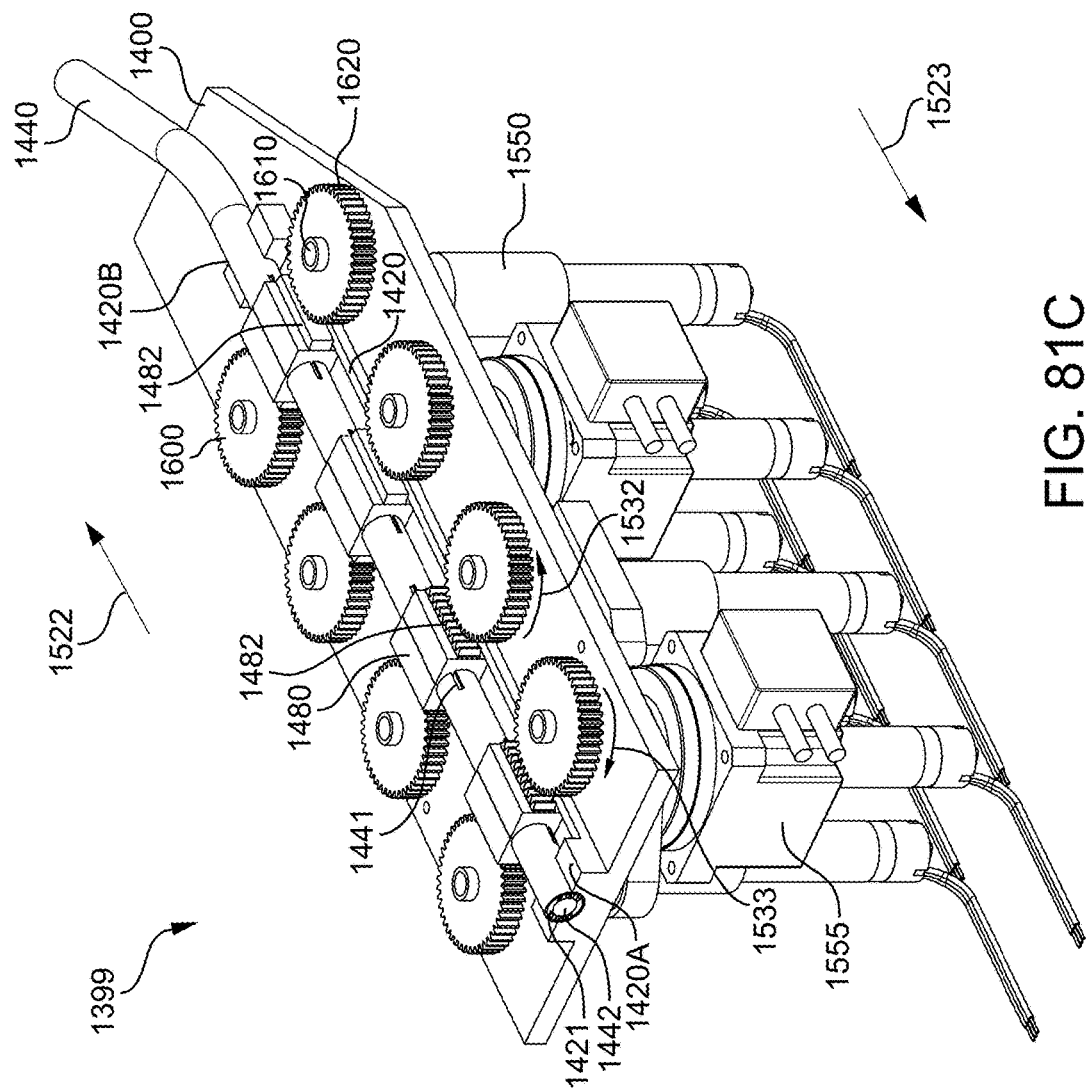

FIGS. 76A, 76B, and 76C are geometric diagrams of cable length calculation parameters of the present teachings;

FIG. 77 is a flowchart of a method for tensioning actuators for a surgical robot;

FIG. 78 is a flowchart of a method for sensing the status of a load sensor;

FIG. 79A is a schematic block diagram of a configuration of a control system for tensioning and displacing an actuator;

FIG. 79B is a schematic block diagram of another configuration of the control system for tensioning and displacing an actuator;

FIG. 79C is a schematic block diagram of the tensioning system of the present teachings;

FIG. 80A is a schematic diagram of an equipment tunnel of the present teachings;

FIG. 80B is a schematic diagram of an equipment tunnel engaged with a driving component of the present teachings;

FIG. 81A is a schematic diagram of an actuation set-up of the present teachings;

FIG. 81B is a schematic diagram of an actuation set-up in an exploded format of the present teachings; and FIG. 81C is a schematic diagram of actuation set-up of FIGS. 81A and 81B with a second configuration of driven component of the present teachings.

DETAILED DESCRIPTION

Figure 1:
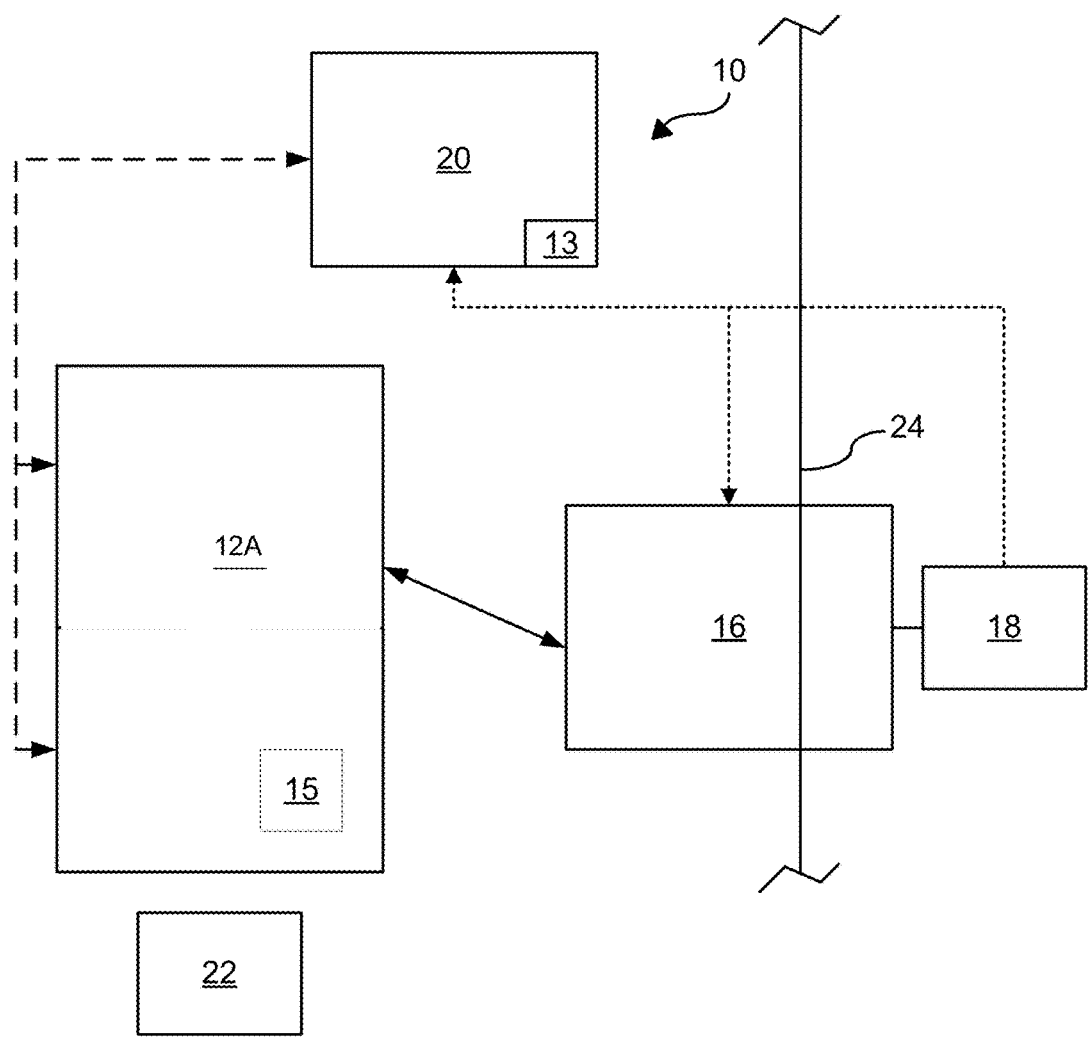
FIG. 1 is a schematic block diagram of the system of an configuration of the present teachings.

In accordance with some configurations of the present teachings, and now referring to FIG. 1, a surgical system 10 for performing surgical procedures is shown. The system 10 may also be used for other medical procedures such as endoscopic procedures. In general, the surgical system 10 can include, but is not limited to including, user interface 12A and surgical robot 16. Robot 16 can include at least one controllable element which can be used to operate on a patient 18. Such an element may be introduced into an anatomical feature or cavity of patient 18 to operate on a surgical target or may help to position other parts of robot 16 for surgery. User interface 12A can communicate with robot 16 to control and receive feedback and/or data from robot 16. Multiple displays and user input devices can be included in user interface 12A. Likewise, multiple robots 16 may be included in a surgical system 10. Multiple displays and/or user input devices may, for example, be desirable for teaching/educational purposes or for scenarios in which robot 16 includes more controllable elements than are easily controlled by a single physician.

Continuing to refer to FIG. 1, user interface 12A can display an image captured and relayed to user interface 12A from imaging or vision system 13. Imaging system 13 may be part of robot 16 and may be introduced into robot 16 during a surgery. Imaging/vision system 13 may be controlled by robot 16. In alternative configurations, imaging/vision system 13 may be an optional auxiliary component 20 which may not be controlled directly by robot 16. An image displayed at user interface 12A can provide a view of the surgical site allowing a surgeon 22 to control robot 16 with visual feedback. User interface 12A can include any of a variety of displays such as a monitor, touch screen, tablet, or the like. In configurations where user interface 12A is capable of receiving user inputs (e.g. a touch screen), a user such as surgeon 22 may interact with user interface 12A to pan, zoom, or otherwise manipulate the field of view shown on a display of user interface 12A. Additionally, other display functionalities (e.g. take photograph, record video, or control of the robot 16) may also be commanded through user interface 12A.

Continuing to refer to FIG. 1, surgeon 22 can interact with user interface 12A to control operation of robot 16. In the example configuration, user interface 12A can move controllable elements (e.g. arms or surgical tools) of robot 16 about and/or along various degrees of freedom during a surgical procedure. User interface 12A may have multiple portions which are separately controllable by different parts of the body of surgeon 22 (e.g. right hand, left hand, right foot, left foot, etc.). Additionally, user interface 12A may have multiple portions which can control different portions or functionalities of robot 16. If user interface 12A does not include a touch screen, user interface 12A may include one or more structures which can be displaced by surgeon 22 to provide input commands to robot 16. These structures may vary from configuration to configuration and any suitable type of interface may be used. In some configurations, one or more joystick, trigger, scroll wheel or ball, etc. may be displaced by surgeon 22 to control robot 16. In alternative configurations, user interface 12A may mimic the working ends of the surgical tools being used in a procedure. This may allow surgeon 22 to operate the surgical tools as if performing an open surgery. In still other configurations, user interface 12A may be exoskeletal. In such configurations, user interface 12A can be donned by surgeon 22 and inputs can be provided to user interface 12A as the body of surgeon 22 moves.

Continuing to refer to FIG. 1, in various configurations, user interface 12A can provide feedback, such as haptic feedback, to surgeon 22. This feedback may be, but is not limited to, force feedback which can make the effort needed to displace a portion of user interface 12A proportional to the amount of force being exerted through a drive system of robot 16. Vibratory feedback or other tactile feedback may also be utilized. Auxiliary components 20 can optionally be included in or interface with surgical system 10. Auxiliary components 20 can include, but are not limited to including, vision or imaging system 13 such as an endoscope, an irrigation or insufflation system, lighting system, and/or suction system. An API may be provided to facilitate the interface between components of surgical system 10 and auxiliary components 20. Any component described herein as auxiliary component 20 may in alternative configurations, be included as a portion of robot 16 and vice versa. At least one controller 15 may also be included as part of surgical system 10. The at least one controller 15 may perform a number of functions such as, but not limited to: analyzing user inputs to the user interface 12A and generate commands for the robot 16 based on these inputs, image processing based on data received from an lighting/vision system 13, controlling the delivery of feedback to the a user such as physician 22.

Continuing to still further refer to FIG. 1, a barrier 24 can segregate one portion of surgical system 10 from the rest of surgical system 10. In some configurations, barrier 24 may separate a single use or multi-use disposable component of robot 16 from a durable component of robot 16 which may not be intended for regular disposal. Barrier 24 may, for example, be a sterility barrier which can separate a sterile portion of surgical system 10 from a non-sterile portion of surgical system 10, creating a sterile field. In some configurations, barrier 24 can be a sterility barrier which can segregate a sterile portion of robot 16 and patient 18 from other components of surgical system 10. In configurations with a disposable, the disposable may be the sterile portion of surgical system 10 which can be isolated from the rest of surgical system 10 by barrier 24. In the representational example shown in FIG. 1, the barrier 24 is depicted with line breaks. This is done to indicate that while sterility barrier 24 will generally have a portion of robot 16 as well as patient 18 on the sterile side, barrier 24 may surround, cover, or otherwise segregate different components of surgical system 10 from a sterile field depending on the configuration.

Figure 2:
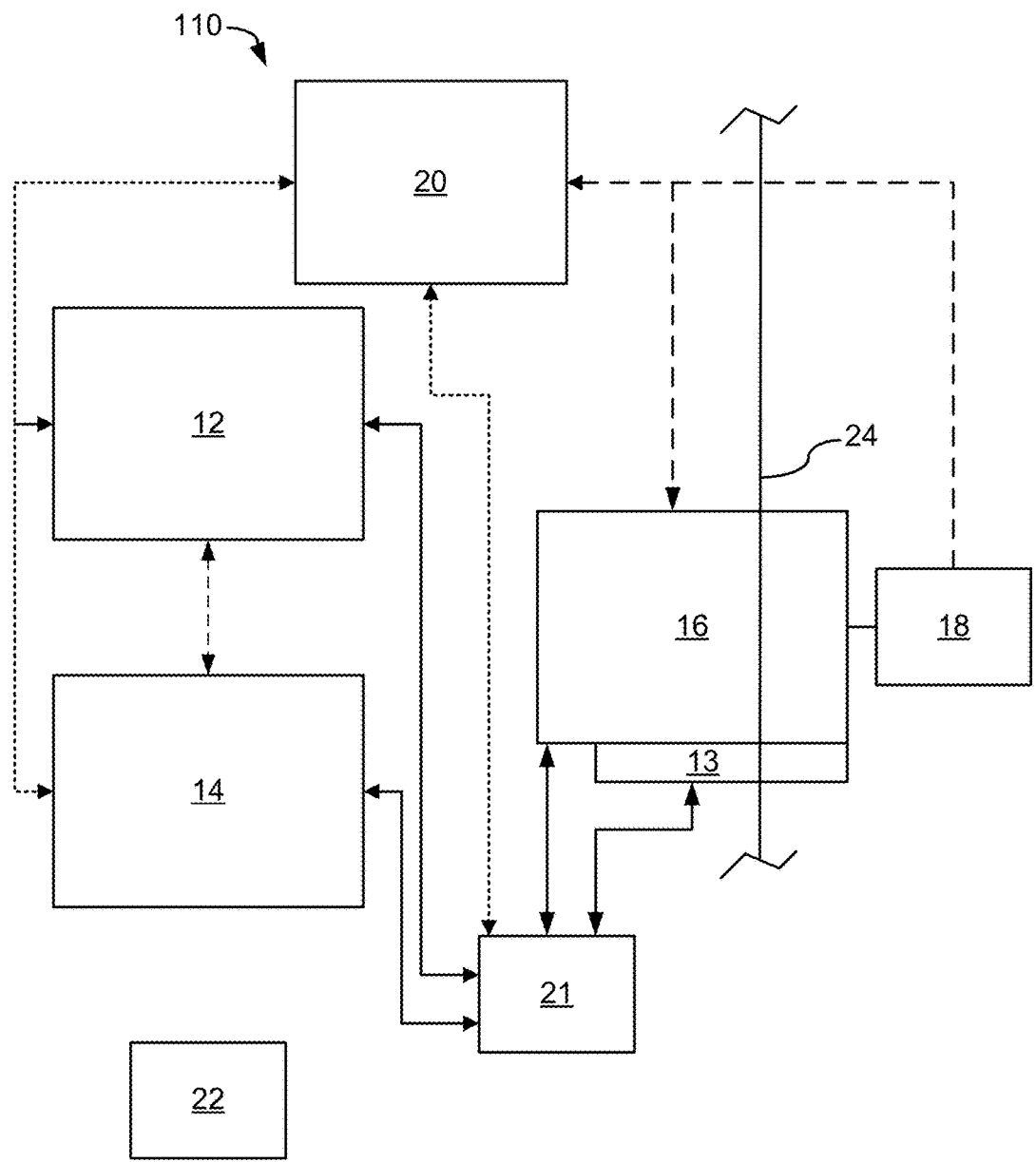
FIG. 2 is a schematic block diagram of the system of another configuration of the present teachings.

Referring now to FIG. 2, user interface 12A (FIG. 1) can include, but is not limited to including, display 12 and user input device 14 that can be, but are not limited to being, physically and electrically remote from each other, and can interface through network 21, among other ways. Further, lighting/vision 13 can be integral with robot 16 and can cross barrier 24 to illuminate surgery on patient 18 for physician 22. Auxiliary components 20 can be optionally included in the system 110.

Figure 3:
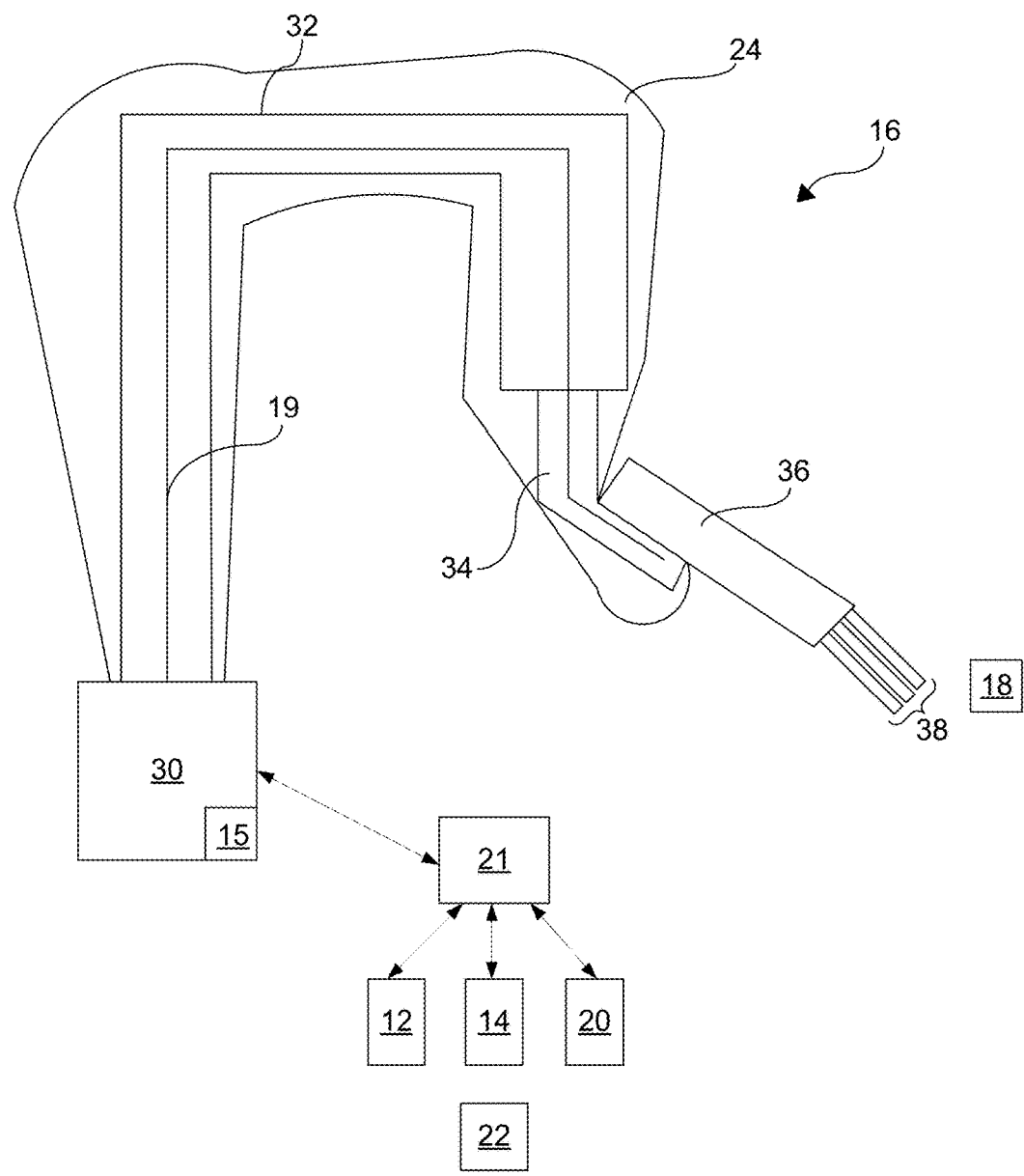
FIG. 3 is a schematic block diagram of a configuration of a robot of the present teachings.

Referring primarily to FIG. 3, surgical robot 16 may be incorporated in surgical system 10 (FIG. 1). Surgical robot 16 can include a base 30 that can support other components of robot 16. Additionally, in some configurations, base 30 may act as a cart which can allow a surgical team to maneuver robot 16 to a desired position. The cart may be a powered cart which can be driven to a desired location or may be an unpowered cart which can be manually moved about. Base 30 may also include electronics components of robot 16 such as processors or controllers 15, memory components, power components, etc. Robot 16 can also include a drive component 34 which can drive operation of a manipulator 36. Drive component 34 may include various motors, hydraulic components, linkages, etc. for driving of manipulator 36. Manipulator 36 can control operation of manipulated component 38 that can be installed in manipulator 36. Manipulated components 38 may include an articulated shaft or lumen (not shown) which can direct a surgical tool or device attached thereto or extending therethrough. Possible surgical tools can include endoscopes, for example, but not limited to, the endoscope described in United States Patent Publication #2014/0221749 entitled Endoscope with Pannable Camera, filed Jan. 31, 2014. Other surgical tools may include, though are not limited to, an imager, cutting tools (e.g. a shaver), retractor, grasper, ablator, illumination source, electrocautery device, stapler, stitching tool, milling cutter, bur tool, rotary cutter, irrigation system outlet, and/or insufflations system outlet. For illustrative purposes, three manipulated components 38 are shown. Any number of manipulated components 38 may be controlled by a manipulator 36. Multiple manipulators 36 may be driven by a single drive component 34. Multiple drive components 34 may also be included to drive at least one manipulator 36.

Continuing to refer primarily to FIG. 3, arm 32 may optionally be positionable by a user and include a number of joints which can allow rotational or translational motion of various segments of arm 32. Such joints can allow arm 32 to position manipulator 36 in an appropriate position for a surgical procedure. In some configurations, base 30 can support robot 16 against tipping when arm 32 is fully extended. Arm 32 may be manually moved into place or may include actuators which may be controlled to drive arm 32 to the desired location. In various configurations, arm 32 may include at least one line 19 to transmit electrical power, data, hydraulic force, fluid, and/or light, for example, but not limited to, between base 30 and driven component 34. The at least one line 19 may also be a fiber optic line which may be used for data transmission or light transmission in some configurations. The at least one line 19 can allow power, data/commands, force, fluid (e.g. irrigation fluid or insufflations gas), and or light to be communicated to driven component 34 from base 30 or another part of surgical system 10 (FIG. 1). Power, data, hydraulics, fluids, illumination, etc., can be controlled by, for example, but not limited to, user input device 14 (FIG. 1).

Continuing to refer to FIG. 3, with respect to hydraulics, in some configurations, base 30 can include master cylinders and motors driving hydraulic fluid through at least one line 19. With respect to fiber optics, light can be transmitted through at least one line 19 and can cross barrier 24 into manipulator 36 to be used in various ways. Including at least one fiber optic line may also allow for the transmission of data. With respect to data, for example, sensors in a drive component 34 may collect and transmit data via the at least one line 19 to a controller 15 in base 30. Additionally or alternatively, sensors located in manipulator 36 and manipulated components 38 can collect and transmit data through barrier 24 to at least one line 19 to be processed in base 30. In another example, and with respect to heat management of, at least one line 19 can be configured to accommodate liquid and/or gas between base 30 and drive component 34 to cool a drive component 34, for example, by thermal conduction. At least one line 19 can conduct water/gas for insufflation and irrigation. At least one line 19 can be used for suction and/or removal of fluid or debris from a surgical site. Controller 15 can, for example, control at least one line 19 to provide services outlined here.

Continuing to still further refer primarily to FIG. 3, barrier 24 can act as a sterility barrier and can segregate manipulator 36 and manipulated components 38 from the rest of robot 16. In some configurations, a portion of barrier 24 can be retained or captured between drive component 34 and manipulator 36. Force may be transferred through this portion of barrier 24 to manipulator 36 to drive manipulator 36. The portion of barrier 24 retained between drive component 34 and manipulator 36 can be a solid and continuous portion of barrier 24. That is, the portion of barrier 24 between drive component 34 and manipulator 36 could be free of voids, orifices, apertures, holes, pass-throughs, or other such interruptions. The integrity of barrier 24 can be maintained as force is transferred through it. Manipulator 36 may latch onto drive component 34 trapping barrier 24 between the two during setup of robot 16. Manipulator 36 and manipulated component(s) 38 may be supplied as single or multi-use disposables. Manipulated components 38 may come pre-installed or pre-assembled into manipulator 36. These portions of the surgical system 10 (FIG. 1) may be provided in a sterile package. Manipulator 36 and manipulated component(s) 38 may be installed into system 10 (FIG. 1) prior to surgery.

FIGS. 4A-4E depict a number of representational views of manipulated components 38. Manipulated components 38 can be at least partially inserted into a patient to perform surgery. In the example configurations, manipulated component 38 is depicted including a shaft 50 for sake of simplicity.

Figure 4A:
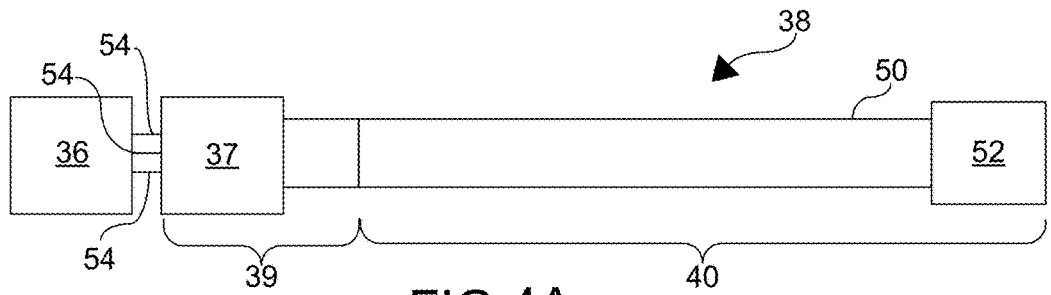
FIGS. 4A-4E are schematic block diagrams of configurations of manipulated components of the present teachings.

Referring now to FIG. 4A, articulated segments 40 may include, but are not limited to including, any combination of: a shaft, a jointed or otherwise articulated shaft, a number of nested shafts, a number of vertebrae-like members or other pivotally/hingedly coupled members, ball and socket members, and/or one or a series of living hinges. Manipulated component 38 may be hollow or include at least one lumen (not shown), and may pass through trocar 37. The lumen (or number of lumens) may serve as a pathway through which surgical tool 52 can be introduced to a surgical site. The lumen(s) may also be used to facilitate insufflations, irrigation, illumination, etc. of a surgical site. Utility components 54 operably connected to manipulated component 38, may be mechanical control, light transmission, information transmission, fluid transmission, and power transmission components. Utility components 54 may extend through a lumen (not shown) shared with one or more other utility component 54 or may each have a dedicated lumen. There may be a variety of different utility components 54 housed within manipulated component 38. A light transmission component may include, for example, a fiber optic bundle, ribbon, light pipe, light projection element, and/or the like. An information transmission component may include, for example, an electrical cable bundle or ribbon. Such a cable or bundle may connect to surgical tool 52 having an imager positioned at the end of manipulated component 38. Such a cable may also be used to transmit power to surgical tool 52. A fluid transmission component may provide a pathway for fluid (e.g. insufflation gas or irrigation fluid) to be introduced into an anatomical feature of a patient.

Still referring primarily to FIG. 4A, manipulated component 38 can include articulated segment, section, or region 40 which can be connected to a variable portion 39 of manipulated component 38. Variable portion 39 can extend into manipulator 36, and can also extend through trocar 37 to facilitate introduction to a patient. Variable portion 39 can be, for example, but not limited to, bendable, articulated, or unbendable. Manipulated component 38 may come pre-assembled into manipulator 36. Likewise, manipulated component 38 may come pre-assembled with utility components 54 already situated therein. As mentioned above, these may be provided in a sterile package. In configurations in which at least one or a portion of utility components 54 is not pre-installed in a manipulator 36 or manipulated component 38, that utility component 54 or portion of a utility component 54 may be similarly packaged. Utility components 54 can be, but are not limited to being, mechanical control components or actuators. Actuators can extend into and along the length of manipulated component 38. Additionally, actuators can extend into manipulator 36 through a void or opening in variable portion 39.

Figure 4B:
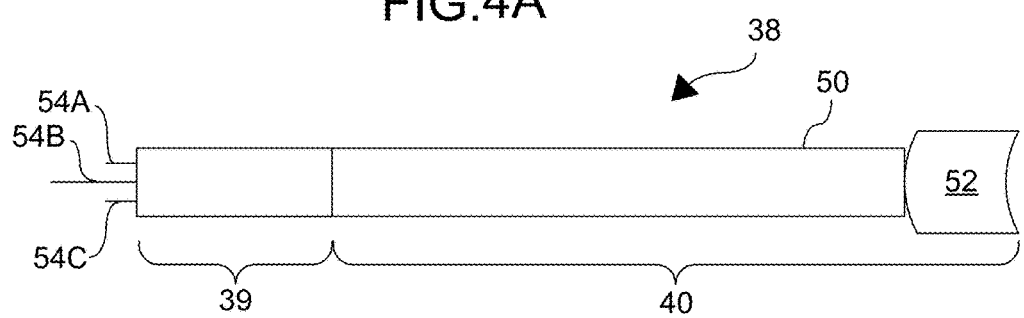

Referring now primarily to FIG. 4B, any suitable number of actuators 54A, 54B, 54C may be included in various configurations. The number of actuators 54A, 54B, 54C may be determined at least in part by the number of individually actuateable components or features in manipulated component 38. In some configurations, a first actuator 54A, second actuator 54B, and third actuator 54C are shown and are depicted as wires for sake of simplicity. In some configurations, the actuators 54A, 54B, 54C may be pushrods, or any other suitable material. Multiple different types of actuators may also be used within the same configuration. For example, some manipulated components 38 may actuate some features with pull wires and actuate others with an actuator which can exert both pull and pushing forces to effect actuation. One or more actuator 54A, 54B, 54C may be associated with a surgical tool 52. In the example configuration shown in FIG. 4B, driving second actuator 54B may actuate surgical tool 52 or an end effector included as part of surgical tool 52. This is shown representationally by surgical tool 52 changing shape (relative to FIG. 4A) in response to displacement of second actuator 54B.

Figure 4C:
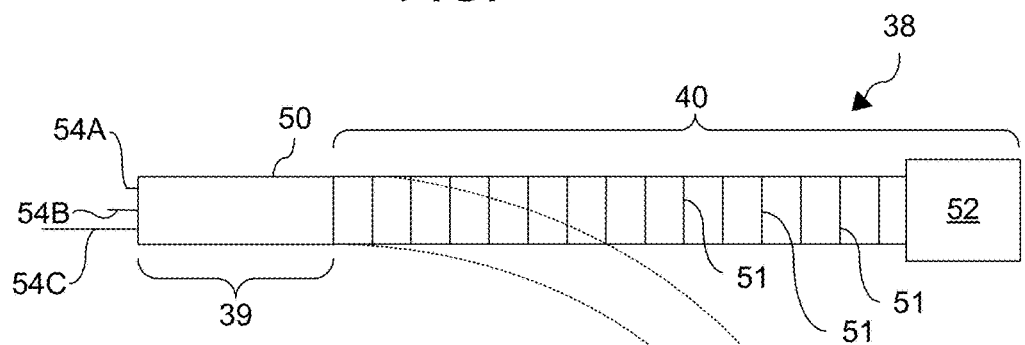

Referring now to FIG. 4C, first actuator 54A, second actuator 54B, and third actuator 54C may be driven to actuate certain features of manipulated component 38. Such actuation may, for example, cause the opening or closing of a jaw or clamp on surgical tool 52 (see FIG. 4B), panning of an imager, camera, and/or lighting system included in surgical tool 52, deployment of a retractor, etc. One or more actuators of first actuator 54A, second actuator 54B, and/or third actuator 54C may be driven to cause displacement of articulated segment 40 about one or more articulations or joints 51 in an articulated segment 40. In response to displacement of the first actuator 54A and third actuator 54C in the illustrative configuration, the articulated segment 40 would be caused to take on the orientation of the dotted outline articulated segment representation 56A. Controlling articulated segment 40 via mechanical control components allows for the invasiveness of a surgery to be minimized. In some instances, such articulation may enable a surgery to be performed through only a single incision in a patient.

Figure 4D:
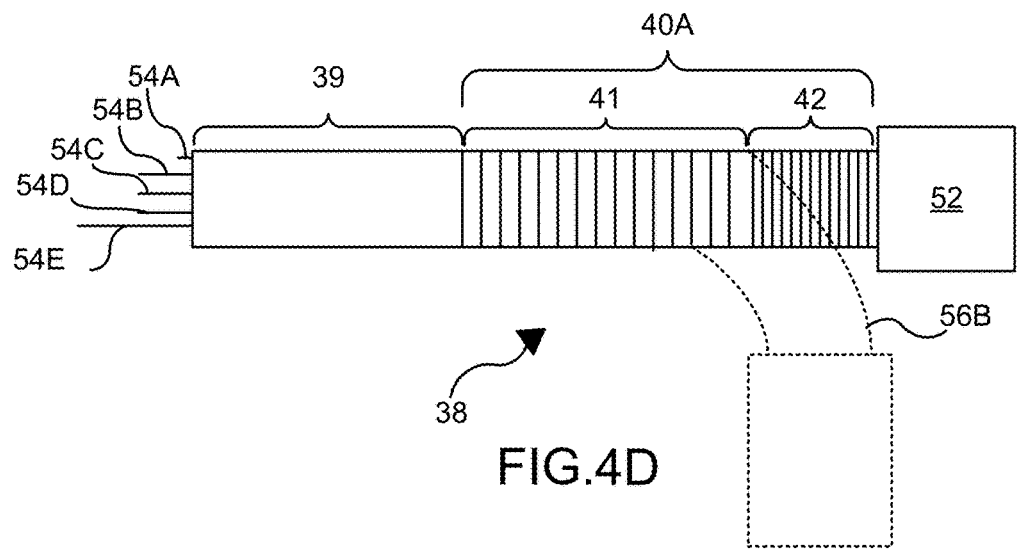

Referring now to FIG. 4D, manipulated component 38 may have multiple regions or segments which can each be articulated to varying degrees. For example, manipulated component 38 may consist of variable segment 39 and articulated segment 40A. Articulated segment 40A may only be a small portion of manipulated component 38. Alternatively, manipulated component 38 may include a number of articulated segments 40A which can be interspersed by intervening variable segments 39. In such configurations, each articulated segment 40A can be articulated to differing degrees. Each region of manipulated component 38 may or may not be independently controllable. Articulated segment 40A can also include gradations of articulation within articulated segment 40A. That is, one or more of portion of an articulated segment 40A may be more densely articulated or jointed than other sections. Alternatively, the density of articulations or joints may progressively increase or decrease along the length of an articulated segment 40A. Manipulated component 38 can include at least one first articulated subsection 41 and at least one second articulated subsection 42. The second articulated subsection 42 may be a distal articulated subsection and the first articulated subsection 41 may be a proximal articulated subsection. Second articulated subsection 42 can be, for example, but not limited to, more densely articulated that other sections of articulated segment 40A, and can allow for precise control of surgical tool 52 when performing a surgery. In configurations where second articulated subsection 42 is more densely articulated then other portions of manipulated component 38, second articulated subsection 42 may be used to perform the bulk of the fine movement and control during a surgery. One or more actuators 54A, 54B, 54C, 54D, 54E may be used to control the first articulated subsection 41 and one or more actuators 54A, 54B, 54C, 54D, 54E may be used to control the second articulated subsection 42. For example, the first actuator 54A and fifth actuator 54E can be used to control second articulated subsection 42, while the second actuator 54B and fourth actuator 54D can be used to control first articulated subsection 41. The remaining third actuator 54C may control the surgical tool 52. In the example configuration, the first actuator 54A and fifth actuator 54E have been displaced. Orientation 56B is shown for illustrative purposes to indicate the position of second articulated subsection 42 as a result of this actuation.

Figure 4E:
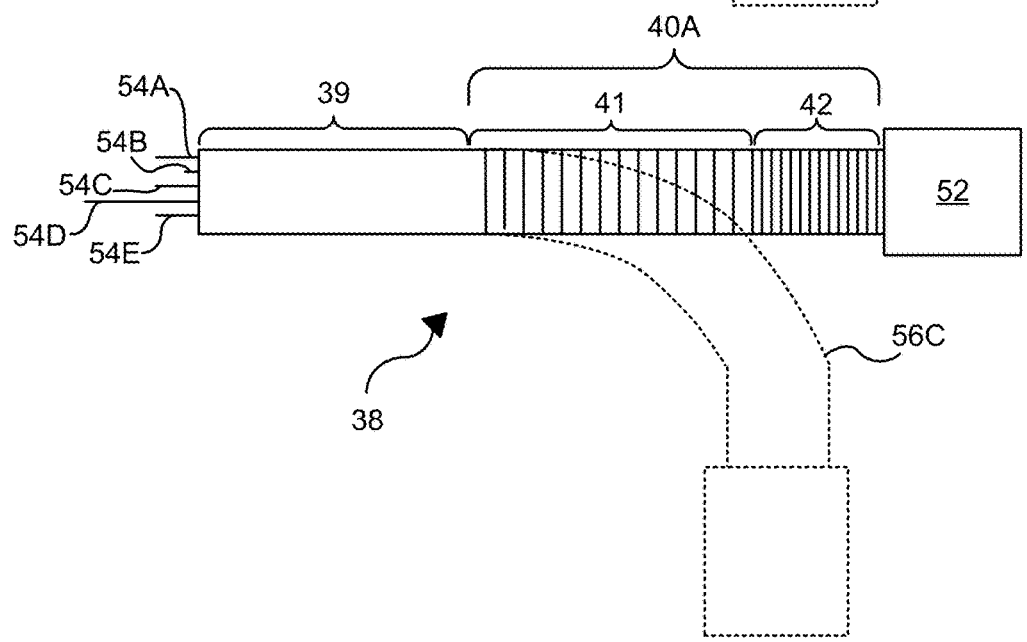

Referring now to FIG. 4E, second articulated subsection 42 may be displaced as a result of any articulation of first articulated subsection 41 or other segments of articulated segment 40A. Any of at least one first articulated subsection 41 may be controlled to more grossly position surgical tool 52 and second articulated subsection 42. Manipulated component 38 can include a number of actuators 54A, 54B, 54C, 54D, 54E which when driven cause articulation of part of the manipulated component 38. To more intricately articulate a manipulator 38 and attached surgical tool 52, additional actuators 54A, 54B, 54C, 54D, 54E can be used. The actuators 54A, 54B, 54C, 54D, 54E are arranged to control the articulated segment 40A of FIG. 4E as described above in relation to FIG. 4D. In the example configuration, the actuators 54B, and 54D controlling the first articulated subsection 41 have been actuated. Orientation 56C is shown for illustrative purposes to indicate the position of the articulated segment 40A as a result of this actuation.

Figure 5:
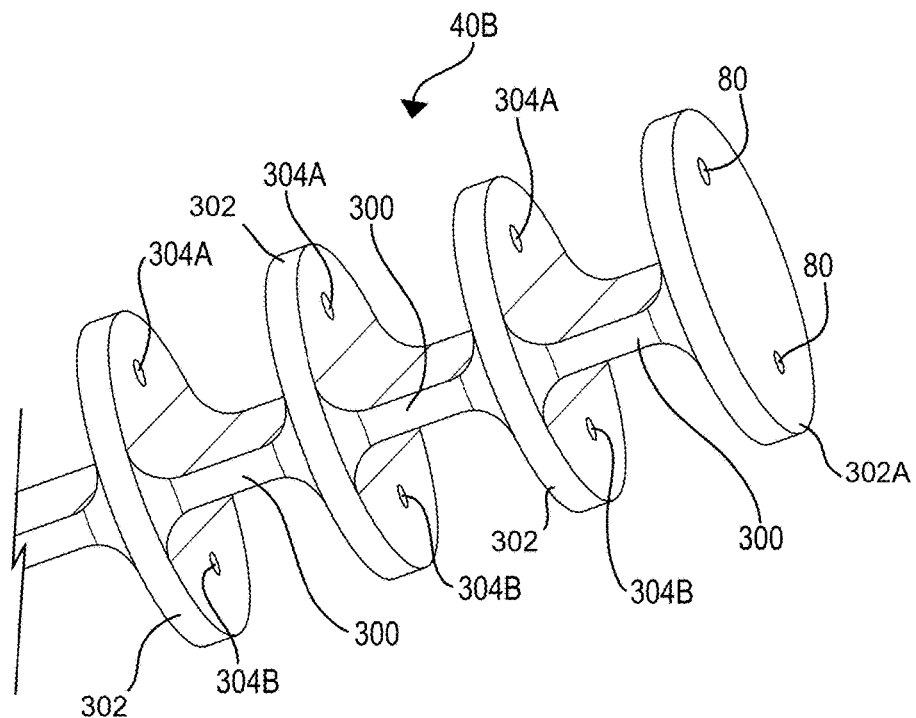
FIGS. 5-9 are schematic diagrams of living hinges of the present teachings.

Referring now primarily to FIG. 5, articulated segment or section 40B may be constructed in a number of different ways. In some configurations, articulated segment 40B may incorporate one or number of living hinges 300 which may be acted on to articulate the articulated segment 40B to a desired configuration or orientation. The living hinges 300 of the articulated segment 40B may span between a number of interceding bodies 302. The interceding bodies 302 may, for non-limiting example, be rigid and may provide either an anchor point 80 or points 80 for one or more actuator 54 (FIG. 4A). Some of the interceding bodies 302 may instead include a pass-through 304A, 304B or multiple pass-throughs 304A, 304B through which actuators (see, e.g. 54A of FIG. 4B) may extend. Exerting forces via the actuators (see, e.g. 54A of FIG. 4B) can cause one or more of living hinges 300 (depending, for example, on the anchor point 80 of the actuator) to be bent. By exerting forces through actuators (see, e.g. 54A of FIG. 4B) selectively, articulated segment 40B may consequentially be bent into a desired orientation. Such a stack of living hinges 300 may be used to form part or the entirety of an articulated segment 40B. Depending on the configuration, articulated segment 40B constructed from a stack of living hinges 300 which may be manufactured as a single part. This part may be a molded part in some configurations. Alternatively, the part may be machined or printed using a material additive process such as three dimensional printing. The interceding bodies 302 can be, for example, but not limited to, disc-like members. Though only three living hinges 300 are shown, any suitable number of living hinges 300 and interceding bodies 302 may be included to create an articulated segment 40B of desired length.

Continuing to refer primarily to FIG. 5, each interceding body 302 of the articulated segment 40B can includes a first pass-through 304A and a second pass-through 304B. The first pass-throughs 304A and second pass-throughs 304B of adjacent interceding bodies 302 may be substantially axially aligned with each other. Each actuator (see, e.g. 54A of FIG. 4B) for an articulated segment 40B may be anchored into an anchor point 80. In the example configuration in FIG. 5 the anchor points 80 are shown in a terminating interceding body 302A. Actuators 54 (see, e.g. 54A of FIG. 4B) may be anchored in interceding bodies 302 other than the terminating interceding body 302A for the series depending on the configuration. As described above, when force is exerted by one or more actuators (see, e.g. 54A of FIG. 4B) in a coordinated fashion, articulated segment 40B may bend in a desired manner. In some configurations, a series of living hinges 300 and interceding bodies 302 may be covered by a tube, sheath, or flexible sleeve 50 (FIG. 4A) when articulated segment 40B is fully assembled.

Figure 6:
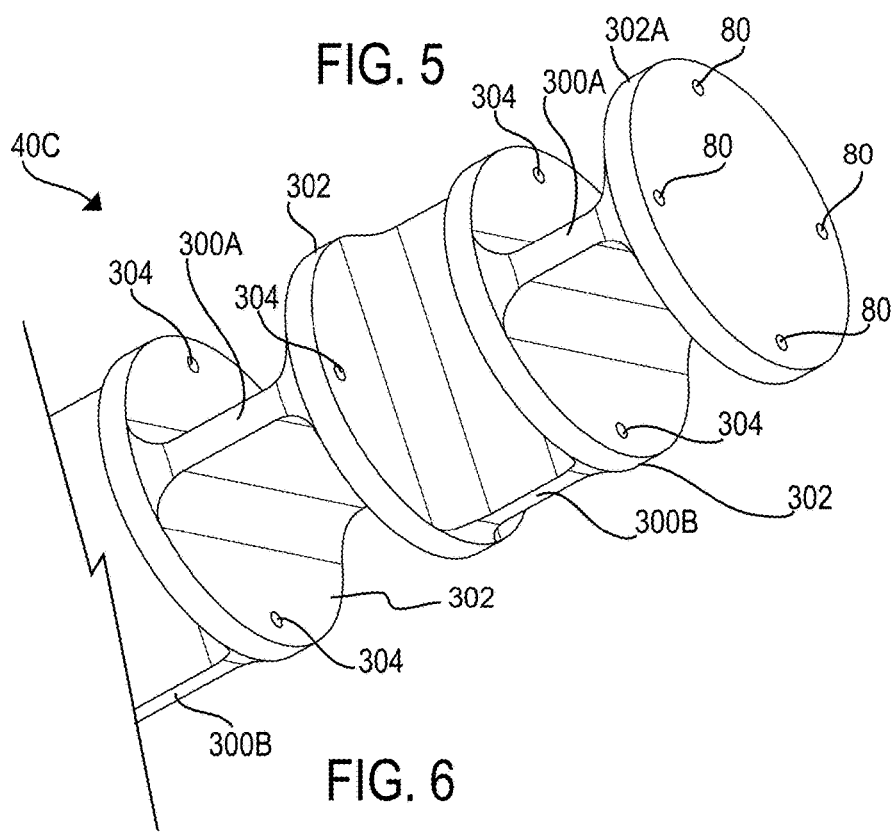

Referring now to FIG. 6, another configuration of an articulated segment 40C with first living hinges 300A, second living hinges 300B, and interceding bodies 302 including pass-throughs 304 is shown. Similarly to as shown in FIG. 5 a terminal interceding body 302A of the articulated segment 40C includes anchor points 80 for actuators (see, e.g. 54A of FIG. 4B). First living hinges 300A can be angularly offset with respect to second living hinges 300B. For non-limiting example, the first and second living hinges 300A, 300B may be positioned perpendicular to or substantially at right angles to any directly adjacent living hinge(s) 300A, 300B. First living hinges 300A can bend articulated segment 40C in a first plane (e.g. up and down), and second living hinges 300B can bend articulated segment 40C in a second plane (e.g. left and right). Each of interceding bodies 302 can include, for example, but not limited to, four pass-throughs 304. Each pass-through 304 can extend through either first living hinges 300A or the second living hinges 300B. Actuators (see, e.g. 54A of FIG. 4B) may be ganged into cooperating sets which may be operated to bend the articulated segment 40C in a set of directions. For example, actuators (see, e.g. 54A of FIG. 4B) which extend through pass-throughs 304 disposed opposite one another could be ganged to allow for coordinated bending of the articulated section 40C in a plane. By operating the sets of ganged actuators (see, e.g. 54A of FIG. 4B) in conjunction with one another, articulated segment 40C may be positioned in a wider range of orientations than the articulated segment 40B (FIG. 5).

In configurations including an articulated segment 40C with multiple articulated sub sections, a first articulated subsection 41 (FIG. 4D) may include a number of first living hinges 300A that are in line with each other or which all allow bending in the same plane. A second articulated subsection 42 (FIG. 4D) may include a number of second living hinges 300B that are in line with each other, but at an angle (e.g. a right angle), to the first living hinges 300A (FIG. 5) in first articulated subsection 41 (FIG. 4D).

Figure 7:
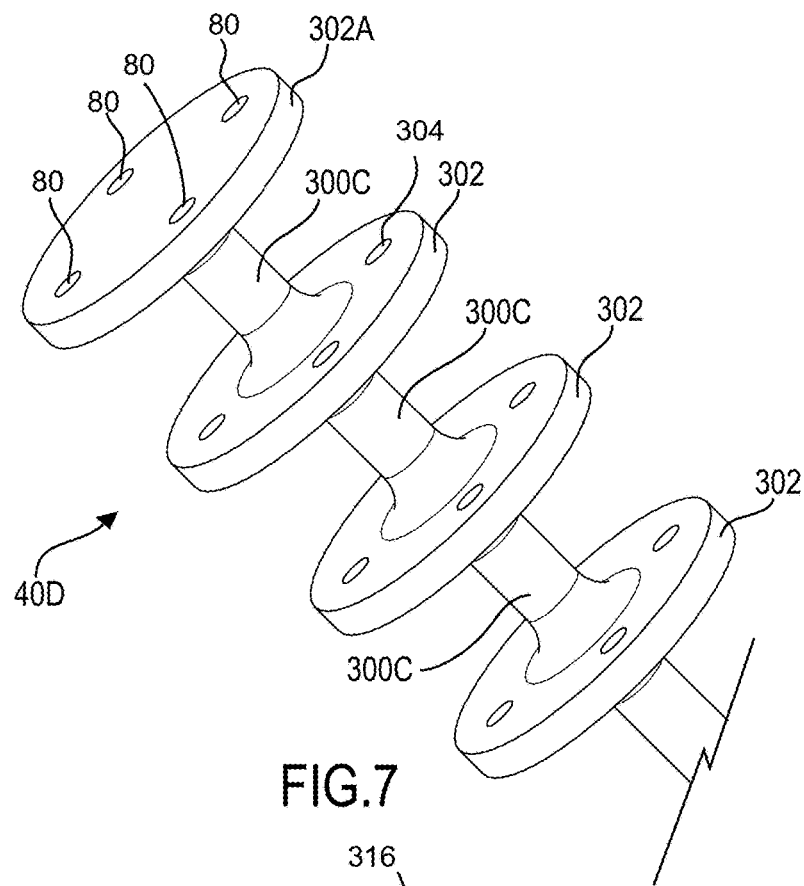

Referring now to FIG. 7, an articulated segment 40D in which living hinges 300C are separated by interceding bodies 302 is shown. The living hinges 300C can be, for example, but not limited to, cylindrical or columnar bodies, and can be made from, for example, but not limited to, a flexible material. Living hinges 300C can be bent in any direction with substantially the same force. If desired, living hinges 300C can be given an elliptical cross sectional shape or any other cross sectional shape. Having an asymmetric cross sectional shape can allow living hinges 300C to bend more freely in a first set of planes when compared to a second set of planes. Interceding bodies 302 can, for example, but not limited to, be disc-like. Each interceding body 302 can include a number of pass-throughs 304, for example, four. In some configurations, interceding bodies 302 need not include four pass-throughs 304. Instead, interceding bodies 302 can include three pass-throughs 304. The number of pass throughs 302 included may depend on the number of actuators (see, e.g. 54A of FIG. 4B) which will be included for an articulated segment 40D. Actuators (see, e.g. 54A of FIG. 4B) can extend through pass-throughs 304 and can be anchored into, for example, but not limited to, anchor points 80 terminating interceding body 302A. Actuators (see, e.g. 54A of FIG. 4B) may be ganged into cooperating sets which may be used alone or together to cause articulated segment 40D to bend into a desired orientation. Actuators (see, e.g. 54A of FIG. 4B) may extend through each set of pass-throughs 304 and be operated in tandem with one another to bend the articulated segment 40D into a desired orientation.

Referring again primarily to FIG. 4A, various articulated segments 40 which are jointed may also be used. Such configurations can incorporate one or a number of joint members that are coupled to one another to act as sets of kinematic pairs. These joint members may be acted on to displace an articulated segment 40 to a desired configuration or orientation. Exerting forces via actuators (see, e.g. 54A of FIG. 4B) included in the articulated segment 40 can cause one or more joint members in the articulated segment 40 to move relative to each other. The number of joint members displaced can depend on anchor point 80 (FIG. 5) of actuator (see, e.g. 54A of FIG. 4B) and the types of joints involved. By exerting forces via actuators (see, e.g. 54A of FIG. 4B) selectively, an articulated segment 40 may consequentially be bent into a desired orientation.

Figure 8:
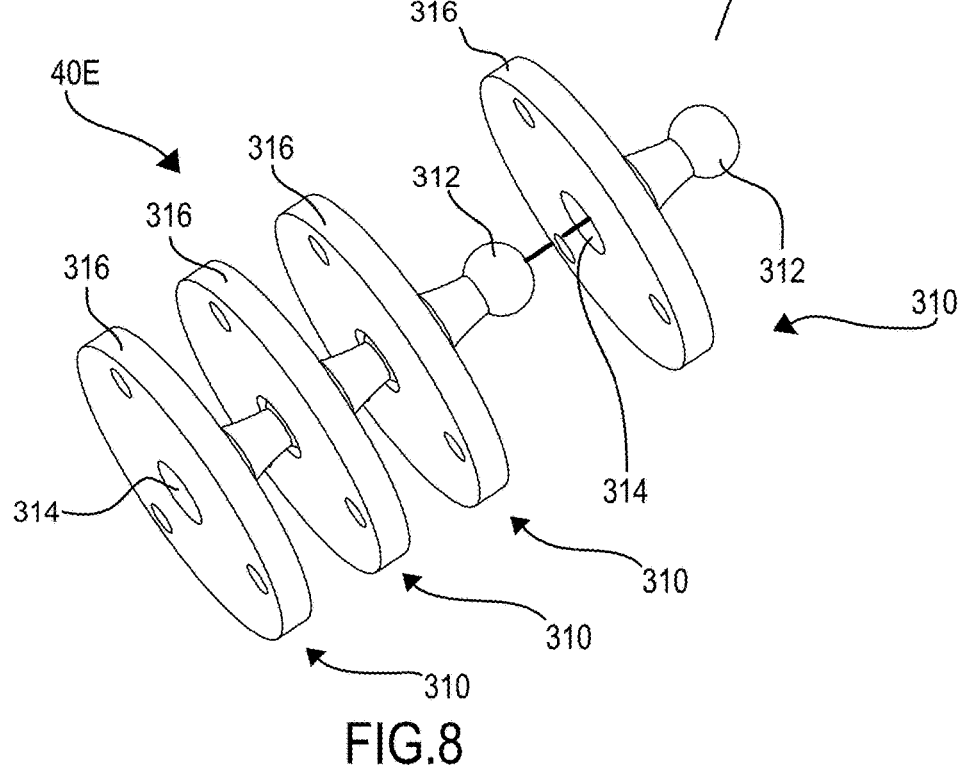

Referring now to FIG. 8, an articulated segment 40E constructed of a number of joint members 310 that are kinematically connected is shown. The joint members 310 can, for non-limiting example, be ball and socket type joints. Any other variety or combination of joint types may be used in other configurations. The illustrated articulated segment 40E includes four joint members 310. Any number of joint members 310 may be included to make an articulated segment 40E of a desired length. Each joint member 310 can include ball 312 and socket 314. Ball 312 can be sized to fit and be retained within socket 314 of an adjacent joint member 310. Joint members 310 can also include flange 316 which can include a number of pass-throughs 304. Alternative configurations may not include flange 316, but rather any type of projections within which the pass-throughs 304 may be located. Such projections may be radially disposed.

Figure 9:
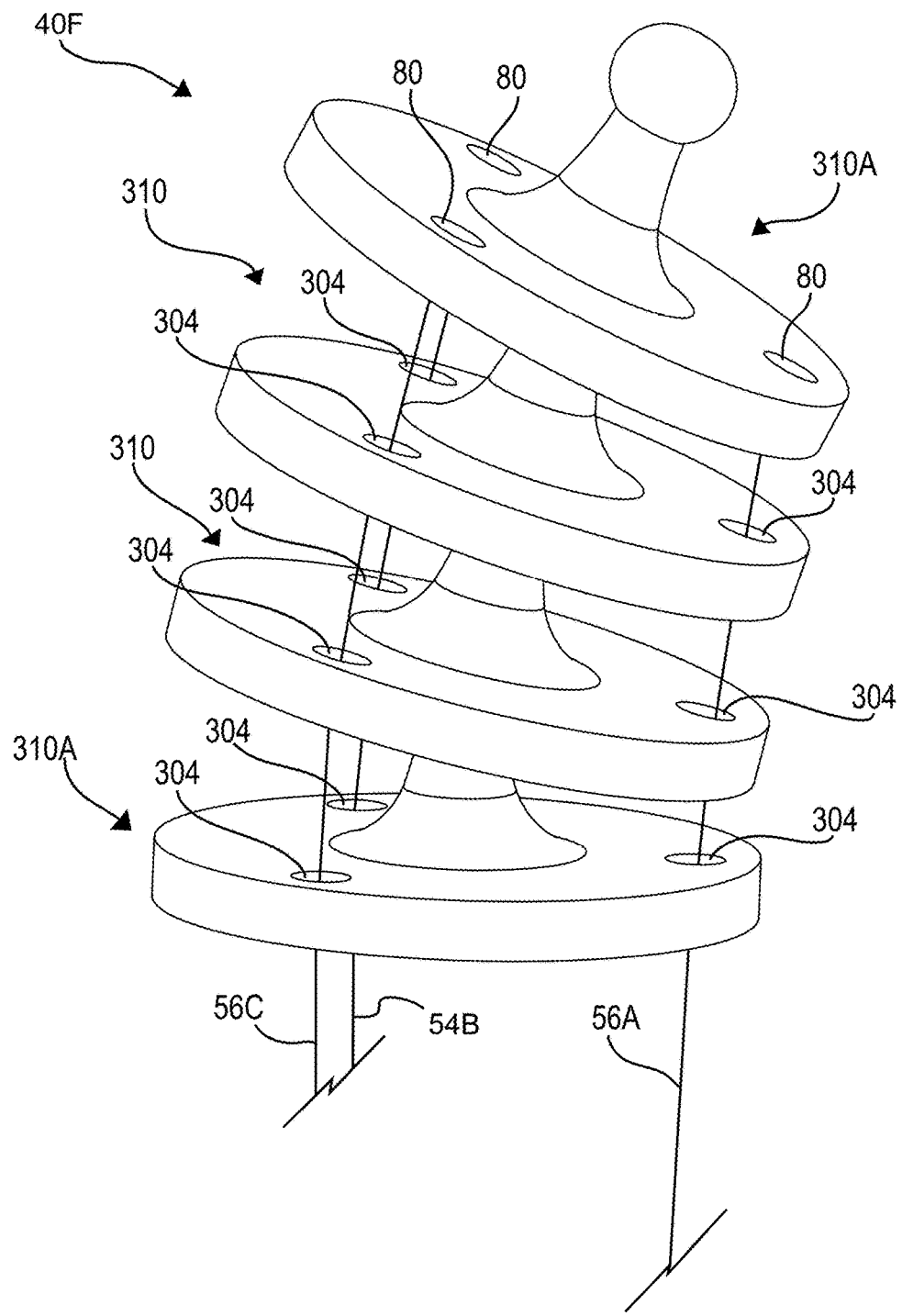

Referring now to FIG. 9, an assembled view of the articulated segment 40F is shown. A number of actuators 54A, 54B, 54C, for example, may extend through pass-throughs 304 in the joint members 310. Each of the first actuator 54A, second actuator 54B, and third actuator 54C may be anchored into an anchor point 80 in one of the joint members 310. In the example configuration, the actuators 54A, 54B, 54C are anchored into anchor points 80 in the terminal joint member 310A. In some configurations, the actuators 54A, 54B, 54C may be wires. The actuators 54A, 54B, 54C may be operated in concert with one another to cause articulated segment 40E to take on a desired orientation. Articulated segment 40E is shown in an actuated position. The second actuator 54B and third actuator 54C have been fed out while first actuator 54A has been pulled in, causing articulated segment 40E to bend.

Figure 9A:
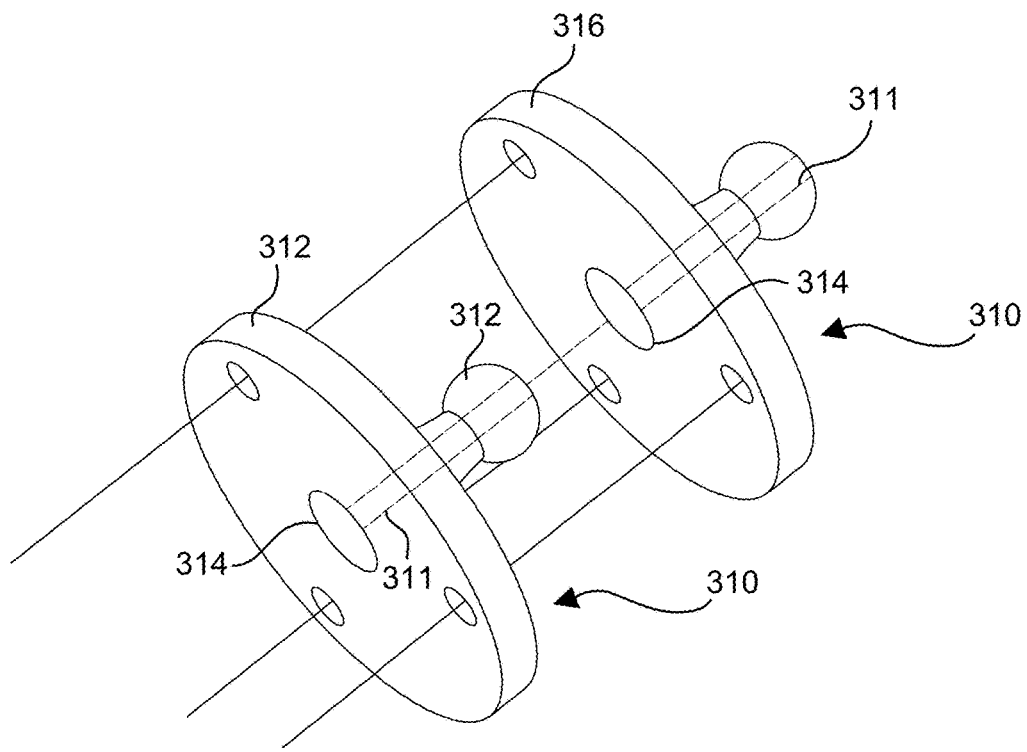
FIGS. 9A and 9B are schematic diagrams of another configuration of the articulated section of the present teachings.
Figure 69:
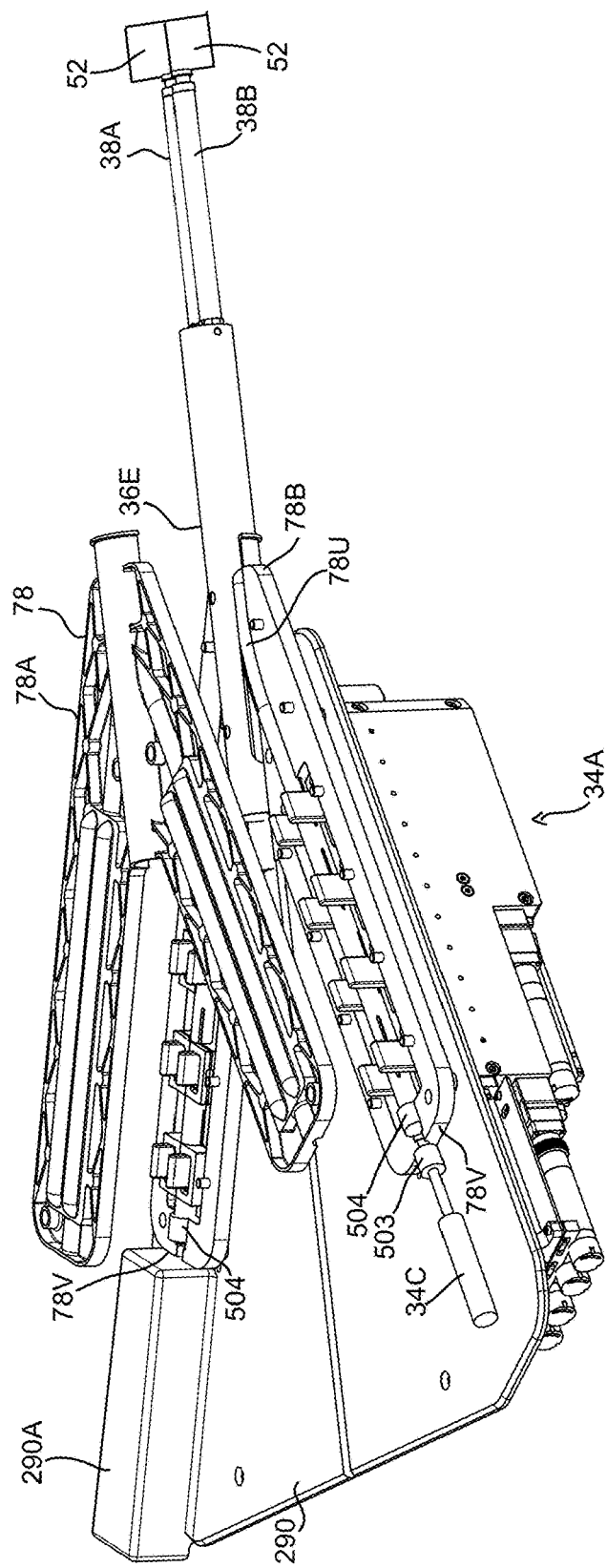

Referring now to FIG. 9A articulated section 40E can include joint members 310 aligned such that the joint of ball 312 and socket 314 of subsequent joint members 310 unite when assembled. Joint members 310 can be configured to have a channel 311 which can extend from the socket 314 to the ball 312 of the joint member 310. When an articulated segment 40E is assembled, the channel 311 in each joint member can align with one another and provide a continuous pathway through articulated section 40E. In some configurations, channel 311 can be configured to receive at least a portion of a surgical tool 52 (FIG. 4A) or auxiliary component 20 (FIG. 1) used during the surgical procedure. The portion received in channel 311 can be, but is not limited to being substantially flexible or pliant and may be passively bent as articulated section 40E is articulated. The portion of a surgical tool 52 (FIG. 4A) or auxiliary component 20 (FIG. 1), which is received in channel 311 can move relative to movement of joint members 310. For example, the portion of the surgical tool 52 (FIG. 4A) or auxiliary component 20 may rotate relative to the joint members 310 when a force is imparted to it via a rotational drive component 34C (FIG. 69). Additionally, a surgical tool 52 (FIG. 4B) or auxiliary component 20 (FIG. 1) may be actuated or controlled via an associated actuator 54B (FIG. 4B). For example, displacing one or more actuator 54B (FIG. 4B) may open and/or close jaws of a surgical grasper. In some configurations, channel 311 may house a flexible cannula or tube configured to receive at least a portion of the surgical tool 52 (FIG. 4A) or auxiliary component 20 (FIG. 1).

Figure 9B:
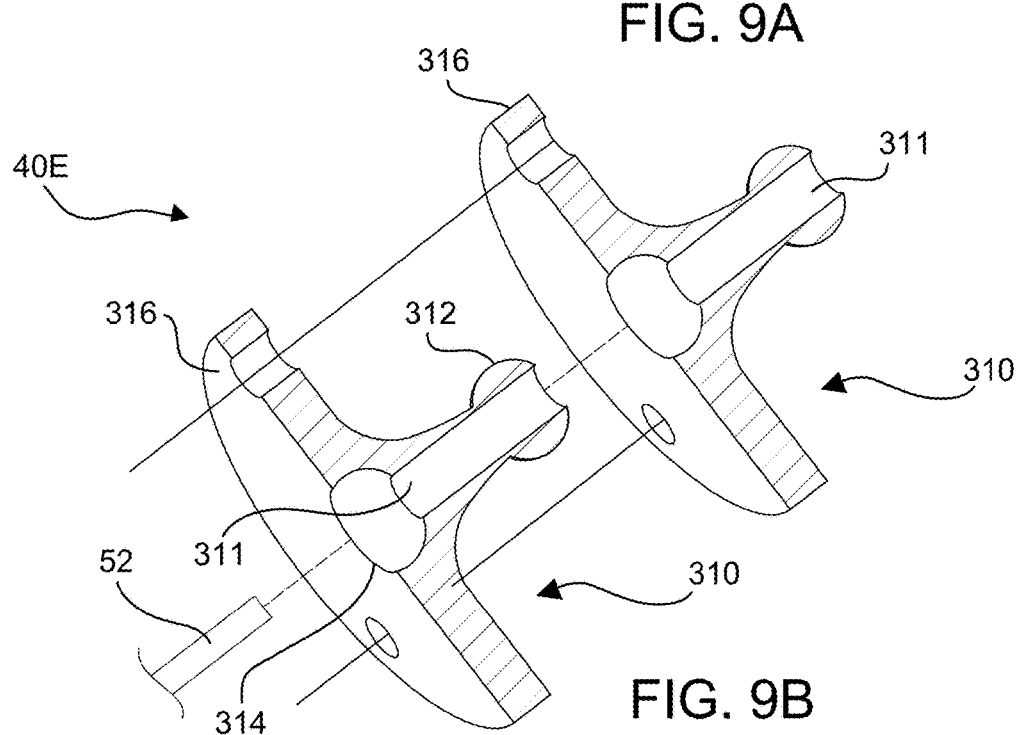

Referring now to FIG. 9B, a cross section of articulated section 40E is depicted. Channel 311 extending from the socket 314 to ball 312 of each joint member 310 of the articulated segment 40E is shown. In some configurations, more than one channel 311 may be included in each joint member 310 of articulated section 40E. A surgical tool 52 may be inserted through the pathway created by the channels 311 to introduce the tool 52 to the surgical site. Alternatively, a portion of a surgical tool 52 or auxiliary component 20 (FIG. 1) may reside in the pathway created by the channels 311.

Figure 10:
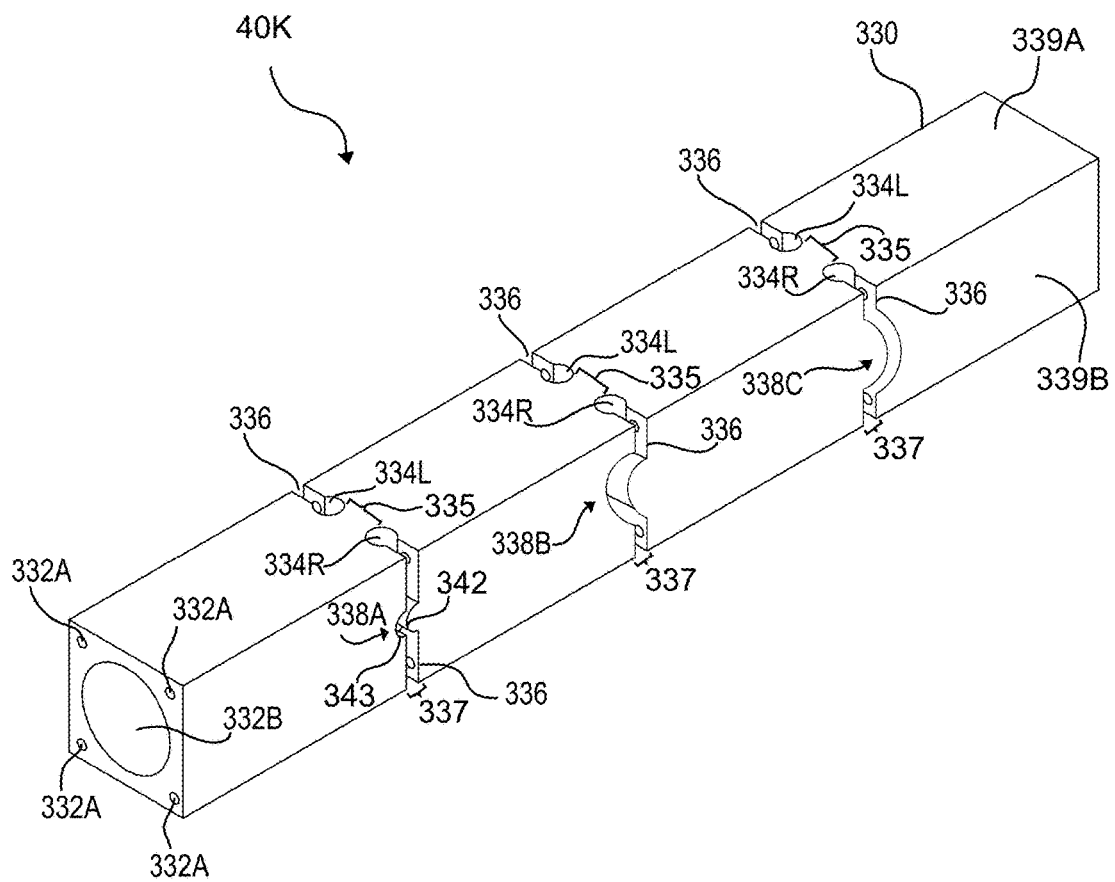
FIG. 10 is a schematic diagram of a configuration of an articulated segment including an elongate structure and lumens of the present teachings.

Referring now primarily to FIG. 10, articulated segment 40K can include elongate structure 330 with first lumens 332A and second lumen 332B. Elongate structure 330 can be, for example, roughly square or rectangular in cross section though could have any other cross-sectional shape (e.g. round, hexagonal, octagonal). Articulated segment 40K may be, for example, but not limited to, a single piece (e.g. an extrusion). In various configurations, articulated segments 40K may be, for example, but not limited to, nylon or a similarly bendable material. Second lumen 332B and first lumens 332A can be of a plurality of different diameters. First lumens 332A can act as actuator guide paths through which respective actuators 54 (FIG. 3A) may extend. Actuators (see, e.g. 54A of FIG. 4B) may be, for example, but not limited to, wires or cables. Second lumen 332B may be, for example, of a larger diameter than first lumens 332A. Second lumen 332B may be used to introduce one or more surgical tools to articulated segment 40K or manipulated component 38 (FIG. 3A). The second lumen 332B may be centrally disposed while the first lumens 332A may be peripherally disposed.

Still referring to FIG. 10, articulated segment 40K can include living hinges 335. The living hinges 335 can be generated by a variety of cutouts 337. This arrangement can allow elongate structure 330 to bend about living hinges 335 when actuators (see, e.g. 54A of FIG. 4B)) attached to portions of elongate structure 330 are displaced. Cutouts 337 can include sets of holes 334L, 334R which can be disposed upon opposing faces of elongate structure 330. Sets of holes 334L, 334R can include left holes 334L and right holes 334R which flank a medial partition which forms a living hinge 335. Each living hinge 335 can be continuous with the rest of elongate structure 330. In configurations in which elongate structure 330 is round in cross section, each hole of sets of holes 334L, 334R may be disposed 180° from the other. Left holes 334L and right holes 334R may be angularly offset from one another, for example, but not limited to, by 20-50°. Left holes 334L and right holes 334R can be round or any other shape. The size and/or spacing of left holes 334L and right holes 334R can vary, though in the example configuration the holes 334L, 334R are depicted as having a uniform size and spacing. In some configurations, first face 339A, second face 339B, third face (not shown) and fourth face (not shown) may include holes. The holes may be arranged in an alternating relationship if desired. For example, every other set of holes 334L, 334R may be angularly offset, for example, but not limited to, by 90° from one another. In an example configuration, every other set of holes 334L, 334R may be on first face 339A and opposing third side face (not shown), while the intervening sets of holes would be on second side 339B and fourth face (not shown) opposite the second face 339B. Other permutations are possible as well. For instance every third or fourth set of holes 334L, 334R could be angularly offset from the others. Other shapes of elongate structures 330 could offer additional possibilities. For example, a hexagonal shape could allow for sets of holes 334L, 334R to alternate about the three pairs of opposing faces.

Continuing to still further refer to FIG. 10, cutouts 337 can include a number of channels 336. Each channel 336 may be associated with a set of holes 334L, 334R. Each channel 336 can be, for example, but not limited to, continuous with at least one of left hole 334L and right hole 334R. Each channel may extend from any of left hole 334L and right hole 334R to an axially aligned hole on the opposing face of the elongate structure 330. In the example configuration, channels 336 can extend from one of a right hole 334R or left hole 334L to an axially aligned left hole 334L or right hole 334R on the third face (not shown) of elongate structure 330. The spacing of channels 336, relationship between channels 336 and set of holes 334L, 334R, as well as the relationship between channels 336 and faces) may differ in various configurations. The arrangement of set of holes 334L, 334R and channels 336 (and therefore living hinges 335) can be chosen to provide the ability to bend elongate structure 330 in desired orientations. Channels 336 can also serve as stops. The widths of channels 336 can be adjusted to cause the range of motion to increase or decrease. As the width is decreased, the allowed range of motion can also decrease. Thus, the point at which the stop will be encountered can be controlled by the width of a channel 336.

Continuing to refer to FIG. 10, channels 336 can also include features which can act as an interlocks and which may create barriers or obstacles which may inhibit torsional distortion during operation. Specifically, geometric features 338A, 338B, 338C can require rotation about the long axis of the elongate structure 330 to also be accompanied by translation about that axis. As a torsional force generally does not favor translational displacement, geometric features 338A, 338B, 338C may effectively lock articulated segment 40K in an orientation when a torsional force is applied. Geometric features 338A, 338B, 338C can include a projection or protuberance 342 which may be received by a receiving recess 343. In the example configuration, protuberance 342 can extend from a first wall of a channel 336 while receiving recess 343 can be recessed into the opposing face of that channel 336. The form of geometric features 338A, 338B, 338C may differ in other configurations.

Figure 11:
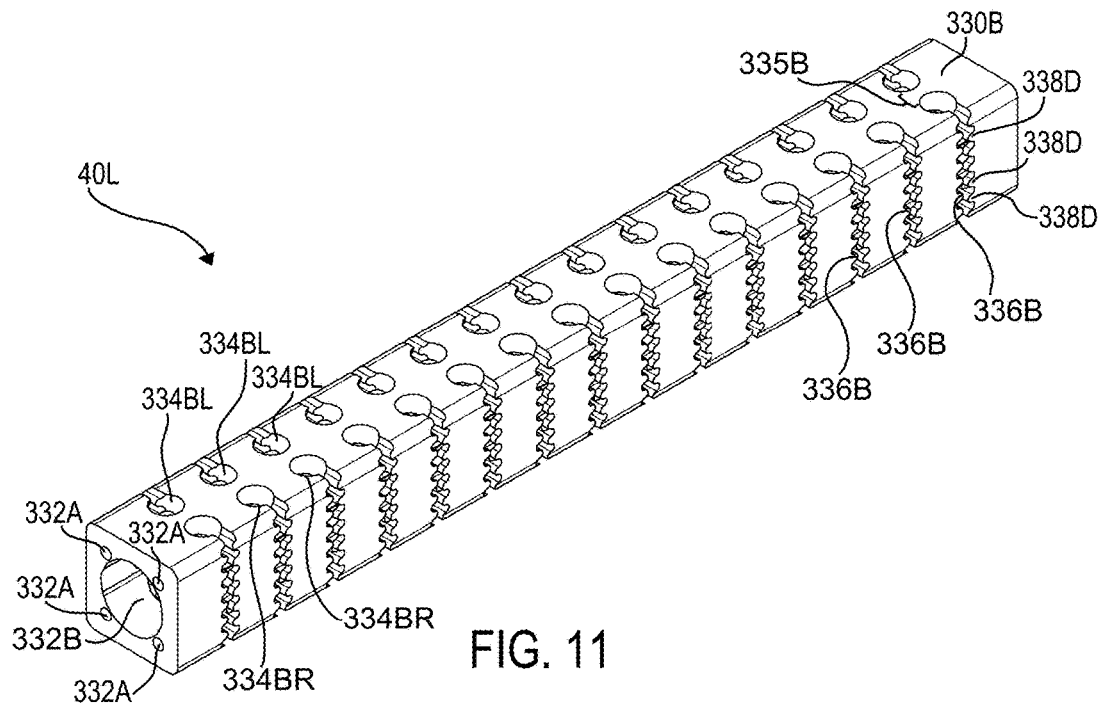
FIG. 11 is a schematic diagram of another configuration of an articulated segment including lumens of the present teachings.

Referring now to FIG. 11, articulated segment 40L can include first lumens 332A and second lumen 332B which can extend along the length of an elongate structure 330B. Elongate structure 330B can include holes 334BL, 334BR and channels 336B which can create living hinges 335B. When actuators (see, e.g. 54A of FIG. 4B) which can be anchored to elongate structures 330B are displaced in a controlled manner, elongate structures 330B can bend about living hinges 335B into a desired orientation. Geometric features 338D in channels 336B can be, but are not limited to being, wavy or teethed. Each of waves 344 can interlock sections of elongate structure 330B. Such an arrangement helps to ensure that one or more of geometric features 338D is engaged regardless of the orientation of elongate structure 330B.

Figure 12:
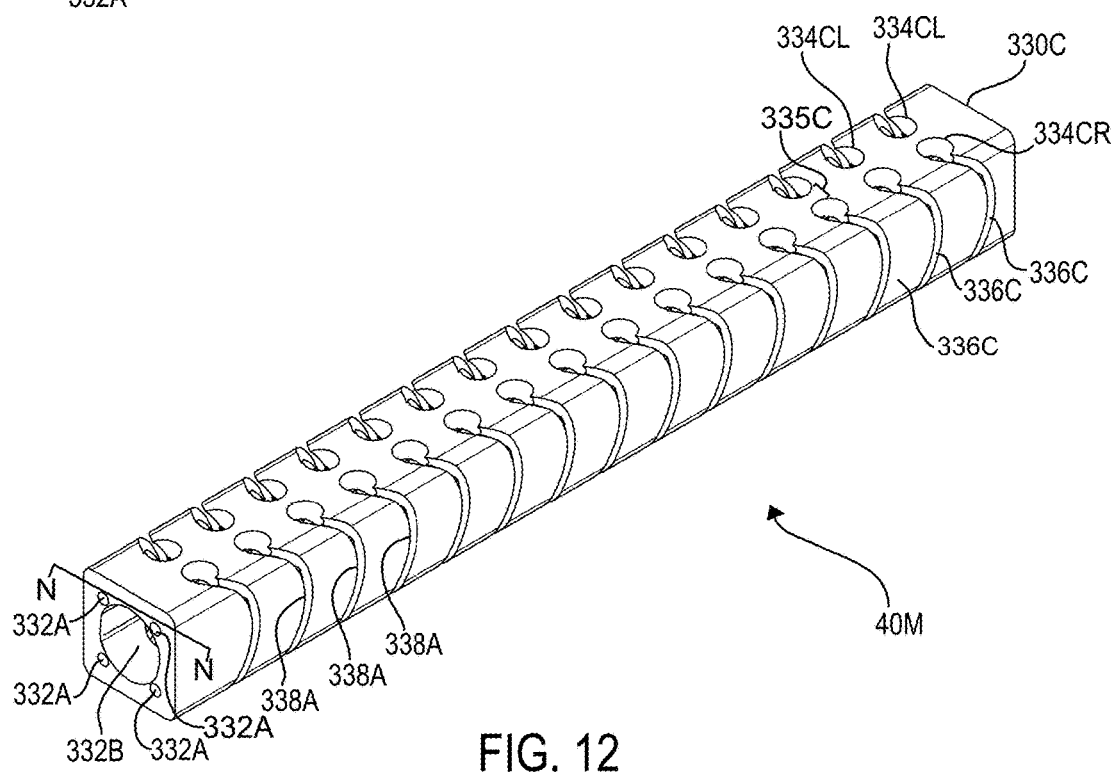
FIG. 12 is a schematic diagram of yet another configuration of an articulated segment including lumens.

Referring now to FIG. 12, articulated segment 40M can include first lumens 332B and second lumen 332A which can extend along the length of an elongate structure 330C. Elongate structure 330C can include holes 334CL, 334CR and channels 336C which can create living hinges 335C. When actuators (see, e.g. 54A of FIG. 4B) which can be anchored to elongate structures 330C are displaced in a controlled manner, elongate structures 330C can bend about living hinges 335C into a desired orientation. Channels 336C can be shaped to interlock sections of elongate structure 330C. Channels 336C can be curved slots which are recessed into elongate structure 330C. Channels 336C can be continuous with set of holes 334CL, 334CR. The width of channels 336C can be selected to limit the range of articulation in elongate structure 330C.

Figures 13, 14:
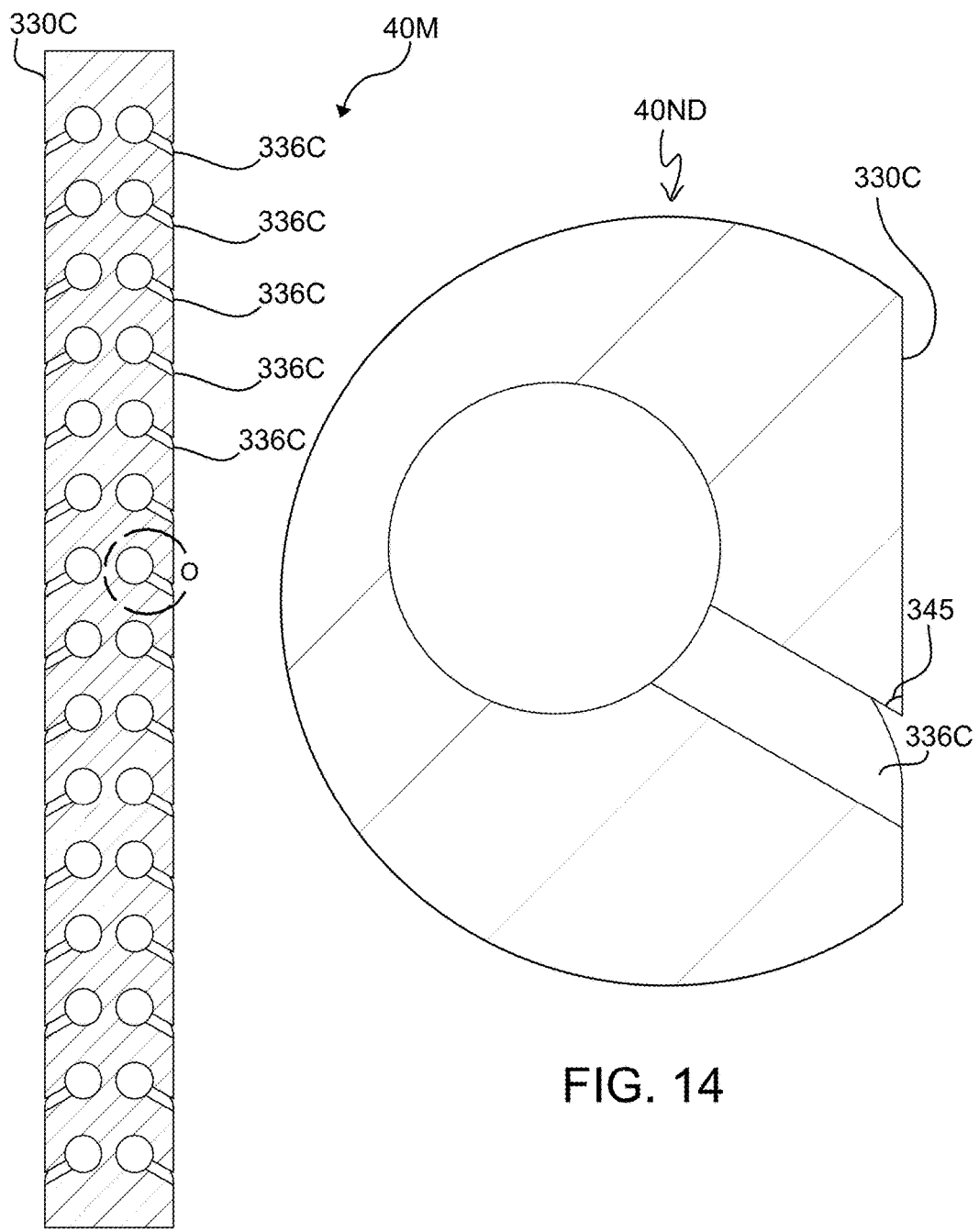
FIG. 13 is a schematic diagram of a cross section of the articulated segment in FIG. 12.
FIG. 14 is a schematic diagram of a detailed view of region O in FIG. 13.

Referring now to both FIGS. 13 and 14, channels 336C in articulated segment 40M are recessed into the elongate structure at angle 345 (FIG. 14). Angle 345 may, for example, be an acute angle (e.g. 30-60° or 45°) with respect to the face of elongate structure 330C in which channel 336C is disposed. Channel 336C can be cut into elongate structure 330C using a hole saw type angular cutter. Alternatively, elongate structure 330C may be a single molded part. Angle 345 may be selected to increase or decrease the range of motion of articulated segment 40M.

Figure 15:
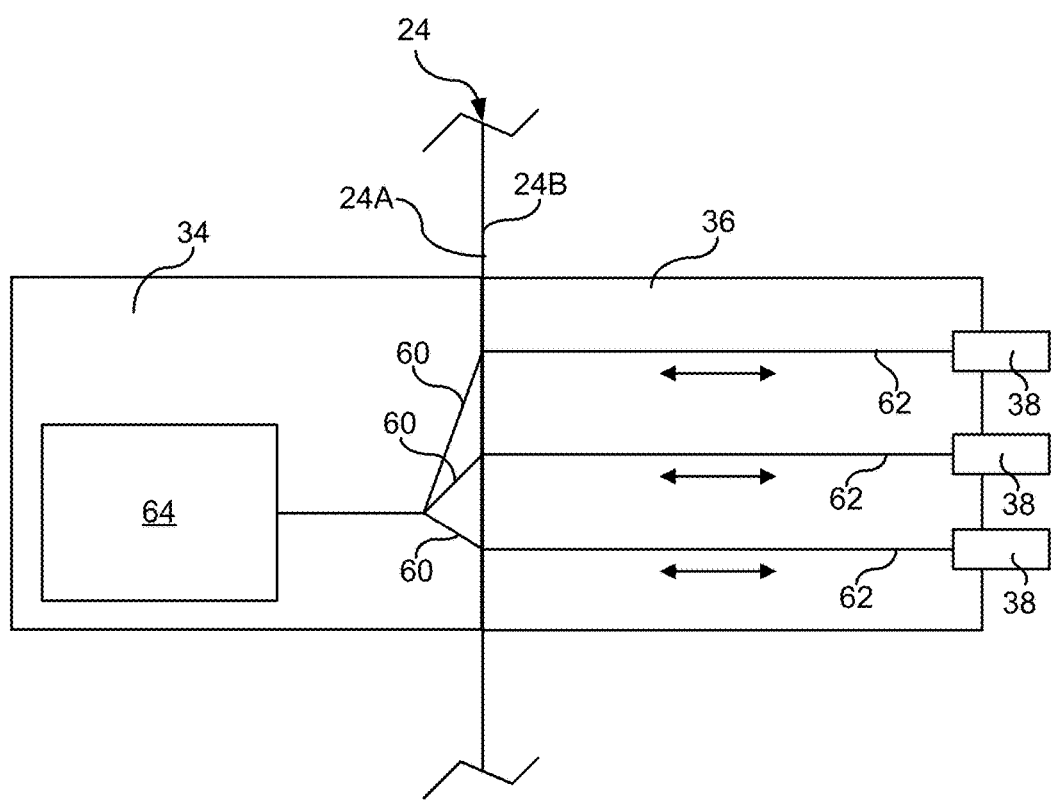
FIG. 15 is a schematic block diagram of a drive component and a manipulator of the present teachings.

Referring now to FIG. 15, drive component 34 and manipulator 36 with operably coupled manipulated components 38 are shown. Drive component 34 can be separated or segregated from manipulator 36 by barrier 24. A portion of barrier 24 can be retained between drive component 34 and manipulator 36. Drive component 34 can include a number of drive elements 60 which can be arranged to act on driven elements 62. Drive elements 60 can be driven by at least one force or motion generating element 64. Each driven element 62 can cause actuation of an actuator (see, e.g. 54A of FIG. 4B) in manipulated component 38. Alternatively, driven element 62 may function as actuator (see, e.g. 54A of FIG. 4B) and directly actuate manipulated component 38. Drive elements 60 and driven elements 62 may each be a single element or a grouped collection of elements. For example, each drive element 60 may include a number of individually actuatable components. Each of these individually actuatable components may act on individual or multiple companion components of a respective driven element 62. As a result, each drive element 60 can be controllable to cause actuation of one or more independently actuatable features of manipulated component 38 via driven elements 62. The number of individually actuatable elements in each drive element 60 and driven element 62 may be determined at least in part based on the number of independently actuatable features in manipulated component 38.

Continuing to refer to FIG. 15, force or motion generating element 64 may, for example, be one or more or a combination of motors, a hydraulic actuation system, or any other arrangement. In the example configuration, force or motion generating element 64 is shown as part of drive component 34. In other configurations, for example, those where a hydraulic system is used, the force or motion generating element 64 may not be entirely housed in the drive component 34. For example, hydraulic master cylinders may be positioned in base 30 (FIG. 3) or in another location remote to drive component 34. Hydraulic lines may then extend from the master cylinders to drive component 34 to act on drive elements 60. It may be desirable to use a fluid-based system for force or motion generating element 64 as it may aid in heat management. Additionally, since the master cylinders can be located externally from robot 16 (FIG. 3), a fluid based system may allow for drive component 34 to be made with a smaller form factor.

Continuing to refer to FIG. 15, drive elements 60 can transfer force to the driven elements 62 on the opposing side of barrier 24. Force may be transmitted from first barrier side 24A to second barrier side 24B (and vice versa) in any of a variety of ways. In some configurations, force is transmitted by translational displacement of at least a portion of drive element 60. This displacement may in turn cause displacement of driven element 62. In other configurations, force is transmitted by rotational displacement of at least a portion of drive element 60. Torque may then be conveyed across barrier 24 to drive driven element 62. In still other configurations, both translational and rotational displacement may be transmitted. Driven elements 62 may be driven by both rotational and translational displacement of the drive elements 60. Additionally, some drive elements 60 may be controlled by different types of force or motion generating elements 64. For example, some may be motor driven while others are controlled by a hydraulic system. In some configurations, barrier 24 may be substantially or entirely stationary as the force is transmitted from first barrier side 24A to second barrier side 24B and vice versa. That is, barrier 24 may displace slightly, but displacement of barrier 24 is not necessary nor the primary means by which force is transmitted. In other configurations, barrier 24 or a portion of barrier 24 may displace about one or more degrees of freedom as the force is transferred from, for example, first barrier side 24A to second barrier side 24B. In some configurations, the degree(s) of freedom about which barrier 24 displaces may be the same as those of drive element 60 and/or driven element 62. In other configurations, drive element 60 and/or driven element 62 may displace about one or more first degrees of freedom while barrier 24 displaces about one or more second degrees of freedom. For a specific example, drive element 60 and companion driven element 62 may displace about a roll axis while barrier 24 may nutate about an axis transverse (e.g. perpendicular) to the roll axis.

Continuing to refer to FIG. 15, in configurations where torque is transferred from drive element 60 to second barrier side 24B, the torque can be transferred substantially or entirely without rotating barrier 24 material or requiring a rotating seal in barrier 24. That is, rotation of barrier 24 may occur to a small degree, but is not necessary nor the primary means by which torque is transmitted to, for example, second barrier side 24B. Various configurations which transmit such force across barrier 24 without rotating barrier 24 or a portion of barrier 24 will be described elsewhere herein.

Figure 16:
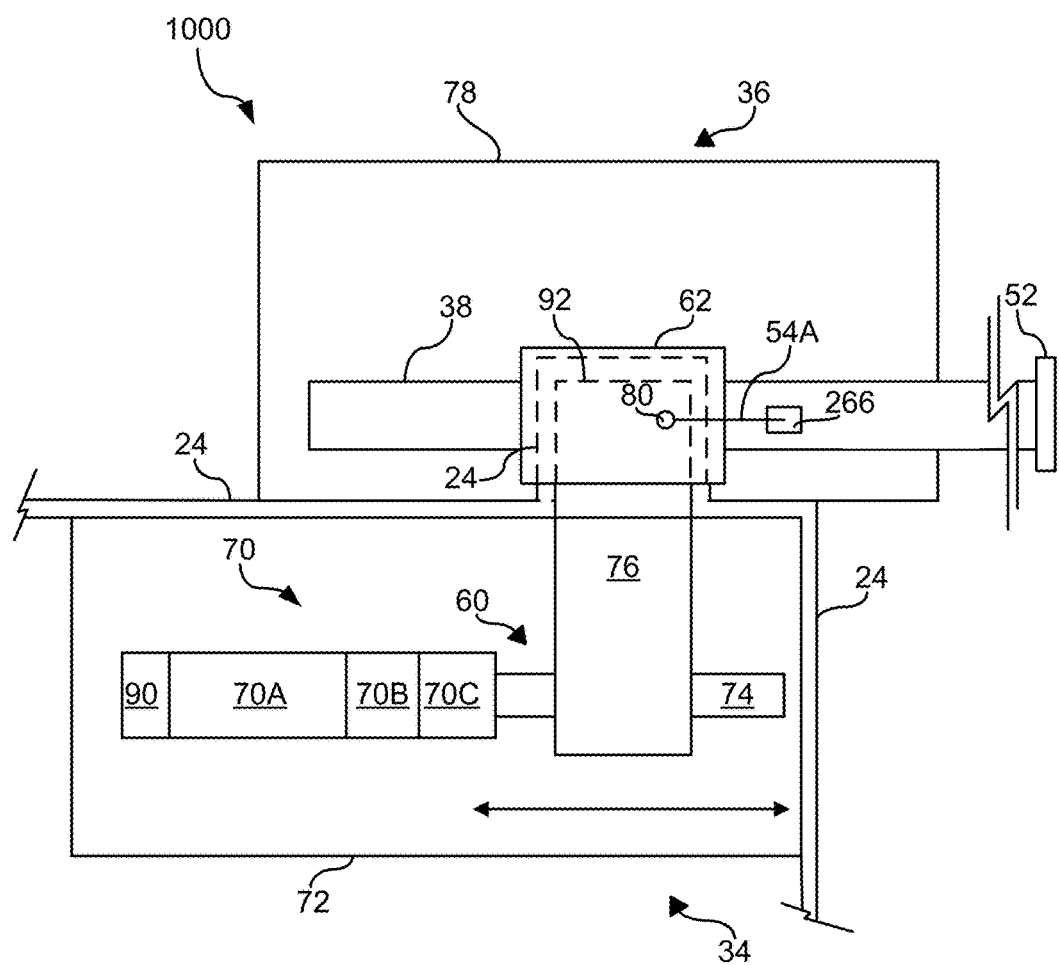
FIG. 16 is a schematic block diagram of some configurations of a system of the present teachings.

Referring now to FIG. 16, system 1000 can include drive component 34 and manipulator 36 that can be engaged with one another through barrier 24. Drive component 34 can include drive element 60. Drive element 60, driven element 62, and barrier 24 can displace in the same degree of freedom when motion is transmitted across barrier 24. Drive element 60 can be driven by a motion-generating element such as, for example, but not limited to, a motor assembly 70. Motor assembly 70 can include motor 70A, gear head 70B, and bearing 70C for a portion of drive element 60, for example, but not limited to, drive screw 74. Motor 70A may be any suitable variety of motor such as, for example, but not limited to, a brushless DC motor. Gear head 70B may be, though is not limited to being, a planetary gear head. The gear ratio of gear head 70B may be chosen to suit the needs of a given application as would be appreciated by one skilled in the art. In some configurations, the gear ratio may be 1:1. Bearing 70C may be, for example a spindle bearing. Drive element 60 can include, but is not limited to including, drive screw 74 and nut 76. Drive screw 74 may be, for example, but not limited to, a lead screw or a ball screw. As motor 70A commutates, drive screw 74 can rotate. In turn, nut 76 can move along the length of drive screw 74. Various encoders and sensors may be included in the present configuration to measure movement of nut 76 along drive screw 74 as well as measure an amount of force being transmitted at one or more points in the load path. To keep nut 76 from displacing in undesired degrees of freedom, nut 76, may also ride along a bearing such as a linear bearing which can run parallel to drive screw 74. Motor assembly 70 and drive screw 74 may be replaced respectively by a hydraulic cylinder and piston if a hydraulic configuration is desired.

Continuing to refer to FIG. 16, system 1000 can further include, but is not limited to including, nut 76 which may include projection 92 which can extend out of drive component housing 72. In system 1000, projection 92 can be a blade shaped protuberance. The portion of nut 76 external to drive component housing 72 (i.e. projection 92) may be covered by barrier 24. In some configurations, barrier 24 may include preformed or bonded-in pockets or sleeves continuous with the rest of barrier 24. These preformed or bonded-in pockets may fit around blade or projection 92. Various configurations of barriers 24 are further described elsewhere herein. Projection 92 may project into manipulator housing 78 and engage with driven element 62. In such configurations, driven element 62 may be a block with a slot which can receive blade or projection 92. In other configurations, nut 76 and/or drive element 60 may magnetically couple to driven element 62 through barrier 24. As nut 76 travels along the length of drive screw 74, driven element 62 can be displaced. Driven element 62 may ride along a one or more bearing in manipulator 36 to constrain driven element 62 from moving in undesired degrees of freedom.

Continuing to still further refer primarily to FIG. 16, driven element 62 may be attached to one or more actuator 54A which can actuate a feature of manipulated component 38 or surgical tool 52. Actuator 54A can be fixedly anchored to driven element 62 at anchor point 80. As the driven element 62 is displaced, the actuator 54A may advance in or out of manipulated component cutout 266. Since manipulated component 38 can be fixedly attached to manipulator 36, displacement of actuator 54A can exert an actuating force on or at the actuated feature of manipulated component 38 or surgical tool 52. As would be appreciated by one skilled in the art, any number of driven elements 62 may be included in manipulator 36 and may be driven by any suitable number of drive elements 60 in drive component 34.

Still referring to FIG. 16, each motor assembly 70 can be also associated with one or more position sensor 90 which can be used to provide feedback as to the position of components of drive element 60. Position sensor 90 can be a motor encoder which can sense rotation as motor 70A commutates. Feedback from position sensor 90 may be communicated to a location remote from drive component 34, for example, via suitable cabling or lines 19 (FIG. 3) in arm 32 or through wireless communications. Any suitable variety of position sensor 90 may be used. For example, if position sensor 90 is a motor encoder, any suitable variety of encoder may be used such as optical, magnetic, or capacitive varieties. In other configurations, drive element 60 may additionally or alternatively be associated with a potentiometer for example. In still other configurations, nut 76 may include a magnet whose travel is monitored by position sensor 90 including one or more magnetic sensors such as a Hall effect sensor, a Hall effect sensor array.

Figure 17A:
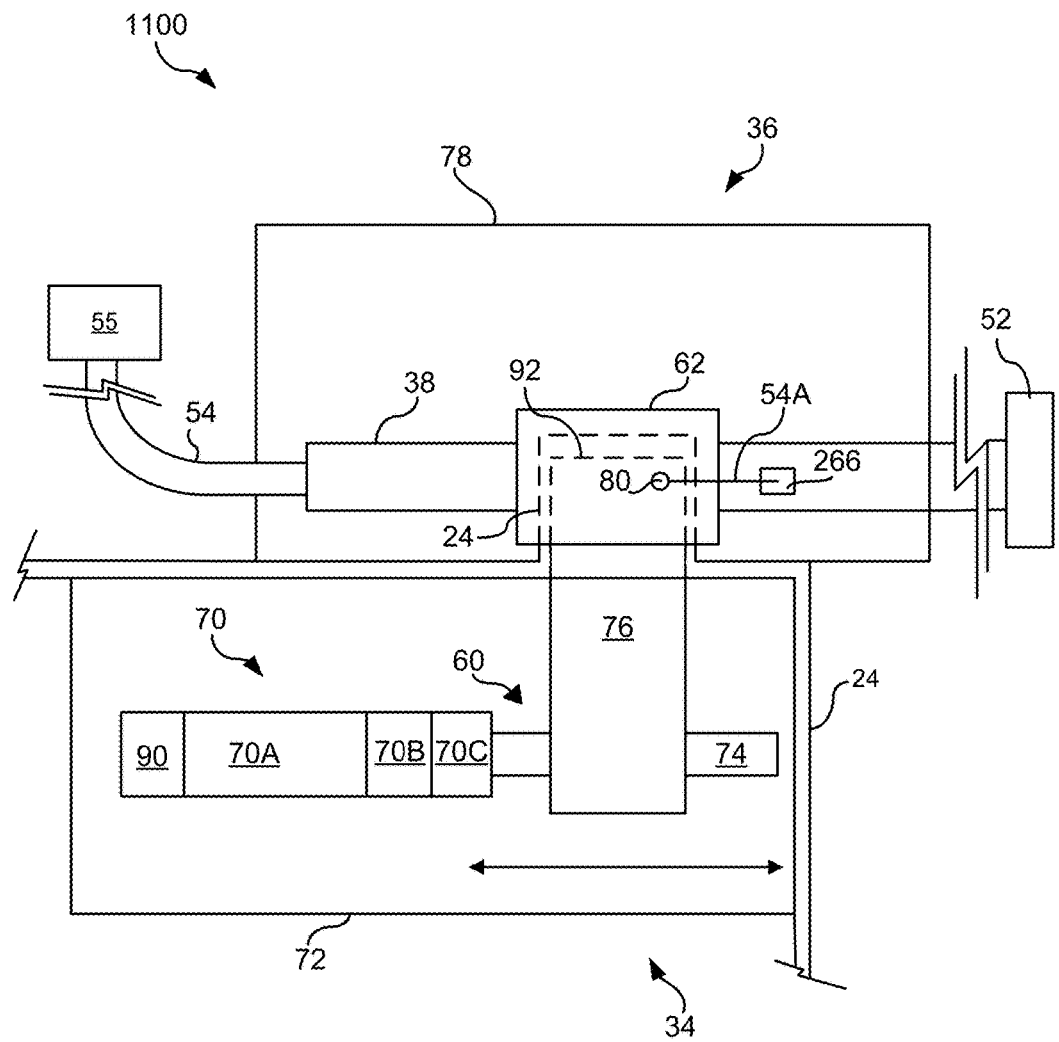
FIG. 17A is a schematic block diagram of another configuration of a system of the present teachings.

Referring now to FIG. 17A, system 1100 can include drive component 34 and manipulator 36 that can be engaged with one another through barrier 24. System 1100 can further include utility component 54 that can enter manipulated component 38 through manipulator housing 78. Utility component 54 may be, for example, a mechanical control, light transmission, information transmission, fluid transmission, and/or power or data transmission component. As shown, utility component 54 does not pass through barrier 24 and is depicted entirely on one side of barrier 24. In configurations where barrier 24 serves as a sterility barrier, utility component 54 may come pre-packaged in a sterile environment. For instance, utility component 54 may be included as part of an assembly that can include manipulator 36 and manipulated component 38, where the assembly can be packed in a sterile package. Alternatively, utility component 54 may be packed individually in its own sterile package. Utility component 54 can be connected to source 55 which may differ depending on the type of utility component 54. In configurations where the utility component 54 is a mechanical control component, the source 55 may be a motion generating element. In configurations where utility component 54 can be a fluid transmission component, source 55 may be an irrigation pump, or insufflations gas source/reservoir. In configurations where utility component 54 is a light transmission component, source 55 may be a light source for a fiber optic line, for example. In configurations where utility component 54 is a power transmission component, source 55 may be a power outlet, battery or battery bank, or other power source. In configurations where utility component 54 is a data transmission component, source 55 may be a processor which may, for example, send and receive data to or from surgical tool 52, for example, but not limited to, an imager.

Figure 17B:
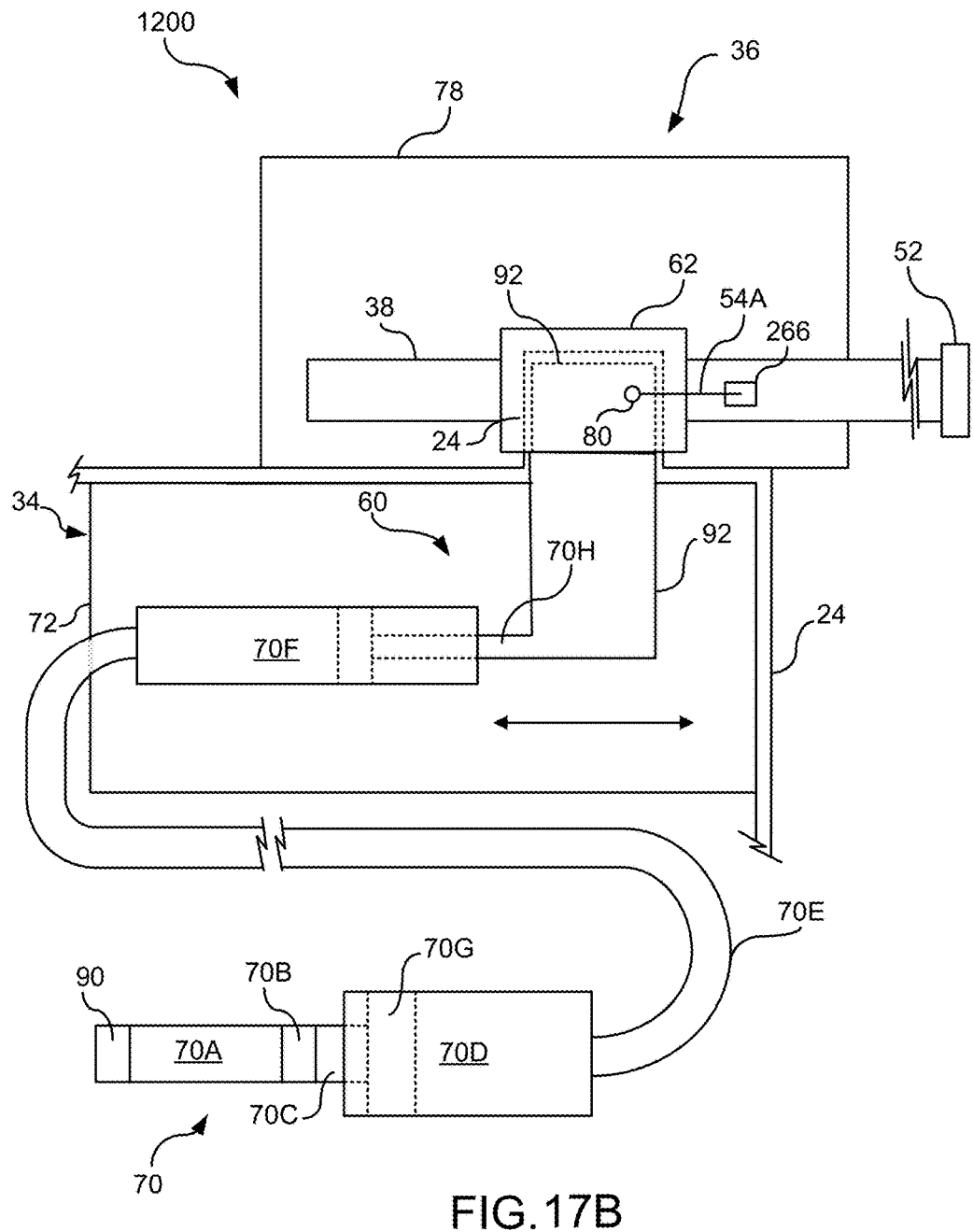
FIG. 17B is a schematic block diagram of yet another configuration of a system of the present teachings.

Referring now primarily to FIG. 17B, system 1200 can include drive component 34 and manipulator 36 which can be engaged with one another through barrier 24. In some configurations, drive element 60 is hydraulically driven. System 1200 can include, but is not limited to including, motor assembly 70 which can be attached to a master cylinder 70D. Master cylinder 70D can be in communication with a hydraulic line 70E. Hydraulic line 70E can extend from master cylinder 70D to slave cylinder 70F. As motor assembly 70 displaces piston 70G, piston 70G may displace fluid in hydraulic line 70E. This in turn can cause displacement of a slave piston 70H. In system 1200, slave piston 70H can include projection 92 which can extend into manipulator housing 78 and causes displacement of driven element 62. Motor assembly 70 and master cylinder 70D can be, for example, located remotely from driven component 34 to reduce the size of driven component 34 as well as simplify heat management. Motor assembly 70 and master cylinder 70D may be placed in any suitable location. In some configurations, any motor assemblies 70 and master cylinders 70D may be placed in base 30 (FIG. 3). Hydraulic line or lines 70E from master cylinders 70D may, for example, extend along arm 32 (FIG. 3) to slave cylinder or cylinders 70H.

Referring now primarily to FIG. 18, drive component 34 can include motor assemblies 70. The motor assemblies 70 may be powered and commanded from a location remote to drive component 34. For example, power and commands from controller 15 (FIG. 3) base 30 (FIG. 3) may be communicated to drive component 34 via various cabling or lines 19 (FIG. 3) in arm 32 (FIG. 3). Each motor assembly 70 can also be associated with a motor encoder 90A which senses rotation as a motor of a motor assembly 70 commutates. Feedback from motor encoder 90A may be communicated to a location remote from drive component 34, for example, via suitable cabling or lines 19 (FIG. 3) in arm 32 (FIG. 3). Motor assemblies 70 can be arranged into first deck 71A and second deck 71B that can be positioned above first deck 71A to minimize the size of drive component 34. Drive component 34 can include, for example, but not limited to, a number of first projections 92A as well as a number of second projections 92B. As the motor assemblies 70 are powered, the first projections 92A and the second projections 92B controlled by each motor assembly 70 may be displaced. In some configurations, each first projection 92A and each second projection 92B can be driven by individual motor assemblies 70. In other configurations, one motor assembly 70 may drive multiple first projections 92A and multiple second projections 92B (e.g. with a suitable gearing arrangement). For example, in some configurations one motor assembly 70 may be used to drive two projections 92A, 92B to displace equally, in the same or opposite directions. This may be desirable in configurations where actuators 54A (FIG. 4B), such as pull wires, are used to actuate a manipulated component 38 (FIG. 16) as it would help ensure that one actuator (see, e.g. 54A of FIG. 4B) may be pulled or spooled in at the same rate another actuator (see, e.g. 54A of FIG. 4B) is spooled in or out.

Figure 19:
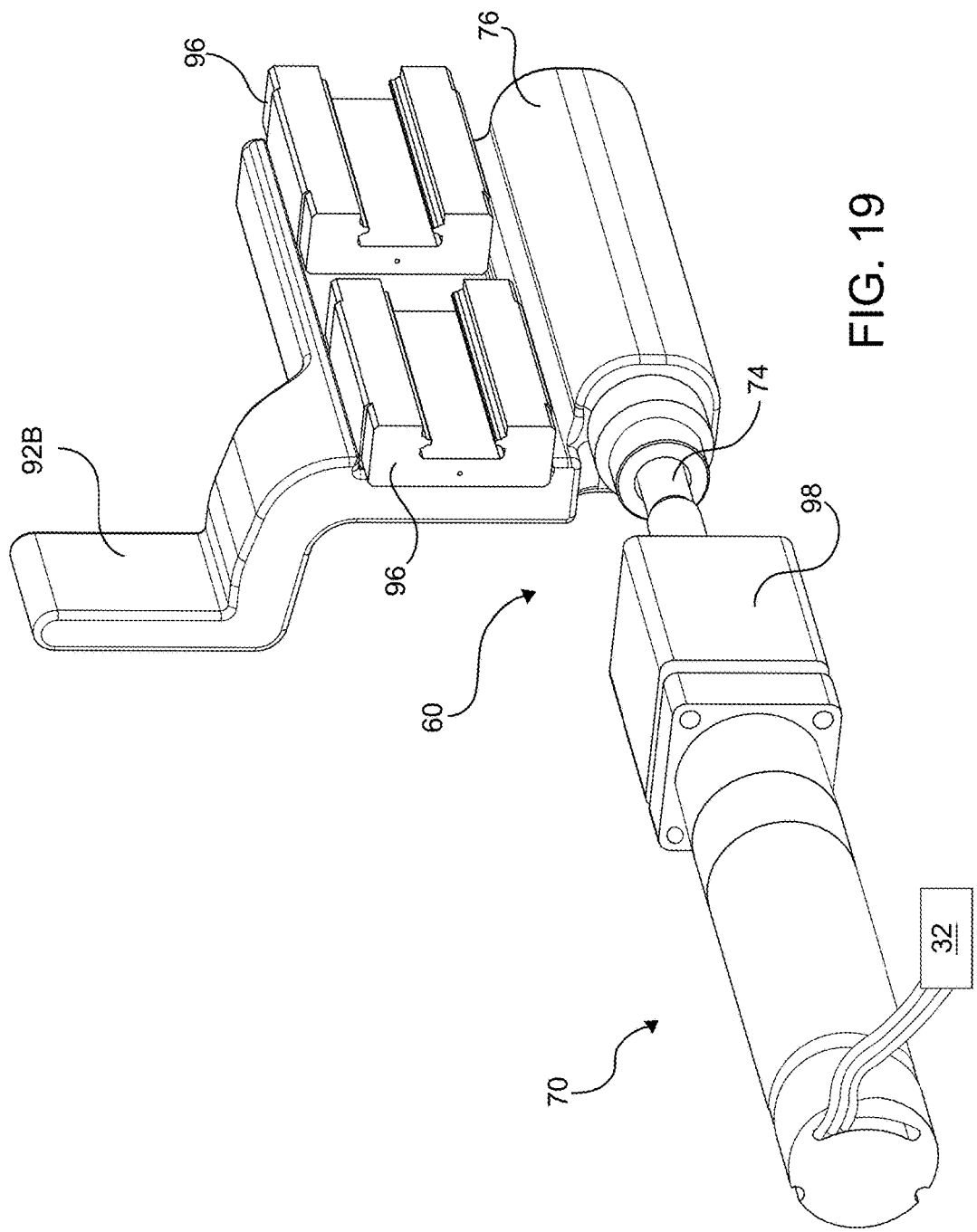
FIG. 19 is a schematic diagram of a motor assembly and drive element of the present teachings.

Referring now primarily to FIG. 19, motor assembly 70 and drive element 60 are shown. Drive element 60 can include a drive screw 74 and nut 76 which can interface with drive screw 74. Drive screw 74 can be generally coaxial with motor assembly 70. Motor assembly 70 can drive screw 74, and the rotation of drive screw 74 can cause nut 76 to travel along drive screw 74. The projection 92 can be shaped such that the force generated in drive element 60 can be transmitted off axis with respect to drive screw 74 and motor assembly 70. In the specific configuration shown, projection 92 can exert force along an axis which is substantially parallel to the axis of the motor assembly 70 and drive screw 74. Projections 92 can be an integral part of each nut 76 or projections 92 can be separate components which are coupled onto each of nuts 76. Projections 92 may also be attached to each nut 76 in a modular fashion. For example, if a nut 76 drives two driven elements 62, an additional projection 92 may be coupled to the nut 76 (or coupled to the projection 92 which is already attached to the nut 76). Nuts 76 may ride along a bearing. In the example configuration, each of nuts 76 can have at least one bearing saddle 96 either attached to nut 76 or as an integral part thereof, for example. Nut 76 can have, for example, but not limited to two saddles 96 coupled to nut 76. A load sensor 98 may be placed in the load paths associated with each motor assembly 70. Load sensors 98 may be, for example, but not limited to, load cells, strain gauges, and any of the load sensor 98 configurations described herein. Load sensors 98 can provide information about the amount of force that is being transmitted to manipulated component 38 (FIG. 16). Load sensors 98 are further described elsewhere herein.

Figure 20:
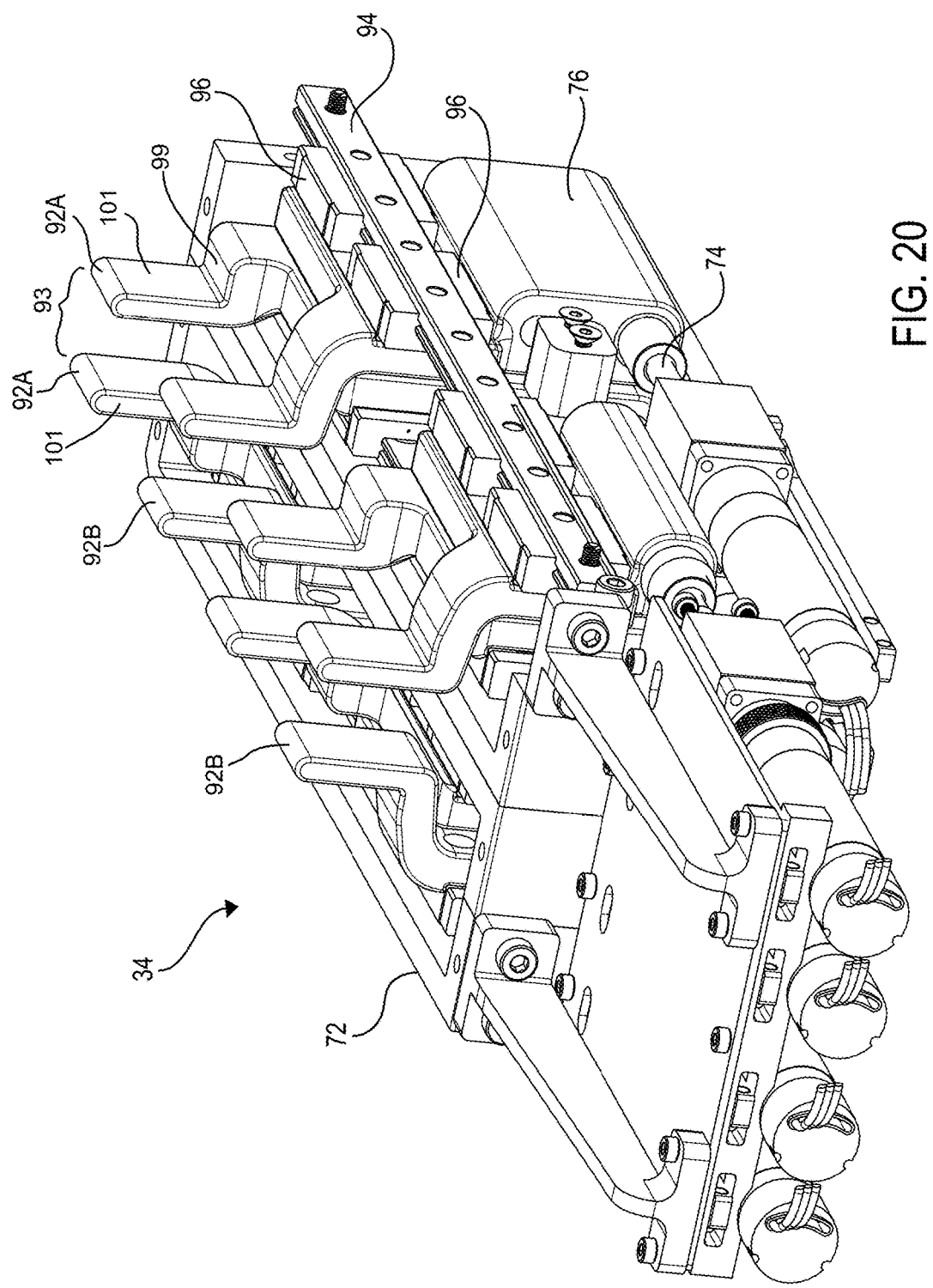
FIG. 20 is a schematic diagram of a drive component having a portion of a drive component housing.

Referring now primarily to FIG. 20, drive component 34 is depicted with a portion of the drive component housing 72 removed. Bearing saddles 96 of nuts 76 can each travel along linear motion bearing 94. The linear motion bearing 94 can be, but is not limited to being, a dovetailed slide bearing. Nuts 76 can be spaced on linear motion bearings 94 such that they do not contact and/or interfere with one another during operation of drive component 34. The linear motion bearings 94 for a drive component 34 can include medial linear motion bearings and lateral linear motion bearings to reduce the longitudinal dimension of drive component 34. In some configurations, the linear motion bearings 94 may include two pairs of lateral and medial bearings. The lateral and medial bearings can be parallel to one another. Each bearing can be shared by two nuts 76. Thus, though the configuration accommodates eight nuts 76, the longitudinal dimension of the linear motion bearings 94 need not be greater than what is necessary to accommodate two nuts 76 with adequate spacing between them. Medial distance 93 between projections 92A, 92B can be minimized to reduce footprint of manipulator 36 (FIG. 16). Each of first projections 92A and second projections 92B can be "L" shaped. Legs 99 of the "L" shapes can be sized such that vertical spans 101 can be aligned in a desired plane. The form of projections 92A, 92B may differ from configuration to configuration. For example, instead of including a bend or forming an "L", projections 92A, 92B may extend at an angle from the body of the nut 76. The angle can allow for a straight path from the nut 76 to the axis to which force can be transmitted. Arced or "S" shapes, and other non-straight projections 92A, 92B may also be used. In other configurations, for example those in which the number of projections 92A and 92B on a nut 76 is greater than one, all projections 92A, 92B may not be aligned on the same plane. Instead, projections 92A, 92B connected to a single nut 76 may be on parallel planes, for example.

Figure 21:
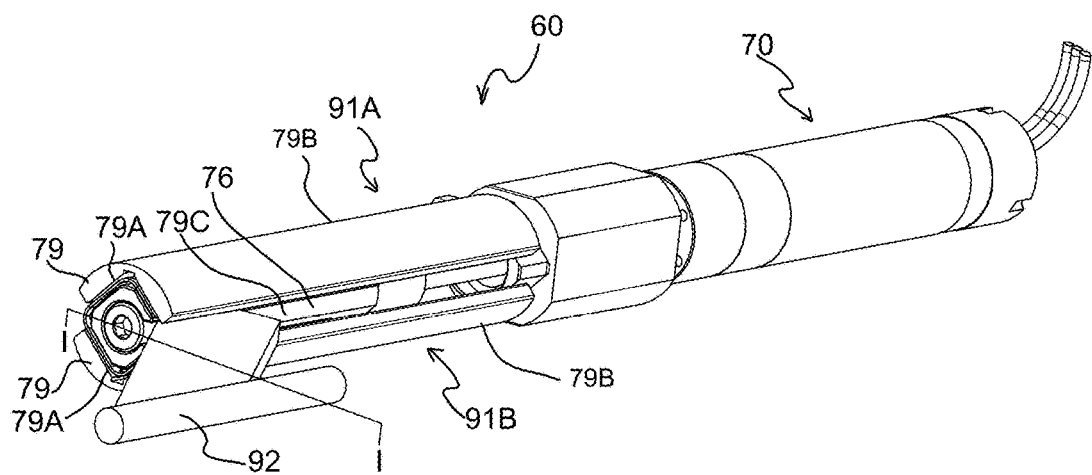
FIG. 21 is a schematic diagram of an alternate configuration of a motor assembly and drive element of the present teachings.

Referring now primarily to FIG. 21, an alternate example configuration of a motor assembly 70 and drive element 60 is shown. A configuration of linear motion bearings 94 (FIG. 20), which can guide the travel of nut 76, can be first linear needle bearing assembly 91A and second linear needle bearing assembly 91B. Linear needle bearing assemblies 91A, 91B can be highly stiff and can be capable of being subjected to high moment loads which may be present with nut 76 having projection 92 that transmits force to an off axis location. Each of linear needle bearing assemblies 91A, 91B can have housing 79 including interior face 79A which can be, for example, but not limited to, "V" shaped, and which can serve as a raceway for roller cages 71D (FIG. 23) of linear needle bearings 91A, 91B. In other configurations, another component of linear needle bearing assemblies 91A, 91B may provide the raceway instead of housing 79. Exterior faces 79B of housings 79 can be arced or rounded to allow for linear needle bearing assemblies 91A, 91B to be compact. Nut 76 can be held in place between the linear needle bearing assemblies 91A, 91B. Gap 79C between first linear needle bearing assembly 91A and second linear needle bearing assembly 91B can allow projection 92 to extend away from nut 76 and transmit force to a desired axis. A desired axis can be an axis along which a driven element 62 (FIG. 16) can be displaced. Travel limiters 57 (FIG. 23) may be included in linear needle bearing assemblies 91A, 91B to prevent movement of nut 76 outside of a predetermined range. The travel limiters 57 (FIG. 23) may be mechanical stops such as walls which block travel of a nut 76 in various configurations.

Figure 22:
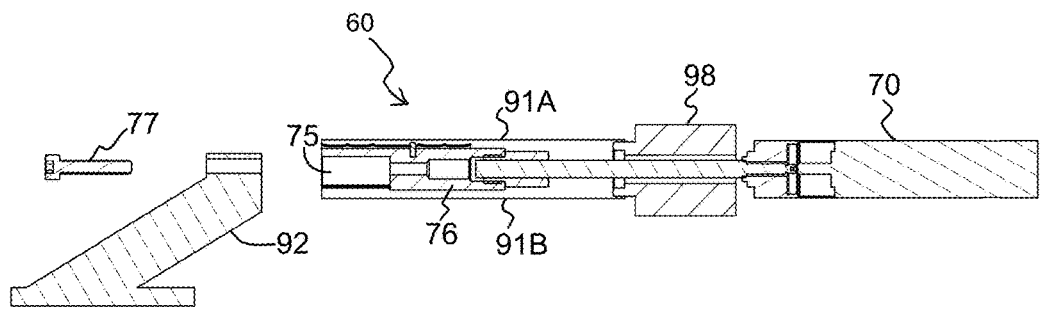
FIG. 22 is a schematic diagram of a medial cross section I-I (FIG. 21) including a nut of the present teachings.

Referring now primarily to FIG. 22, a medial cross section taken at I-I (FIG. 21) is shown. A nut 76 that can be constructed such that it may be used with any of a variety of different projections 92 is included. Specifically, nut 76 can include receiving feature 75 into which a projection 92 may be coupled. Each of the variety of different projections 92 may include a portion which may fit within the receiving feature 75. A desired projection 92 can be, for example, but not limited to, removably coupled to nut 76 via fastener 77. Any suitable fastener 77 may be used. In alternative configurations, projection 92 need not be removably coupled and may be ultrasonically welded, solvent bonded, glued, or otherwise permanently attached to nut 76. A load sensor 98 which may measure load in the load path of the drive element 60 is also included in FIG. 22.

Figure 23:
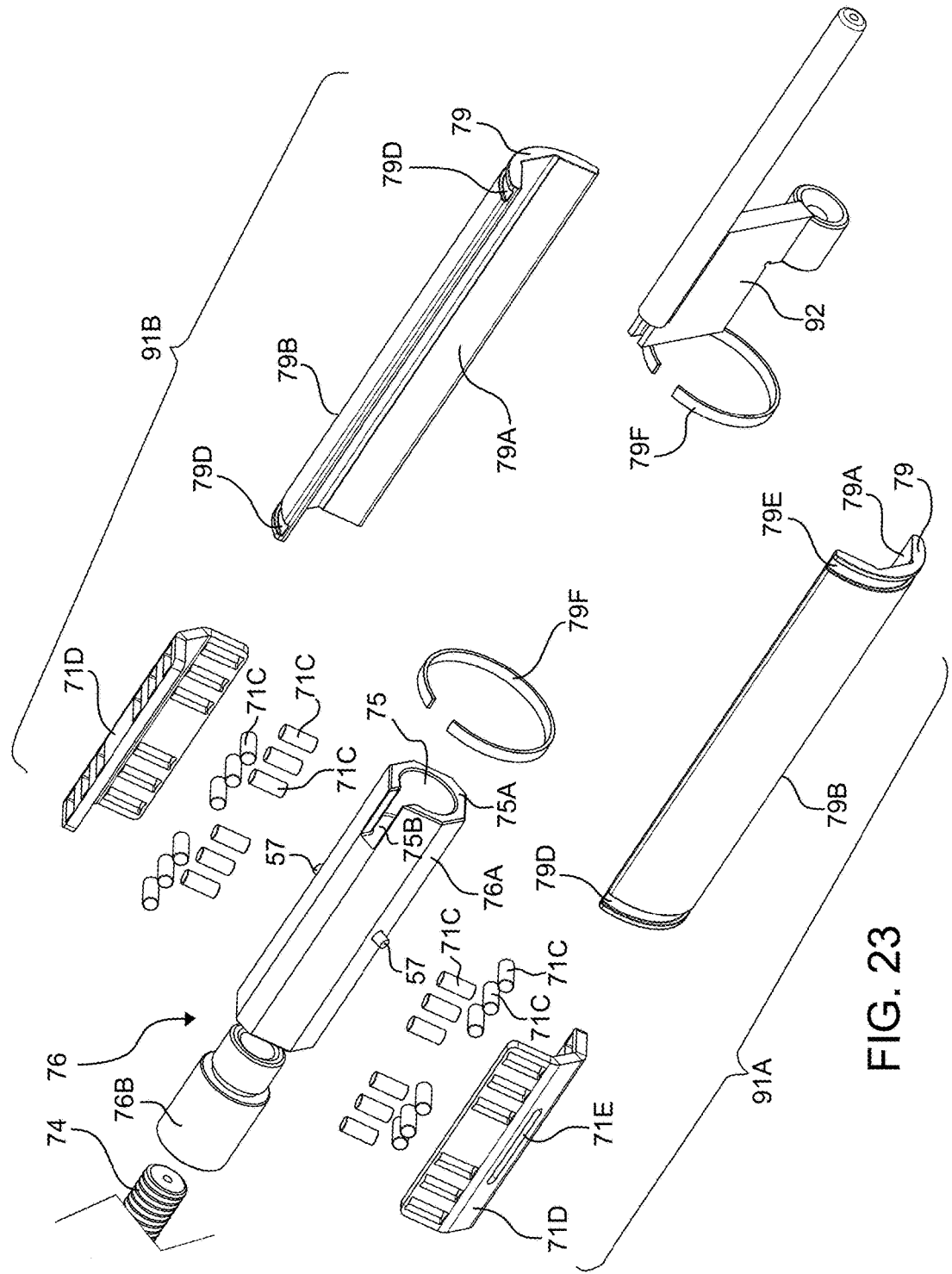
FIG. 23 is a schematic diagram of an exploded view of a number of linear needle bearing assemblies of the present teachings.

Referring now primarily to FIG. 23, an exploded view of a number of linear needle bearing assemblies 91A, 91B is shown. Linear needle bearing assemblies 91A, 91B can include housing 79. Exterior faces 79B of housings 79 can be arched or rounded. First recess 79D and second recess 79E can be included in exterior face 79B and can be sized to cooperate with retainer 79F which can hold two housings 79 together when linear needle bearing assemblies 91A, 91B are fully assembled. In the example configuration, retainer 79F can be, but is not limited to being, a retaining ring, or any other suitable retainer 79F, for example, but not limited to C-clips, pins, and/or threaded fasteners. Interior faces 79A can be, but are not limited to being, roughly "C" shaped, and serve as a raceway for needle bearings 71C of linear needle bearing assemblies 91A, 91B. Each of linear needle bearing assemblies 91A, 91B can include, for example, twelve needle bearings 71C. The number of linear needle bearings 71C in linear needle bearing assemblies 91A, 91B may differ depending on the size of needle bearings 71C and the forces expected to be present on needle bearings 71C. In some configurations, needle bearings 71C may be 1-2 mm in diameter and twelve needle bearings 71C may be included per linear needle bearing assembly 91A, 91B. Each of needle bearings 71C may be received in needle bearing cage 71D when linear needle bearing assembly 91A, 91B is fully assembled. Needle bearing cages 71D can be shaped to fit against interior faces 79A of housings 79 to allow needle bearings 71C to utilize interior faces 79A as a raceway.

Continuing to refer to FIG. 23, nut 76 can include first portion 76A and second portion 76B. First portion 76A and second portion 76B may couple together when assembled. In alternative configurations, nut 76 may be a single, monolithic component. Nut 76 may be shaped to allow needle bearing cage 71D to fit around nut 76 when linear needle bearings 91A, 91B are fully assembled. In an example configuration, first portion 76A of nut 76 can be shaped to accommodate the "C" like shape of needle bearing cages 71D and to allow needle bearings 71C to use the exterior of first portion 76A of nut 76 as a race. First portion 76A can be, but is not limited to being, octagonal in cross section. Nut 76 may be adapted to translationally displace in response to a rotational displacement of drive screw 74. In the example configuration, second portion 76B may be engaged with drive screw 74, and second portion 76B may be caused to translationally displace. When second portion 76B is attached to first portion 76A, nut 76 may displace. Second portion 76B may differ depending on the type of drive screw 74 being used. For example, second portion 76B may be a ball nut if a ball screw is used. If a lead screw is used, second portion 76B may be a split nut, half nut, or other suitable type nut. Alternatively, second portion 76B may include a threaded receiving feature which may be threaded onto drive screw 74.

Continuing to still further refer primarily to FIG. 23, needle bearing cages 71D can each include slot 71E (only the slot 71E of linear needle bearing assembly 91A is visible in FIG. 23). Slots 71E can cooperate with travel limiters 57 extending from first portion 76A. Travel limiters 57 can be, for example, but not limited to, projections or protuberances which can extend outwardly from first portion 76A. When fully assembled, travel limiters 57 extend into slots 71E. When nut 76 travels within linear needle bearing assemblies 91A, 91B, travel limiters 57 can prevent needle bearing cages 71D and needle bearings 71C seated therein from movement beyond a predetermined range. For example, travel limiters 57 may be employed to prevent needle bearing cages 71D and needle bearings 71C from traveling out of housings 79. At the ends of the displacement range allowed by travel limiters 57, travel limiters 57 may abut against an edge of slots 71E. At this point needle bearing cages 71D and needle bearings 71C may be unable to further displace in that direction and travel will effectively be limited with a mechanical stop. The lengths of slots 71E can be, but are not limited to being, substantially equal. In alternative configurations, travel limiters 57 may not be included on nut 76, but may be included on housings 79. For example, in some configurations, protuberances, which can serve as travel limiters 57, may extend into slots 71E from interior face 79A. In other configurations, interior face 79A may include one or a number of raised features which can limit the displacement range of needle bearings 71C and needle bearing cages 71D. To prevent the linear needle bearing assemblies 91A, 91B from rotating about the drive screw's 74 axis, at least one keyed feature may be included on one or both the linear needle bearing assemblies 91A, 91B. This keyed feature may, for example, be a projection extending from housing 79 that would encounter a stationary element which acts as a mechanical interference. Alternatively, a projection from a stationary element may extend into a receiving structure in the linear needle bearing assemblies 91A, 91B. In some configurations, rotation may be inhibited by fitting projection 92 into notch 75B in receiving structure 75 of nut 76.

Still referring to FIG. 23, the nut 76 can be constructed such that it may be used with any of a variety of different projections 92. Specifically, nut 76 can include receiving feature 75 into which projection 92 may be coupled. Receiving feature 75 can be a recess into nut end 75A. Receiving feature 75 can also include notch 75B to accommodate a portion of projection 92 when projection 92 has been coupled into receiving feature 75. Any suitable method for coupling projection 92 into receiving feature 75 may be used. Fastener 77 (FIG. 22) may be used in some configurations. Alternatively, projection 92 may be permanently coupled into receiving feature 75.

Figure 24:
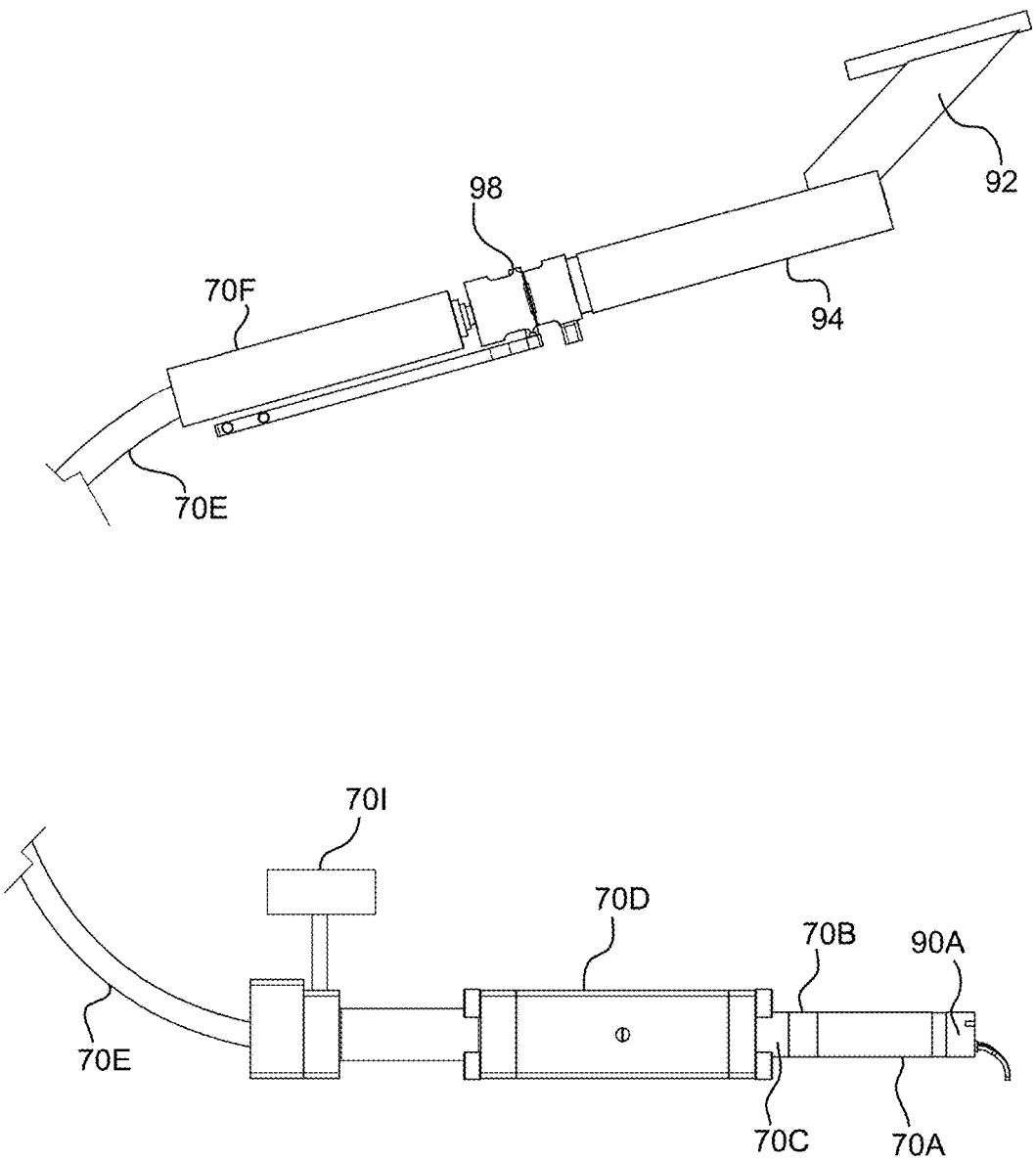
FIG. 24 is a schematic diagram of a drive element that can be operated electrohydraulically.

Referring now primarily to FIG. 24, drive element 60 can be operated electrohydraulically. Drive element 60 can include, for example, but not limited to, a hydraulic slave cylinder 70F. Slave cylinder 70F can include piston 70H (see FIG. 17B) which may be displaced to cause displacement of projection 92. Projection 92 may act on driven element 62 (FIG. 17B) to actuate a feature of manipulated component 38 (FIG. 17B). Slave piston 70H may be guided by at least one linear motion bearings 94. Any suitable linear motion bearings 94 may be used, such as, though not limited to, those described in FIG. 23 and elsewhere herein. The projection 92 may be an integral part of the slave piston 70H (FIG. 17B) in some configurations. In alternative configurations, slave piston 70H (FIG. 17B) may be constructed such that it may be used with any of a variety of different projections 92. Specifically, slave piston 70H (FIG. 17B) can include a receiving feature (similar to receiving feature 75 of FIG. 23) into which projection 92 may be coupled. In some configurations, an intervening body (not shown) may be included between slave piston 70H (FIG. 17B) and projection 92. In such configurations, displacement may be transmitted through the intervening body to projection 92. A hydraulic master cylinder 70D can be included and can drive slave cylinder 70F though hydraulic line 70E. Hydraulic master cylinder 70D can be driven by motor assembly 70. Motor assembly 70 may cause displacement of piston 70G (see FIG. 17B) in master cylinder 70D. When piston 70G (FIG. 17B) is displaced, slave piston 70H (FIG. 17B) in hydraulic slave cylinder 70F may consequently be displaced since the master cylinder 70D and slave cylinder 70F are connected via hydraulic line 70E. To monitor displacement, a position sensor 90 may be associated with the motor assembly 70 or another component such as a part of drive element 60. At least one pressure sensor 70I may also be included to monitor pressure in hydraulic line 70E.

Figure 25:
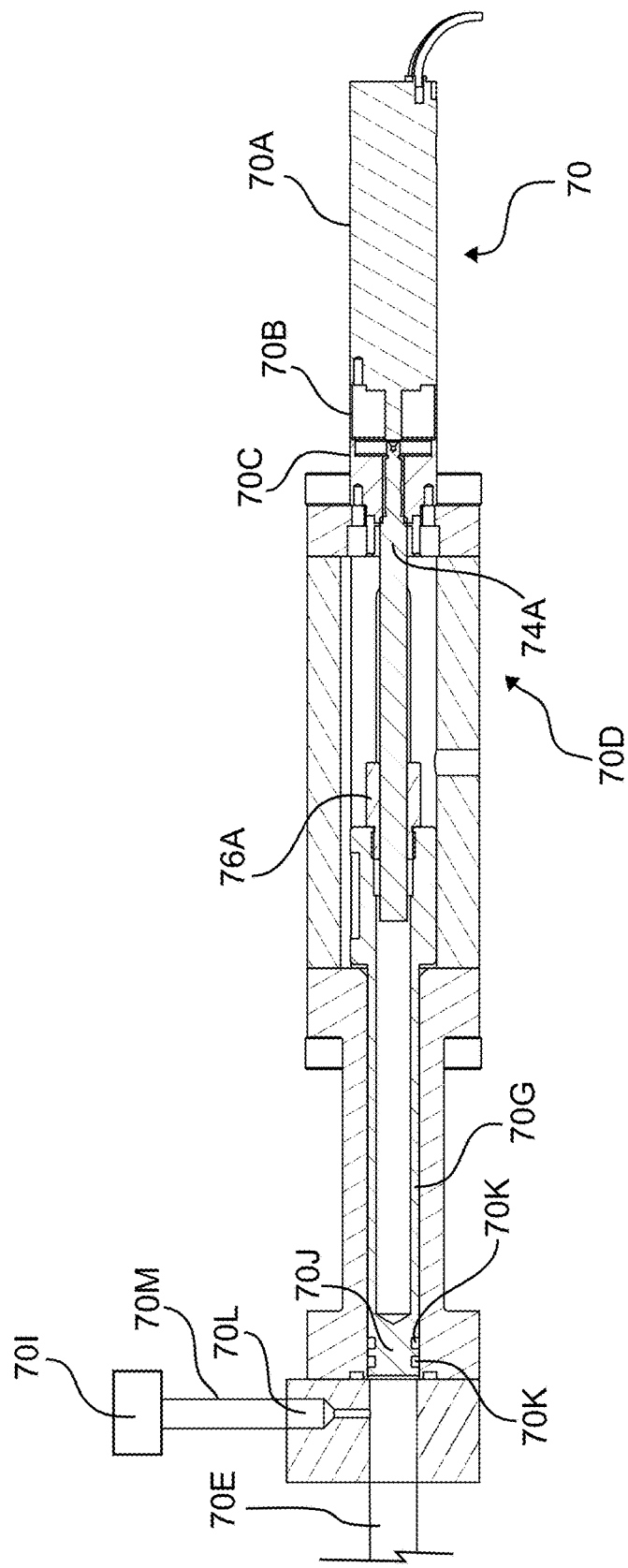
FIG. 25 is a schematic diagram of a cross sectional view of a motor assembly and a hydraulic master cylinder of the present teachings.

Referring now to FIG. 25, motor assembly 70 can include motor 70A, gearhead 70B, and bearing 70C for drive screw 74A. Rotation of drive screw 74A may in turn cause translational displacement of nut 76A. Nut 76A may move in tandem with master cylinder piston 70G. In some configurations, master cylinder piston 70G and nut 76A may be coupled to one another. When master cylinder piston 70G displaces, fluid in attached hydraulic line 70E may also be displaced. Head 70J of master cylinder piston 70G can include a number of sealing members 70K, for example, but not limited to, o-rings or a similar gasketing member, which can ensure that fluid does not escape from hydraulic line 70E. Pressure tap 70L can be attached to line 70M leading to at least one pressure sensor 701. Pressure sensor 701 may collect data related to the pressure in hydraulic line 70E via pressure tap 70L and line 70M. Data from at least one pressure sensor 701 may be provided to a controller as feedback.

Figure 26:
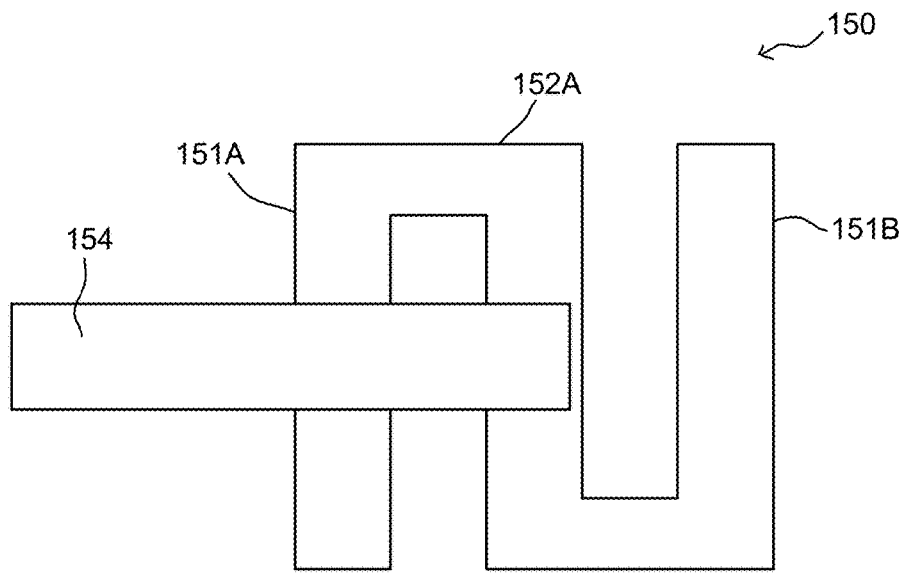
FIG. 26 is a schematic block diagram of a load sensor of the present teachings.

Referring primarily to FIG. 26, load sensor 98 (FIG. 20) may be associated with each motor 70 (FIG. 20) in drive component 34 (FIG. 20). Load sensor 98 (FIG. 20) may be any of a variety of conventional load sensor types. Alternatively, load sensor 98 (FIG. 20) may have, for example, electrical components that can be remote and physically isolated from the load path. Load sensor 98 (FIG. 20) may include, disposed in a load path, mechanical component 150 that can, for example, deform or displace in proportion to the load. This deformation may in turn be sensed or monitored by an electrical component of load sensor 98 (FIG. 20) which is located remotely from the load path. Mechanical component 150 can include, but is not limited to including, a compliant member which may be a deformable body 152A. Deformable body 152A may have first end 151A and second end 151B. The example deformable body 152A shown in FIG. 26 is unloaded. Deformable body 152A can be shaped, for example, as an "S" beam. In other configurations, the shape of deformable body 152A may be any shape or configuration. Mechanical component 150 may optionally include projection or flag 154 that can amplify any deformation of deformable body 152A. Projection 154 may be coupled onto a deformable body 152A or be an integral part of a deformable body 152A.

Figure 27:
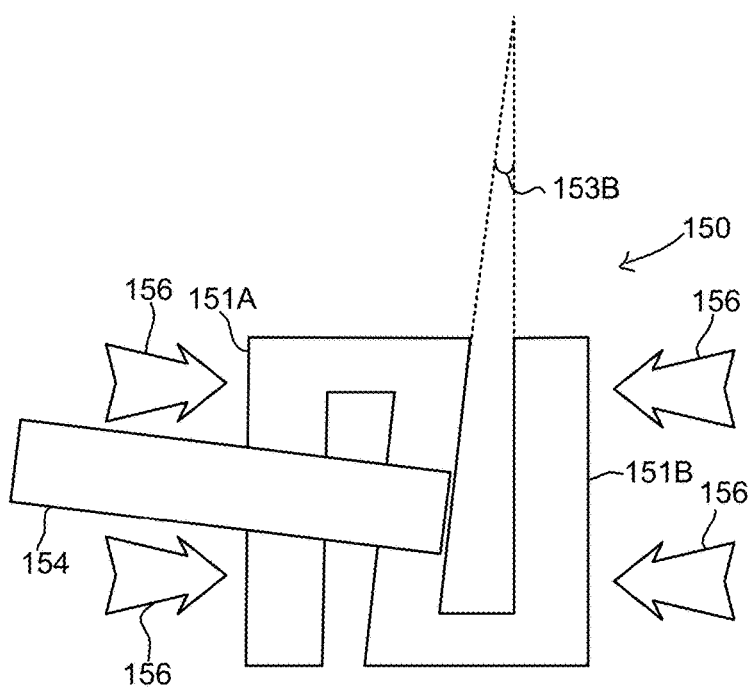
FIG. 27 is a schematic block diagram of a configuration in which load is applied.

Referring primarily to FIG. 27, when load 156 is applied to at least one of first end 151A and second end 151B, at least a portion of the deformable body 152A can distort from its unloaded shape (see, e.g. FIG. 26). The shape of deformable body 152A may be chosen based on where it is desired that the distortion occurs or how it is desired deformable body 152A will distort. Cross piece 153A can distort under load 156. More specifically, angle 153B of cross piece 153A with respect to first end 151A and second end 151B can be changed. The amount of distortion may be sensed or monitored to determine load 156 being applied to mechanical component 150.

Still referring to FIG. 27, the amount of distortion that can occur for various ranges of loads 156 on deformable body 152A may be controlled by altering the shape and/or structure of deformable body 152A. In some configurations, it may be desirable that deformable body 152A deform a greater amount or at a greater rate under a first range of load conditions as opposed to a second range of load conditions. For example, it may be desired that deformable body 152A distort a greater amount or at a greater rate under low load conditions than high load conditions. This may allow deformable body 152B to displace a greater amount under load conditions which may be expected in a given device. In specific configurations, deformable body 152A can be constructed such that a first range of loads 156 can include loads from zero to fifty pounds. The second range of loads 156 can include, for example, any load 156 above fifty pounds. In the first range of loads 156, deformable body 152A may freely distort in proportion to load 156. In the second range of loads 156, deformable body 152A may be more resilient to distortion or substantially unable to distort.

Figure 28A:
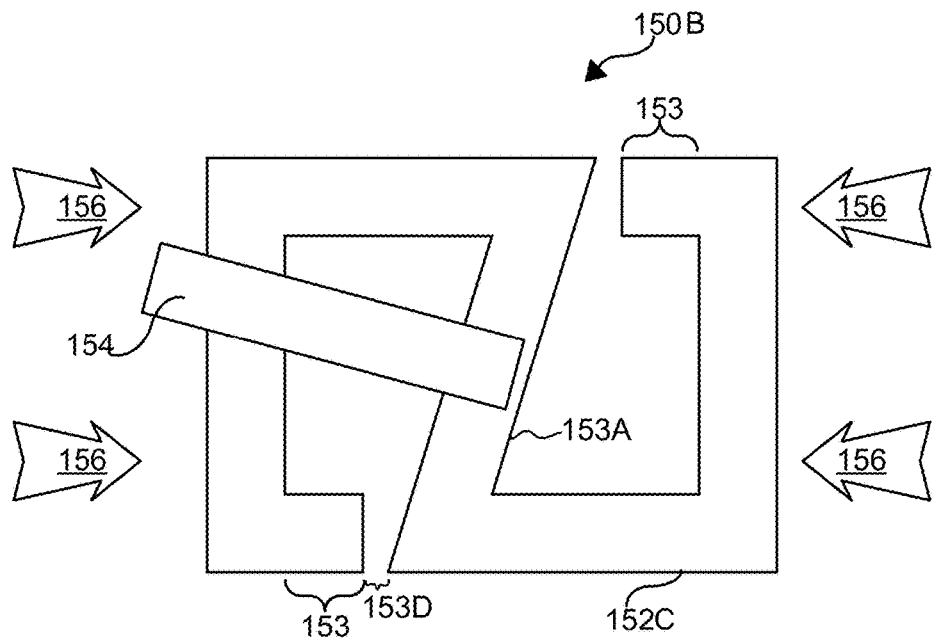
FIG. 28A is a schematic block diagram of a mechanical component including a deformable body and stop projections.

Referring now to FIG. 28A, mechanical component 150B can include deformable body 152C can include stop projections 153 that can extend toward cross piece 153A. As load 156 increases on deformable body 152C, gap 153D between stop projection 153 and cross piece 153A can decrease. Eventually, cross piece 153A will contact stop projections 153 and be inhibited from continued displacement as load 156 increases. The amount of load 156 at which this contact can occur may be the upper bound of the first load range. In some specific configurations, the amount of load 156 at which contact occurs can be, for example, but not limited to, about fifty pounds. The amount of load at which contact occurs can be controlled based on the structure, material, and geometry of deformable body 152C. Deformable body 152C may thus be constructed such that distortion of deformable body 152C can provide higher resolution of load 156 at low load conditions or in a first range of loads. A target resolution can be, for example, but not limited to, less than 0.1 lbs. In some configurations, the target resolution in the first range of load conditions may be less than 0.1 lbs while mechanical component 150B may provide a more binary type indication in the second range of load conditions. For example, in the second range of load conditions, mechanical component 150B may serve to provide a yes or no indication of whether the amount of load 156 applied is within the second range.

Figure 28B:
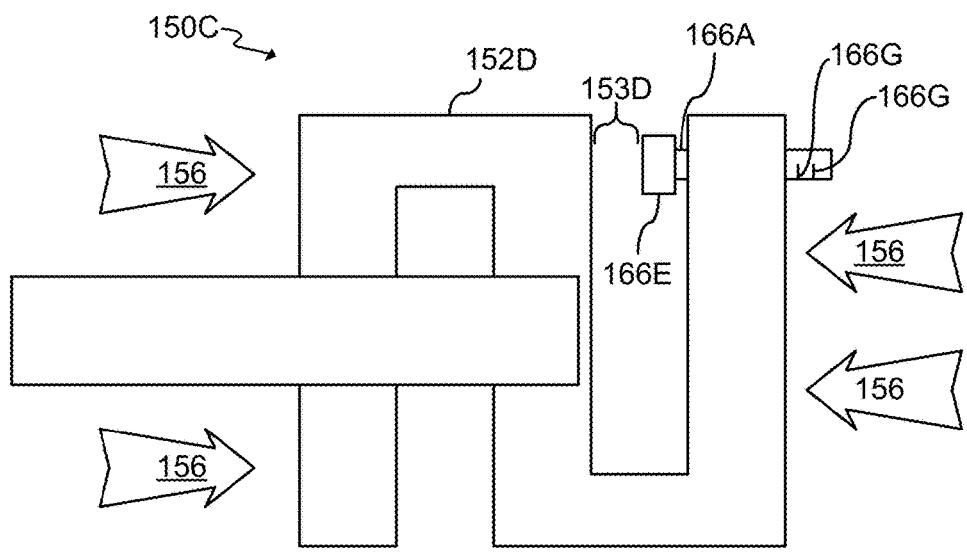
FIG. 28B is a schematic block diagram of a mechanical component include a threaded insert instead of stop projections.

Referring primarily to FIG. 28B, mechanical component 150C can include threaded insert 166A instead of stop projections 153 (FIG. 28A). Threaded insert 166A may be advanced or retreated a desired amount out of deformable body 152D to alter the size of gap 153D. Movement of threaded insert 166A may change the point at which stop 166E can be encountered and may alter the force necessary before stop 166E is encountered. Thus load ranges may be flexible and possibly user-defined, for example. Threaded insert 166A and/or deformable body 152D may include markings 166G which can indicate the amount of load 156 at which stop 166E will be contacted to facilitate defining the desired range. In the example configuration, the shown threaded insert 166A provides a compression stop.

Figure 28C:
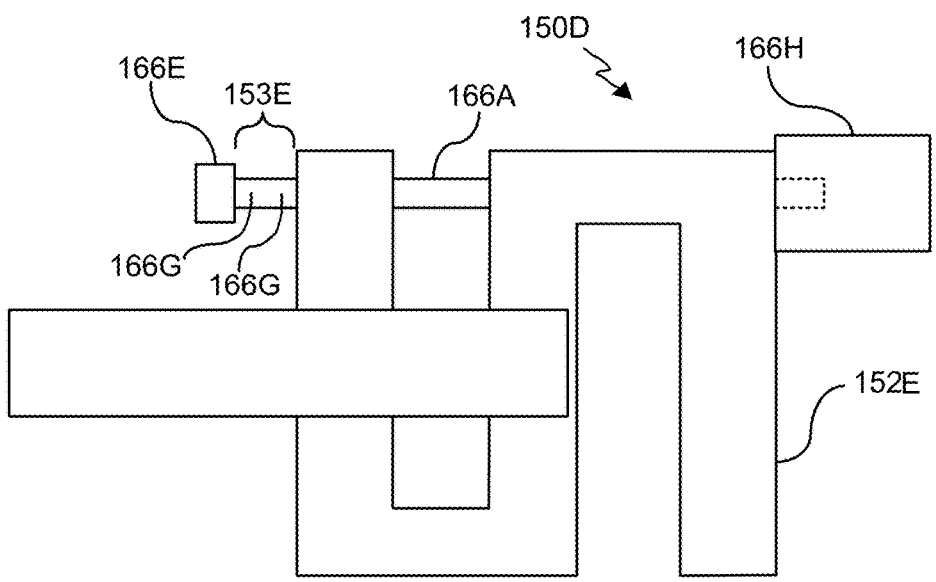
FIG. 28C is a schematic block diagram of a mechanical component including a threaded insert to provide a tension stop.

Referring now to FIG. 28C, mechanical component 150D can include threaded insert 166A to provide a tension stop. Threaded insert 166A may be inserted through deformable body 152E and anchored into stationary element 166H. This may be accomplished with a threaded engagement. Threaded insert 166A may also be partially or completely threaded, or not threaded at all but instead bonded/welded to stationary element 166H or coupled to stationary element 166H with a fixative, interference fit, or any other arrangement. Threaded insert 166A may not affect the distortion of deformable body 152E until gap 153E decreases to zero and deformable body 152E encounters head or stop 166E of threaded insert 166A.

Figure 28D:
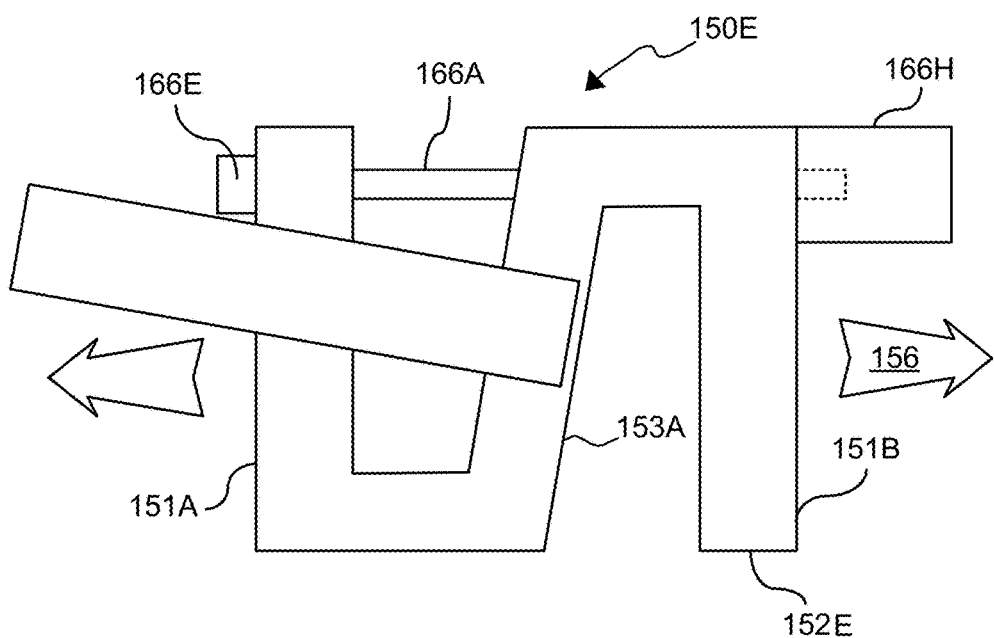
FIG. 28D is a schematic block diagram of a configuration in which force is applied to a deformable body.

Referring now to FIG. 28D, deformable body 152E may distort when tensile force 156 is applied in mechanical component 150E. Angle 153B (FIG. 27) of cross piece 153A with respect to first end 151A and second end 151B of deformable body 152E may be changed. Applying tensile force can cause deformable body 152E to stretch out and elongate. Since threaded insert 166A can be fixedly coupled to stationary element 166H, deformable body 152F may only be stretched by tension until first end 151A of deformable body 152E abuts head 166E of threaded insert 166A.

Figure 28E:
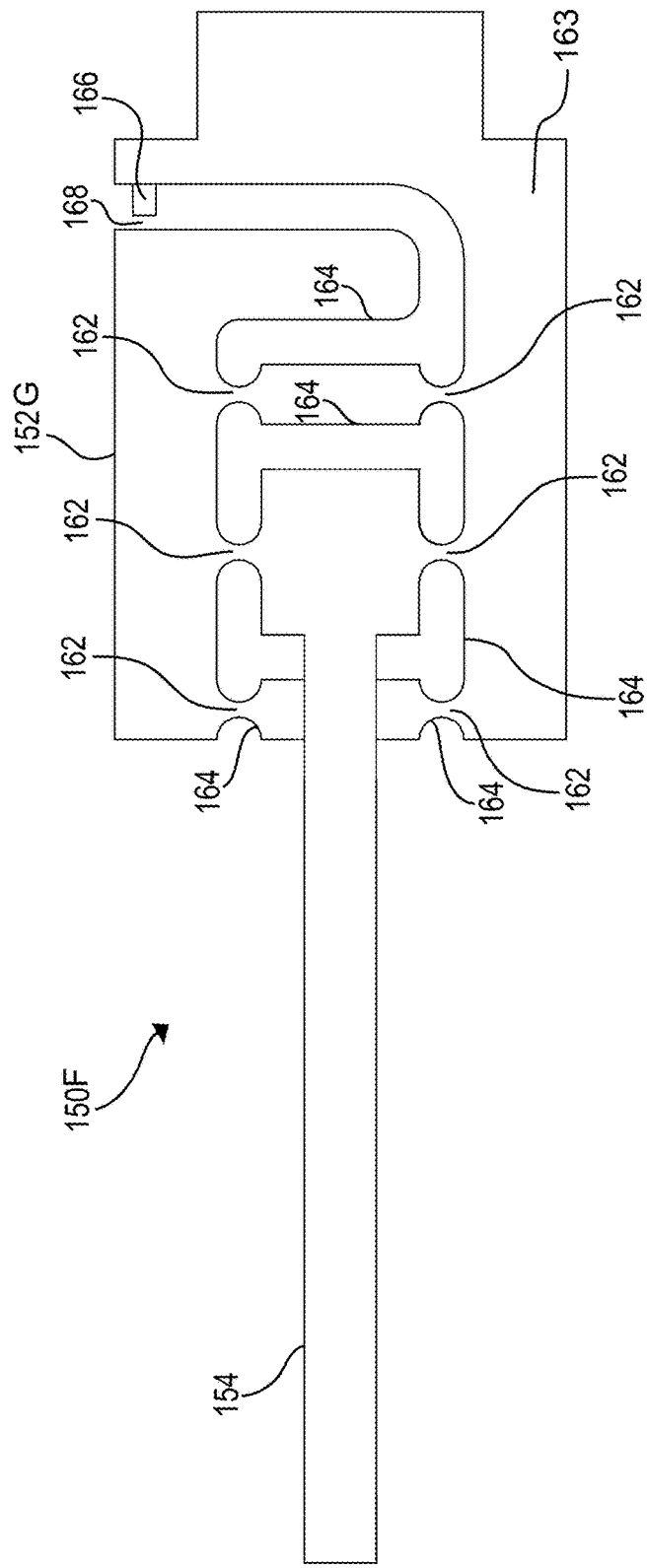
FIG. 28E is a schematic block diagram of a deformable body of the present teachings.

Referring now to FIG. 28E, the manner in which deformable body 152G can distort can also be influenced by the shape of deformable body 152G. In some configurations, deformable body 152G may be coupled or mounted to a component of a drive system which may displace due to run-out in part of the drive system. To mitigate any effect of run-out or to allow for more lenient run-out tolerancing, mechanical component 150F may be constructed such that it has a low tendency to displace due to any rotation about a secondary axis or as a consequence of any other rotational eccentricities in a drive shaft. Deformable body 152G can include a number of thinned spans 162 which can be defined by channels 164 recessed or cutout through deformable body 152G. Lateral portions 163 of deformable body 152G can be relatively thick and serve as buttresses against distortion due to run out. Lateral portions 163 of deformable body 152G may also serve to accept threaded insert 166A (FIG. 28D). At least one side of deformable body 152G can include gap 168. The form of the deformable body 152G and the arrangement of channels 164 and thinned spans 162 may be selected to cause deformable body 152G to be resilient against undesired distortions. In some configurations, the form of deformable body 152G and the arrangement of channels 164 and thinned spans 162 can cause deformable body 152G to generally behave as a number of four bar linkages. Such parallelogram frame configurations may buttress deformable body 152G against undesired deformation. Additional channels 164 and thinned sections 162 may be added to increase the amount of distortion caused by a given load. Mechanical component 150F can also include stop surface 166. When deformable body 152G is distorted under pressure, gap 168 between stop surface 166 and the rest of deformable body 152G can decrease until contact is made with stop surface 166. Stop surface 166 can limit or prevent distortion of deformable body 152G when the load on deformable body 152G reaches a desired amount. Mechanical component 152G can, for example, but not limited to, be more responsive to a first range of loads than it is to a second range of loads. Stop surface 166 may be replaced or supplemented with threaded insert 166A (FIG. 28D). In configurations including flag or projection 154, projection 154 may be sized to create a desired amount of amplification of the distortion of deformable body 152G. When load 156 (FIG. 28D) is present, displacement of a point on the portion of projection 154 most distal to deformable body 152G will be approximately equal to the length of the projection multiplied by radian angle of projection 154 with respect to its unloaded position. A longer projection 154 may be used to create more amplification.

Figure 29:
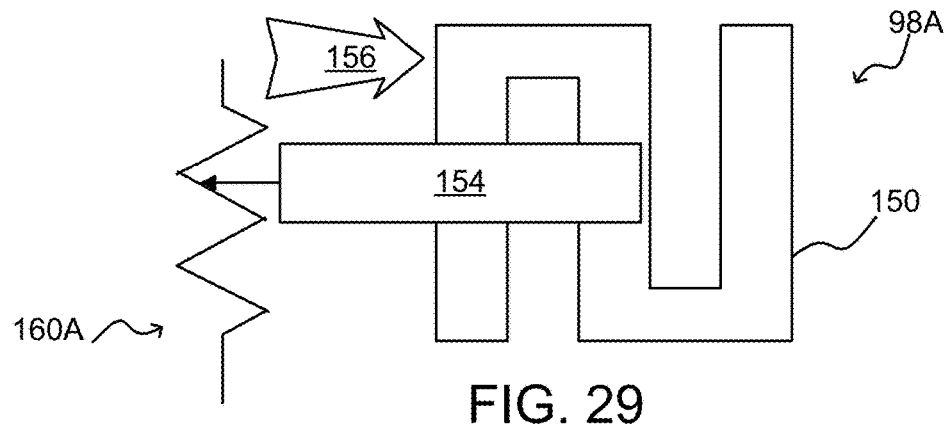
FIG. 29 is a schematic block diagram of a load sensor including an electrical component such as a potentiometer.

Referring now to FIG. 29, load sensor 98A can include electrical component 160A, for example, but not limited to, a potentiometer. If electrical component 160A is a potentiometer, when projection 154 is displaced, a wiper can be moved across the resistive element of the potentiometer changing the resistance. By measuring the resistance, it is possible to determine the amount of displacement of projection 154. As the amount of displacement is proportional to load 156, load sensor 98A may determine load 156 using the value of the measured resistance.

Figure 30A:
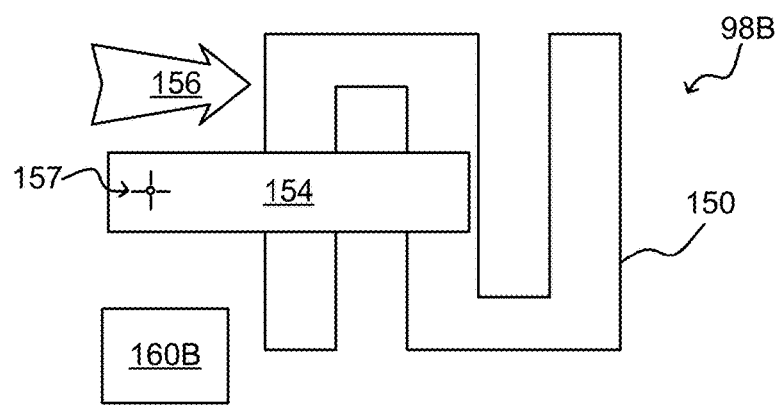
FIG. 30A is a schematic block diagram of a load sensor including an electrical component such as an optical sensor.

Referring now to FIG. 30A, load sensor 98B can include electrical component 160B, for example, but not limited to, an optical sensor. Any variety of optical sensor may be used, for example, but not limited to, a laser displacement sensor. Alternatively, a camera may be used to monitor and track the location of projection 154 over time. In some configurations, projection 154 may include fiducial reference 157, for example, but not limited to, a grid or pattern, color marking, or the like which may aid in tracking of displacement of projection 154, and therefore determination of load 156.

Figure 30B:
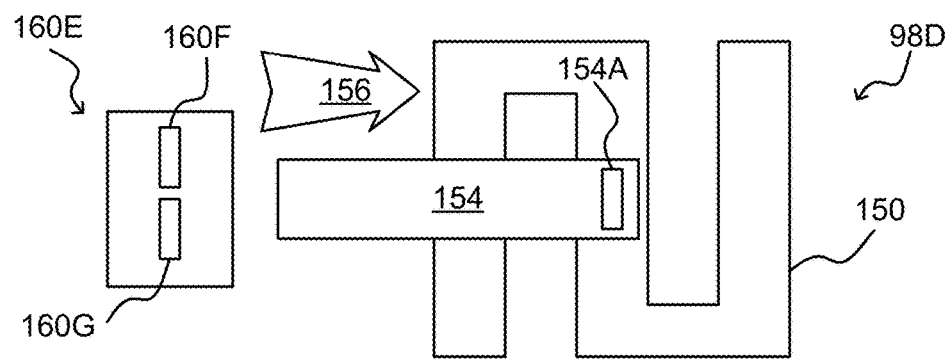
FIG. 30B depicts a representational configuration of a load sensor including an electrical component having a light emitter and reflected light receiver.

Referring now to FIG. 30B, load sensor 98D can include electrical component 160E. Electrical component 160E may include light emitter 160F and light receiver 160G. Light emitter 160F may shine light onto reflective projection 154A on mechanical component 150. Reflective projection 154A may reflect light from light emitter 160F to light receiver 160G. As load 156 on mechanical component 150 changes, the orientation of reflective projection 154A may also change. As a result, the light reflected from reflective projection 154A may be reflected to a different portion of light receiver 160G. Light emitter 160F may, for example, include one or more laser or concentrated light beam emitter. Reflective projection 154A may include a light colored or mirrorized surface on which light from light emitter 160F can be projected. Light receiver 160G may include one or an array of light receivers 160G which may be reflected light receivers such as optical sensors. As mechanical component 150 distorts in proportion to load 156, the location and/or intensity of the reflected light may be tracked and therefore a determination of load 156 may be made.

Figure 30C:
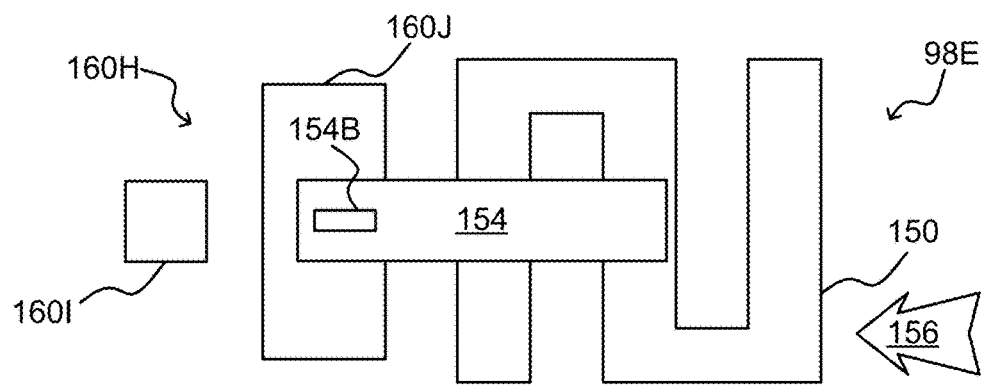
FIG. 30C depicts a representational configuration of a load sensor including an electrical component having a light emitter and an optical sensor.

Referring now to FIG. 30C load sensor 98E can include electrical component 160H. Electrical component 160H may include light source 160I and optical sensor 160J. Optical sensor 160J may, for example, include a camera having a CCD or CMOS chip. Light source 160I may produce light which can illuminate part of projection 154. Optical sensor 160J may be placed such that the shadow of projection 154 falls within the field of view of optical sensor 160J. The position of the shadow may be tracked by optical sensor 160J and therefore a determination of load 156 may be made. In some configurations, light source 160I may be placed on one side of projection 154 while optical sensor 160J may be placed on an opposing side of projection 154. Alternatively or additionally, projection 154 may include one or more slit, slot, void, aperture or the like 154B through which light from light source 160I may pass. As projection 154 displaces in proportion to load 156 on mechanical component 150, slit 154B may change location. Optical sensor 160J may monitor the location of slit 154B instead or in addition to the location of projection 154 shadow to determine the amount of distortion of mechanical component 150. The distortion may be analyzed to determine load 156 on mechanical component 150.

Figure 31A:
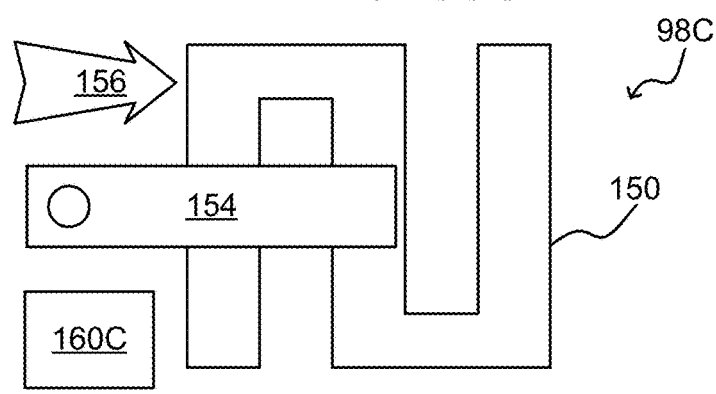
FIG. 31A is a schematic block diagram of a load sensor including an electrical component such as a Hall sensor.

Referring now to FIG. 31A, load sensor 98C can include the electrical component 160C, for example, but not limited to, a magnetic sensor such as a Hall effect sensor or Hall effect sensor array. In such configurations, at least one magnet 158, for example, but not limited to, a neodymium rare earth magnet, may be attached or embedded in projection 154. In configurations where electrical component 160C includes a Hall effect sensor, when projection 154 displaces, the Hall effect sensor may be used to determine the position of projection 154 based on the Hall voltage created by the magnetic field of at least one magnet 158. Any number of other sensing arrangements may be used, for example, but not limited to, capacitive, ultrasonic, and inductive sensing.

Figure 31B:
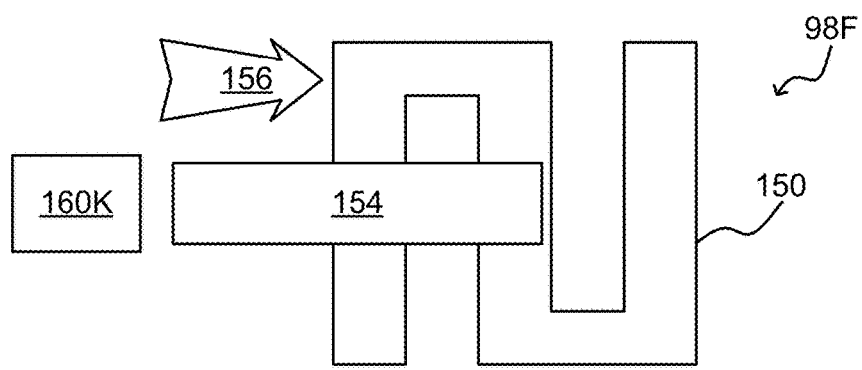
FIG. 31B is a representational configuration of a load sensor including an electrical component with a non-contact sensor.

Referring now the FIG. 31B, load sensor 98F may include electrical component 160K with a contact free sensor. The sensor may, for example, be an inductive or capacitive sensor. As projection 154 displaces in proportion to load 156 on mechanical component 150, the capacitance and inductance may change predictably based on the location of projection 154. The values of the capacitance and inductance may be monitored to determine the location of projection 154 and consequently the amount of load 156 on mechanical component 150.

Figure 32:
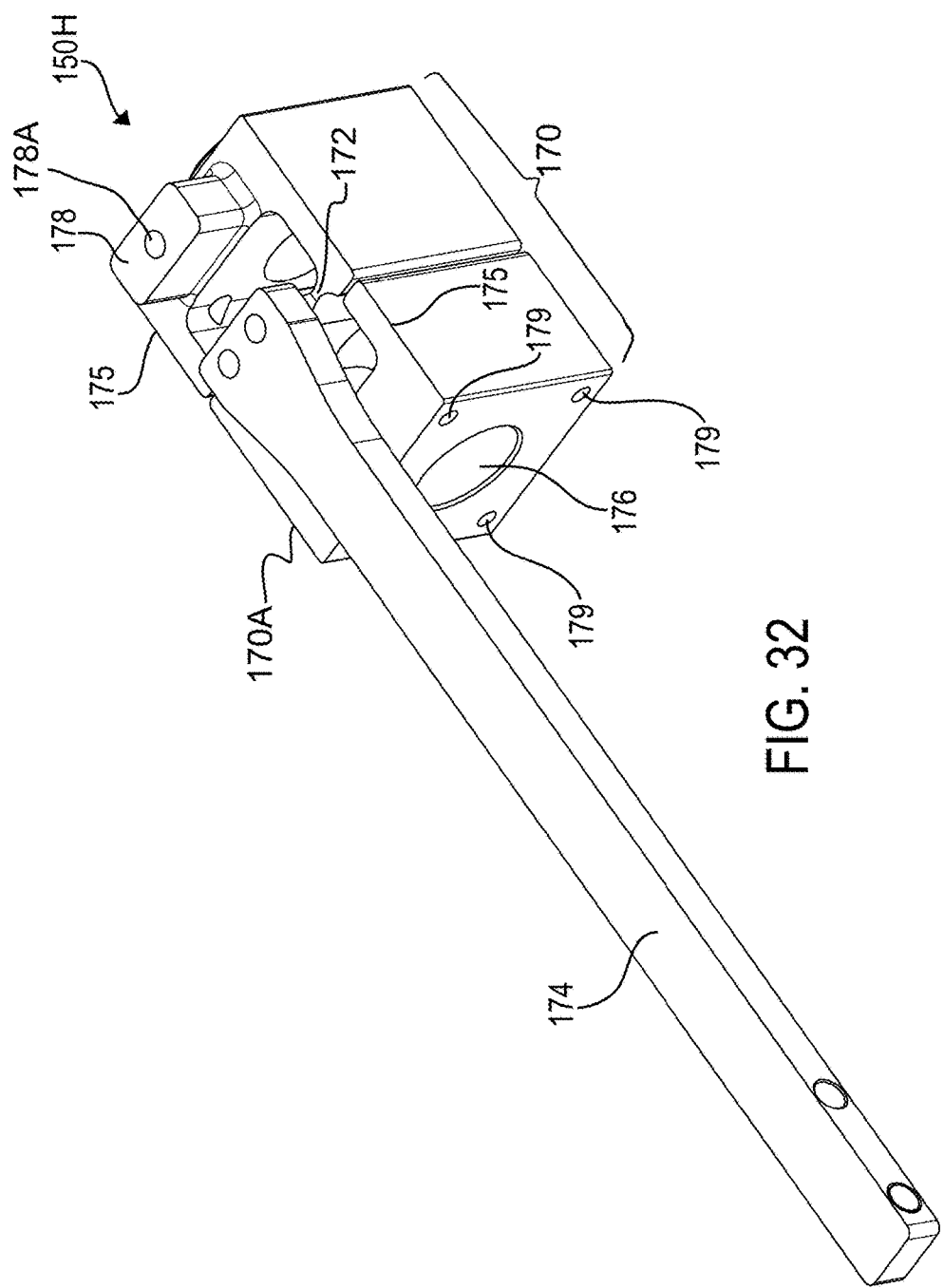
FIG. 32 is a schematic diagram of a right front top perspective view of a mechanical component of a load sensor of the present teachings including an "S" beam.
Figure 33:
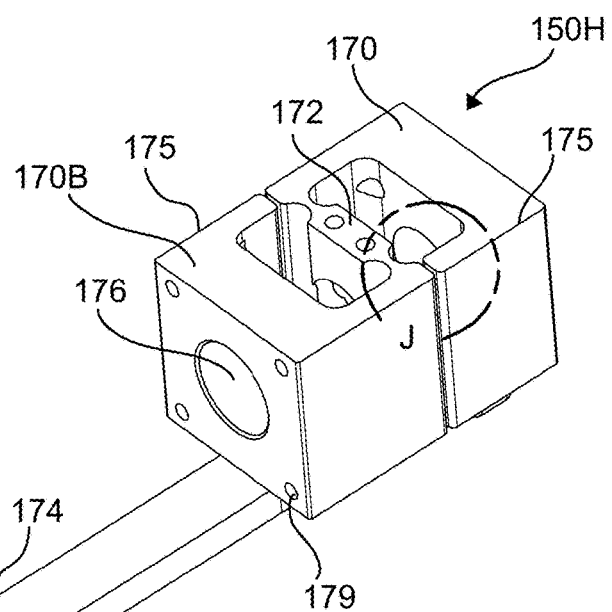
FIG. 33 is a schematic diagram of a left rear bottom perspective view of a mechanical component of a load sensor of the present teachings.

Referring now primarily to FIGS. 32 and 33, mechanical component 15011 can include "S" beam 170. Projection 174 can be coupled to center cross piece 172 of "S" beam 170. Projection 174 may be attached to center cross piece 172 in any suitable manner, for example, but not limited to, via fasteners. Alternatively, projection 174 may be integrally formed as part of "S" beam 170. The length ratio of projection 174 to "S" beam 170 can be, but is not limited to being, about 3:1. Void 176 can run through "S" beam 170 in a substantially parallel direction to projection 174 when projection 174 is in its unloaded position. Void 176 may be sized to accommodate drive screw 74 (FIG. 16) or other portion of a drive element 60 (FIG. 16). In some configurations, void 176 may be sized such that at least a portion of motor assembly 70 (FIG. 16) may be placed inside of void 176. "S" beam 170 can also include stop projections 175 (described elsewhere herein). Mechanical component 15011 can also include mounting feature 178 that may include, but is not limited to including, a raised plateau with threaded hole 178A. "S" beam 170 can be attached to a stationary housing (e.g. drive component housing 72 (FIG. 18)) using mounting feature 178 to help to ensure that any displacement of "S" beam 170 is a result of load deviations in the load path associated with "S" beam 170. In other configurations, mounting feature 178 may be a mounting bracket or rail. In other configurations, multiple mounting features 178 may be included. For example, mounting feature 178 may be included on both first face 170A (FIG. 32) and second face 170B (FIG. 33) of "S" beam 170. "S" beam 170 can also include a number of threaded holes 179 that can allow "S" beam 170 to be coupled to motor assembly 70 (FIG. 16), bearing (such as linear needle bearing assemblies 91A (FIG. 21) and 91B (FIG. 21)), or other portions of drive element 60 (FIG. 16).

Figure 34:
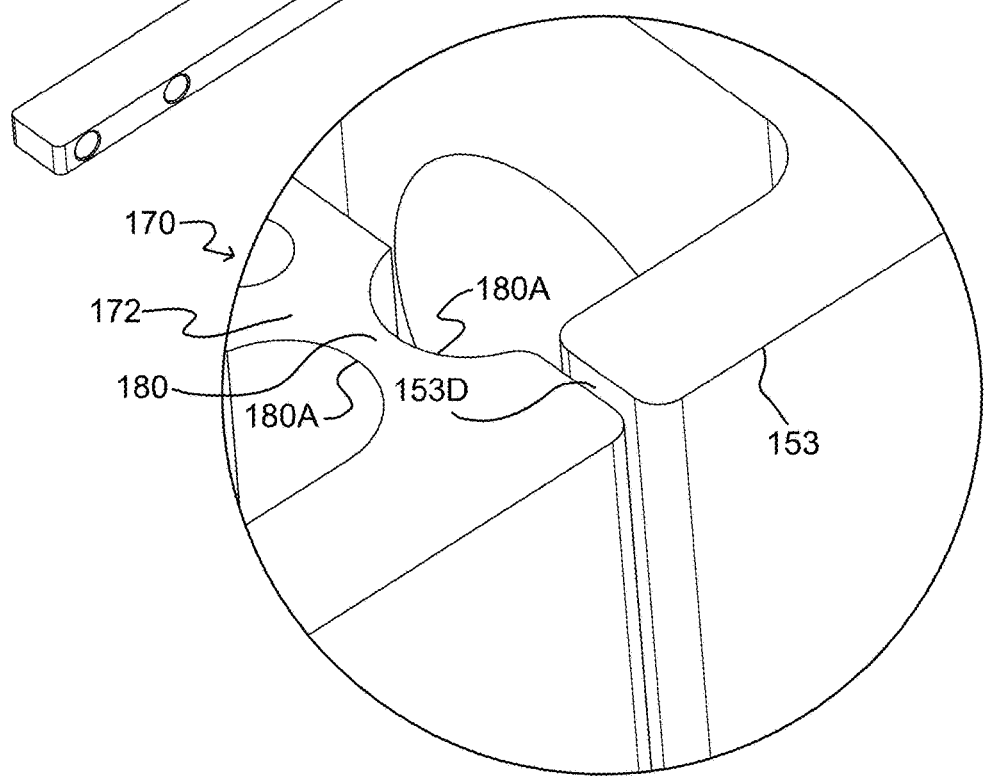
FIG. 34 is a schematic diagram of an enlarged view of a cross piece including a thin portion proximal to the body of an "S" beam of the present teachings.

Referring now to FIG. 34, an enlarged view of region J of FIG. 33 is depicted. "S" beam 170 can include stop projection 153. Gap 153D can be present between stop projection 153 and cross piece 172. Cross piece 172 can include thin or flexible portion 180 which is most proximal to the body of "S" beam 170. Thin portions 180 may be included at each end of cross piece 172. Thin portion 180 can act as an elastically deformable segment. For structural strength, thin portion 180 can have, for example, but not limited to, arched walls 180A. In other configurations, this need not be the case. The location and thickness of thin portions 180 may be chosen to help "S" beam 170 to have a desired displacement behavior under given load conditions. Additionally, the material chosen for "S" beam 170 may be selected, among other characteristics, for its elastic modulus and yield strength. Possible materials can include, but are not limited to including, any metal, composites, and other material such as plastic, magnesium, steel, aluminum, and titanium. In applications where low loads are anticipated, a plastic or material such as magnesium may be used. In high load applications, a material such as steel may be used. In other applications, materials such as aluminum or titanium may be used.

Figure 35A:
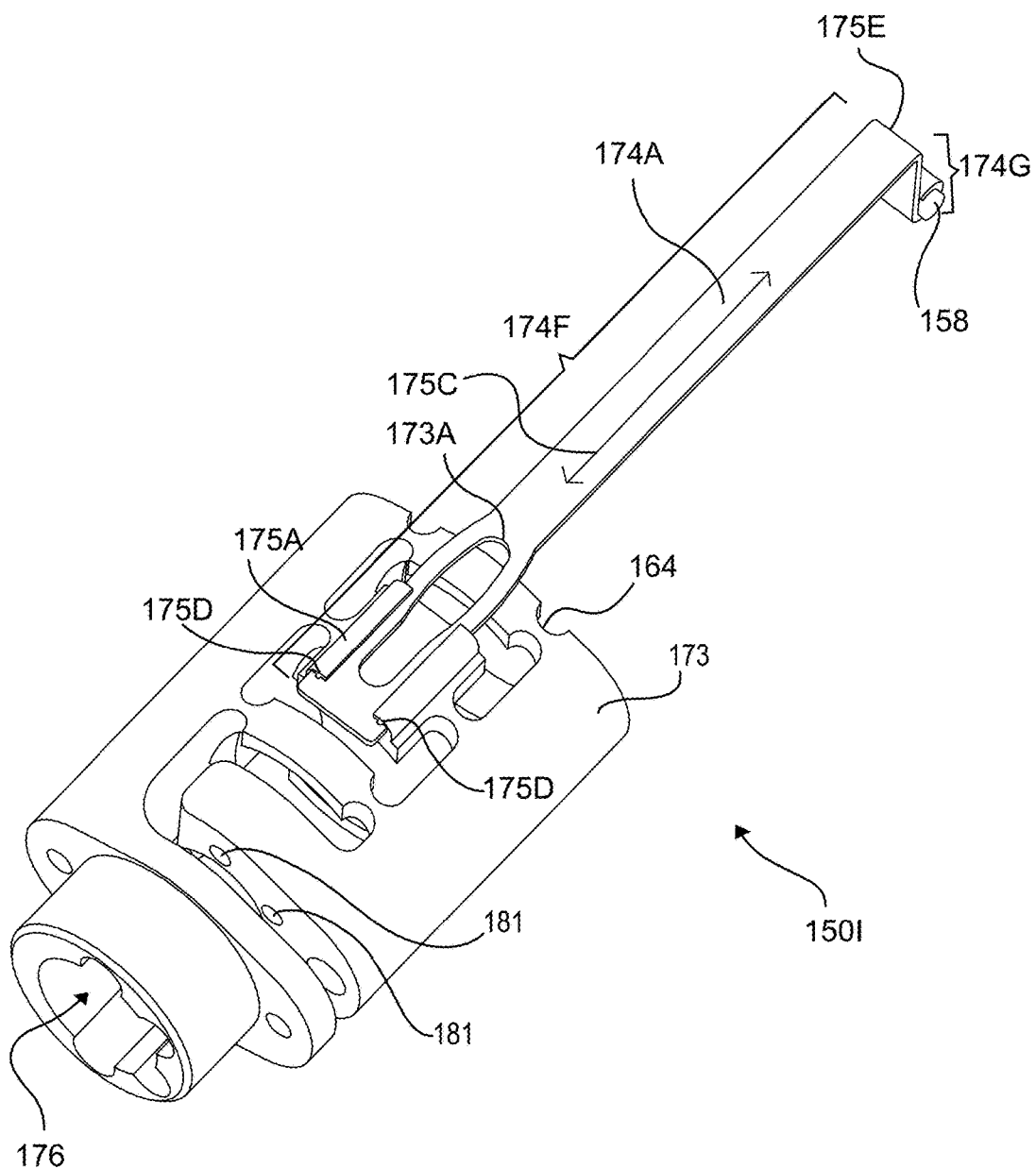
FIG. 35A is a schematic diagram of a load sensor mechanical component including a deformable body.

Referring primarily to FIG. 35A, mechanical component 1501 can include deformable body 173 that can be designed to mitigate any affect of run-out on deformable body 173 during operation. Deformable body 173 can also include a number of mounting points 181 which may allow deformable body 173 to attach to a stationary housing (e.g. drive component housing 72 (FIG. 16)), motor assembly 70 (see FIG. 35B) for an associated drive train, and/or a bearing (e.g. linear needle bearings 91A and/or 91B (FIG. 21)). Void 176 can be sized such that motor assembly 70 (FIG. 35B) can be at least partially housed within deformable body 173. Additionally, void 176 can be sized to allow a drive screw 74 to extend into deformable body 173 to engage with the motor assembly 70 (FIG. 35B) housed therein.

Still referring to FIG. 35A, deformable body 173 can include flag or projection 174A which may be coupled to it. Projection 174A can be mounted in shoe 175A. Projection 174A and/or shoe 175A may include a detent or step feature which can help to position and/or lock projection 174A in place when mechanical component 1501 is assembled. In alternative configurations, shoe 175A can allow projection 174A to be slid back and forth along, for example, but not limited to, axis 175C of projection 174A. Thus the amount of displacement of magnet 158 in projection 174A for a given load can be altered. When projection 174A has been slid to a position, one or more set screw or the like may be used to hold projection 174A in position. Projection 174A can also include cutout 173A which can allow projection 174A to be compressed slightly when in shoe 175A. Cutout 173A can allow the section of projection 174A received in shoe 175A to act as a spring which can exert a force against walls 175D of shoe 175A. This force can help to retain projection 174A in shoe 175A. Projection 174A can include bend 175E which can place magnet 158 behind and/or in line with motor assembly 70 (FIG. 5), possibly allowing space savings. Bend 175E may divide projection 174A into pre-bend portion 174F and post bend portion 174G. If necessary, a magnetic shielding material such as mu metal may be included to shield a motor assembly 70 (FIG. 16) and/or a portion of projection 174A. Projections 174A may differ from the shapes described herein. The shape or form of projection 174A can be chosen to best suit any space constraints which may be present in various applications.

Figure 35B:
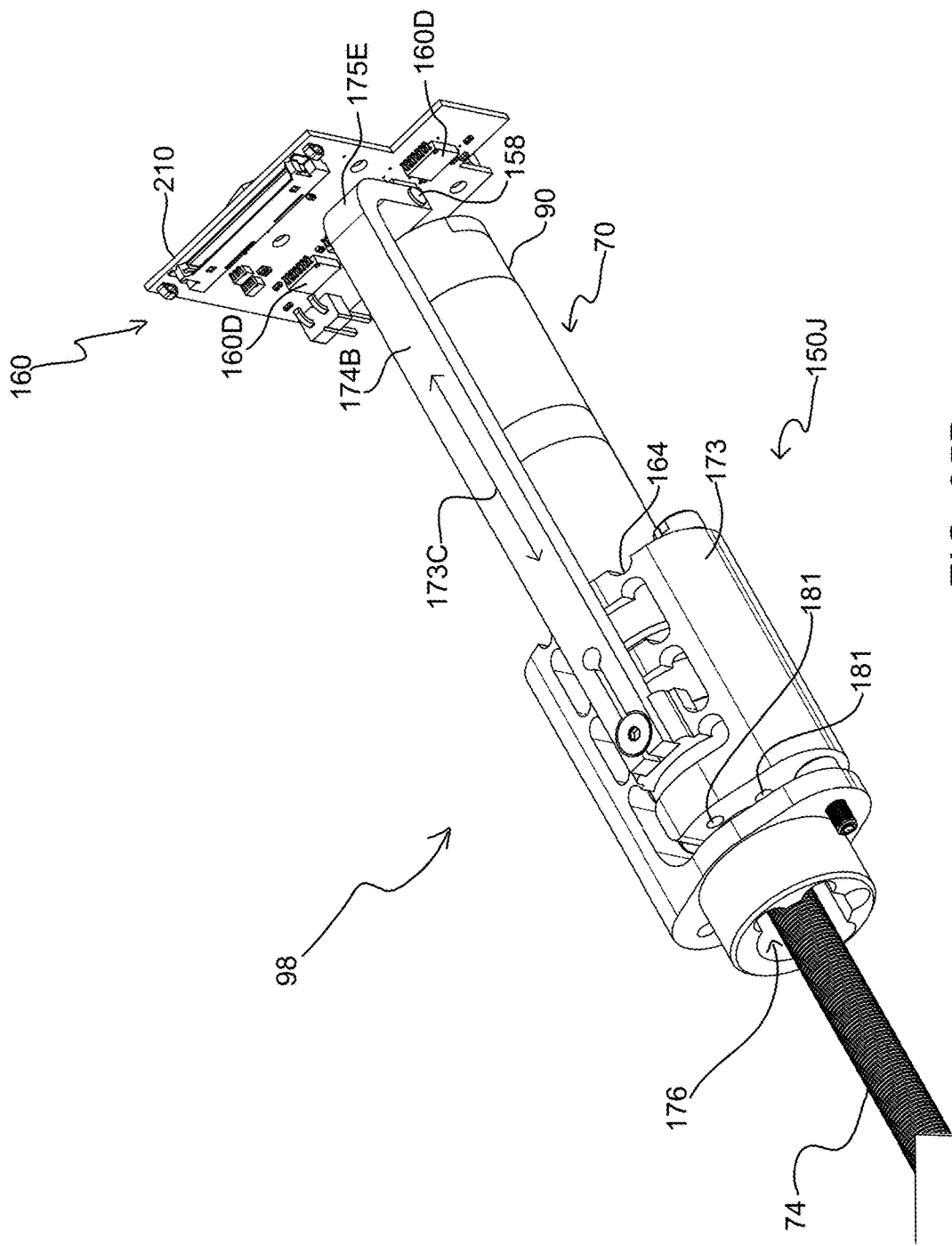
FIG. 35B is a schematic diagram of a load sensor mechanical component including a threaded insert extending into a deformable body.

Referring now to FIG. 35B, load sensor 98 can include mechanical component 150J and electrical component 160. Void 176 in mechanical component 150J can be sized such that motor assembly 70 can be at least partially housed within deformable body 173. Motor assembly 70 may be attached to mechanical component 150J via mounting points 181. Additionally, void 176 can be sized to allow drive screw 74 to extend into deformable body 173 to engage with motor assembly 70. As flag or projection 174B is displaced, magnet 158 attached to projection 174B may sweep along a path within range of a number of Hall effect sensors 160D arrayed on PCB 210 included as part of electrical component 160 of load sensor 98. The data provided from Hall effect sensors 160D may be processed by controller 15 (FIG. 1) to determine the location of magnet 158. Since the location of magnet 158 is dependent on the amount of load 156 (FIG. 31) applied to the mechanical component 150J, the position data can be used to determine the amount of load 156 (FIG. 31). Electrical component 160 composed of a Hall effect sensor array may be similar to that described in United States Patent Publication #20130184676 entitled System, Method, and Apparatus for Estimating Liquid Delivery, filed Dec. 21, 2012.

Figure 35C:
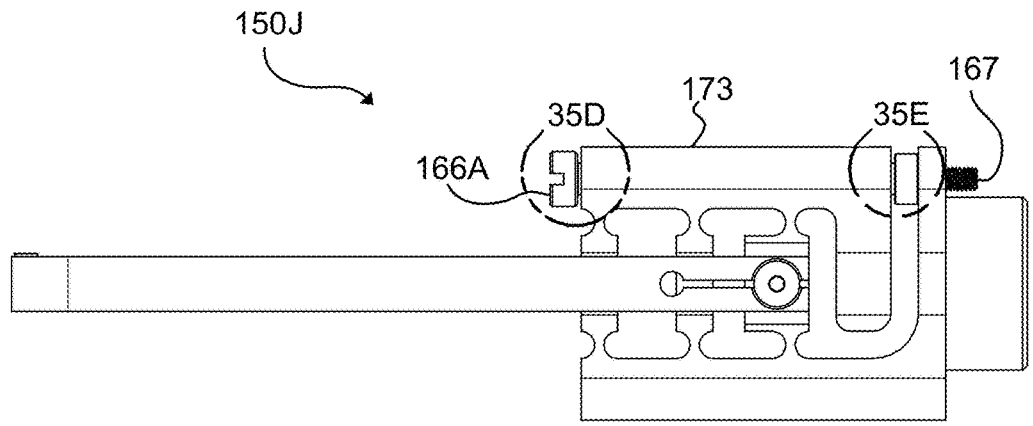
FIG. 35C is a schematic diagram of a threaded insert and a nut showing a tension stop gap and a compression stop gap.

Referring now to FIG. 35C, mechanical component 150J can include insert 166A which may be a threaded insert extending into or through deformable body 173. Mechanical component 150J can also include an adjustable spacer such as nut 167 on threaded insert 166A. Threaded insert 166A and nut 167 can provide compression and tensile stops for deformation of deformable body 173. Threaded insert 166A may be used to cause deformable body 173 to deform a greater amount or at a greater rate under a first range of load conditions as opposed to a second range of load conditions.

Figure 35D:
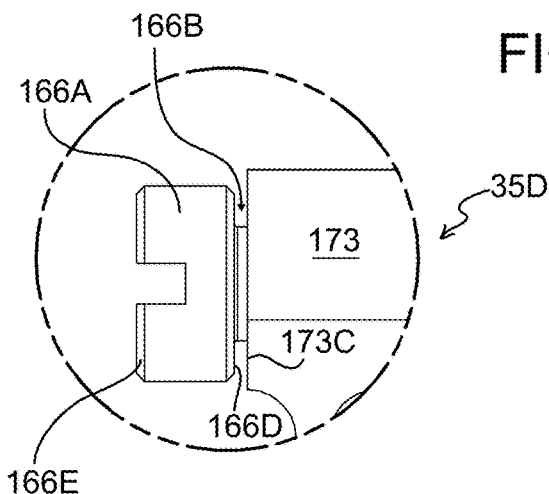
FIG. 35D is a schematic diagram of a compression stop gap occupying a space between a nut and a deformable body.
Figure 35E:
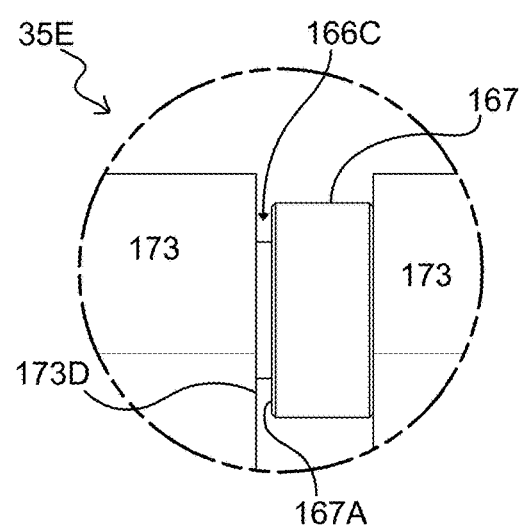
FIG. 35E is a schematic diagram of a cross sectional view taken at the horizontal mid-plane of the load sensor mechanical component shown in FIG. 35B.

Referring now also to FIGS. 35D-35E (respectively enlarged views of regions 35D and 35E of FIG. 35C), in the example configuration threaded insert 166A and nut 167 are disposed such that tension stop gap 166B (FIG. 35D) and compression stop gap 166C (FIG. 35E) are present. Tension stop gap 166B (FIG. 35D) can occupy a space between threaded insert first face 166D (FIG. 35D) and deformable body first face 173C (FIG. 35D). Compression stop gap 166C (FIG. 35E) can occupy a space between nut face 167A (FIG. 35E) and second face 173D (FIG. 35E) of deformable body 173. Second face 173D (FIG. 35E) can be on the opposite side of deformable body 173 from first face 173C (FIG. 35D). The size of tension stop gap 166B (FIG. 35D) may be selected to define a first range of tensile load conditions over which deformable body 173 may be substantially free to distort or deform. Loads in a second tensile load range outside of the first tensile load range may cause little or no distortion of deformable body 173 as the stop provided by threaded insert 166A (FIG. 35D) may be encountered and prevent further distortion. Size of compression stop gap 166C (FIG. 35E) may be selected to define a first range of compressive load conditions over which deformable body 173 may be substantially free to distort or deform. Loads in a second compressive load range outside of the first compressive load range may cause little or no distortion of deformable body 173 as the stops provided by threaded insert 166A (FIG. 35D) and nut 167 (FIG. 35E) may be encountered and prevent further distortion. In some configurations, threaded insert 166A (FIG. 35D) may be advanced or retreated a desired amount into or out of deformable body 173 to alter the size of gaps 166C (FIG. 35E) and 166B (FIG. 35D). The advancement or retreating, in turn, can alter the load at which the stops are encountered. The ranges may be flexible and possibly user-defined, for example. Threaded insert 166A (FIG. 35D) and/or deformable body 173 may include markings 166G (FIG. 28B) which can indicate the amount of load 156 (FIG. 28A) at which a stop will be contacted to facilitate defining the desired range.

Referring now to FIG. 35D, when a tensile force is exerted on deformable body 173, tension stop gap 166B can decrease. A mechanical stop can be encountered when first face 166D of head 166E of threaded insert 166A and first face 173C of deformable body 173 contact. The force at which faces 166D, 173C contact may be the boundary between the first tensile load range and second tensile load range. Additionally, head 166E of threaded insert 166A may be replaced with a second nut (not shown) which can engage with a thread (not shown) on the end of threaded insert 166A. The second nut could be advanced along the thread to alter the size of tension stop gap 166B. The second nut could be placed in a position suitable for a desired first tensile load range.

Referring now to FIG. 35E, compression stop gap 166C can occupy a space between nut first face 167A and deformable body second face 173D. A size of compression stop gap 166C may be selected to define a first range of compressive load conditions over which deformable body 173 may be substantially free to distort or deform. When a compressive force is exerted on deformable body 173, compression stop gap 166C can decrease. A mechanical stop can be encountered when first face 167A of nut 167 and second face 173D of deformable body 173 contact. The force at which these faces 167A, 173D contact may be the boundary between the first compressive load range and second compressive load range. Different sized nuts 167 may be used to alter the size of compression stop gap 166C. The nut 167 used may be chosen to suit the force values desired for the first compressive load range.

Figure 35F:
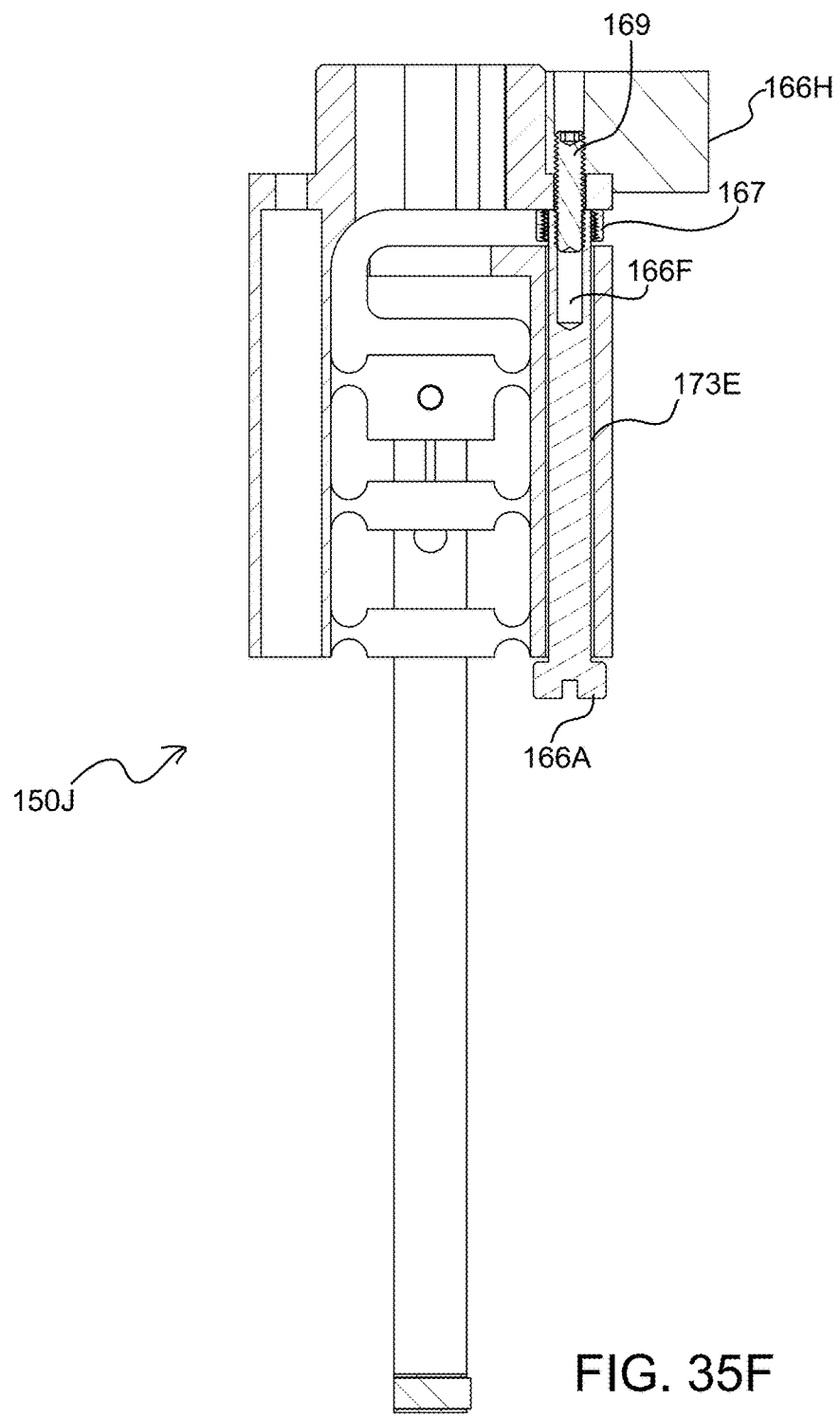
FIG. 35F is a cross sectional view taken of FIG. 35C.

Referring primarily to FIG. 35F, threaded insert 166A may extend through threaded insert accepting hole 173E. In some configurations, less than the entire portion of threaded insert 166A can be threaded and threaded inserted 166A may not be in threaded engagement with threaded insert accepting hole 173E. A configuration in which less than the entire portion of threaded insert 166A can be threaded can allow deformable body 173 (FIG. 35C) to distort freely over the desired load ranges. In some configurations, only the portion of threaded insert 166A onto which nut 167 is mated may be threaded. Threaded insert 166A can include threaded mounting hole 166F. Threaded mounting hole 166F can allow fastener 169 to couple into threaded insert 166A. Fastener 169 may fixedly couple threaded insert 166A to stationary element or structure 166H which can ensure that threaded insert 166A does not displace during loading of deformable body 173 (FIG. 35C). In other configurations any other suitable method of fixing the position of threaded insert 166A may be used.

Figure 36:
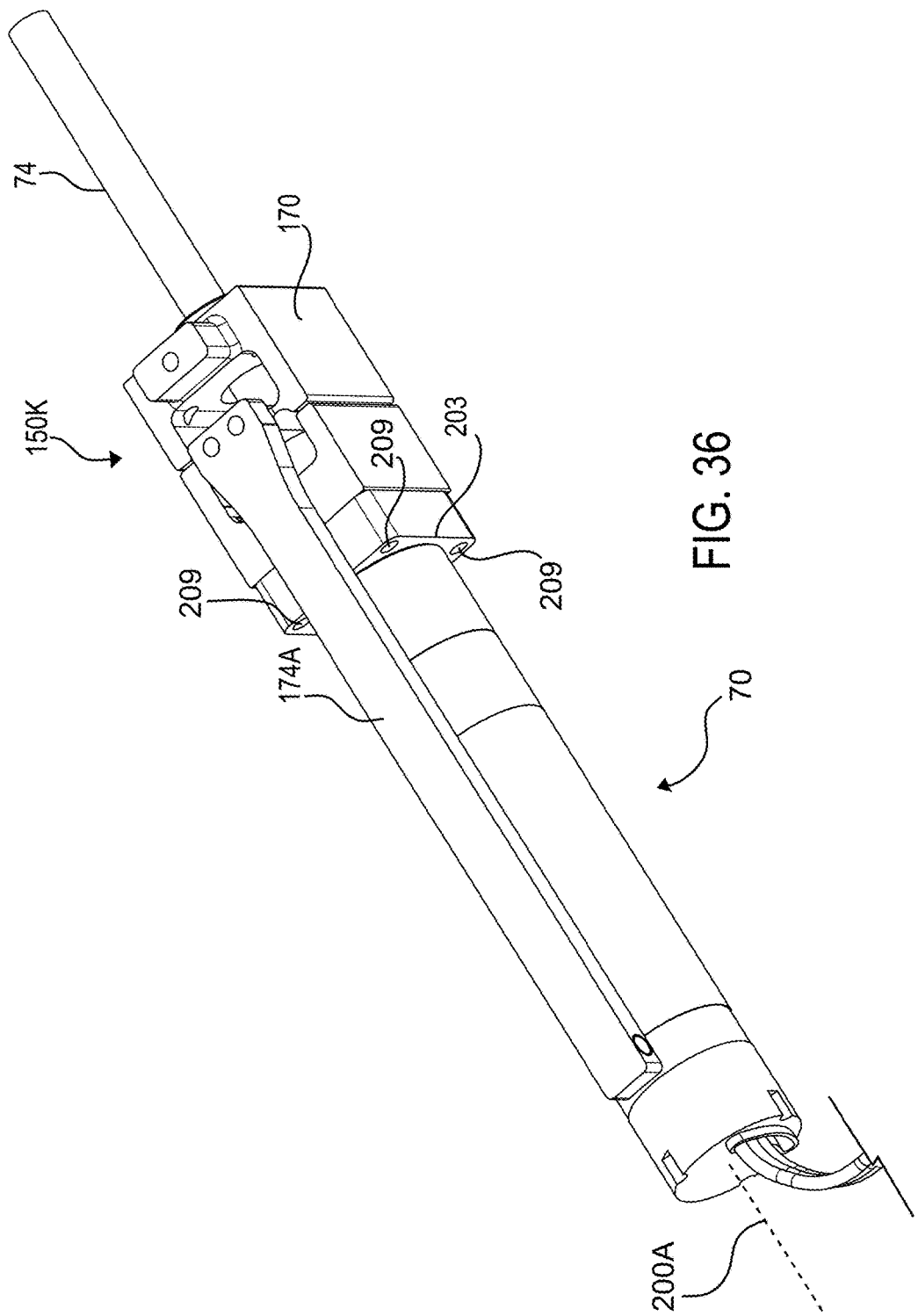
FIG. 36 is a schematic diagram of a motor assembly arranged to drive a drive screw.

Referring now primarily to FIG. 36, motor assembly 70 can be arranged to apply force to drive screw 74. The arrangement including motor assembly 70 and drive screw 74 can include mechanical component 150K. Mechanical component 150K can include "S" beam 170. Coupling block 203 can be attached to motor assembly 70 and can be used in some configurations to facilitate joining of motor assembly 70 to "S" beam 170. Coupling block 203 can include threaded holes 209 which can allow, for example, but not limited to, fasteners (not shown) to couple "S" beam 170 to coupling block 203. Any other suitable means of coupling motor assembly 70 to "S" beam 170 may be used. Flag or projection 174A attached to "S" beam 170 can extend parallel to longitudinal axis 200A of motor assembly 70 and has clearance 200B (FIG. 37) over motor assembly 70. This configuration can allow for size reduction of a load sensor 98 (FIG. 35B) and motor assembly 70 pair.

Figure 37:
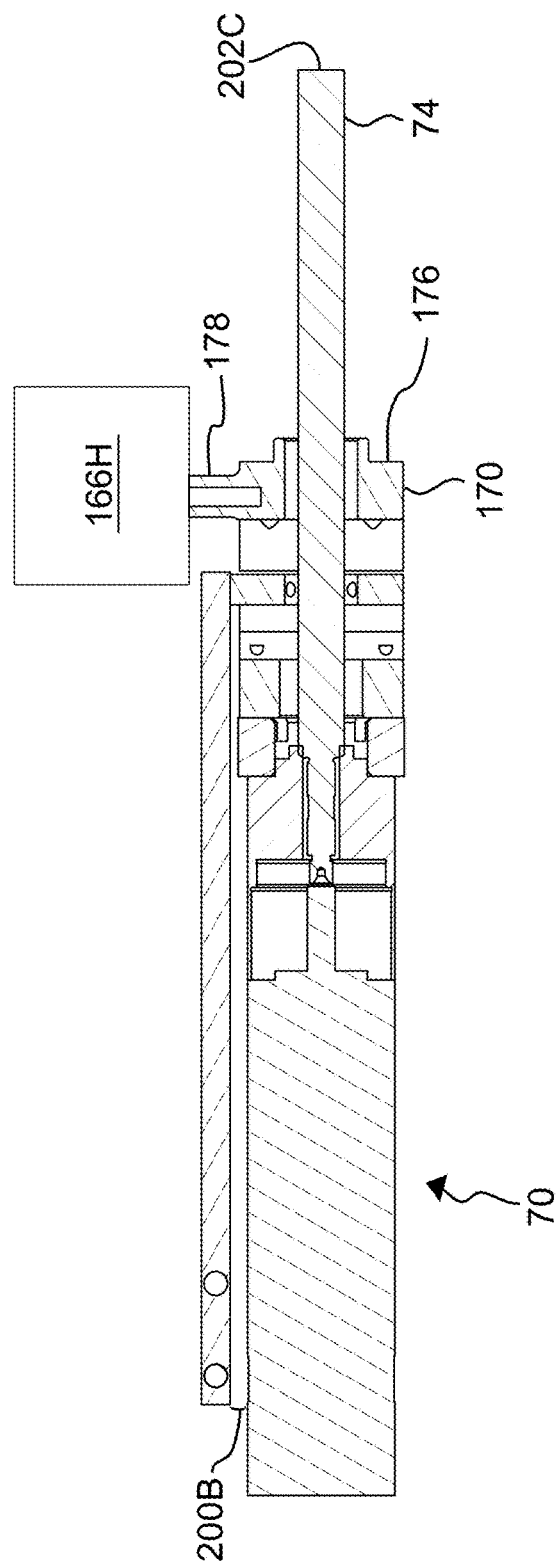
FIG. 37 is a schematic diagram of a medial cross section of the configuration depicted in FIG. 36.

Referring now primarily to FIG. 37, drive screw 74 can pass through void 176 in "S" beam 170. Mounting feature 178 may be included on "S" beam 170 and may be used to couple a portion of "S" beam 170 to stationary structure or housing 166H. In some configurations, motor assembly 70 is free floating and not fixedly coupled to stationary housing 166H. As the load in the drive path increases, motor assembly 70 and drive screw 74 may displace. Since "S" beam 170 is coupled to motor assembly 70, but fixed to stationary housing 166H, "S" beam 170 can deform as a result of this displacement. In other configurations, another portion of the drive train may be floating. For example, end 202C of lead screw 74 driven by motor assembly 70 may be retained in a slip coupling (not shown). Alternatively, motor assembly 70 may include gear head 70B (FIG. 36) whose gears are wide enough to allow for some axial displacement between them during operation.

Figure 38:
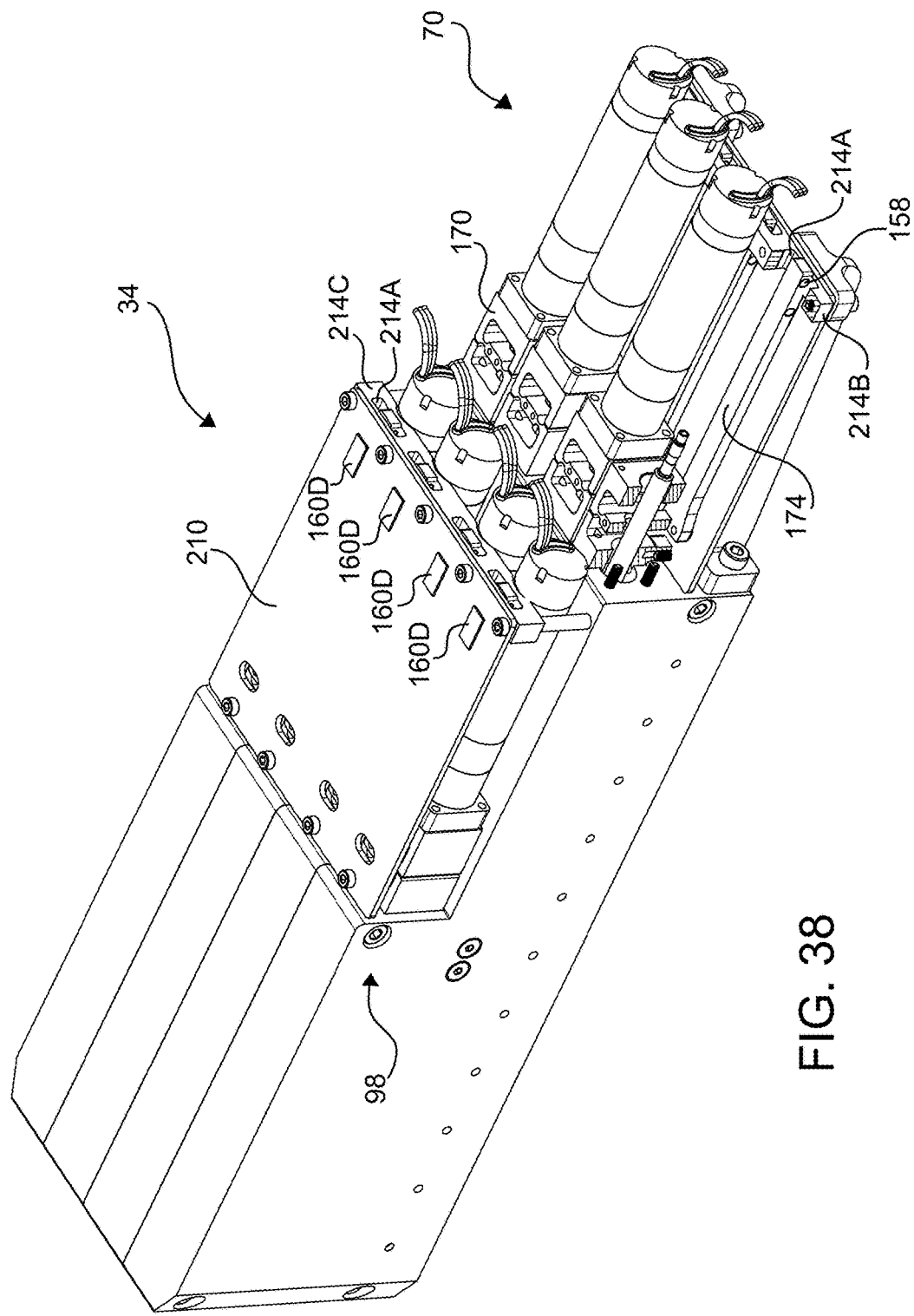
FIG. 38 is a schematic diagram of "S" beams of a number of load sensors.

Referring now to FIG. 38, "S" beams 170 of a number of load sensors 98 (FIG. 35B) can be included in a drive component 34. In configurations where a motor assembly 70 is free floating, or not fixedly coupled to drive component 34, as a load is exerted on motor assembly 70 through associated drive screw 74 (FIG. 37), motor assembly 70 may displace slightly. The displacement may cause "S" beam 170 (FIG. 37) to be distorted. The distortion of "S" beam can cause projection 174 to displace from an orientation in which it is substantially parallel to motor assembly 70. The displacement of projection 174 may be read by a sensor on electrical component 160 (FIG. 35B) of load sensor 98 (FIG. 35B). In some configurations, the sensor may be at least one Hall effect sensor 160D which can track the position of magnet 158 on projection 174. One or multiple sensors such as Hall effect sensors 160D can be included on PCB 210 of electrical component 160 (FIG. 35B) to allow for a cross comparison between Hall effect sensors 160D when any one of projections 174 moves. Such a cross comparison may help to detect displacement of projections 174 with a greater degree of certainty, provide redundancy in the system, and be useful in fault detection. A pair of tracks 214B, 214C can be included as part of drive component 34 and can include slots 214A into which the ends of projections 174 extend. Tracks 214B, 214C may constrain movement of projection 174 during operation which may help to increase the accuracy of load sensor 98 (FIG. 35B). Accuracy in this context indicates minimizing deviations of magnet 158 from an expected path that could alter output from Hall effect sensors 160D and skew a load reading.

Figure 39:
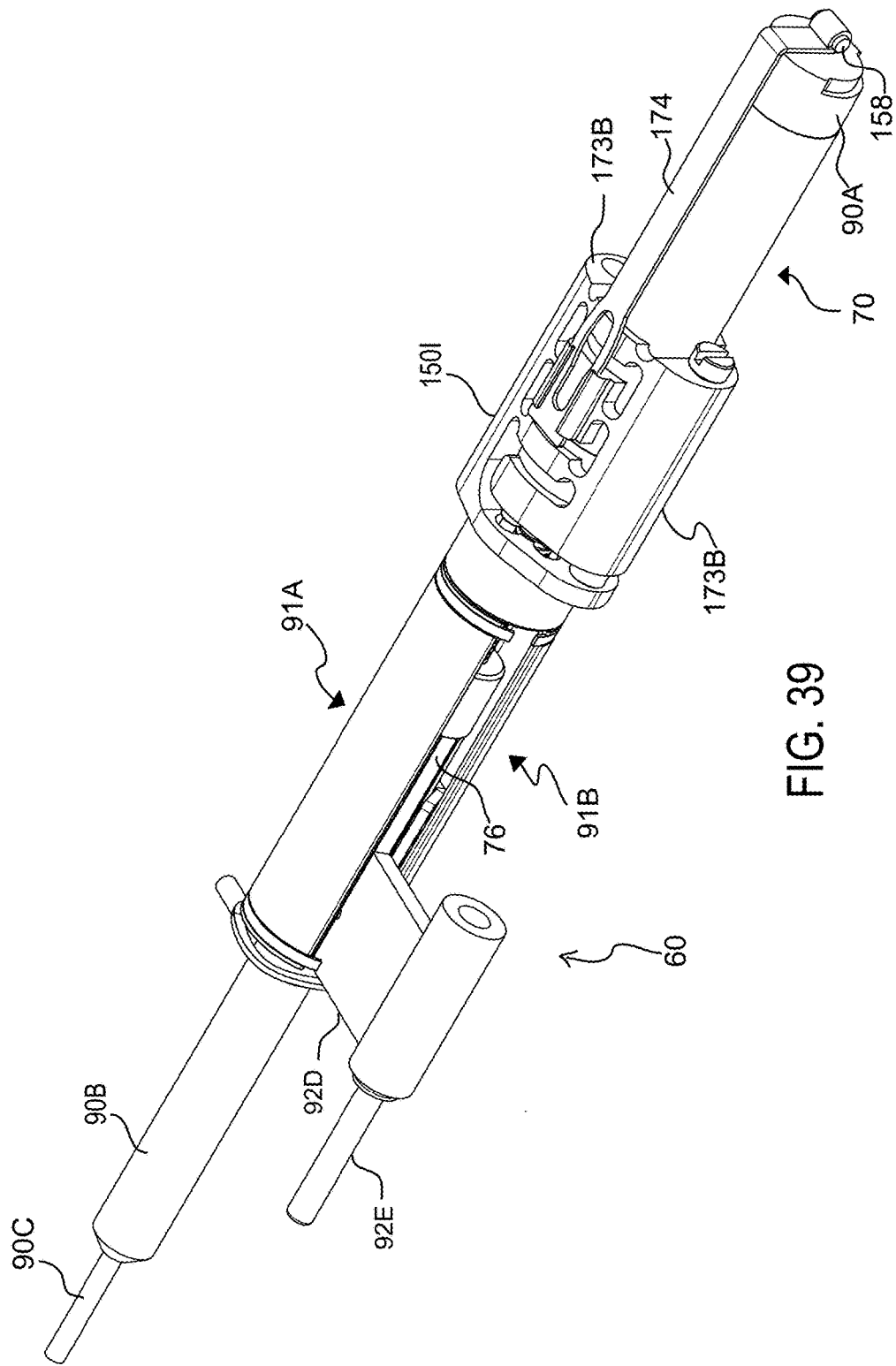
FIG. 39 is a schematic diagram of a motor assembly and an associated drive element.
Figure 40:
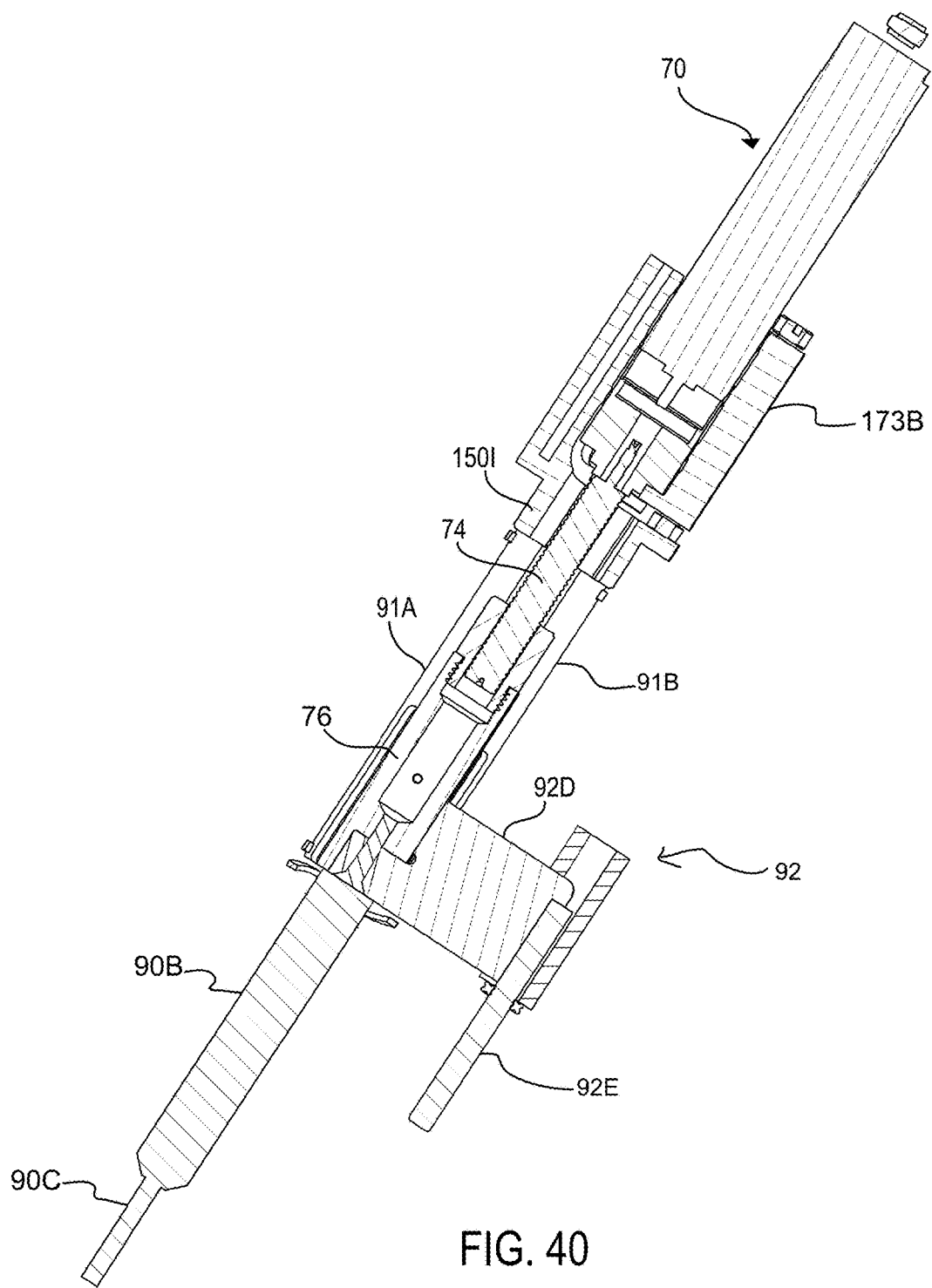
FIG. 40 is a schematic diagram of a medial cross section of the configuration depicted in FIG. 39.

Referring now to FIGS. 39-40, views of motor assembly 70 and associated drive element 60 driving including a lead screw 74 are shown. "V" shaped linear needle bearing assemblies 91A and 91B can attach to mechanical component 1501 for load sensor 98 (FIG. 35B). Motor assembly 70 can be partially housed within mechanical component 1501 and can be mounted to mechanical component 1501. Lateral portions 173B of mechanical component 1501 can be thickened to prevent distortion of mechanical component 1501 due to run out. Nut 76 of the driven element 60 can be constructed to be used with any of a variety of different projections 92 (FIG. 40). Projection 92 (FIG. 40) may not be an integral part of nut 76. Projection 92 (FIG. 40) may be attached to nut 76 using any coupling method, for example, but not limited to, a fastener. The coupling method may allow the same nut 76 to be used with any of a plurality of projections 92 (FIG. 40). Projection 92 (FIG. 40) can include projection body 92D and interfacing portion 92E. Projection body 92D can span the distance from nut 76 to the axis to which it is desired to transmit force. Interfacing portion 92E may be placed in line with the axis to which it is desired to transmit force and may be the portion of the projection 92 (FIG. 40) through which force is ultimately transferred.

Still referring to FIG. 39-40, drive element 60 can include, for example, but not limited to, position sensors 90A (FIG. 39) and 90B (FIG. 40). Specifically, motor encoder 90A (FIG. 39) and linear potentiometer 90B (FIG. 40) can be included. Linear potentiometer 90B (FIG. 40) may have wiper 90C (FIG. 40) which can move with or can be connected to nut 76. Wiper 90C (FIG. 40) may move across the resistive element of potentiometer 90B (FIG. 40) as nut 76 is shuttled back and forth within linear needle bearing assemblies 91A, 91B. Linear potentiometer 90B (FIG. 40) may provide feedback as to the position of nut 76 and projection 92 as they are displaced by operation of the motor assembly 70. The position of the nut 76 and projection 92 (FIG. 40) may also be tracked by the number of encoder counts from motor encoder 90A (FIG. 39). When used in conjunction with linear potentiometer 90B (FIG. 40), tracking of encoder counts may provide a level of redundancy and allow for cross-checking of feedback data from any of position sensors 90A (FIG. 39) and 90B (FIG. 40) monitoring movement of drive element 60.

Figure 40B:
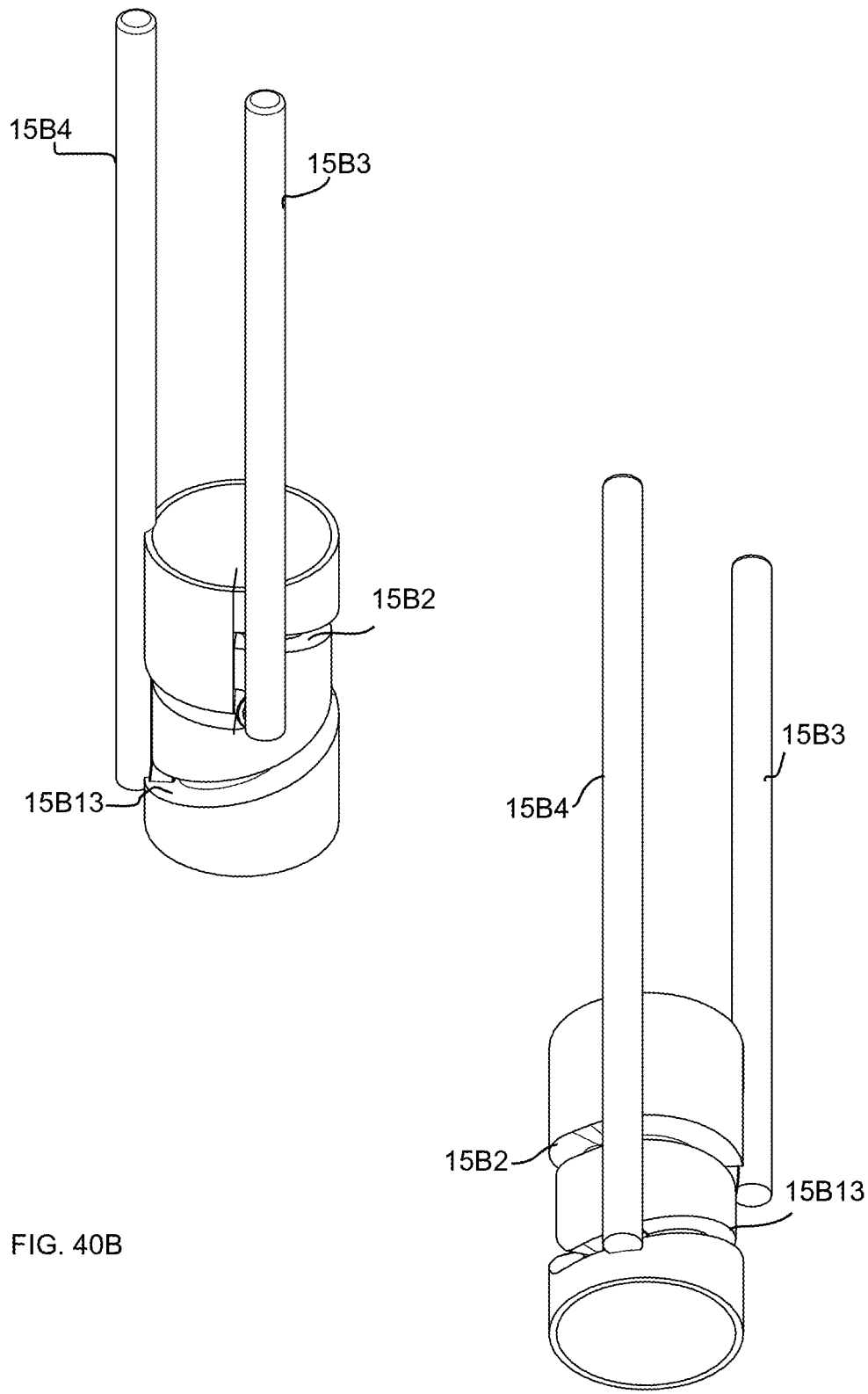
FIG. 40B is a schematic diagram of the double cams of the present teachings.
Figure 40C:
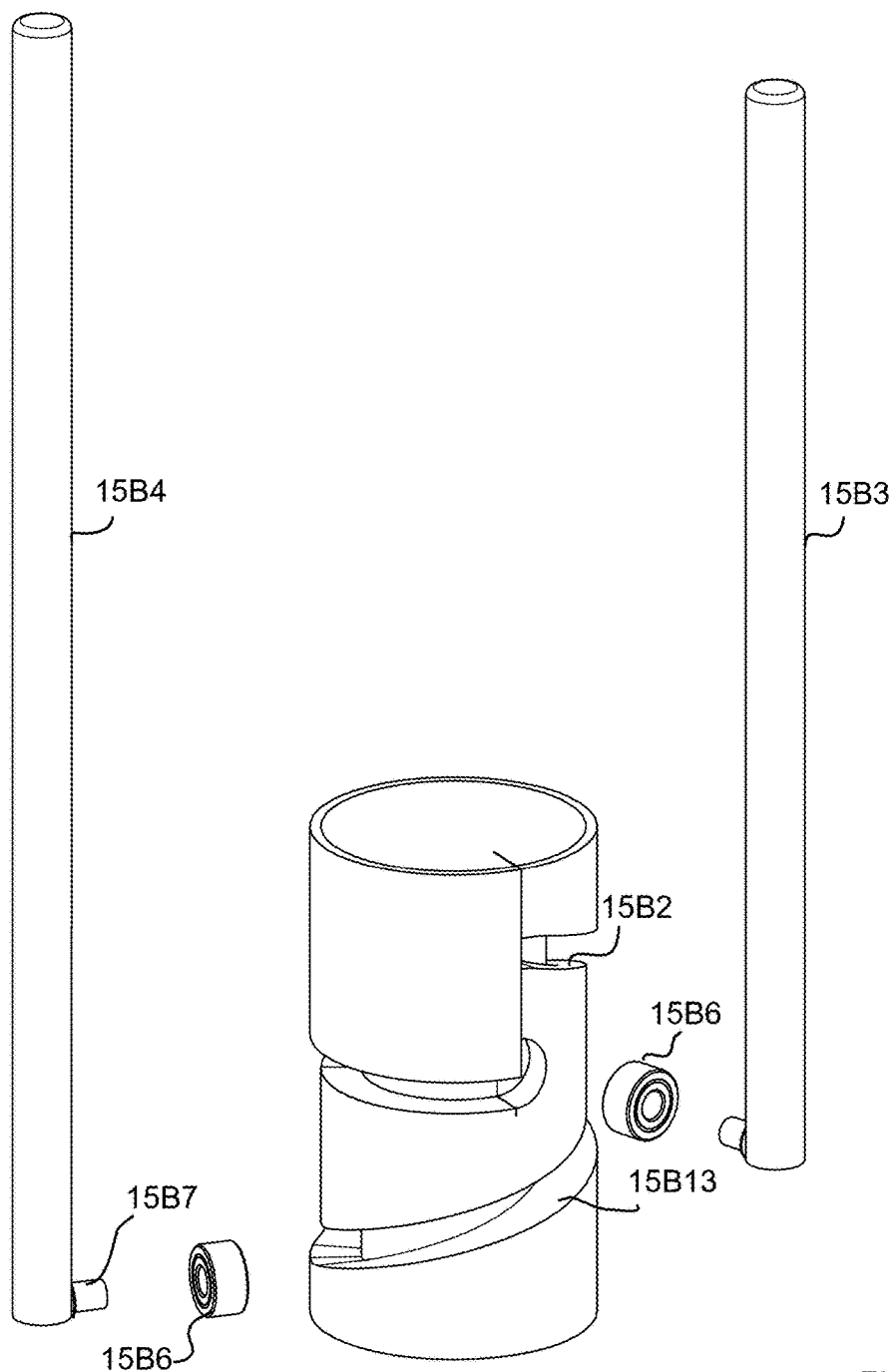
FIG. 40C is a schematic diagram of an explosion of the double cams of FIG. 40B.
Figure 40E:
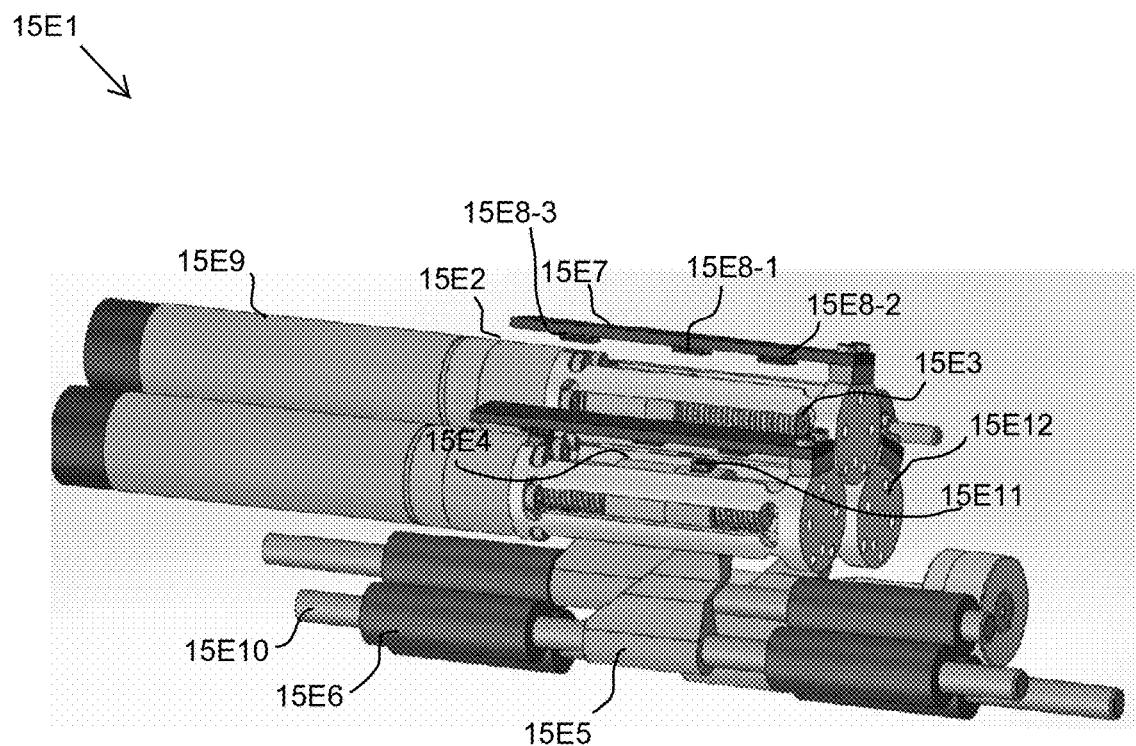
FIG. 40E is a pictorial representation of an actuation assembly including the flexure of the present teachings.
Figure 40F:
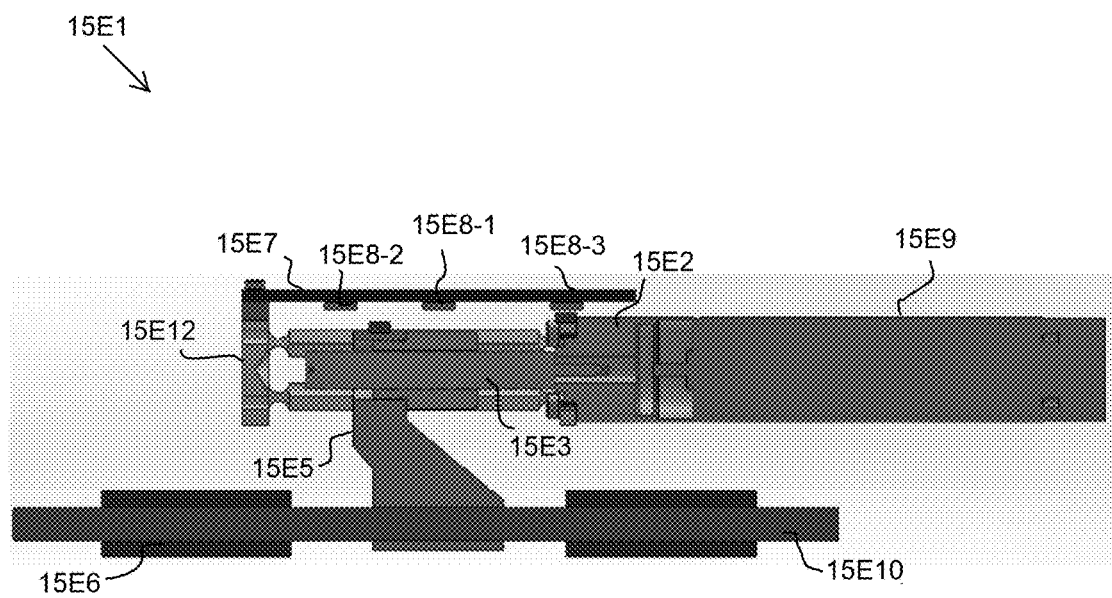
FIG. 40F is a schematic diagram of a cross section of the actuation assembly of FIG. 40E.
Figure 40G:
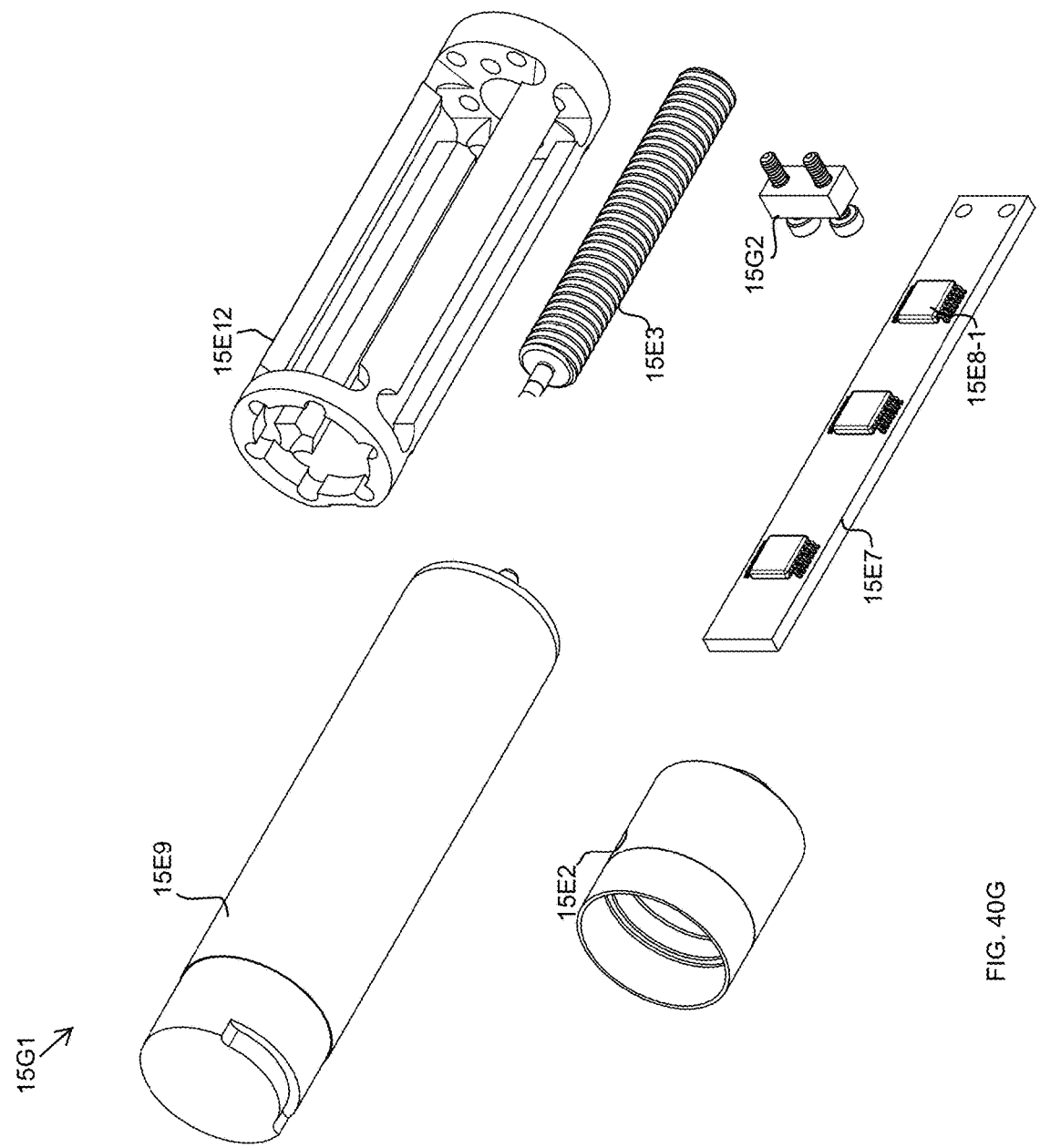
FIG. 40G is a schematic diagram of an explosion of the ball screw/flexure of the actuation assembly of FIG. 40E.
Figure 40I:
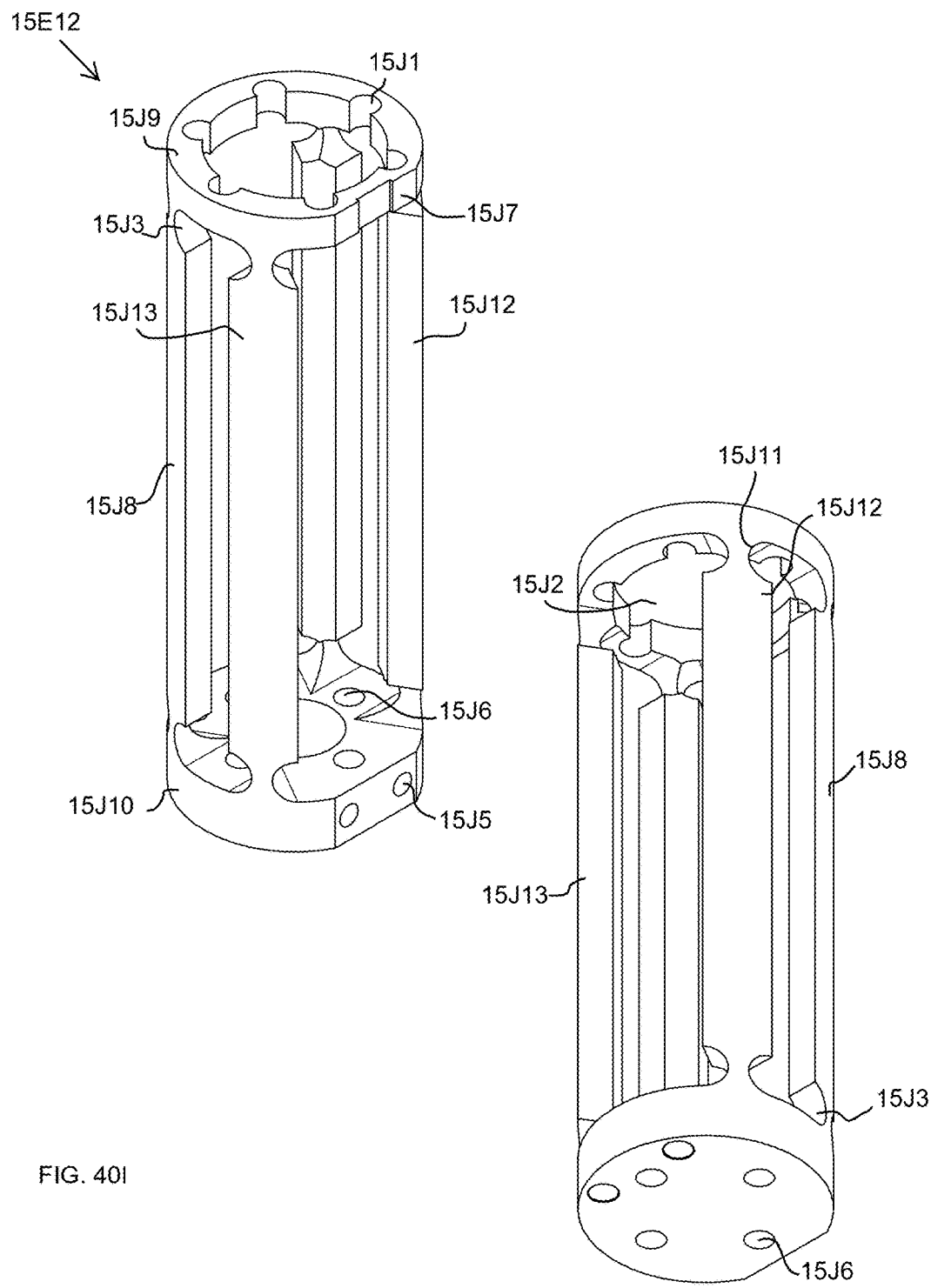
FIG. 40I is a schematic diagram of the flexure of the present teachings.
Figure 40J:
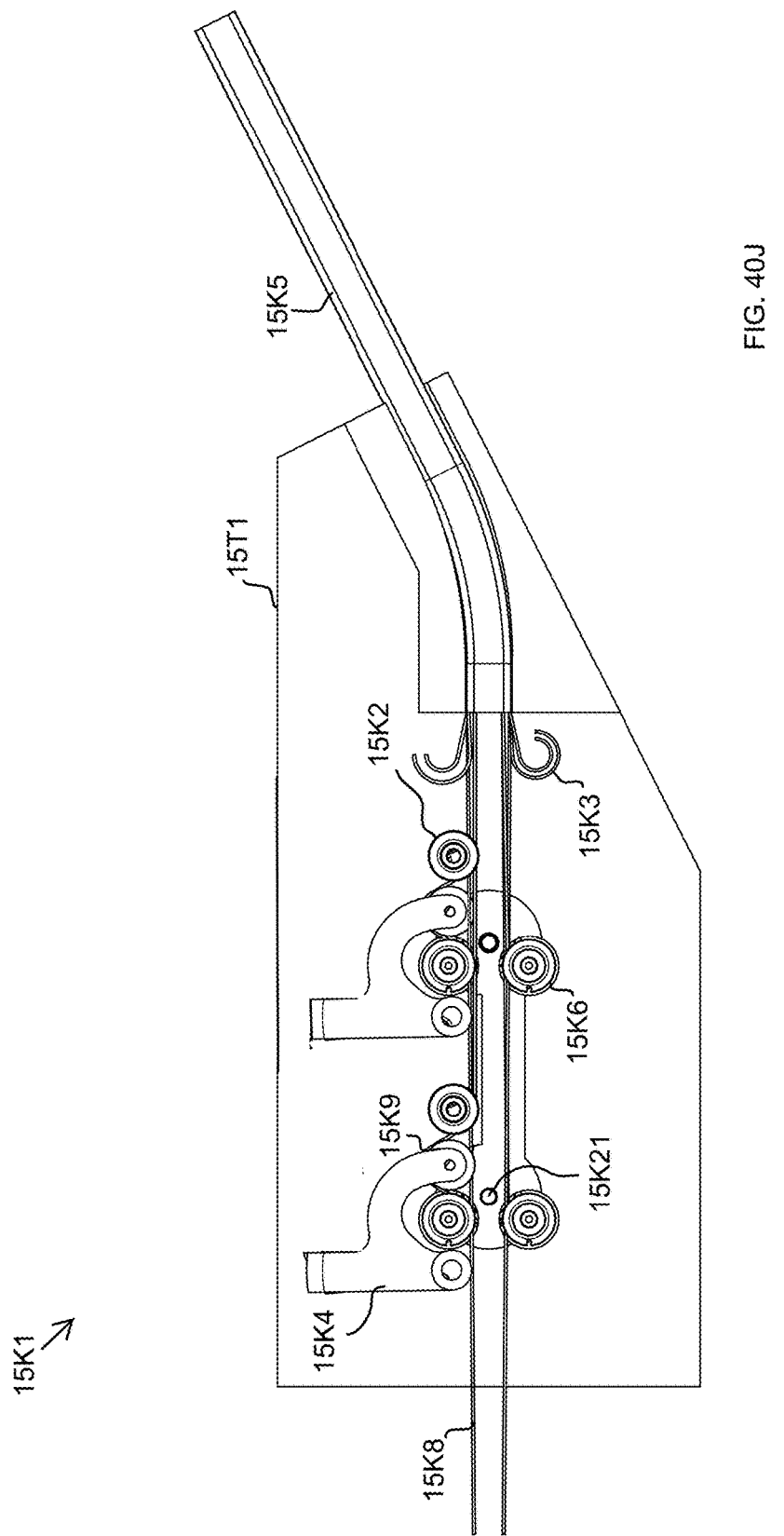
FIGS. 40J and 40K are schematic diagrams of cable tensioning and lumen pathway of the present teachings.
Figure 40K:
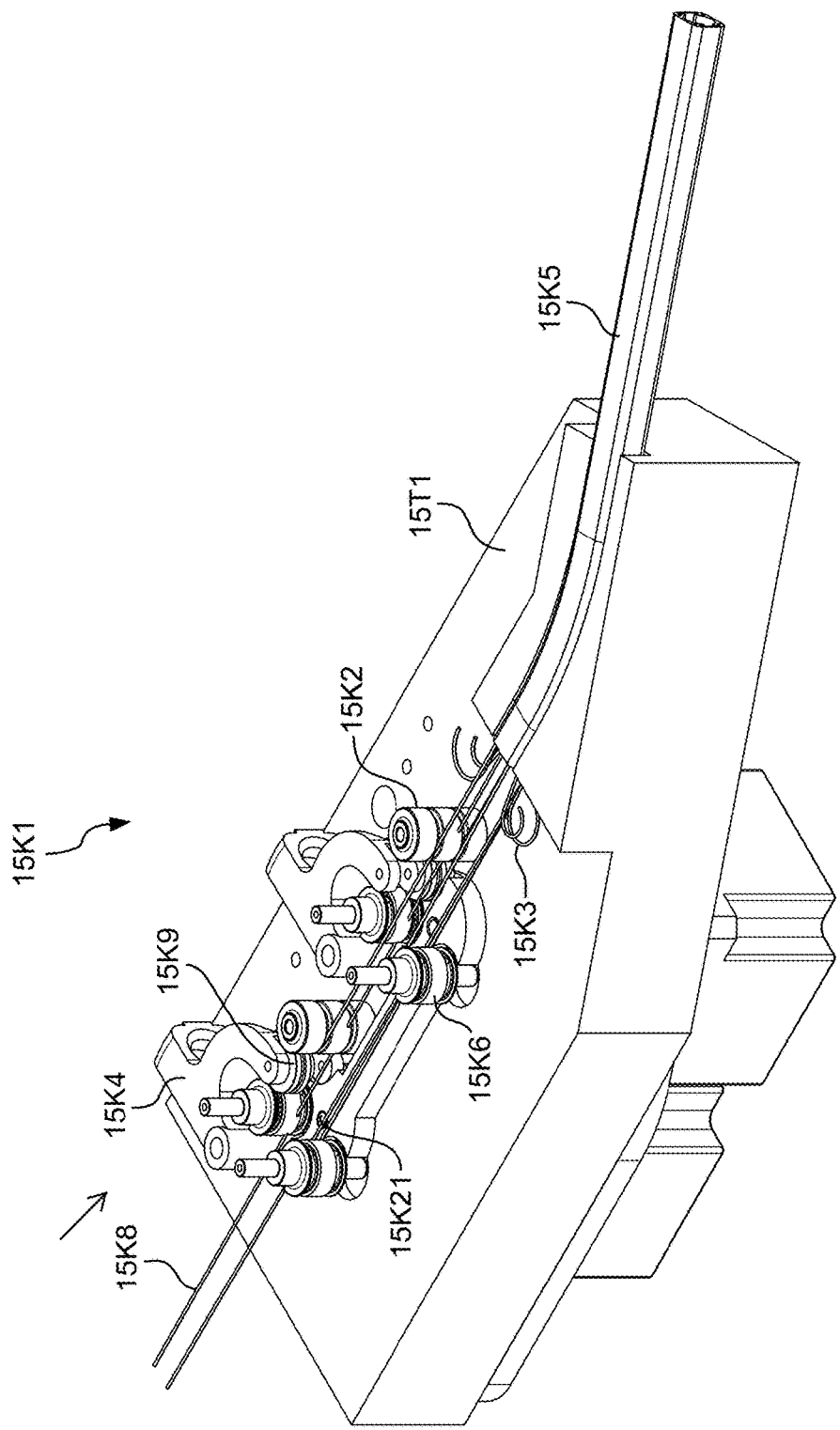
Figure 40L:
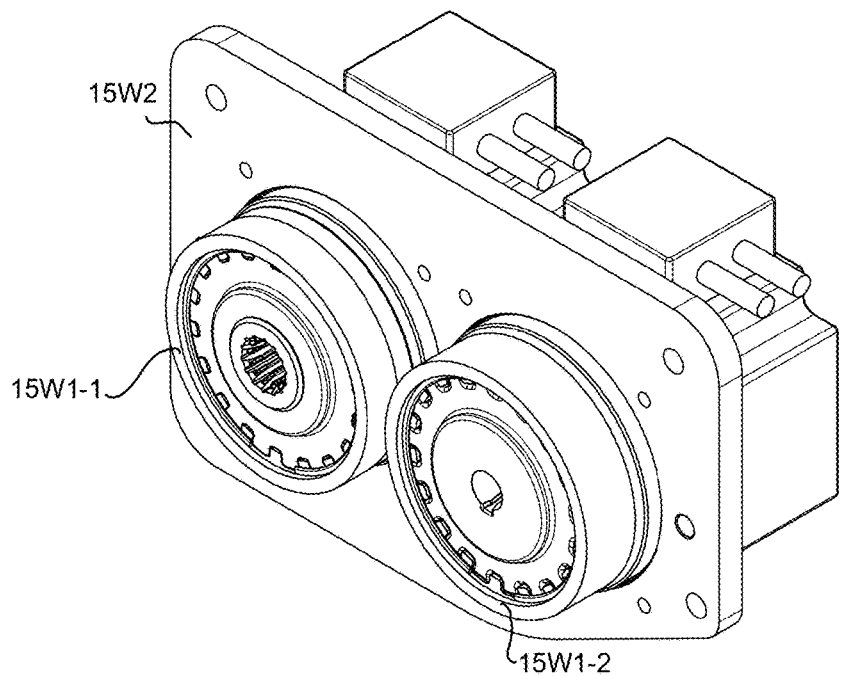
Figure 1:
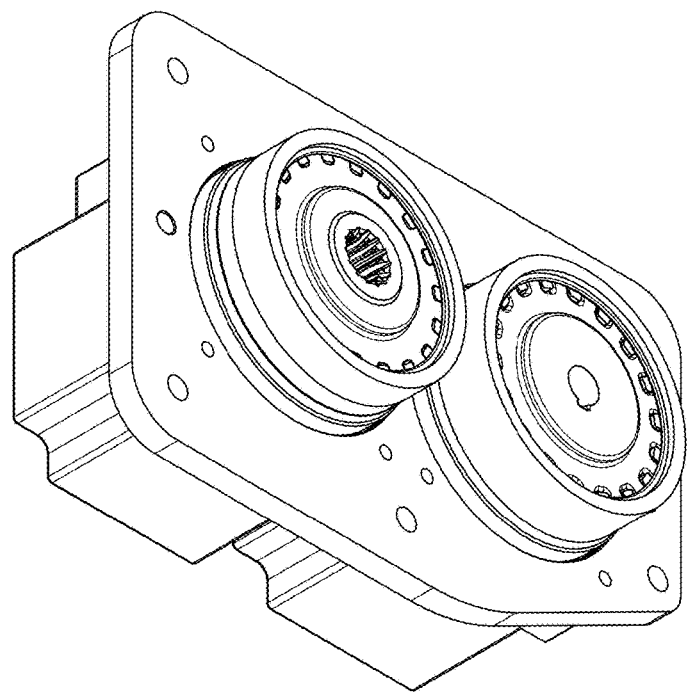
Figure 40L:
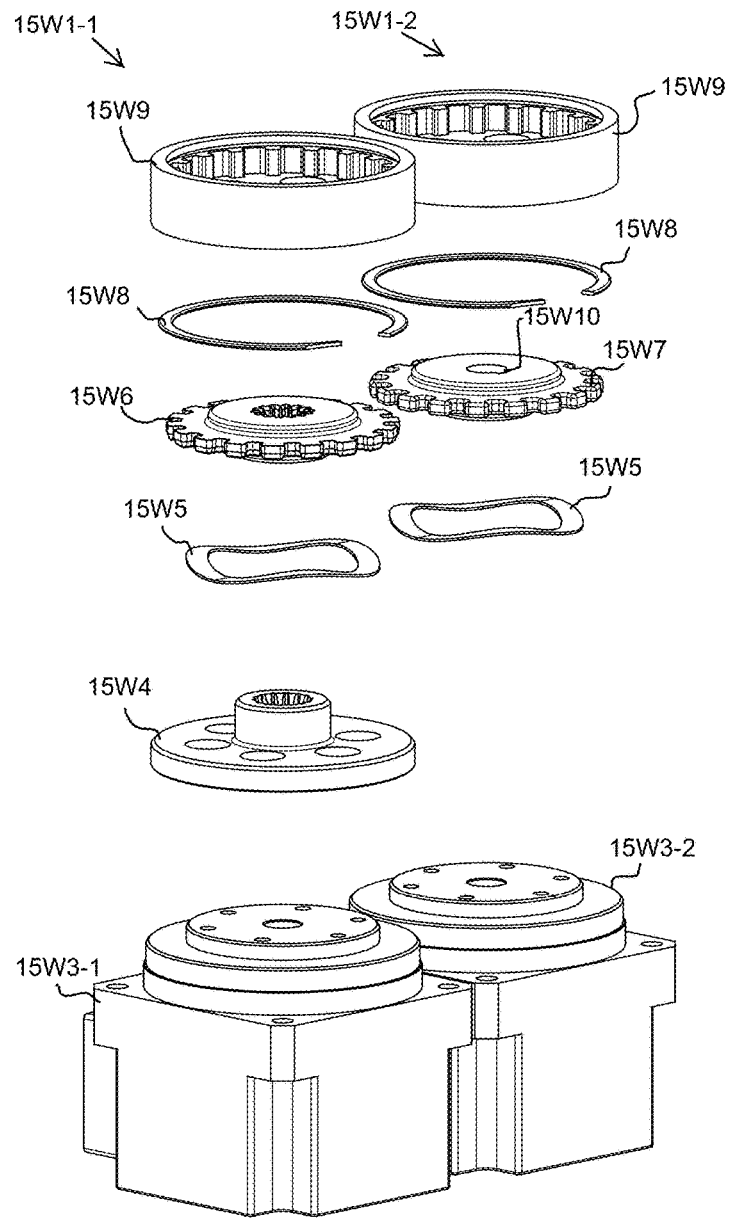
Figure 2:
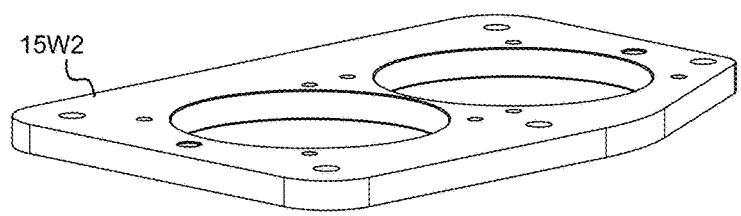
Figure 40M:
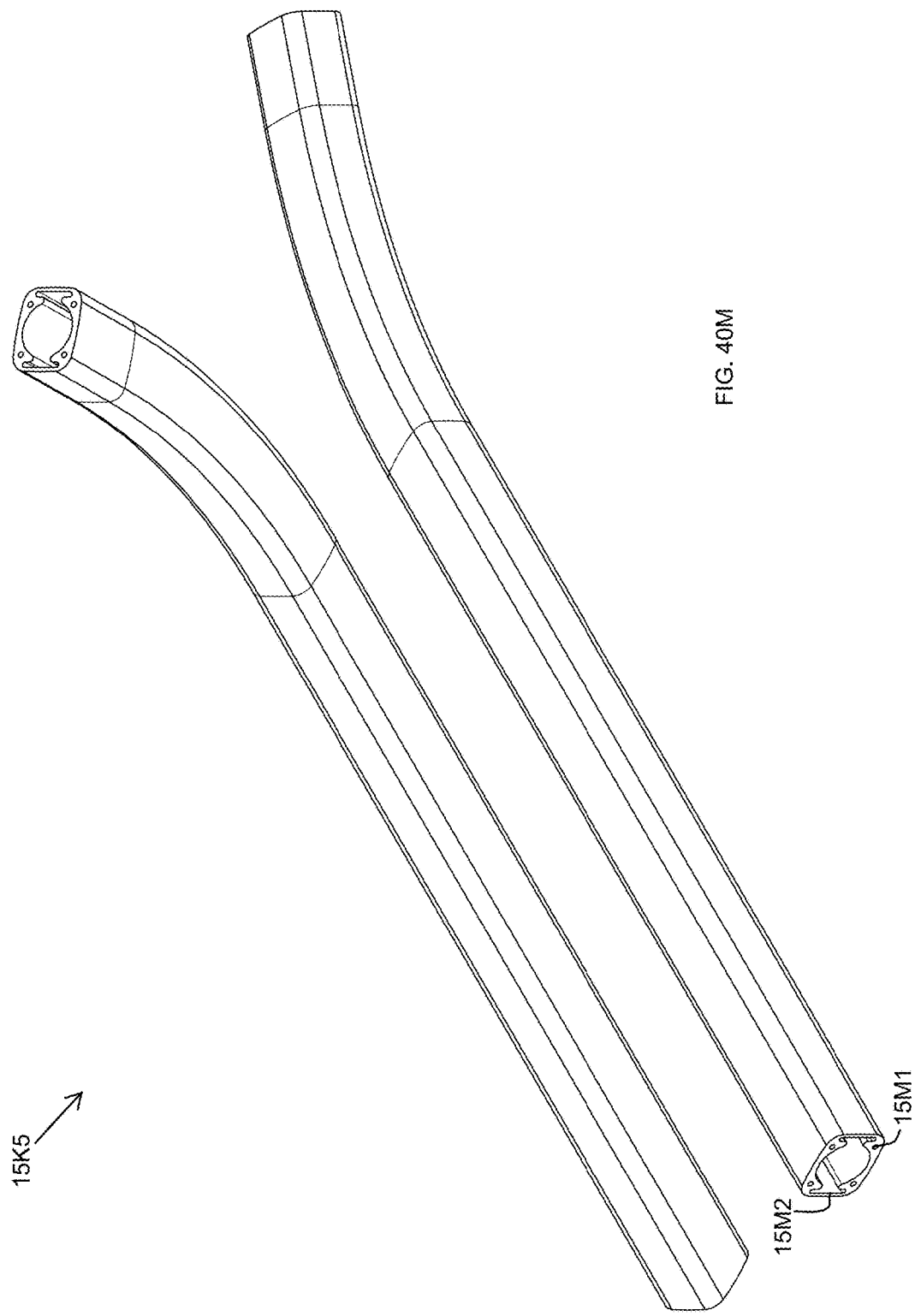
FIG. 40M is a schematic diagram of the lumen of the present teachings.
Figure 40O:
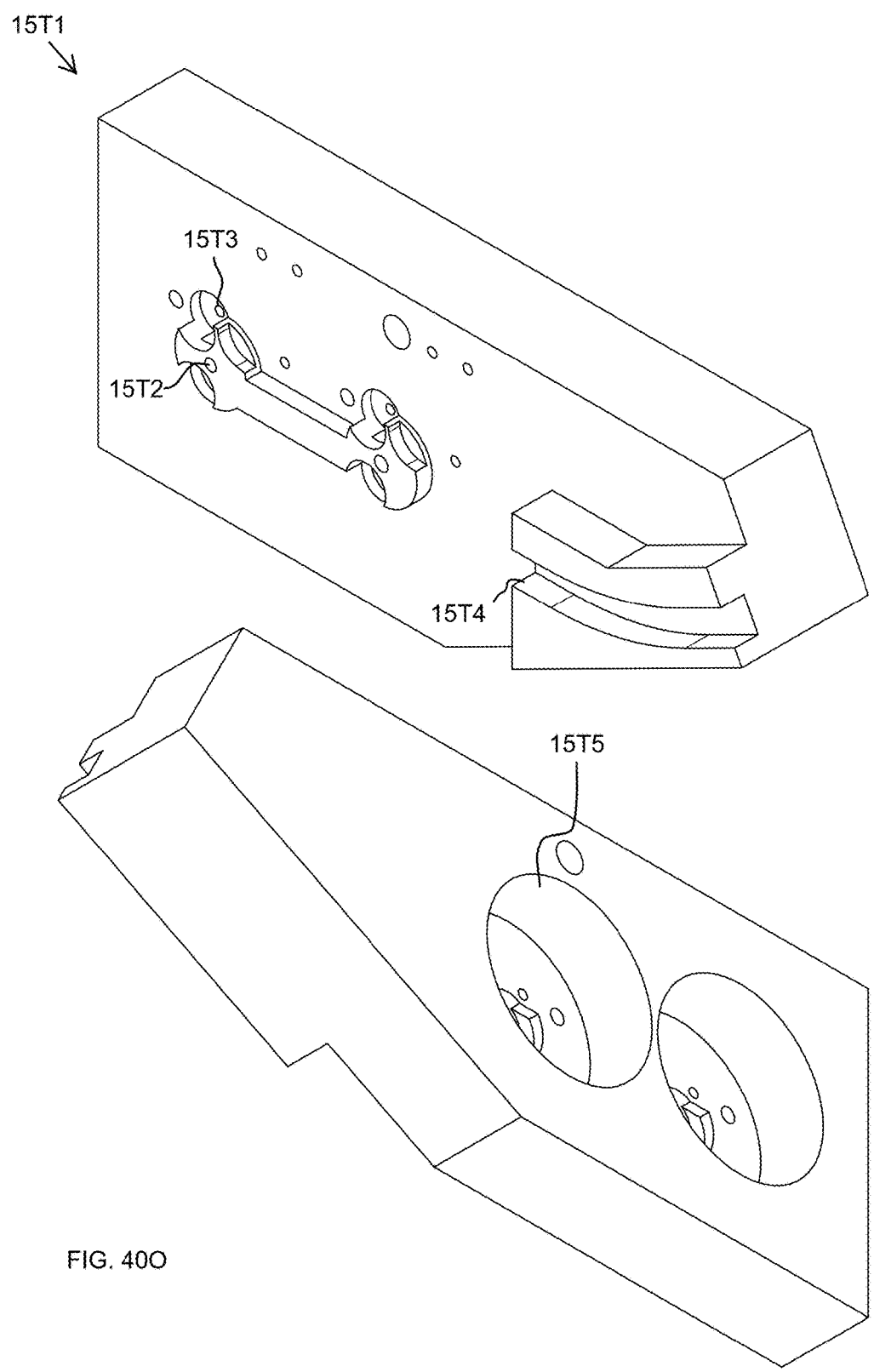
FIG. 40O is a schematic diagram of a first configuration of the capstan housing of the present teachings.
Figure 40T:
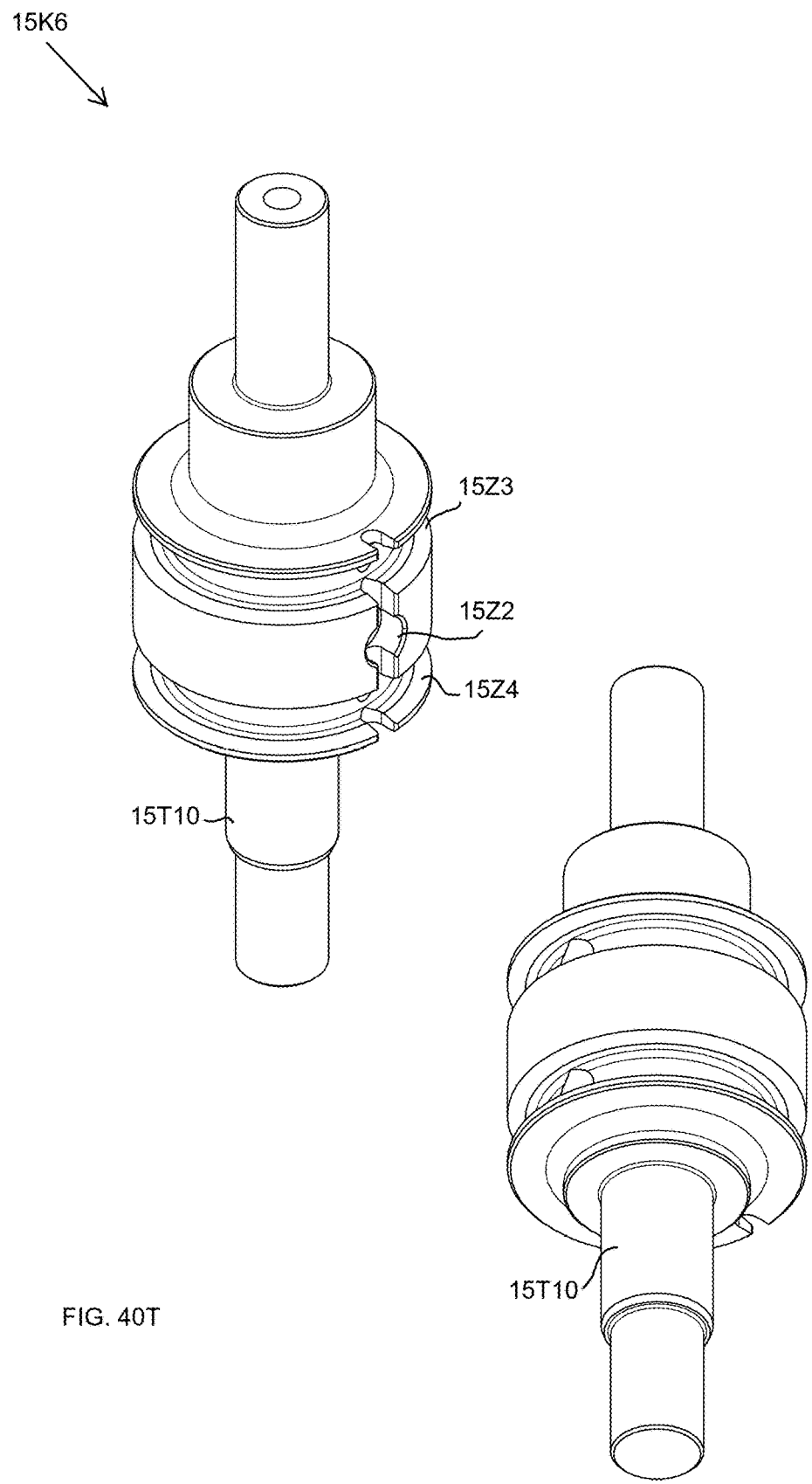
FIG. 40T is a schematic diagram of the capstan shaft of the present teachings.
Figure 40A:
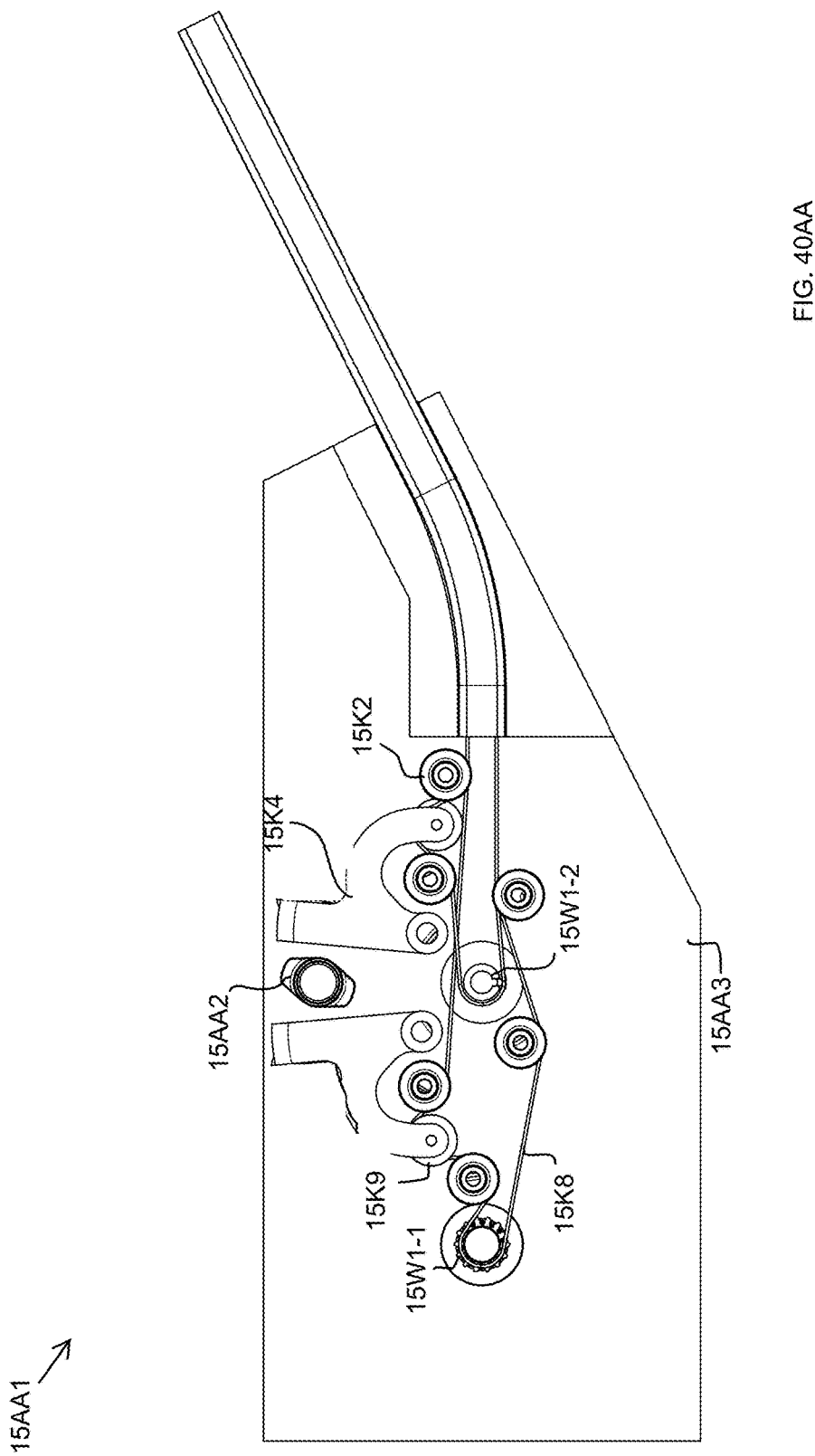
Figure 40B:
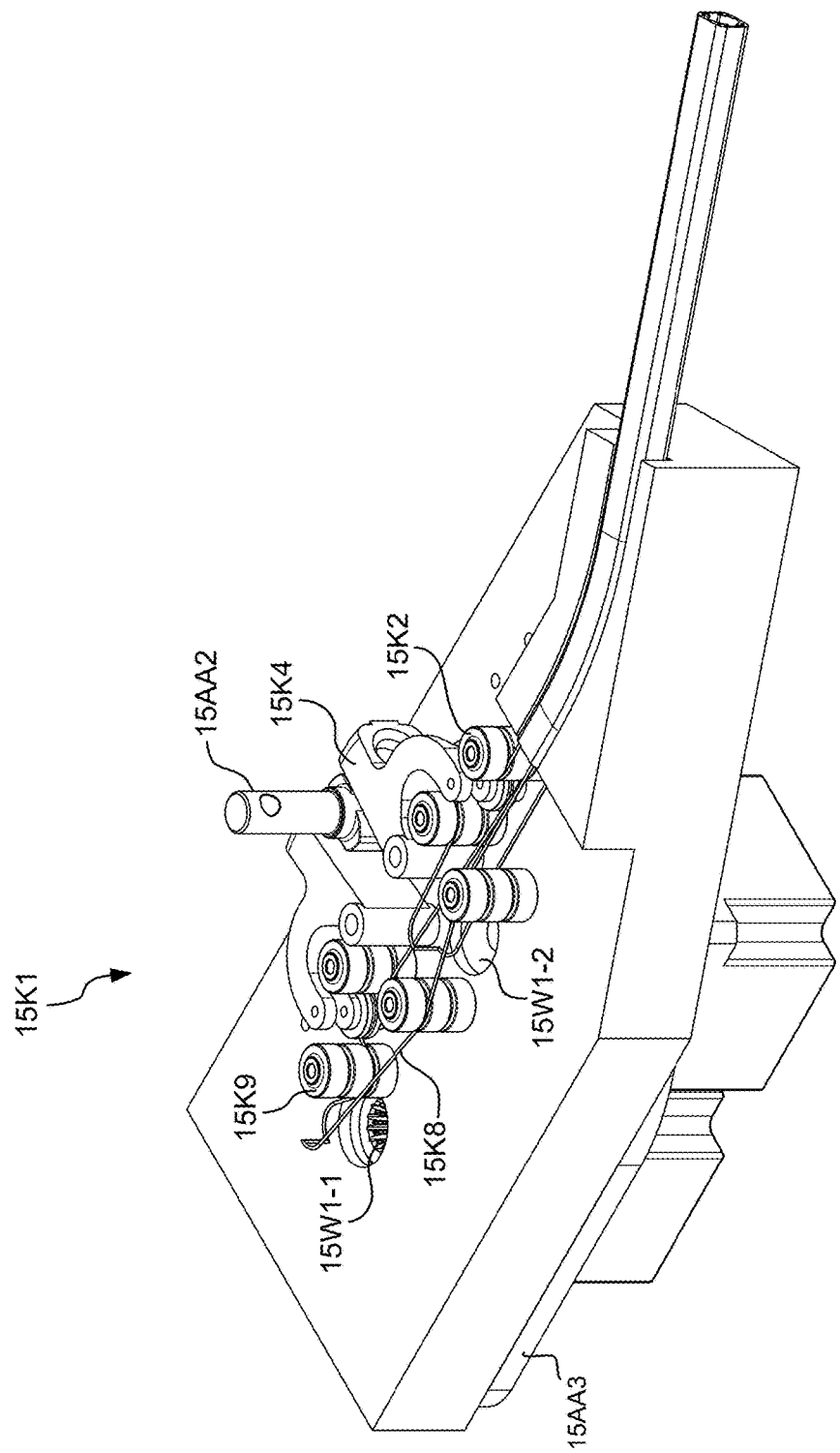

Referring now to FIGS. 40A-1, 40A-2 and 40A-3, in some configurations, one motor 15B1 can be used, and cams 15B2/15B13 can drive jaw open/close drive pins 15B3/15B4, respectively. In some configurations, there can be one section of rotation of cams 15B2/15B13 that can park pins 15B3/15B4 in retracted position 15B5 (FIG. 40A-1). Jaw open/close pins 15B3/15B4 can be positioned at jaw closed extreme travel 15B9 (FIG. 40A-2) based on the position of cams 15B2/15B13 at jaw closed position 15B10 (FIG. 40A-2). Jaw open/close pins 15B3/15B4 can be positioned at opposite extreme of travel 15B11 (FIG. 40A-3) based on the position of cams 15B2/15B13 at opposite extreme of travel 15B12 (FIG. 40A-3). In some configurations, the subassembly including cams 15B2/15B13 and motor 15B1 can be floated axially along output pins 15B3/15B4, and a spring (not shown) can be applied to the subassembly that could remove backlash from the system.

Referring now to FIG. 40B, cams 15B2/15B3 can be shaped according to the desired positioning of jaw open/close pins 15B3/15B4. Jaw open/close pins 15B3/15B4 can be positioned in cams 15B3/15B4 respectively based on the desired relative movement of jaw open/close pins 15B3/15B4.

Referring now to FIG. 40C, jaw open/close pins 15B3/15B4 can include rollers 15B6 that can mount upon jaw open/close pins 15B3/15B4 at mounting peg 15B7. Rollers 15B6 can enable movement of jaw open/close pins 15B3/15B4 within tracks formed by cams 15B2/15G13.

Referring now to FIG. 40D, the track of jaw open/close pin 15B3 (FIGS. 40A-1 through 15A-3) (and therefore the height of jaw open/close pin 15B3 (FIGS. 40A-1 through 15A-3)) can be tracked for cam 15B2 according to cam center line 15D1, and the track of jaw open/close pin 15B4 (FIGS. 40A-1 through 15A-3) can be tracked for cam 15B13 according to cam center line 15D4. Negative slope section 15D3 of cam center line 15D1 indicates that jaw open/close pin 15B3 (FIGS. 40A-1 through 15A-3) is descending during its travel in this part of the cam track of cam 15B2. Positive slope section 15D2 of cam center line 15D4 indicates that jaw open/close pin 15B3 (FIGS. 40A-1 through 15A-3) is ascending during its travel in this part of the cam track of cam 15B13. In some configurations, a 115° offset between cam 15B2 and cam 15B13 (indicated by the 11.54 dimension) can position jaw open/close pins 15B3/15B4 to raise and lower according to a pre-defined schedule, for example, in opposite directions as indicated by the opposing track slopes 15D3/15D2. Cams 15B2/15B13 (FIG. 40B) can rotate 240° as shown by the 24.09 dimension, making the total cam rotation 355°. The stroke of each of jaw open/close pins 15B3/15B4 (FIGS. 40A-1 through 15A-3) is indicated by the 10 mm dimension.

Referring now to FIGS. 40E and 40F, with respect to rotational compliance, the reaction torque created by the motor/gearbox/ballscrew can be measured by rotational flexure 15E12. In particular, the torque applied to the ballscrew shaft can be measured by measuring the reaction torque applied to the housing of gearbox 15E2. Actuator assembly 15E1 can include, but is not limited to including, motors 15E9 coupled with gearboxes 15E2 and integrated ball screw shafts 15E3. Ballnut 15E4 can travel within rotational flexure 15E12. Gooseneck arms 15E5 can transfer the axial load from ballnuts 15E4 to pins 15E10 that can be channeled through linear ball bearings 15E6. Sensor drivers mounted upon printed circuit board 15E7 can receive sensor data from sensors 15E8-1 through 15E8-3 such as, for example, but not limited to, Hall sensors. Sensors 15E8-1 and 15E8-2, in collaboration with magnet 15E11, can collect sensor data that can be used to measure, for example, the approximate absolute position of ballnut 15E4, and in turn the approximate absolute position of actuator pin 15E10. Sensor 15E8-3 can collect sensor data that can be used to measure the rotational displacement of the assembly of gearbox 15E2 and motor 15E9. The axial force in the shaft of ballscrew 15E3 can be measured based on the rotational spring rate of flexure 15E12 and the pitch and efficiency of ballscrew 15E3. The rotation of flexure 15E12 near gearbox 15E2 can have travel limits that can prevent over-rotation and yielding of flexure 15E12. The coupling between gearbox 15E2 and flexure 15E12 can include a bushing material such that flexure 15E12 is free to rotate.

Referring now to FIG. 40G, flexure assembly 15G1 can include, but is not limited to including, motor 15E9, gearbox 15E2, ballscrew 15E3, PCB 15E7, flexure 15E12, and PCB spacer 15G2. Motor 15E9, coupled with gearbox 15E2, can drive ballscrew 15E3. Flexure 15E12 can surround ballscrew 15E3 and can provide for rotation of flexure assembly 15G1 that can be measured based on data collected from sensor 15E8-3. Sensor 15E8-3 can be mounted upon PCB 15E7. PCB 15E7 can be mounted upon flexure using, for example, PCB spacer 15G2. PCB 15E7 can process data from sensor 15E8-3 to determine the rotation of flexure assembly 15G1.

Referring now to FIG. 40H, ballscrew 15E3 can include connect shaft 15H1 that can operably couple ballscrew 15E3 with gearbox 15E2 (FIG. 40G). Ballscrew 15E3 parameters can vary according to the requirements of ballnuts 15E4 (FIG. 40E).

Referring now to FIG. 40I, flexure 15E12 can include, but is not limited to including, gearbox mounting cavities 15J1 and housing mounting cavities 15J6. PCB 15E7 (FIG. 40E) can be mounted upon flexure 15E12 at mounting cavities 15J5. Flexure 15E12 can include sensor indent 15J7 that can provide space for sensor 15E8-3 (FIG. 40E). Flexure 15E12 can include legs 15J8 that can flexibly couple flexure gearbox end 15J9 with flexure PCB mount end 15J10. Cut-outs 15J11 can control flexibility of flexure 15E12. Cavity 15J2 between surrounding legs 15J12/15J13 can accommodate ballnut 15E4 (FIG. 40E) and gooseneck arms 15E5 (FIG. 40E).

Referring now to FIG. 40J, tensioning assembly 15K1 can enable controlled movement of control cables 15K8 through lumen 15K5. The layout of tensioning assembly 15K1 upon cable drive capstan housing 15T1 can enable clear access through the pulley mesh and lumen 15K5 that can enable, for example, but not limited to, introduction and transit of an instrument through lumen 15K5. Tensioning assembly 15K1 can include, but is not limited to including, swing arms 15K4 that can enable tension to be supplied to cables 15K8 around capstan shafts 15K6, cable idler grooves 15K2, and cable take-up idlers 15K9. Cables 15K8 can terminate in capstan shafts 15K6. Pulley box drive shaft 15K21 can terminate flush with cable drive capstan housing 15T1. Spur gear 15Y5 (FIG. 40S) of pulley box drive shaft 15K21 can operably couple cable drive actuator modules 15K20 (FIG. 40L) to the cabling/pulley assembly through gear mesh with a gear (not shown) mounted upon capstan shaft 15K6 at shaft collar 15T10 (FIG. 40T). Cable drive actuator modules 15K20 (FIG. 40L) can propel control cables 15K8 within lumen 15K5. Cable drive capstan housing 15T1 can provide a mounting and coupling platform for the elements of tensioning assembly 15K1. Deployment cables 15K3 can be used for the deployment stage of flexure, allowing manual tensioning. Pulley box assembly 15K1 can include at least one pulley box drive shaft 15Y1 that can operably couple cable drive capstan housing 15T1 with cable drive assemblies 15W1 at cavity 15T2.

Referring now to FIG. 40K, cable drive actuator modules 15K20 can be operably coupled to cable drive capstan housing 15T1 through cable drive actuator plate 15W2.

Referring now to FIG. 40L-1, cable drive actuator module 15K20 can include cable drive actuator plate 15W2 and at least one cable drive assembly 15W1-1/15W1-2.

Referring now to FIG. 40L-2, cable drive assembly first configuration 15W1-1 can include, but is not limited to including, hollow shaft actuator 15W3-1 such as, for example, but not limited to, HARMONIC DRIVE® FHA-C size 11. Cable drive assembly first configuration 15W1-1 can include a frictional interface that can include the combination of harmonic drive output shaft 15W6/15W7, retaining ring 15W8, first harmonic drive output hub 15W4, and wave washer 15W5. Wave washer 15W5 can be positioned between first harmonic output drive 15W4 and harmonic drive output shaft 15W6 to provide spring action to reduce/avoid backlash. Retaining ring 15W8 can be positioned atop harmonic drive output shaft 15W6. Second harmonic drive output hub 15W9 can be mounted upon harmonic drive 15W3-1, optionally followed by first harmonic output drive 14W4, depending upon the shaft interconnection style. The frictional interface can be disposed within second harmonic drive output hub 15W9.

Referring now to FIG. 40M, lumen 15K5 can include, but is not limited to including, cable runs 15M1 that can house control cables 15K8, and cable accommodations 15M2 that can accommodate deployment cables 15K3.

Referring now to FIG. 40N, swing arm 15K4 can include, but is not limited to including, pivot pin cavity 15N1 that can enable rotation of swing arm 15K4. Swing arm 15K4 can include pulley cavities 15N2-1/15N2-2 that can each accommodate one of pulleys 15K9 (FIG. 40P). Control cables 15K8 (FIG. 40J) can thread through pulleys 15K9 (FIG. 40P) and can be tensioned by swing arm 15K4 when swing arm 15K4 rotates.

Referring now to FIG. 40O, capstan housing 15T1 can include drive shaft cavity 15T2 that can receive pulley box drive shaft 15 K21 (FIG. 40J). Capstan housing 15T1 can include first geometry 15T3 that can accommodate gear mesh, second geometry 15T4 that can accommodate lumen 15K5 (FIG. 40M), and third geometry 15T5 that can accommodate cable drive assemblies 15W1-1/15W1-2 (FIG. 40L-1).

Referring now to FIG. 40P, swing arm pulley 15K9 can include cable run 15U2 that can accommodate control cable 15K8 (FIG. 40J). In some configurations, one of swing arm pulleys 15K9 can be mounted in first pulley cavity 15N2-1 (FIG. 40N) in one of swing arms 15K4, and another of swing arm pulleys 15K9 can be mounted in second pulley cavity 15N2-2 (FIG. 40N) in another of swing arms 15K4.

Referring now to FIG. 40Q, pulley 15K2 can include cable runs 15V2/15V3 that can accommodate control cables 15K8 (FIG. 40J) along the path from lumen 15K5 (FIG. 40M) through swing arm pulleys 15K9 to capstan shaft 15K6 (FIG. 40T). Control cable 15K8 (FIG. 40J) can run through one of cable runs 15V2/15V3 depending on which of pulley cavities 15N2-1/15N2-2 (FIG. 40N) house swing arm pulleys 15K9 (FIG. 40P).

Referring now to FIG. 40R, pulley drive shaft bearing 15R1 can mount upon pulley box drive shaft 15K21 (FIG. 40S) and can couple pulley box drive shaft 15K21 (FIG. 40S) with cable drive actuator module 15K20 (FIG. 40L-1).

Referring now to FIG. 40S, pulley box drive shaft 15K21 can include housing shaft 15Y4 that can be received by capstan housing 15T1 (FIG. 40O) at drive shaft cavity 15T2 (FIG. 40O). Pulley box drive shaft 15K21 can include spur gear 15Y5 that can mesh with at least one gear mounted at shaft collar 15T10 (FIG. 40T) to drive the movement of control cables 15K8 (FIG. 40J). Pulley box drive shaft 15K21 can include drive key 15Y2 that can operably couple with shaft key 15W10 (FIG. 40L-2) to position pulley box drive shaft 15K21.

Referring now to FIG. 40T, capstan shaft 15K6 can include cable termination cavity 15Z2 that can house a termination point of control cable 15K8 (FIG. 40J). Control cable 15K8 (FIG. 40J) can traverse either or both of cable runs 15Z3/15Z4 on the way to termination point 15Z2.

Capstan shaft 15K6 can accommodate at least one gear at shaft collar 15T10, the gear being meshed with spur gear 15Y5 (FIG. 40S), the movement of which can be driven by harmonic drive assemblies 15W1-1/15W1-2 (FIG. 40L-2).

Referring now to FIGS. 40AA and 40BB, tensioning assembly second configuration 15AA1 can include the parts described herein with respect to tensioning assembly 15K1. Additionally, tensioning assembly 15AA1 can include cam 15AA2 that can enable reducing the tension on swing arms 15K4 (FIG. 40N) to accommodate placement of control cables 15K8. Tensioning assembly second configuration 15AA1 can include capstan housing second configuration 15AA3 that can enable a second configuration of pulley placement and cable routing geometry.

Referring now to FIG. 40CC, cam 15AA2 can include cam ears 15CC1-1/15CC1-2 that can, when oriented to be flush with swing arms 15K4 (FIG. 40AA), spread swing arms 15K4 (FIG. 40AA) to reduce the force on cables 15K8 (FIG. 40AA). Cam 15AA2 can include cam shaft 15CC2 that can be received by capstan housing second configuration 15AA3 (FIG. 40DD) at cavity 15DD1 (FIG. 40DD).

Figure 41:
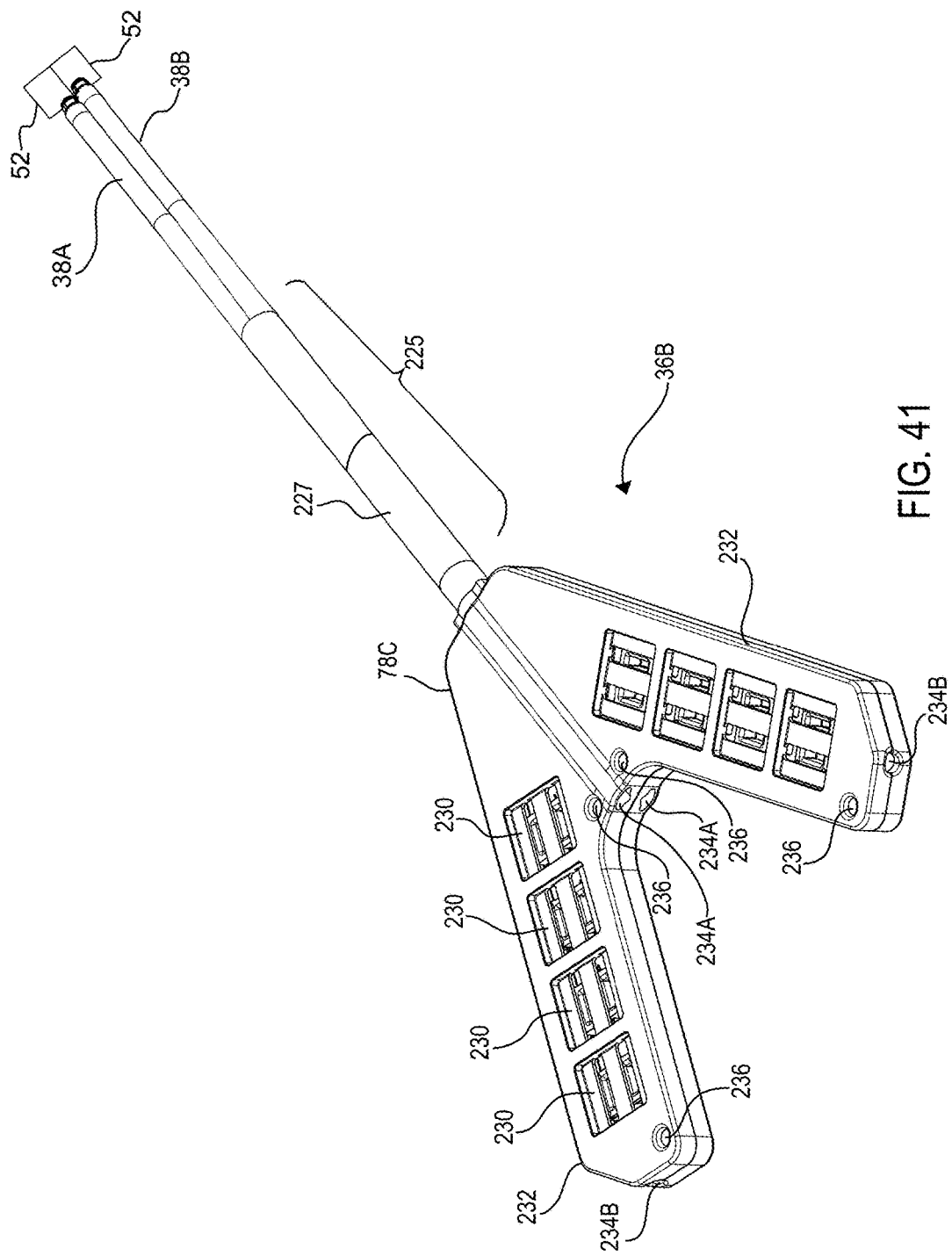
FIG. 41 is a schematic diagram of a bottom perspective view of a manipulator and a number of manipulated components of the present teachings.

Referring primarily to FIG. 41, a bottom perspective view of manipulator 36B and a number of manipulated components 38A, 38B are depicted. Manipulator 36B can include manipulator housing 78C which can include or be coupled to trocar 225 through which first manipulated component 38A and second manipulated component 38B and/or auxiliary components 20 (FIG. 1) may be introduced into patient 18 (FIG. 1). Outer conduit 227 of trocar 225 can cover the interior of trocar 225 that may house any number of interior lumens. Manipulator housing 78C can be, for example, but not limited to, "V" shaped and can include a number of fenestrations 230 in each arm 232 of the "V". Fenestrations 230 can allow for drive elements 60 (FIG. 16) to interface with driven elements 62 (FIG. 16) located in manipulator 36B. In other configurations, manipulator housing 78C may be any other shape. For example, manipulator housing 78C may be a thin box-like shape. In such configurations, fenestrations 230 may be organized into two parallel rows. Other configurations may have at least one manipulated component 38 or three or more manipulated components 38 and include a suitable number of fenestrations 230 for the number of manipulated components 38. For example, in a configuration with three manipulated components 38, manipulator housing 78C may be a thin box-like shape with three rows of fenestrations 230.

Still referring primarily to FIG. 41, a number of ports 234A, B can be included in manipulator housing 78C to insert surgical tools 52 or auxiliary components 20 (FIG. 1) into patient 18 (FIG. 1). In some configurations, ports 234A can extend to lumens within trocar 225. Ports 234B in the arms of the "V" of manipulator housing 78C can also extend into lumens in trocar 225. Ports 234A, B can allow for surgeon 22 (FIG. 1) to insert or remove any number of tools 52 in/out of patient 18 (FIG. 1) during a surgery. In some configurations, one of more of ports 234A or ports 234B may not be included. For instance, in some configurations, ports 234B may not included. In such configurations, surgical tool(s) 52 maneuvered about by manipulated component 38 may not be swappable during a surgery. Manipulator 36B could include pre-selected surgical tools 52 for a particular surgery already attached to manipulated components 38.

Still referring primarily to FIG. 41, manipulator 36B can also include a number of recesses 236 which can mate against drive component 34 (FIG. 16). Recesses 236 may serve as locating features to align with pins or other projections on drive component 34 (FIG. 16). Recesses 236 can help to ensure that manipulator 36B is properly installed onto drive component 34 (FIG. 16) during set-up. In some configurations, a latch or the equivalent may be included to retain manipulator 36B in place on drive component 34 (FIG. 16). Alternatively, interface structure 290 (FIG. 49) may be included between manipulator 36B and drive component 34 (FIG. 16).

Figure 42:
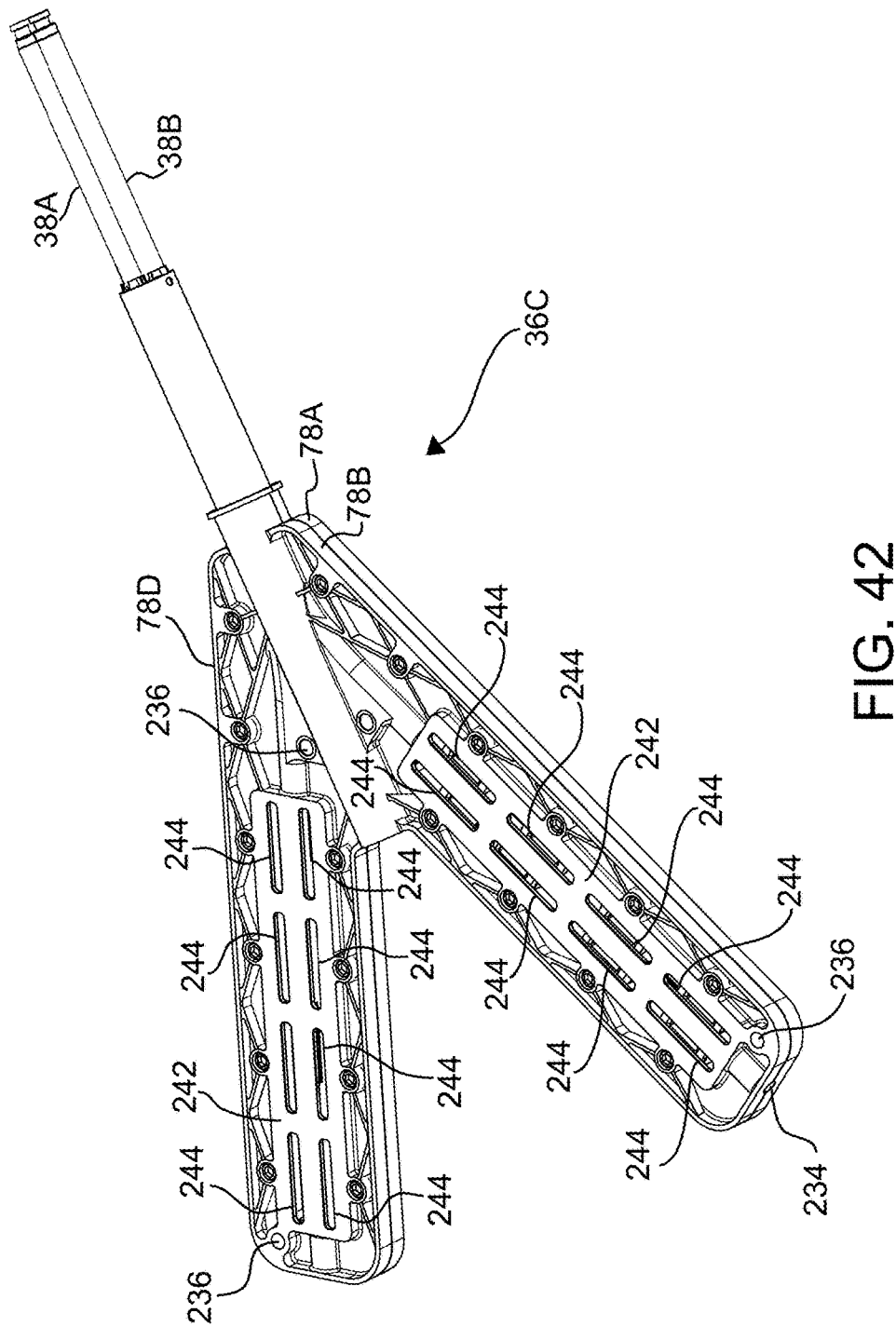
FIG. 42 is a schematic diagram of a manipulator housing shell capturing and retaining driven elements of the present teachings.

Referring now primarily to FIG. 42, manipulator housing 78D can be a shell which can capture and retain driven elements 62 (FIG. 16) of manipulator 36C. Manipulator housing 78D shell can provide the lumens for ports 234. Proximal ends of manipulated components 38A, 38B may be retained within manipulator housing 78D. Manipulator housing 78D can include, but is not limited to including, first housing piece 78A and second housing piece 78B which can be coupled together with a number of fasteners (not shown). Each of first housing piece 78A and second housing piece 78B may be identical for ease of manufacturing. Alternatively, first housing piece 78A and second housing piece 78B may differ. First housing piece 78A and second housing piece 78B may snap fit, friction fit, be bonded together, etc. to form manipulator housing 78D in various configurations. Additionally, in some configurations, manipulator housing 78D may be a clamshell which can hinge closed around the portions of manipulator 36C and/or manipulated components 38A, 38B housed within manipulator housing 78D. Manipulator housing 78D can be optimized for manufacture as a molded part.

Still referring primarily to FIG. 42, manipulator housing 78D can include slotted plateau structures 242. Slots 244 in slotted plateau structures 242 can be arranged in substantially parallel pairs and can allow drive elements 60 (FIG. 16) to interface with driven elements 62 (FIG. 16) housed within manipulator housing 78D. In some configurations, slotted plateau structures 242 may only be included on the side of manipulator housing 78D which is intended to be adjacent to drive component(s) 34 (FIG. 16).

Figure 43:
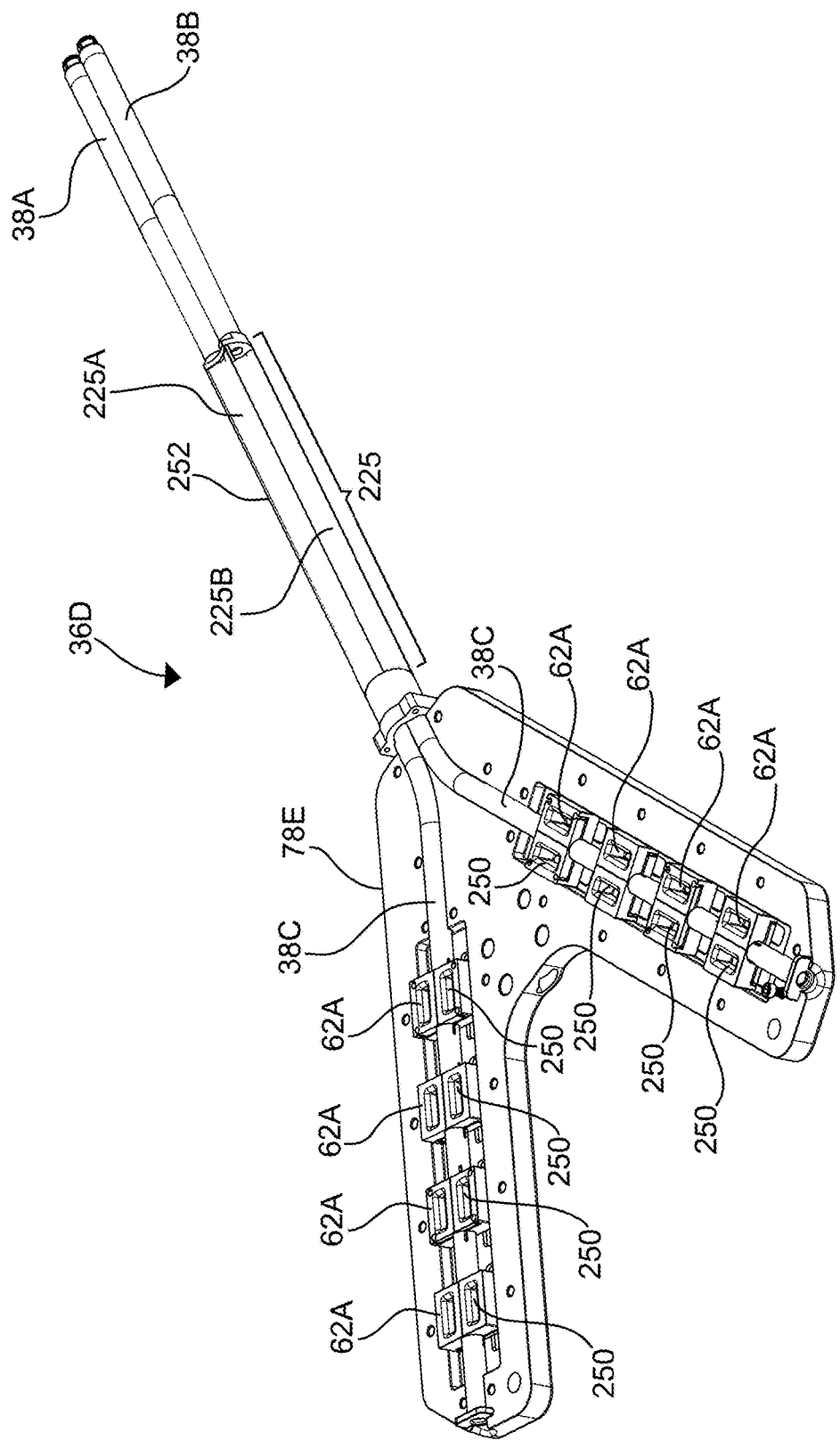
FIG. 43 is a schematic diagram of a portion of manipulator housing exposing driven elements of the present teachings.

Referring primarily to FIG. 43, a configuration of manipulator 36D is depicted. A portion of manipulator housing 78E is not shown in order to expose driven elements 62A. Driven elements 62A can be block-like structures, and the faces of driven elements 62A proximal to manipulated components 38A, 38B can be contoured to fit snuggly against first end 38C of manipulated components 38A, 38B. Driven elements 62A can include receiving structure 250 into which a portion of drive element 60 (FIG. 16) may be inserted. The form of receiving structure 250 may be chosen based upon the portion of drive element 60 (FIG. 16) which is intended to interface with driven element 62A. Receiving structure 250 can be, for example, but not limited to, a rectangular slot or socket into which drive element 60 (FIG. 16) can extend when manipulator 36D is in place on drive component 34 (FIG. 16).

Still referring primarily to FIG. 43, divider 252 can be included inside trocar 225. Outer conduit 227 (FIG. 41) of trocar 225 has been removed in FIG. 43 to expose divider 252. Multiple dividers 252 may be used in alternative configurations. Divider 252 can separate the interior of trocar 225 into a number of individual lumens, for example, but not limited to first lumen 225A and second lumen 225B. Each of the individual lumens may or may not be fluidically isolated from other lumens depending on the configuration. Divider 252 can have a cross-sectional shape selected, for example, to create a desired number of lumens and to define a cross-sectional shape for each lumen. In some configurations, divider 252 may be "X" shaped and may partially define first lumen 225A and an opposing lumen (not shown). Divider 252 may also partially define laterally disposed second lumen 225B and another lumen (not shown) opposite second lumen 225B. First lumen 225A and an opposing lumen may have a larger cross-sectional area than second lumen 225B and another laterally disposed lumen. The lateral lumens may be dedicated, for example, to manipulated components 38A, 38B.

Figure 44:
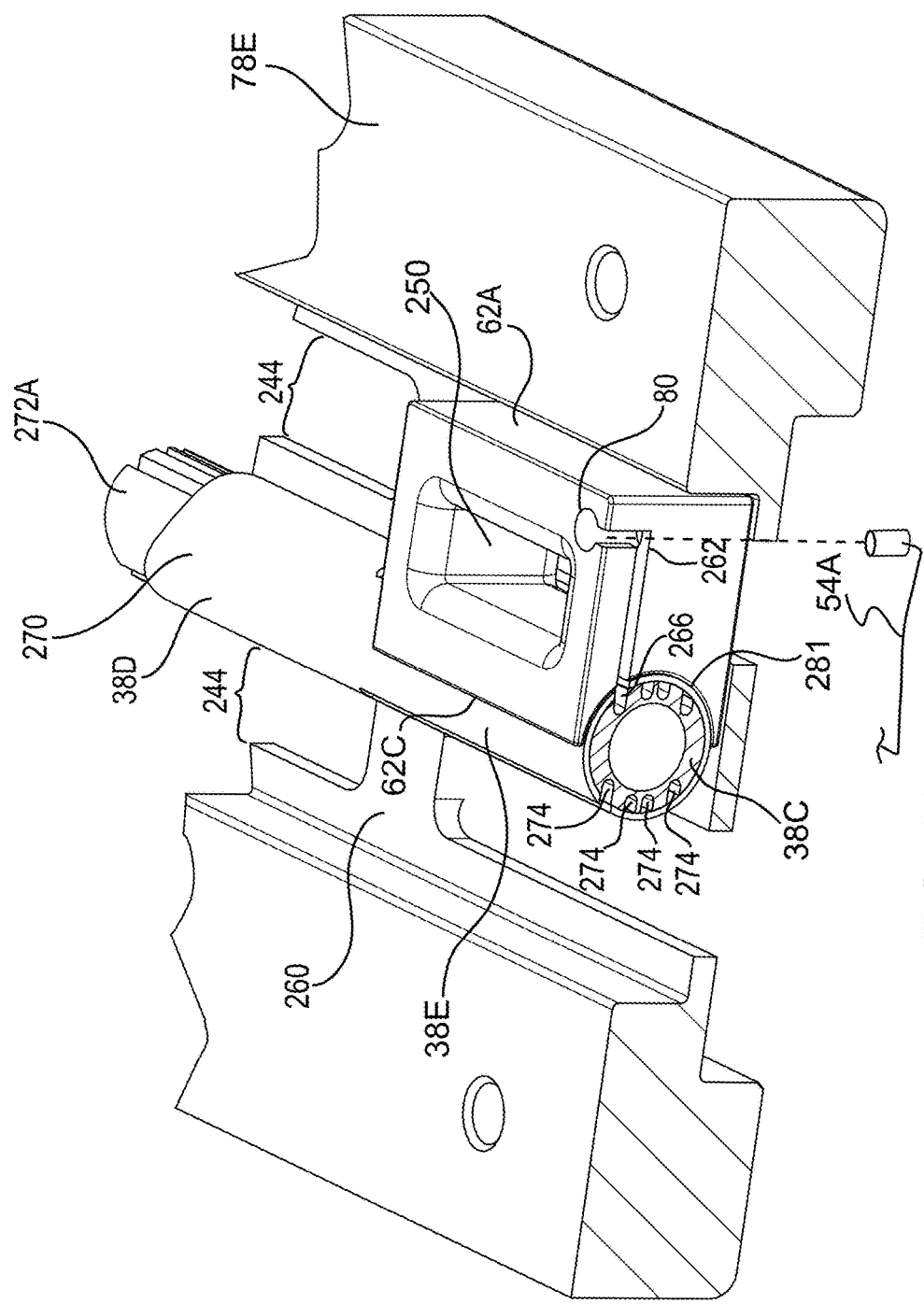
FIG. 44 is a schematic diagram of a driven element and a manipulated component of the present teachings.

Referring now to FIG. 44, an enlarged, detailed view of one of driven elements 62A and a portion of manipulator 36D is shown. Side 281 of driven element 62A adjacent to proximal end 38C of manipulated component 38D can be shaped such that side 281 can fit around and accommodate at least a portion of manipulated component 38D. Driven element 62A can fit, for example, in recess or trough 260 within manipulator housing 78E. When manipulator 36D is fully assembled, driven element 62A can be captured within manipulator housing 78E. In some configurations, driven element 62A may be captured between two pieces of manipulator housing 78E. Only one piece of the manipulator housing 78E is shown in FIG. 44. Receiving structures 250 of driven elements 62A can align with slots 244. Driven element 62A may be displaced within manipulator 36D. During displacement, driven element 62A may ride along bearings. For example, outer surface 270 of proximal end 38C of manipulated component 38D may serve as a bearing for driven element 62A. Recess or trough 260 in manipulator housing 78E may also serve as a bearing surface for driven element 62A. The bearings can, among other things, constrain driven element 62A from displacement in undesired degrees of freedom. In some configurations, driven element 62A may ride along a different number and/or type(s) of bearings. For example, in some configurations, one of a driven element 62A or a manipulated component 38D may include rails or a similar structure which can cooperate with a recessed track in the other of driven element 62A and manipulated component 38D. In some configurations, driven element 62A may not contact manipulator housing 78E. A rail or track may also be included on a portion of manipulator housing 78E such as trough 260.

Figure 46:
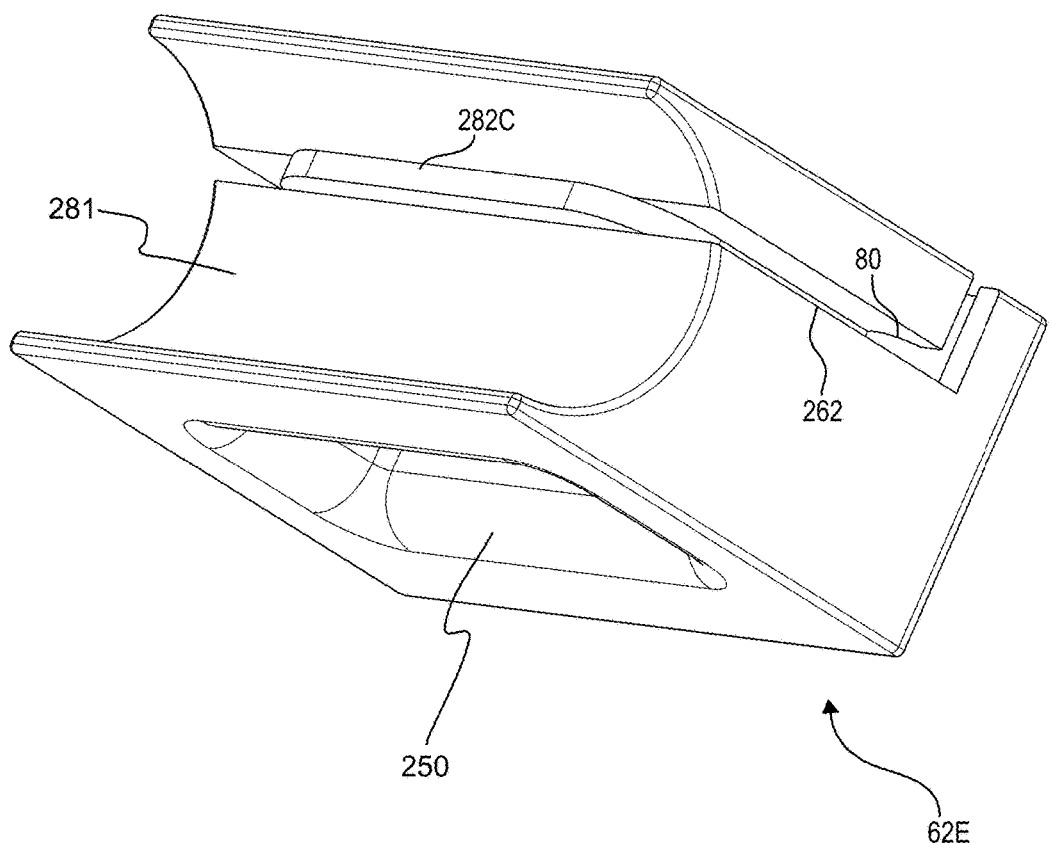
FIG. 46 is a schematic diagram of rails that extend from a face of the present teachings.

Continuing to refer primarily to FIG. 44, driven element 62A can include channel 262 which can lead to anchor point or anchor feature 80. Anchor point 80 can be, for example, but not limited to, a recess or well. Channel 262 can be cut into driven element 62 and anchor feature 80 may be recessed into the top face of driven element 62 in a position which can line up with cutout 266. Channel 262 can be, for example, but not limited to, located on the same horizontal or longitudinal plane as cutout 266. When assembled, anchor point 80 may anchor actuator 54A which may be a pull wire. Actuator 54A can extend from well/anchor point 80, through channel 262, and into cutout 266. Actuator 54A can run the length of manipulated component 38D until reaching the feature of manipulated component 38D which actuator 54A actuates. When driven element 62A is displaced, actuator 54A can pull on the actuated feature of manipulated component 38D or can be fed back into manipulated component 38D to control manipulated component 38D. Such an arrangement can allow for relatively simple control of manipulated component 38D in that a straight pull on actuator 54A can affect actuation of manipulated component 38D. This arrangement can simplify manufacture and can allow the system to operate predictably which can facilitate processor assisted control of manipulated component 38D. Cutouts 266 in outer surface 270 of manipulated component 38D may be used as the tracks for a rail such as rail 282B (FIG. 46). When driven element 62A displaces within manipulator 36D, rail 282B (FIG. 46) may travel along the length of and be guided by the walls of cutout 266.

Referring still primarily to FIG. 44, manipulated component 38D can include outer wall 270 which can define a conduit through which various utility components 54 (FIG. 4A) such as actuators 54A, surgical tools 52 (FIG. 4A), or auxiliary components 20 (FIG. 1) may extend. Routing insert 272A may be placed within manipulated component 38D and can extend along the length of manipulated component 38D. Routing insert 272A can abut the interior surface of manipulator sheath 38E leaving a lumen in the interior of manipulated component 38D. In other configurations, routing insert 272A may not be placed within manipulated component 38D but rather be an integral part of sheath 38E of manipulated component 38D. Routing insert 272A can include at least one routing channel 274 that can provide a pathway for actuators 54A. At least one routing channel 274 can be recessed into routing insert 272A, and can be sized to be only slightly larger, for example, but not limited to, 10-30% larger in diameter than actuator 54A which can extend along routing channel 274. Actuator 54A can be a wire or other element which may not be compressionally stiff along its longitudinal axis. If at least one routing channel 274 is only slightly larger than actuator 54A, the potential for actuator 54A to bunch and jam when letting out slack can be minimized if actuator 54A extends along routing channel 274. Dimensioning at least one routing channel 274 slightly larger than actuator 54A could allow actuator 54A to displace without excessive friction, possibly helping to ensure a smooth and predictable actuation. Actuator 54A may extend along and up to the entire length of routing channel 274. The point at which actuator 54A exits routing channel 274 can be in line with and very near anchor point 80. Since a number of pulleys or other routing elements external to manipulator 36D are not required, actuators 54A can be constrained within a controlled path for up to their entire length.

Figure 45:
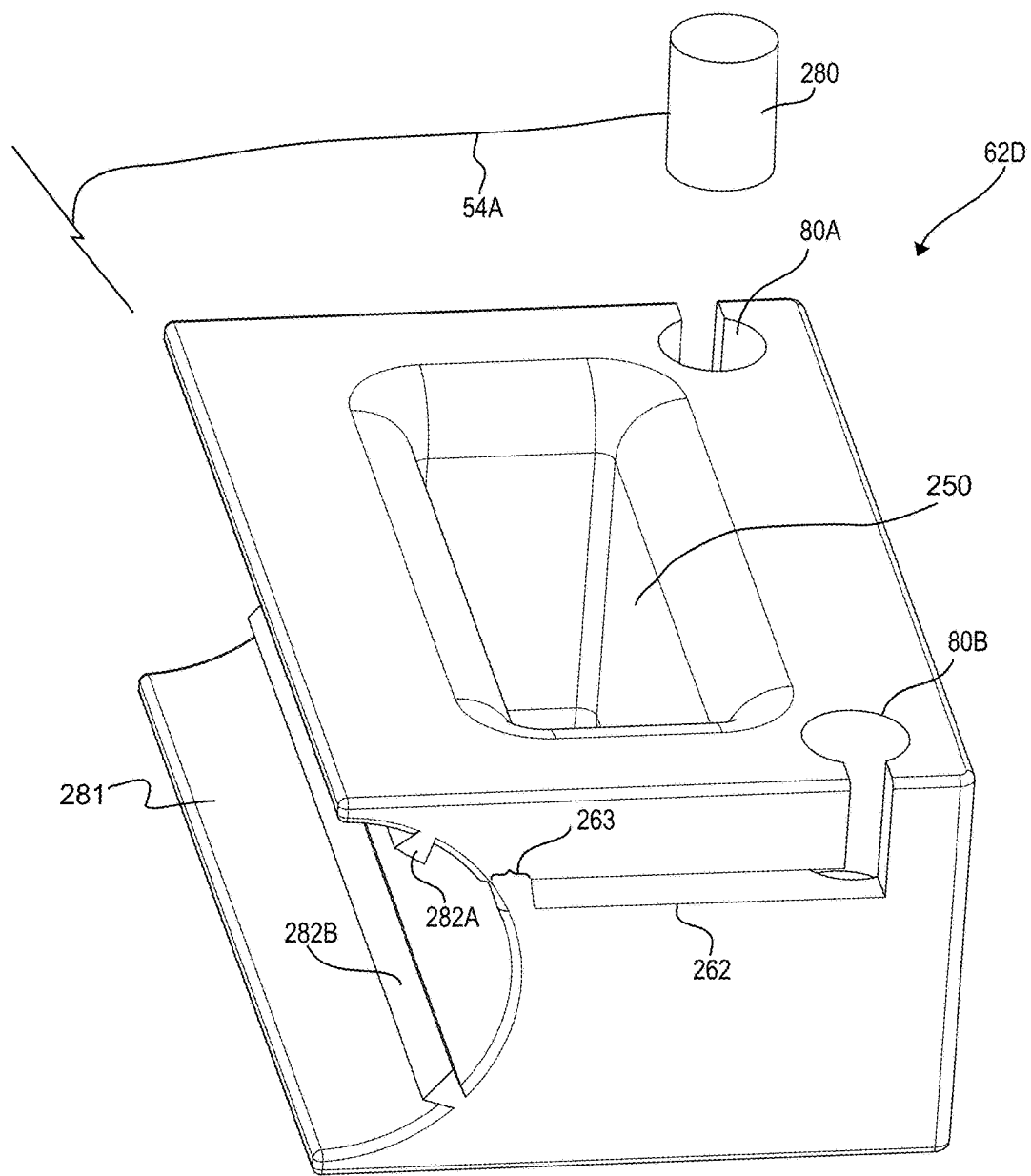
FIG. 45 is a schematic diagram of a driven element including anchor points of the present teachings.

Referring primarily to FIG. 45, driven element 62D can include first anchor point 80A and second anchor point 80B. Each of anchor points 80A, 80B may anchor separate actuators 54A. Actuator 54A can be terminated, for example, with crimp or bead 280 which can be, for example, but not limited to, sized such that it fits within one or both of anchor points 80A, 80B. Crimp or bead 280 may be glued or otherwise bonded into place. In configurations with two or more actuators 54A attached to driven element 62D, a piece of material may form bridge 263 over channel 262 leading to, for example, second anchor point 80B. Bridge 263 may be disposed proximal to the outer surface 270 (FIG. 44) of a manipulated component 38D (FIG. 44) when the device is fully assembled. Actuator 54A may be routed under bridge 263 to constrain actuator 54A such that it exits manipulated component 38D (FIG. 44) at a controlled angle. Driven element 62D can be used with a plurality of anchor points 80A, 80B even if actuator 54A is not anchored to each anchor point 80A, 80B. Thus the same mold can be used to fabricate driven element 62D for each side of manipulated component 38D (FIG. 44). Rails 282A, 282B can extend from face 281 of driven element 62D. Rails 282A and 282B may ride in tracks recessed into outer wall or surface 270 (FIG. 44) of manipulated component 38D (FIG. 44). Rails 282A, 282B can be, for example, but not limited to, dovetailed. Other types of rails 282A, 282B are possible.

Referring now to FIG. 46, shelf or blade like rail 282C is shown extending from face 281 of driven element 62E. Shelf like rail 282C may ride in a track recessed in outer surface 270 (FIG. 44) of manipulated component 38D (FIG. 44). In some configurations, shelf like rail 282C may ride within channel 262 in manipulator 36D (FIG. 44).

Figure 47:
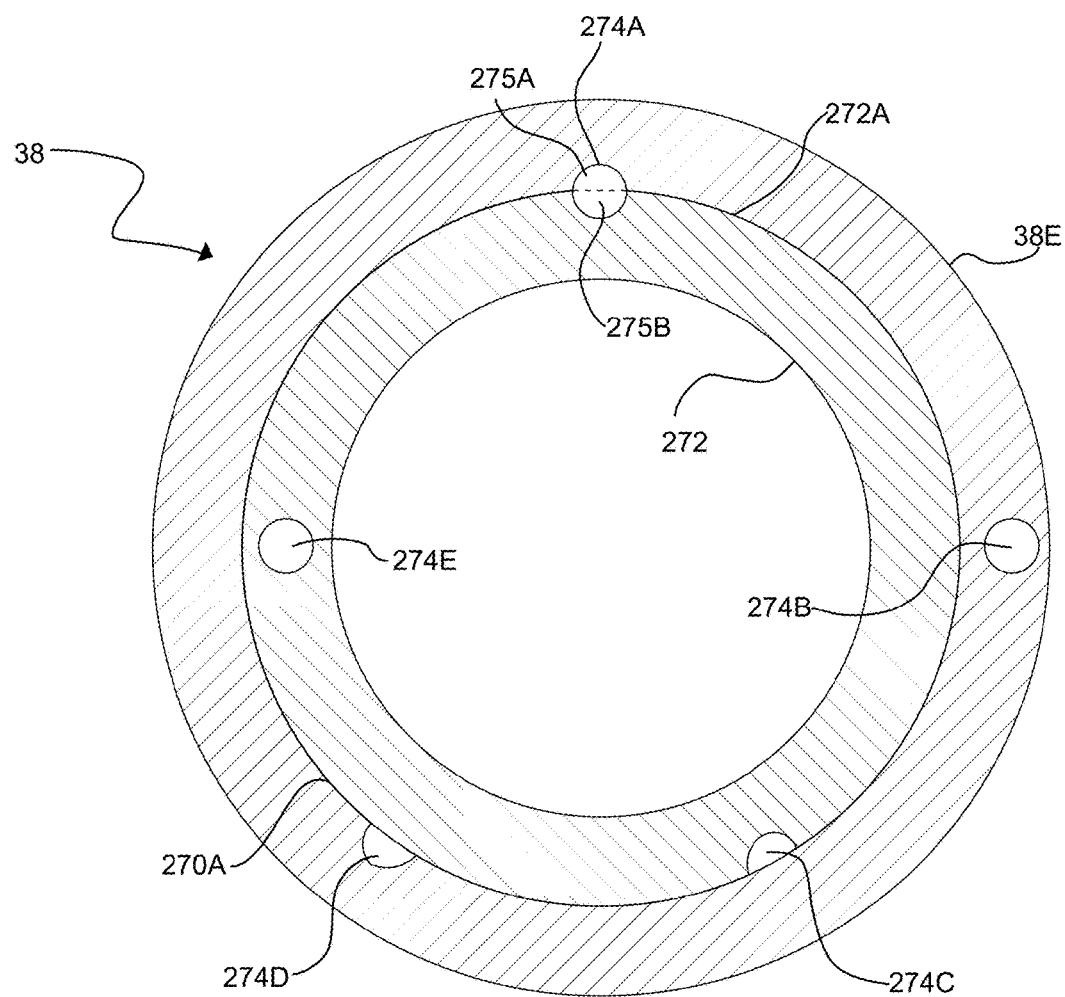
FIG. 47 is a pictorial representation of an outer wall and a routing insert having a number of different routing channels of the present teachings.

Referring primarily to FIG. 47, manipulator sheath 38E and routing insert 272A can include a number of different routing channels 274A-E. Any of routing channels 274A-E or a combination of routing channels 274A-E can be used. First routing channel 274A can have first portion 275A recessed into outer surface 272A of routing insert 272, and second portion 275B recessed into interior surface 270A of manipulator sheath 38E. Second routing channel 274B can be disposed entirely within the wall of manipulator sheath 38E. In some configurations, routing insert 272A may be omitted. Third routing channel 274C can be a trough which can be recessed into outer surface 272A of routing insert 272. Fourth routing channel 274D can be a trough recessed into interior surface 270A of the wall of manipulator sheath 38E. Third routing channel 274C and fourth routing channel 274D can be, for example, but not limited to, "U" shaped. Fifth routing channel 274E can be disposed entirely within routing insert 272A.

Figure 48:
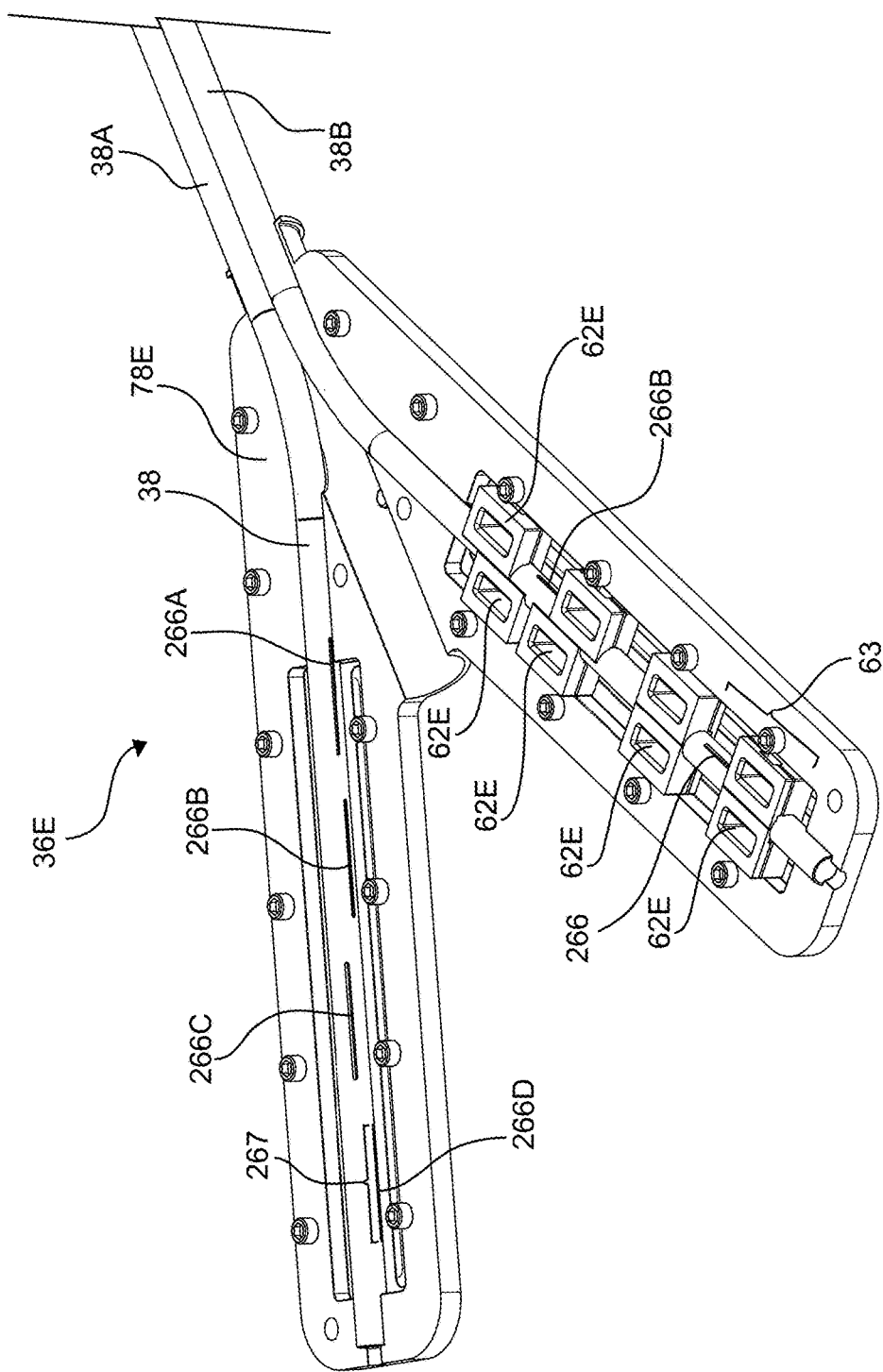
FIG. 48 is a schematic diagram of a manipulator including a manipulator housing and a number of driven elements of the present teachings.

Referring primarily to FIG. 48, manipulator 36E can include manipulator housing 78E and a number of driven elements 62E. Each of manipulated components 38A, 38B can include at least one cutout 266A, 266B, 266C, 266D. Actuators 54A (FIG. 44) such as wires may exit through cutouts 266A-D and may be anchored to driven element 62E. Cutouts 266A, 266B, 266C, 266D may be substantially parallel to one another and can be staggered on different planes. Cutouts 266A, 266B, 266C, 266D may correspond to the location of at least one routing channel 274 (FIG. 44). The number of cutouts 266A, 266B, 266C, 266D may correspond to the number of driven elements 62E which are used to actuate manipulated components 38A, 38B. Cutouts 266A, 266B, 266C, 266D can be substantially equal in cutout length 267, or cutout length 267 for each of cutouts 266A, 266B, 266C, 266D may differ. Cutout length 267 can define displacement range 63 of each driven element 62E. The exit point of actuator 54A (FIG. 44) from cutout 266A, 266B, 266C, 266D can change as driven element 62E is displaced during operation. Cutout length 267 can be chosen such that actuator 54A is able to exit cutout 266A, 266B, 266C, 266D into driven element 62E at any location along the travel path or displacement range 63 of the associated driven element 62E.

Figure 49:
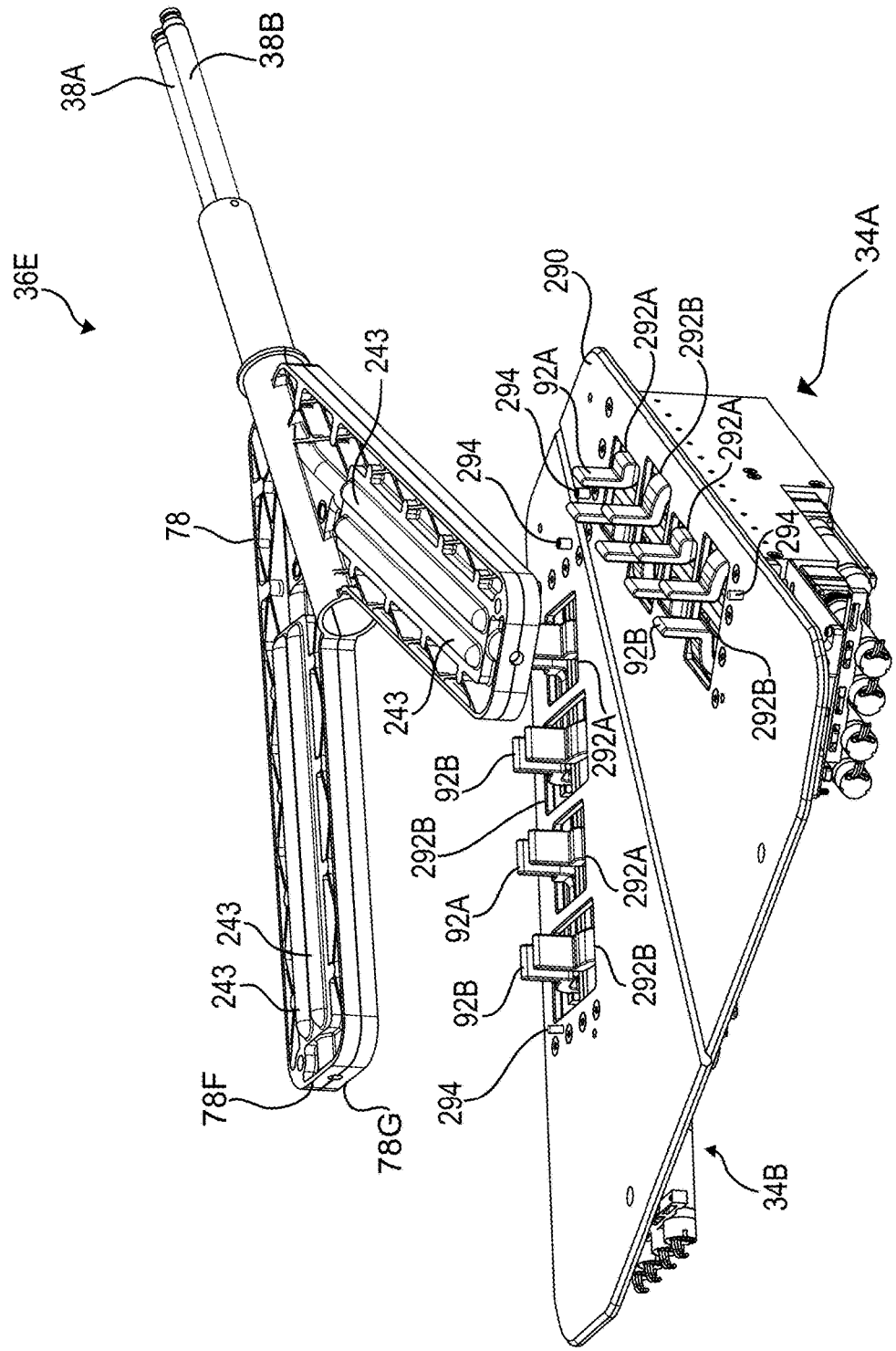
FIG. 49 is a schematic diagram of a manipulator and drive components aligned for operable engagement of the present teachings.

Referring primarily to FIG. 49, manipulator 36E, first drive component 34A and second drive component 34B can be aligned for operable engagement. Barrier 24 (FIG. 16), for example, but not limited to, a sterility barrier, may be placed between manipulator 36E and drive components 34A, 34B. First manipulator housing portion 78F can include anticline or arch structures 243 that can prevent ingress of fluid or detritus into manipulator housing 78 while still accommodating the protrusion of first projections 92A and second projections 92B into manipulator housing 78. Second manipulator housing portion 78G may be joined to first manipulator housing portion 78F to complete manipulator housing 78. Second manipulator housing portions 78G may, for example, include fenestrations 230 (FIG. 41) or slotted plateau features 242 (FIG. 42) to allow projections 92A, 92B of the drive components to enter manipulator 36E.

Still referring primarily to FIG. 49, interface plate 290, for example, but not limited to, a relatively planar, rigid element, can accommodate manipulator 36E and drive components 34A, 34B. Drive components 34A, 34B may be attached to interface plate 290 in any suitable manner. Projections 92A, 92B can extend through apertures 292A, 292B in interface plate 290. Interface plate 290 can include a number of locating projections 294 that can seat into recesses 236 (FIG. 41) of manipulator 36E.

Figure 50:
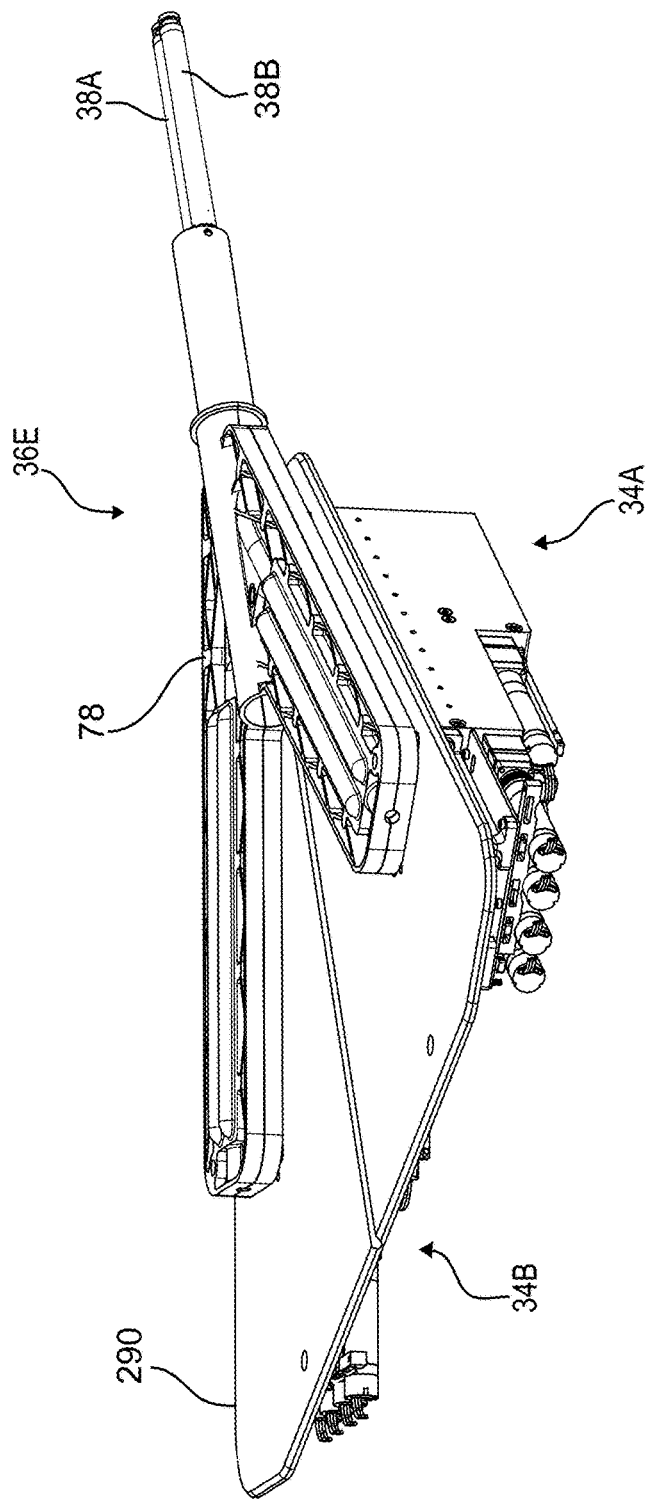
FIG. 50 is a schematic diagram of a manipulator seated onto an interface plate of the present teachings.
Figure 51:
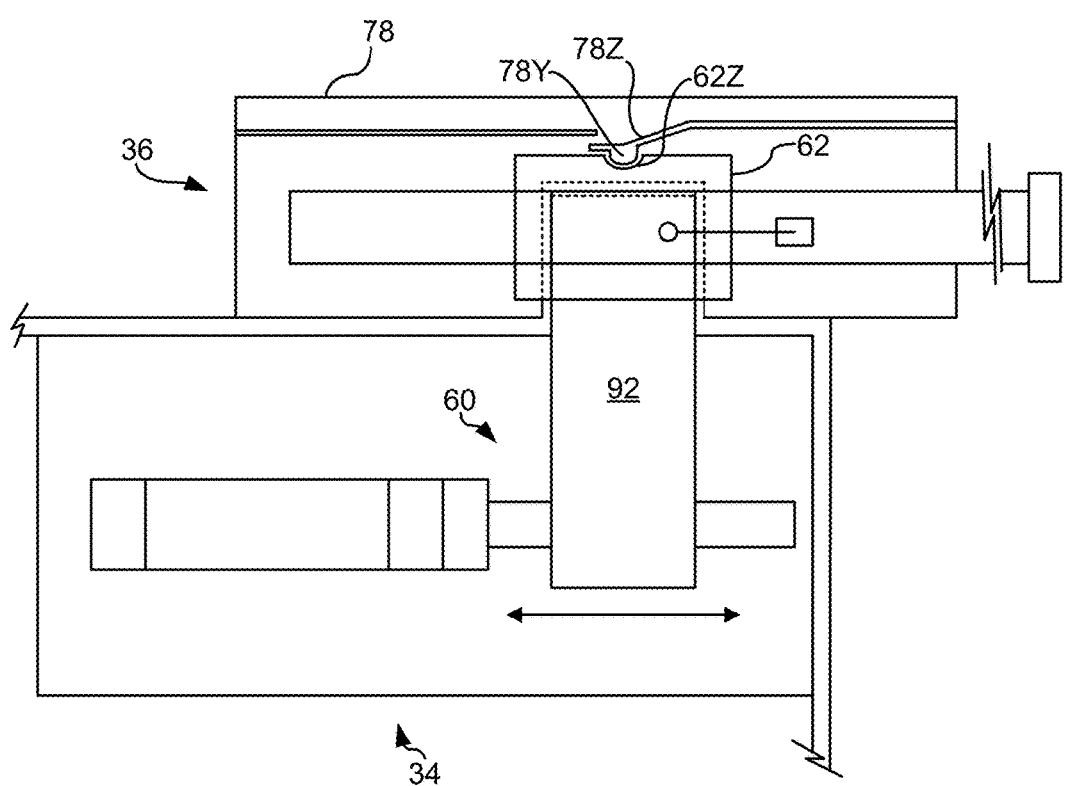
FIG. 51 is a schematic block diagram of a driven element held in a known position to facilitate docking of the manipulator of the present teachings.

Referring primarily to FIG. 50, when manipulator 36E is seated onto interface plate 290, projections 92A, 92B may extend into manipulator housing 78 and engage driven elements 62 (FIG. 51). Interface plate 290 may be omitted in some configurations. In configurations without interface plate 290, manipulator 36E may be attached or installed directly onto one or more drive component 34A, 34B.

Referring now to FIG. 51, driven element 62 may be held in a known position within manipulator 36 to facilitate docking of manipulator 36 onto drive component 34 during setup. The known position may also be referred to as a docking position. Constraining driven element 62 to a docking position may allow drive element 60 to be easily pre-aligned for engagement with driven element 62 upon docking of manipulator 36 to drive component 34. Drive component 34 may, for example, displace projection 92 to an engaging position which would align with the docking position of driven element 62. As manipulator 36 is docked onto drive component 34, projection 92 may engage with driven element 62 as a result of the pre-alignment. After manipulator 36 is docked and projection 92 and driven element 62 are engaged, the constraint holding driven element 62 in the docking position may be removed so that it does not further impede displacement of driven element 62. Any of a variety of different constraints may be used. The constraint may, in some configurations, be a mechanical interference which can contact part of driven element 62 and can prohibit movement of driven element 62 before engagement with drive component 34. After manipulator 36 and drive component 34 are engaged, the constraint may be locked into a stowed or non-interfering position. In some configurations, the displacement of driven element 62 by drive component 34 may provide the force which drives the constraint into the stowed position.

Continuing to refer to FIG. 51, driven element 62 may include detent 62Z. Detent 62Z may be engaged by projection 78Z included in manipulator 36 or manipulator housing 78. In some configurations, projection 78Z can include protuberance 78Y which can seat in detent 62Z. When projection 78Z is engaged in detent 62Z, projection 78Z may hold driven element 62 in a known or docking position. In some configurations, projection 78Z can be a beam which can be cantilevered to a portion of manipulator housing 78. Projection 78Z may be molded integrally with manipulator housing 78 such that it can extend away from a face of manipulator housing 78 and into detent 62Z. Alternatively, projection 78Z may be biased into detent 62Z with a bias member such as a torsion spring.

Figure 52:
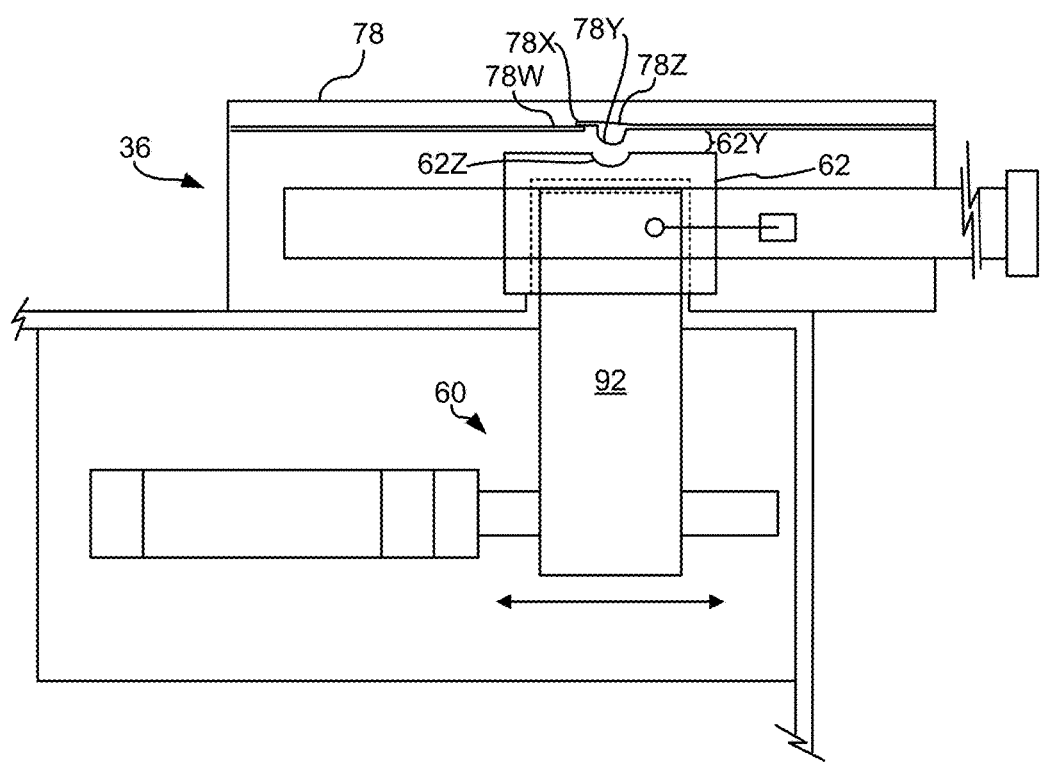
FIG. 52 is a schematic block diagram of a flange to hold the projection in the stowed position of the present teachings.

Referring now to FIG. 52, as drive element 60 displaces driven element 62, projection 78Z may be disengaged with detent 62Z. As projection 78Z is disengaged with detent 62Z, projection 78Z may be forced into and may be retained in a stowed position in which it is out of physical contact with driven element 62. In some configurations, there can be clearance 62Y between driven element 62 and manipulator housing 78. As projection 78Z is disengaged from detent 62Z, projection 78Z, protuberance 78Y may not fit within clearance 62Y and projection 78Z may be forced into a stowed position. Projection 78Z may include flange 78X which can hold projection 78Z in the stowed position once disengaged from detent 62Z. When driven element 62 is disengaged from projection 78Z, flange 78X may first abut and then bend around catch 78W to allow projection 78Z to reach the stowed position. In the stowed position, projection 78Z may be subjected to a restoring force which can urge projection 78Z towards driven element 62. The restoring force may result from bent projection 78Z attempting to restore to its original position or may be the result of a biasing member such as a torsion spring (not shown). Flange 78X may be strong enough to substantially resist deformation under the restoring force. That is, though flange 78X may deform slightly, it may not deform to an extent that it bends around catch 78W.

Figure 53:
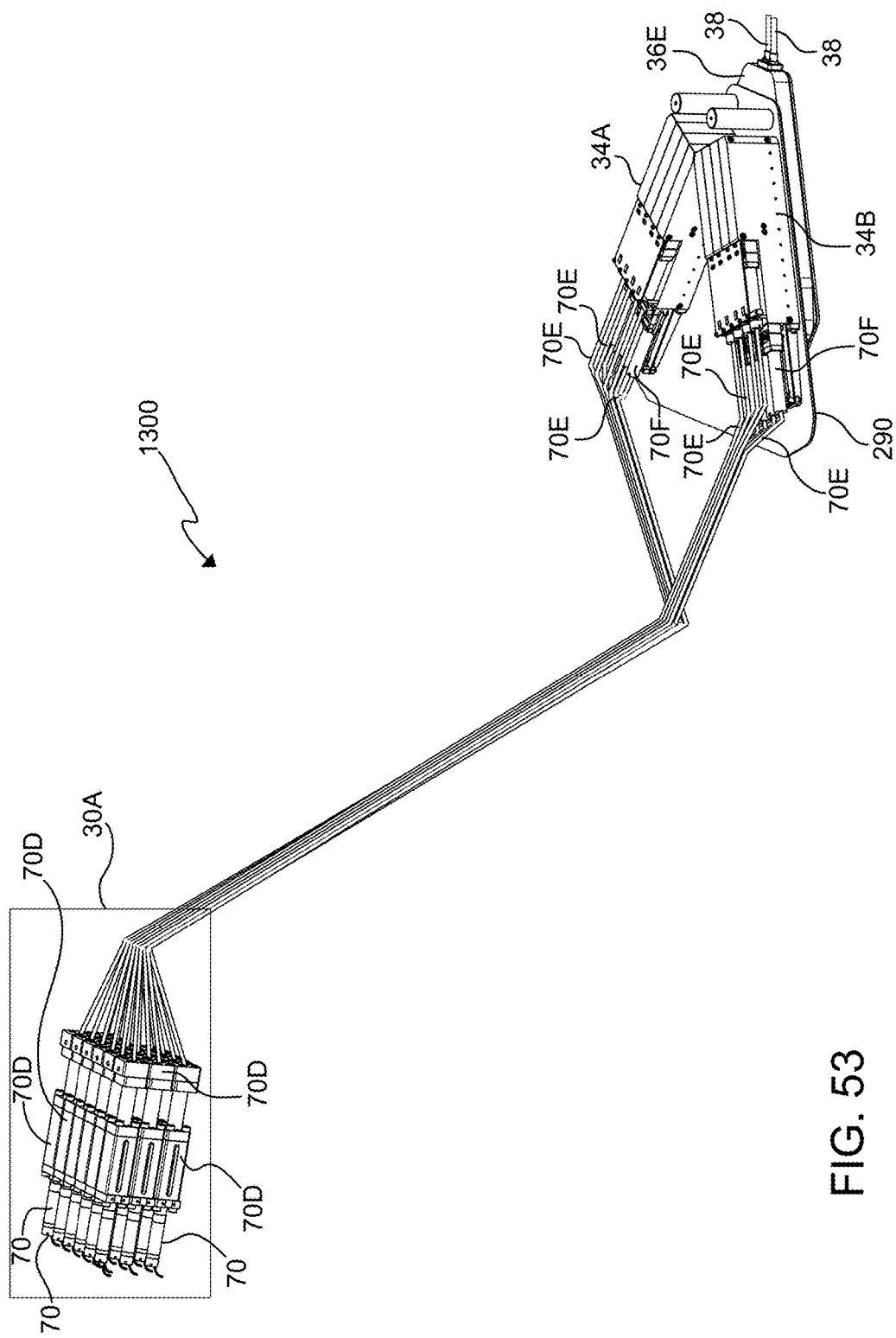
FIG. 53 is a schematic diagram of a hydraulically powered system of the present teachings.

Referring primarily to FIG. 53, hydraulically powered system 1300 can include, but is not limited to including, manipulator 36E, first drive component 34A, second drive component 34B, and interface plate 290. Barrier 24 (FIG. 17B) can also be included. Each of drive components 34A, 34B can be in communication with a number of hydraulic lines 70E. Hydraulic lines 70E can each be in operable communication with each of master cylinders 70D which can be driven by each of motor assemblies 70. When piston 70G (FIG. 17B) in master cylinder 70D is displaced by operation of motor assembly 70, slave piston 70H (FIG. 17B) in slave cylinder 70F can be displaced which can displace drive element 60 (FIG. 17B) in drive component 34A, 34B and driven element 62 (FIG. 17B). As a result, manipulated component 38 can be actuated. In some configurations of system 1300, motor assemblies 70 can be remote from drive components 34A, 34B, and drive components 34A, 34B can be made more compact. Further, in some configurations of system 1300, heat generated by drive component 34A, 34B can be mitigated. Motor assemblies 70 and master cylinders 70D can be located in remote enclosure 30A which may reside in any suitable location within surgical system 10 (FIG. 1). Hydraulic lines 70E may extend from remote enclosure 30A to drive components 34A, 34B. In some configurations, motor assemblies 70 and master cylinders 70D can be included within base 30 (FIG. 3) of surgical robot 16 (FIG. 3), and hydraulic lines 70E can extend along or within arm 32 (FIG. 3).

Figure 54:
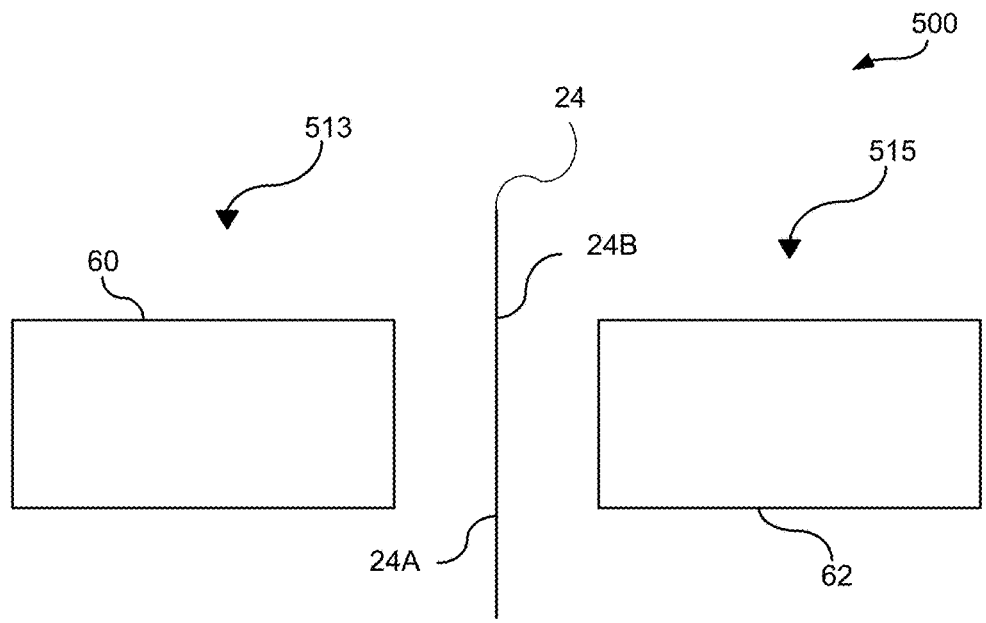
FIG. 54 is a schematic block diagram of a force transmission arrangement of the present teachings.

Referring now primarily to FIG. 54, transmission of force may be performed in a number of ways, for example, but not limited to, via linear or rotational displacement of a component in a first section which can cause displacement of a component in a second section. Generally, a surgical system may employ at least one apparatus comprising one or more shafts with two ends, such as manipulated components 38 (FIG. 16). A first end of manipulated component 38 (FIG. 16) may provide one or more end tools or end effectors which may be surgical tools 52 (FIG. 16). A second end of manipulator 38 (FIG. 16) may interface with a control system which can be configured to control manipulator 38 (FIG. 16) (either manually or with the assistance of a processor) and any end tool or tools 52 (FIG. 16) on the first end. The first end may be referred to herein as a distal end and the second end may be referred to herein as a proximal end. Manipulator 36 (FIG. 16) may be articulated or maneuverable due to plurality of joints provided in manipulator 36 (FIG. 16). Moreover, manipulator 36 (FIG. 16) may also serve as a lumen through which a target anatomical site may be accessed. Surgical instrument 52 (FIG. 16) and/or irrigation/insufflations fluid may be introduced to patient 18 (FIG. 1) via this lumen. Additionally or alternatively, the lumen may carry one or more utility components 54 (FIG. 16) (e.g. light, power, or data transmission components, mechanical control components, fluid conduits, etc. see FIG. 4A). In other configurations, surgical instrument or instruments 52 (FIG. 16) may be engaged at the distal end of manipulator 36 (FIG. 16). In some configurations, manipulator 38 may include a number of wire or cable actuators 54A (FIG. 4B) that may be configured to operate the end-tool or end-effecter 52 (FIG. 16) disposed at the distal end. Actuators 54A (FIG. 16) in manipulator 36 (FIG. 16) may be controlled with an electromechanical or electrohydraulic drive system in various configurations. During a surgical procedure, a portion of manipulator 36 (FIG. 16) and/or end-tool 52 (FIG. 16) may be completely or partially inserted into an anatomical cavity or orifice of patient 18 (FIG. 1).

Continuing to refer primarily to FIG. 54, surgical system 10 (FIG. 1) may include, but is not limited to including, barrier 24 configured to separate a first section of surgical system 10 (FIG. 1) from a second section. In some configurations, barrier 24 may serve as a sterility barrier and segregate non-sterile section 513 from sterile section 515. Location of sterility barrier 24 may differ depending on a surgical procedure, however, the primary purpose may remain the same (i.e. segregation of non-sterile section 513 from sterile section 515). In some configurations, barrier 24 may be placed at a location where a disposable portion of surgical system 10 (FIG. 1) may be attached to a durable portion of surgical system 10 (FIG. 1). Force may be transmitted across barrier 24 from the durable portion to the disposable portion to control components in the disposable portion. Non-sterile section 513 may include a durable portion of system 10 (FIG. 1) which may be used for a number of surgical procedures without requiring a sterilization process such as autoclaving. Non-sterile section 513 may include, for example, but not limited to, components such as electromechanical or electrohydraulic drive components, processing components, other electronic components, a user interface, etc. Sterile section 515 may include, for example, but not limited to, a disposable portion of system 10 (FIG. 1) which may require replacement or sterilization at the end of a surgery.

Continuing to still further refer primarily to FIG. 54, alternatively, barrier 24 may be disposed in a location where actuator 54A (FIG. 16) (which may also be used as a connector) may be configured to engage with end tool 52 (FIG. 16) or an end effecter. The engagement of actuator 54A (FIG. 16) and end-tool 52 (FIG. 16) may be provided at one of the first or second end of manipulated component 38 (FIG. 16). In other configurations, barrier 24 may be disposed at any location towards the distal end of actuator 54A (FIG. 16). Location of barrier 24 may also be chosen based on which components of surgical system 10 (FIG. 1) may be easily sterilized or replaced after one or a limited number of uses and those which are more difficult to replace and sterilize.

Continuing to refer to FIG. 54, barrier 24 may maintain its integrity as force is transmitted from first barrier side 24A to second barrier side 24B. In some configurations, barrier 24 may be, for example, but not limited to, a single continuous blanket, drape, or curtain of material. In other configurations, barrier 24 may be segmented while being functionally equivalent to a single continuous blanket or drape. Barrier 24 may be made of flexible film which may be pliable, durable, wear resistant, impermeable, and light weight. In some configurations, barrier 24 may be composed of a multiple layers of the same or different material. Materials which may be used for barrier 24 can include, but are not limited to, polyurethane. At least a part of barrier 24 may include a coating or material containing an anti microbial agent and/or the barrier 24 may be provided in a sterile package.

Continuing to refer to FIG. 54, in some configurations barrier 24 may not require any tailoring or modification for transmission of force across it. In some configurations, barrier 24 may provide one or more pockets which may accept and/or may be draped over a component on one side of barrier 24. In some configurations, barrier 24 may be configured to undergo modification or may include integral or attached elements in order to complement and facilitate transmission of force using a specific mechanism. Such modification may include, but is not limited to including, fixedly attaching or integrally forming an element with barrier 24 during manufacture. Such an element may be attached to barrier 24 in a manner which can maintain the integrity of barrier 24. That is, after attachment of the element, there may be no gap or other pathway in barrier 24 providing communication from one side of barrier 24 to the other. An element may be attached to barrier 24 in any of a variety of suitable manners. For example, in some configurations, barrier 24 and at least a portion of the element may be made of similar materials which may be ultrasonically welded to one another. Barrier 24 and the element may be laser welded together. Barrier 24 and the element may be solvent bonded together. The element may be attached to barrier 24 with an adhesive. Barrier 24 and the element may be formed integrally with one another during manufacture. In some configurations, the element may be over-molded onto barrier 24. Any other suitable attachment method may also be used. The element may be a built-in bridging element which may be surrounded by a flexible membrane or diaphragm. The bridging element may be configured to engage with one or more components in non-sterile section 513 and/or with one or more components on sterile section 515.

Continuing to refer primarily to FIG. 54, sterile section 515 may include end-tool 52 (FIG. 16) or the end-effecter that may be configured to perform surgical tasks during a surgical procedure. In some configurations, movement of end-tool 52 (FIG. 16) may be governed by a drive system which may be manually operated or controlled by or with assistance of at least one processor. A first set of components which may be configured to direct the surgical procedure may be collectively referred to as drive element 60. Correspondingly, a second set of components which may be configured to be driven automatically, manually, or automatically assisted may be referred to as driven element 62. Drive element 60 may be disposed completely or partially in non-sterilized section 513 and driven element 62 may be disposed completely or partially in sterile section 515 of surgical system 10 (FIG. 1). In some configurations, drive element 60 may operate one or more driven elements 62. Alternatively, single drive element 60 may operate a corresponding driven element 62. Surgical system 10 (FIG. 1) may include a plurality of drive elements 60 and a plurality associated driven elements 62.

Continuing to refer to FIG. 54, drive element 60 and driven element 62 may be arranged to transmit force across barrier 24 with or without physically contacting barrier 24. In other configurations, force may be transmitted across barrier 24 with only one of drive element 60 and driven element 62 in contact with barrier 24. Irrespective of the manner in which barrier 24 interacts with drive element 60 and driven element 62, barrier 24 can retain its integrity as force is transmitted from one side of barrier 24 to the other. The durable components, which may be in non-sterile section 513, may be substantially responsible for directing and controlling aspects of the surgical procedure. For example, the durable components may guide one or more end-tool 52 (FIG. 16) or end-effecter to perform a desired surgical task. Drive element 60 may be included as one of the durable components. One or more of the disposable components, which may be in sterile section 515, may be employed to perform the desired surgical procedure at the target anatomical location. At least a part (e.g. surgical tool 52 (FIG. 16)) of the disposable components, which may be in sterile section 515, may be may be replaced or swapped during a surgery if desired. Driven element 62 may be included as a disposable component.

Continuing to refer to FIG. 54, drive element 60 may be configured to translationally or rotationally displace to cause a transmission of force through barrier 24 to driven element 62. In some configurations, barrier 24 may be partially or completely stationary as a pre-determined force or torque is passed across barrier 24. Though in some configurations barrier 24 may displace, displacement of barrier 24 need not be the primary means by which force is transmitted across barrier 24. A principal function of barrier 24 may be to segregate non-sterilized section 513 from sterile section 515. In some configurations, a plurality of pairs of drive elements 60 and driven elements 62 may be engaged with single barrier 24 at a number of locations on barrier 24. Barrier 24 may be positioned and in some configurations trapped between drive element 60 and driven element 62. In some configurations, a part of drive element 60 may be disposed adjacent to first barrier side 24A of barrier 24 on the non-sterilized side or section 513. A part of cooperating driven element 62 may be disposed adjacent to second barrier side 24B of barrier 24 on sterile side or section 515. Such arrangement may provide a range of mechanisms for force transfer interaction among drive element 60, barrier 24, and driven element 62. One of the force transfer interaction mechanisms may demand a physical contact or engagement of drive element 60 and/or driven element 62 with barrier 24. Another force transfer interaction mechanism may not require a physical contact of part of drive element 60 and part of driven element 62 with barrier 24.

Figure 55:
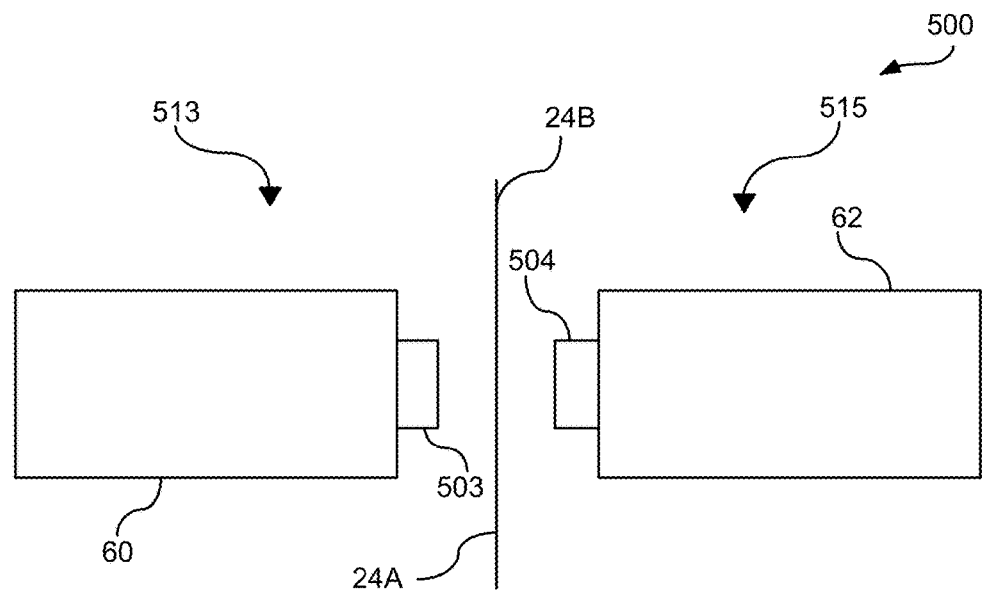
FIG. 55 is a schematic block diagram of another force transmission arrangement of the present teachings.

Referring primarily to FIG. 55, a representational view of force transmission arrangement 500 including drive element 60, barrier 24, and driven element 62 is depicted. Barrier 24 may be disposed at an intermediary location between drive element 60 and driven element 62. Barrier 24 may further include first barrier side 24A and second barrier side 24B. First barrier side 24A may serve as a first barrier interfacing surface on non-sterilized side 513 of surgical system 10 (FIG. 1). Second barrier side 24B may serve as a second barrier interfacing surface on sterile side 515 of surgical system 10 (FIG. 1). Barrier 24 may be large enough to accommodate a plurality of drive element 60 and driven element 62 pairs, and barrier sides 24A, 24B may provide multiple sites where these pairs may transmit force across barrier 24. In some configurations, the site of interaction on first barrier side 24A may be directly opposite the site of interaction with second barrier side 24B for a given drive element 60 and driven element 62 pair. In other configurations, the site of interaction on first barrier side 24A may not be directly opposite the site of interaction on second barrier side 24B. Non-sterilized side 513 can also include first part 503 of drive element 60 which may be configured to wholly or partially interact with barrier 24. First part 503 may also be referred to herein as first barrier interfacing part 503. In some configurations, drive element 60 may include more than one first barrier interfacing part 503. Drive element 60 may be displaced by, for example, but not limited to, an electromechanical or electrohydraulic assembly which can exert a force on drive element 60. Sterilized side 515 may also include second part 504 on driven element 62 which may receive the force transmitted from first barrier interfacing part 503. Second part 504 may also be referred to herein as second barrier interfacing part 504 and may be disposed on sterilized side 515 of surgical system 10 (FIG. 1). First barrier interfacing part 503 in conjunction with second barrier interfacing part 504 may accomplish transmission of force across barrier 24 as drive element 60 is displaced.

Continuing to refer to FIG. 55, first barrier interfacing part 503 may be positioned to interact with first barrier side 24A of barrier 24. Second barrier interface part 504 may be positioned to interact with second barrier side 24B of barrier 24. A mechanism and extent to which first barrier interfacing part 503 interacts with first barrier side 24A may be similar or different from the mechanism and extent to which second barrier interfacing part 504 interacts with second barrier side 24B of barrier 24. In some configurations, a first mechanism for engagement between first barrier interfacing part 503 and first barrier side 24A may be configured to complement a second mechanism for engagement between second barrier interfacing part 504 and second barrier side 24B.

Figure 56A:
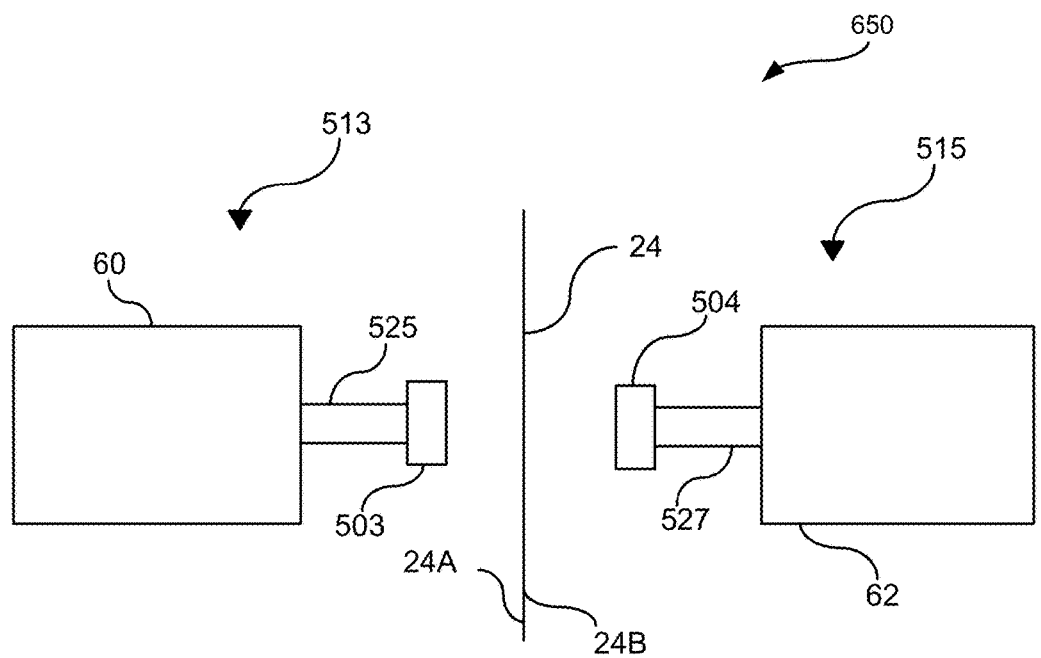
FIG. 56A is a schematic block diagram of yet another force transmission arrangement of the present teachings.

Referring primarily to FIG. 56A, force transmission arrangement 650 can include drive element 60 which may be in communication with first barrier interfacing part 503 via first force carrier 525, and driven element 62 may be in communication with second barrier interfacing part 504 via second force carrier 527. Force carriers 525, 527 may be any linking component(s) capable of transmitting and/or receiving force including, but not limited to, a solid or hollow shaft, drive shaft, piston shaft, a tube or lumen including one or more actuators 54A (FIG. 16) (e.g. cables) that may operate in tandem with or independent of each other, a housing including actuators 54A (FIG. 16) configured to operate on first barrier interfacing part 503 and/or second barrier interfacing part 504, a gear train, or any suitable combination thereof. In other configurations, force carriers 525, 527 may be configured to increase or reduce the force transmitted to and/or received by them from drive element 60 and driven element 62, respectively.

Figure 56B:
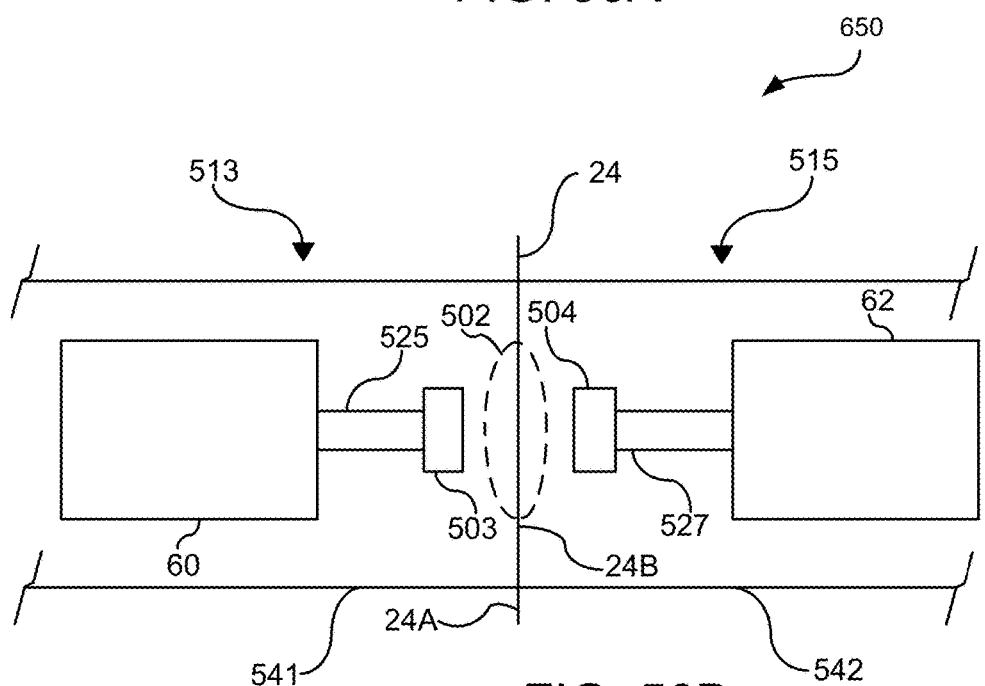
FIG. 56B is a schematic block diagram the housings of the surgical system of the present teachings.

Referring now to FIG. 56B, first housing 541 may be provided on non-sterilized side 513 and second housing 542 may be provided on sterile side 515 of surgical system 10 (FIG. 1). Drive element 60 may be at least partially disposed in first housing 541 and driven element 62 may be at least partially disposed in the second housing 542. Transmission of force across barrier 24 may occur with a portion of drive element 60 and a portion of driven element 62 in physical contact with barrier 24 and/or an element in barrier 24. Such an arrangement may be referred to as a contact mode for force transmission. In other configurations, only one or neither of drive element 60 and driven element 62 may contact barrier 24 or an element in barrier 24. In an arrangement where neither of drive element 60 and driven element 62 contacts barrier 24, force may be transmitted across barrier 24 in a contact-free mode. Irrespective of the mode used for force transmission, barrier 24 may be at least partially disposed or held/trapped between the first housing 541 and second housing 542. Housings 541, 542 may couple together across barrier 24 and consequently trap barrier 24. Housings 541, 542 may house various other components of surgical system 10 (FIG. 1). For example, first housing 541 may house, for example, but not limited to, electromechanical or electrohydraulic components of system 10 (FIG. 1). Second housing 542 may at least partially house manipulated component 38 (FIG. 16). In some configurations, a plurality of drive elements 60 and first barrier interfacing parts 503 may be disposed in first housing 541. The plurality of drive elements 60 and first barrier interfacing parts 503 in first housing 541 may interact with a plurality of driven elements 62 and second barrier interfacing parts 504 in second housing 542.

Figure 57:
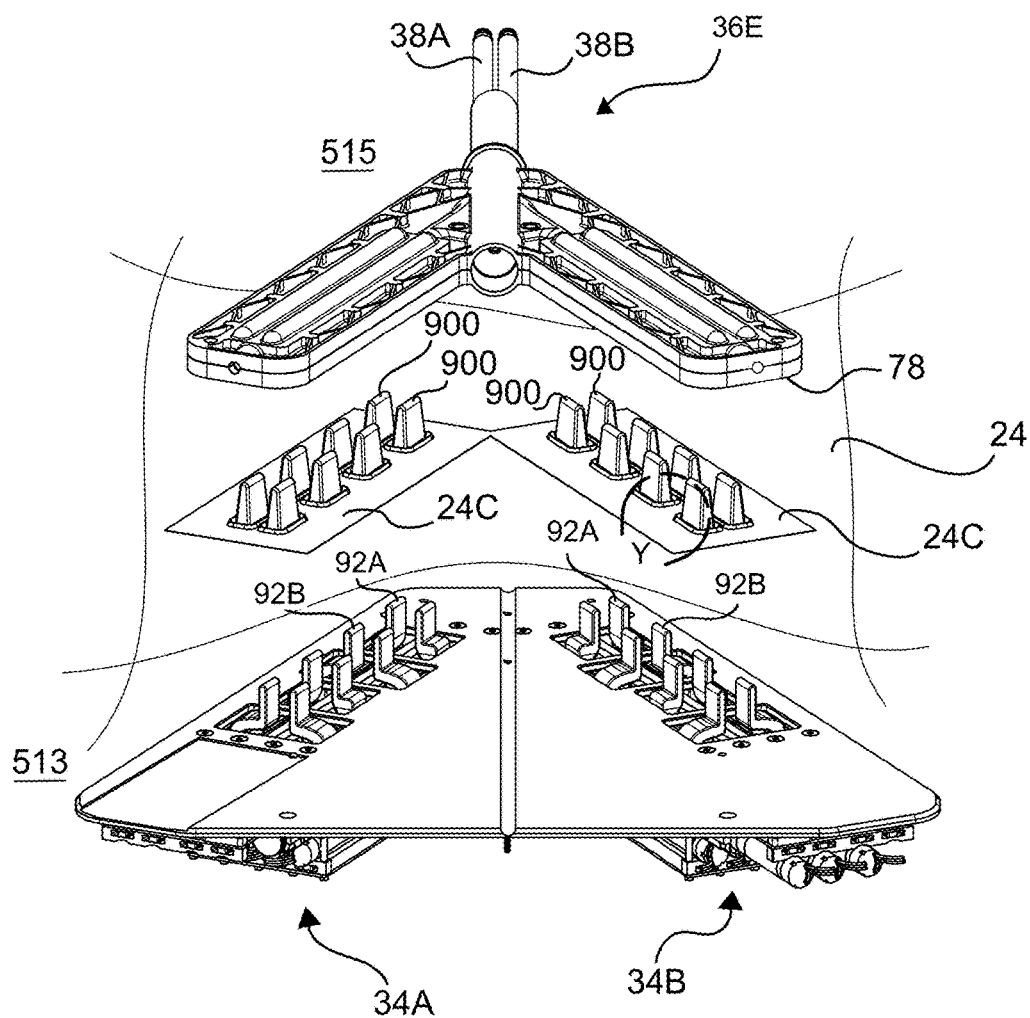
FIG. 57 is an exploded view of an example of a contact arrangement for force transmission of the present teachings.

Referring now to FIG. 57, a contact arrangement for force transmission can include, but is not limited to including, manipulator 36E, interface plate 290, first drive component 34A and second drive component 34B. Drive components 34A, 34B may include a number of drive elements 60 (FIG. 16) which can be operated to displace projections 92A, 92B. In some configurations, projections 92A, 92B can be analogous to first barrier interfacing parts 503 (FIG. 56A). When manipulator 36E is docked on interface plate 290, projections 92A, 92B of drive components 34A, 34B may extend through manipulator housing 78 and into corresponding driven elements 62 (FIG. 16) which may act as second barrier interfacing parts 504 (FIG. 56A). Linear displacement of projections 92A, 92B can cause linear displacement of driven elements 62. The displacement may actuate a feature of manipulated component 38A, 38B and may be transmitted down a force carrier such as actuator 54A (FIG. 16).

Continuing to refer to FIG. 57, barrier 24 can segregate manipulator 36E from drive components 34A, 34B and interface plate 290. Barrier 24 may be a sterility barrier which can separate manipulator 36E on sterile side 515 and drive components 34A, 34B on non-sterile side 513. Barrier 24 can be captured between manipulator 36E and drive components 34A, 34B when manipulator 36E is docked on interface plate 290. Barrier 24 can include pocketed region 24C for each drive component 34A, 34B. Pocketed region 24C may be an integral part of barrier 24 or may be attached to barrier 24 by any suitable means, for example, but not limited to, solvent bond, over mold, and ultrasonic weld. Pocketed region 24C may include a number of pockets 900 which can be shaped to receive projections 92A, 92B. Each of pockets 900 may extend into manipulator 36E and may, for example, project into receiving structure 250 (FIG. 43) of driven element 62 (FIG. 16).

Figure 58:
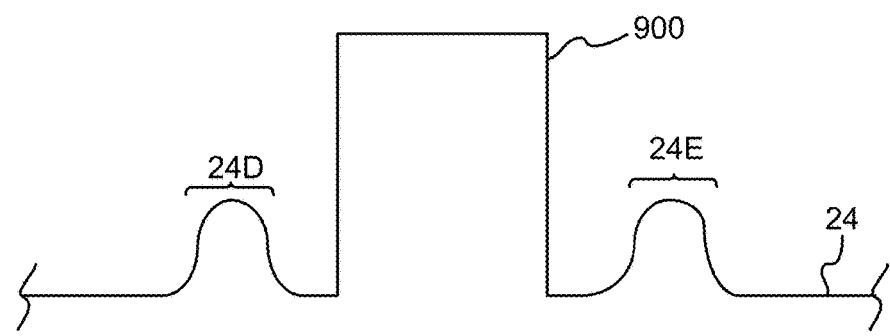
FIG. 58 is a representational view of allowing for linear displacement of the projections of the present teachings.

Referring now primarily to FIG. 58, to allow for linear displacement of the projections 92A, 92B (FIG. 57) and consequent displacement of their respective driven elements 62 (FIG. 16), barrier 24 may include a number of variable regions which can provide for displacement of associated pocket 900. The variable regions may, for example, be made of a stretchable material or may be bellows like. The variable regions may be pleated segments 24D, 24E of barrier 24 (FIG. 57). Pleated segments 24D, 24E may flank or encompass pocket 900 in barrier 24 allowing pocket 900 to be displaced. The amount of displacement may be dependent on the surface area of the pleats in pleated segment 24D, 24E. As pocket 900 displaces in a direction, pleated segment 24D, for example, may become folded or compacted while pleated segment 24E may flatten out in order to allow pocket 900 to displace.

Figure 59:
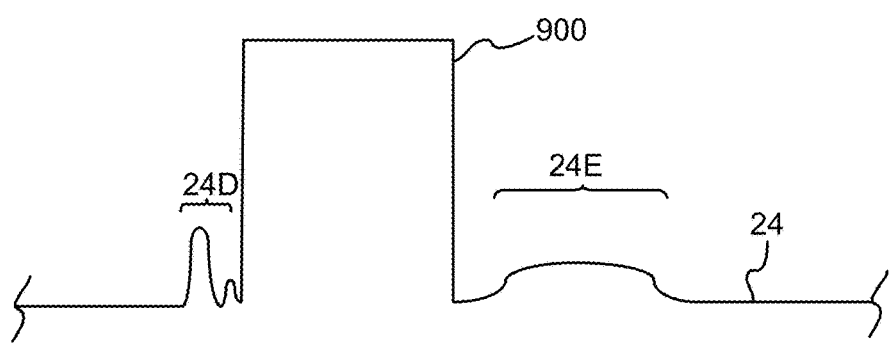
FIG. 59 is a detailed view of a pocket displaced toward a pleated segment of the present teachings.

Referring now to FIG. 59, pocket 900 has displaced, with respect to pocket 900 in FIG. 58, toward pleated segment 24D. As a result, pleated segment 24D can fold up and become compacted. Pleated segment 24E can flatten out allowing for the displacement.

Figure 60:
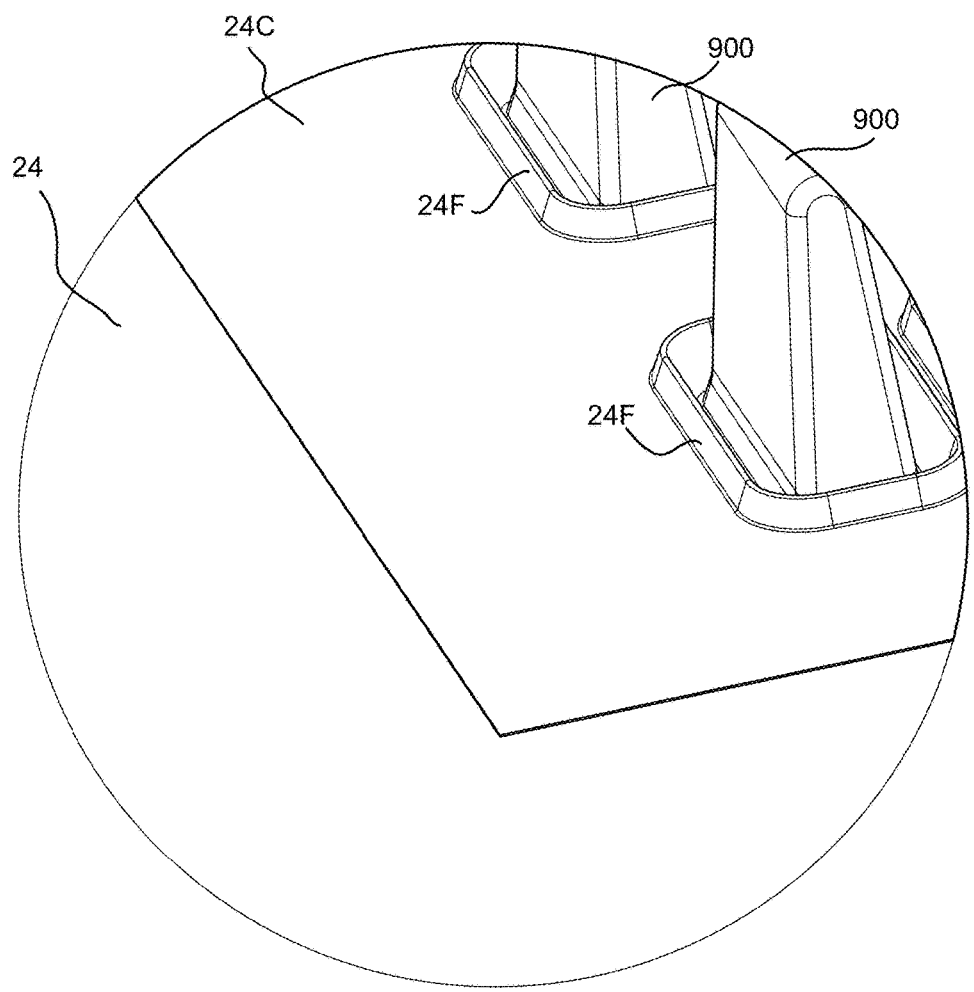
FIG. 60 is a detailed view of a region of FIG. 57.

Referring now to FIG. 60, in region Y of FIG. 57 each of pockets 900 in pocketed region 24C can be encompassed by pleated segment 24F of barrier 24. Pleated segments 24F may fold up and flatten out to allow for pocket 900 to displace. Pleated segments 24F can include a single pleat or multiple pleats.

Figure 61:
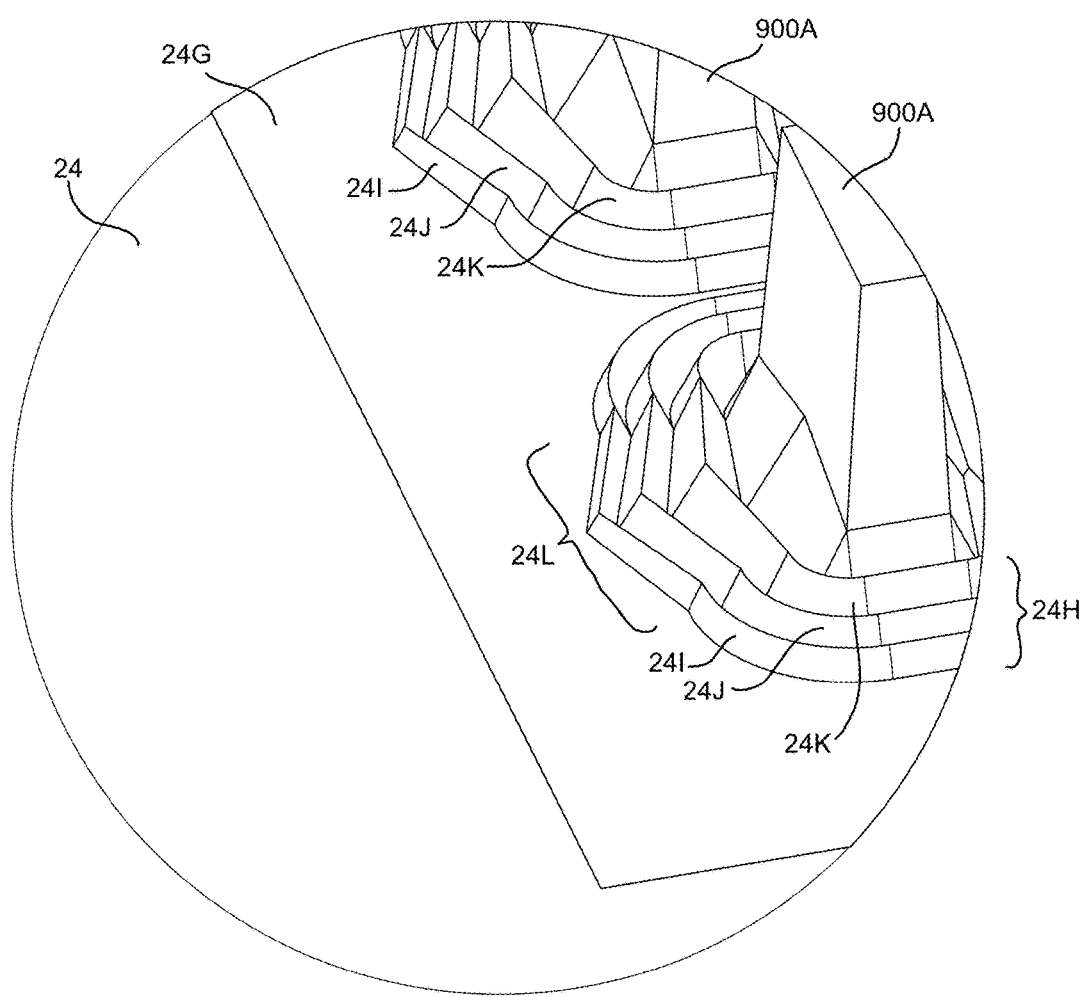
FIG. 61 is an alternative detailed view of the region in FIG. 57.

Referring now to FIG. 61, barrier 24 can include pocketed region 24G. Pocketed region 24G can include pockets 900A which can be encompassed by pleated segment 24H. Pleated segment 24H can include multiple pleats 24I, 24J, 24K. The plurality of pleats 24I, 24J, 24K may allow for increased displacement of a pocket 900A. Additionally, the plurality of pleats 24I, 24J, 24K may help to limit the amount of stress placed on any one pleat 24I, 24J, 24K for a given displacement of pocket 900A. Pleated segments 24H may also include lateral cusps 24L. Lateral cusps 24L may, for example, but not limited to, protrude from pockets 900A in a direction transverse to the linear displacement path of pocket 900A. Lateral cusp 24L may help to direct folding and flattening of pleats 24I, 24J, 24K and may reduce and/or avoid bunching or distorting of unpleated portions of barrier 24.

Figure 62A:
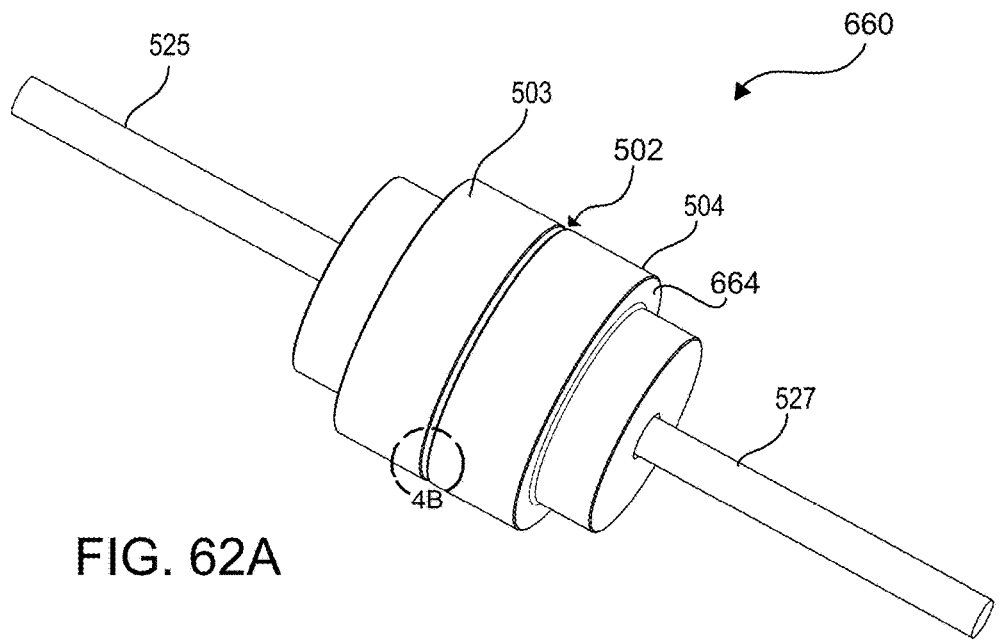
FIG. 62A is a perspective view of an example configuration of a magnetic coupling.

Referring now primarily to FIG. 62A, some configurations of a contact free torque transmission arrangement 660 may comprise the use of one or more magnetic couplings. Use of a magnetic coupling may serve a secondary function of helping to locate and secure first housing 541 (FIG. 56B) to second housing 542 (FIG. 56B) during setup. In some configurations, a magnetic coupling for the torque transmission arrangement 660 may provide a magnet on one of sides 513, 515 (FIG. 56B) and a metallic material on the other of sides 513, 515 (FIG. 56B). The metallic material may also be a magnetized material. In configurations with a magnetic coupling, one or more magnets may function as first barrier interfacing part 503 and another magnet or group of magnets may function as second barrier interfacing part 504. The magnet or magnets in each of barrier interfacing parts 503, 504 may align with magnets having opposing magnetic poles on the other of barrier interfacing parts 503, 504. Any suitable material displaying magnetic properties such as an appropriate transition metal, rare earth metal, or alloy may be used. Magnets containing neodymium can be, but are not limited to be, used in some configurations. In some configurations, the type of magnet used in each of barrier interfacing parts 503, 504 may differ. A first variety of magnet or magnetic material may be included in first barrier interfacing part 503 and a second variety of magnet or magnetic material may be included in second barrier interfacing part 504.

Continuing to refer primarily to FIG. 62A, the magnetic coupling can transmit torque across gap 502. Barrier 24 (FIG. 56B) may be placed gap 502. Each of barrier interfacing parts 503, 504 may be disposed at a pre-determined distance from barrier 24 (FIG. 56B) to transmit a pre-determined force from first barrier interfacing part 503 to second barrier interfacing part 504. Barrier 24 (FIG. 56B) may be placed in gap 502 such that the portion of gap 502 on non-sterile side 513 (FIG. 56B) can be substantially equal to that on sterile side 515 (FIG. 56B). The force may be transmitted as a result of the magnetic attraction and/or repulsion between the poles of the magnet or magnets making up each of barrier interfacing parts 503, 504. In some configurations, first barrier interfacing part 503 may include, but is not limited to including, a first set of magnets or magnetic segments, and second barrier interfacing part 504 may include, but is not limited to including, a second set of magnets or magnetic segments. Barrier interfacing parts 503, 504 may be aligned such that the poles in the first set of magnets or magnetic segments may face opposing poles in the second set of magnets or magnetic segments. Such an alignment may facilitate torque transmission from first barrier interfacing part 503 to second barrier interfacing part 504. Additionally, adjacent magnets or magnetic segments within each barrier interfacing part 503, 504 may be aligned such that their poles are oriented in opposite directions. In other configurations, first barrier interfacing part 503 may include, but is not limited to including, a first single continuous magnet, and second barrier interfacing part 504 may include, but is not limited to including, a second continuous magnet. In still other configurations a monolithic piece of material which has been magnetized to include a plurality of north and south poles (e.g. a radial sintered magnetic ring) may be used for each of first barrier interfacing part 503 and second barrier interfacing part 504.

Continuing to refer primarily to FIG. 62A, barrier interfacing parts 503, 504 may be coupled to one or more force carriers 525, 527 on respective sides of barrier 24 (FIG. 56B). In some configurations, force carriers 525, 527 can be drive shafts. In other configurations, force carrier 525 disposed on non-sterilized side 513 (FIG. 56B) may be included in drive element 60 (FIG. 16) and may rotate force carrier 525. The rotation may, in turn, rotate first barrier interfacing part 503. As a result of the magnetic coupling present between first barrier interfacing element 503 and second barrier interfacing element 504, second barrier interfacing element 504 and second force carrier 527 may rotate in kind with first barrier interfacing element 503. Thus the magnetic relationship between barrier interfacing elements 503, 504 may allow torque to be transmitted across barrier 24 (FIG. 56B). Movement of second force carrier 527 may be transmitted to an actuated component such as surgical tool 52 (FIG. 16).

Figure 62B:
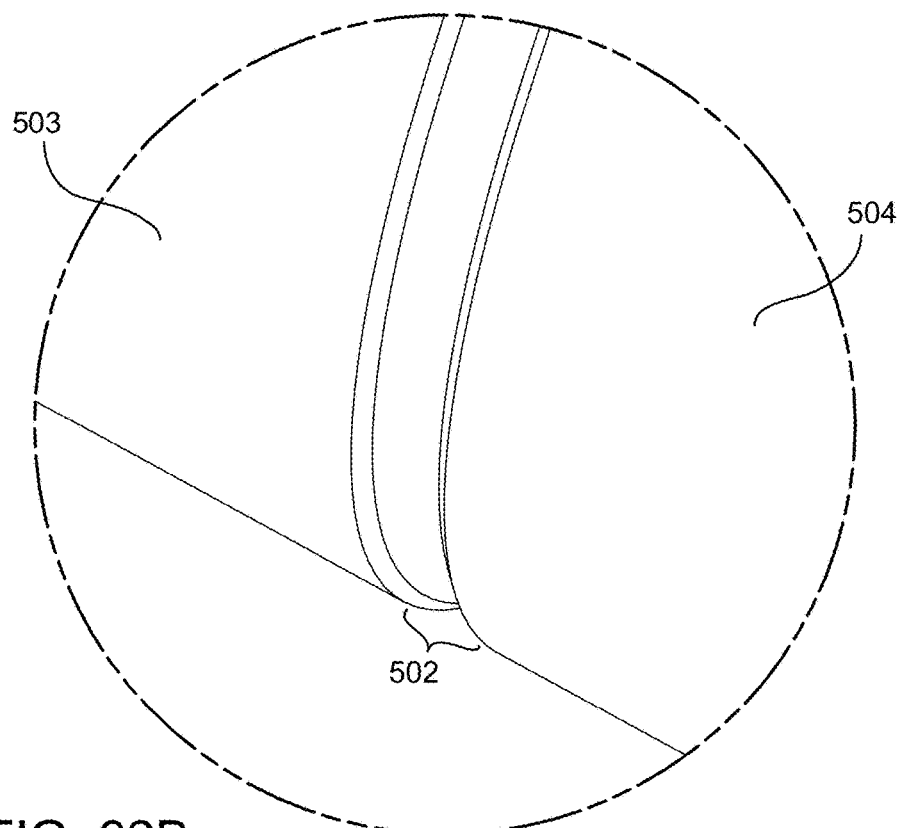
FIG. 62B is an enlarged view of a region in FIG. 62A.

Referring primarily to FIG. 62B, barrier 24 (FIG. 56B) may be disposed in gap 502 during surgery, and gap 502 may be referred to as barrier placement gap 502. Gap 502 may be a predetermined distance which is held substantially constant during operation. The pre-determined distance may be chosen such that barrier 24 may be placed between barrier interfacing parts 503, 504, but not in contact with either barrier interfacing parts 503, 504. The pre-determined distance may be chosen such that a desired amount of torque may be transmitted across it. As the pre-determined distance is increased, the amount of torque transferred may decline. In some configurations, gap 502 may be a distance of about 0.10 to 0.50 inches. In some configurations, gap 502 may be approximately 0.125 to 0.30 inches. The gap 502 may not be symmetric on both sides of the barrier 24. The transmission of force across gap 502 may occur without any disruption to barrier 24. As a result, barrier 24 may function to keep sterile section 515 (FIG. 56B) segregated from non-sterile section 513 (FIG. 56B). The distance of gap 502 may depend on the variety of magnetic couplings used.

Figure 62C:
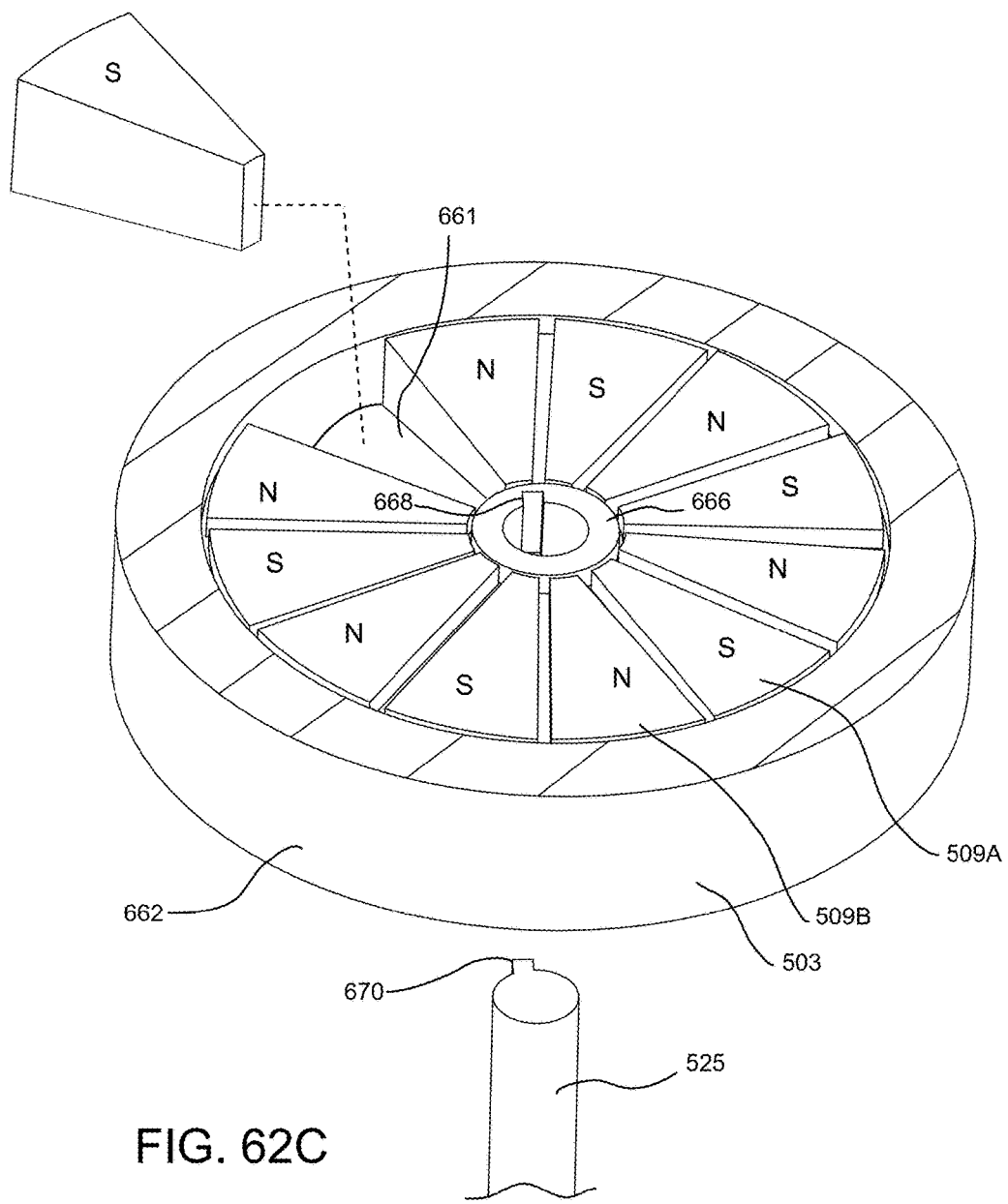
FIG. 62C is a cross-sectional view of an example barrier interfacing part including a number of magnets.

Referring primarily to FIG. 62C, first barrier interfacing part 503 is described, though the description could apply to any barrier interfacing part 503, 504 (FIG. 62A) which can serve as part of a magnetic coupling. Magnets 509A may be arranged to have opposite polarity from adjacent magnets 509B. The number of magnets may differ in various configurations. For example, some configurations may include six magnets 509A, 509B in each barrier interfacing element 503, 504 (FIG. 62A). Each magnet 509A, 509B may be included in housing 662 which may include voids 661 into which the magnets 509A, 509B may be placed during assembly. Housing 662 may be made of any suitable material including, but not limited to, metals, ceramics, glass, and plastics. In some configurations, the material chosen for housing 662 may be chosen from materials which are compatible for bonding to or ultrasonically welding to a force carrier 525 for example. Housing 662 may also be constructed so as to influence the magnetic flux paths of the magnets 509A, B in a desired manner. For example, the magnetic flux paths may be influenced so as to create one or more closed loop paths. In such a configuration, a portion (e.g. face 664 (FIG. 62A) of housing 662 may be made of a metallic material which can create a magnetic circuit in barrier interfacing part 503. In some configurations, housing 662 may be constructed such that magnets 509A, 509B positioned about 180° from each other and can be ganged together in a magnetic circuit. For example, in a configuration with three sets of magnets 509A, 509B, three magnetic circuits may be created with the influence of housing 662. Barrier interfacing part 503, for example, can include receiving feature 666 for force carrier 525 such as, for example, but not limited to, a drive shaft. Receiving feature 666 may be keyed. In some configurations, receiving feature 666 may include notch 668 into which a cooperating feature of force carrier 525 may seat. In some configurations, force carrier 525 may include protuberance 670 which may be received in notch 668 when fully assembled to, for example, ensure that force carrier 525 and barrier interfacing part 503 do not rotate with respect to one another.

Referring now to FIG. 63A, torque transmitting arrangement 672 can include one or more force carriers 525, 527, barrier interfacing parts 503, 504, and barrier 24. Barrier interfacing parts 503, 504 may each include one or more magnet and may magnetically couple with one another when assembled. Barrier placement gap 502 (FIG. 63B) may be configured to receive barrier 24 and also allow a torque transfer from non-sterile side 513 to sterile side 515. The transmission of force may occur without any disruption to barrier 24 and/or contamination of sterile side 515. As a result, barrier 24 may function to keep sterile section 515 divorced from non-sterile section 513.

Referring now to FIG. 63B, first barrier interfacing part 503 may provide a first receiving cavity 523 which can receive first force carrier 525. Second barrier interfacing part 504 may provide second receiving cavity 526 which can receive second force carrier 527. Barrier interfacing parts 503, 504 may also include one or more fastener receiving voids 528, 529 or a similar feature. Any suitable fastener may be inserted into fastener receiving voids 528, 529 to prohibit rotation of force carriers 525, 527 with respect to barrier interfacing parts 503, 504. In some configurations, a different mechanism may be used to couple force carriers 525, 527 to barrier interfacing parts 503, 504. In some configurations, one or both of force carriers 525, 527 may be permanently coupled to barrier interfacing parts 503, 504. In such configurations, the components may be welded (ultrasonically or otherwise) together, coupled with adhesive, or solvent bonded together. Additionally, a threaded coupling or nut and bolt type arrangement may also be used. Any other mechanism which would be apparent to one skilled in the art may be used for coupling barrier interfacing parts 503, 504 with force carriers 525, 527.

Referring now to FIG. 64A, torque transmission arrangement 520 can include drive element 60 with first barrier interfacing part 503, barrier 24, and driven element 62 with second barrier interfacing part 504. Torque transmission arrangement 520 may be a contact arrangement in which a portion of drive element 60 and a portion of driven element 62 contact barrier 24. When in operation, barrier 24 may be in physical contact with one or more parts of drive element 60 and/or in physical contact with one or more parts of driven element 62. The contacted portion of barrier 24 may be referred to as an engagement site. Contact through the engagement site may allow transmission of torque from drive element 60 in non-sterile section 513 to driven element 62 in sterile section 515. Second barrier interfacing part 504 may be configured to receive the transmitted torque and pass it to an actuated feature such as end tool 52 (FIG. 16) to facilitate a surgical task. In some configurations, barrier 24 may not undergo any modification or tailoring. Force may be transferred from first barrier side 24A to the second barrier side 24B with at least a portion of barrier 24 physically contacted and trapped between one or more parts of drive element 60 and one or more parts of driven element 62. In other configurations, barrier 24 may be tailored or modified, for example, but not limited to, configured to provide a receptacle or receiver for receiving one or more parts from non-sterile side 513 and/or one or more parts from sterile side 515. In other configurations, a bridging element or a plurality of bridging elements may be provided as part of barrier 24. The bridging element may be configured to engage part of drive element 60 and/or part of driven element 62.

Continuing to refer to FIG. 64A, reference axis 535 may serve as a rotational axis about which drive element 60 and driven element 62 may rotate. As torque is transmitted from drive element 60 to driven element 62, barrier 24 may be caused to displace. Specifically, as torque is transferred, a nutational "wobble" may occur allowing torque to be transferred without requiring barrier 24 to rotate and without the need for a rotary seal in barrier 24. The displacement of barrier 24 may be described with respect a number of different reference axes, for example, second reference axis or tilt axis 539. Second reference axis 539 may be perpendicular to barrier faces 24A, 24B. Barrier 24 may be held between first barrier interfacing element 503 and second barrier interfacing element 504 such that an angle Ø may be formed between reference axis 535 and tilt axis 539. As torque is transmitted from first barrier side 24A to second barrier side 24B, angle Ø may be maintained. Tilt axis 539 may nutate about reference axis 535 according to first nutation path 537, for example. Tilt axis 539 may also maintain a substantially perpendicular orientation with respect to first barrier side 24A and second barrier side 24B. Dotted indicator 538 indicates the position of tilt axis 539 and barrier 24 after about 180° of rotation of drive element 60 and driven element 62 about reference axis 535. A barrier angle α between first face 24A of barrier 24 and reference axis 535 may also be substantially constant during torque transmission across barrier 24.

Referring now to FIG. 64B, nutation may also be described with respect to a variety of other axes. For example, third reference axis or barrier nutation axis 541 may be used to describe the displacement of barrier 24 as torque is transmitted via torque transmission arrangement 520. Barrier nutation axis 541 may be substantially perpendicular to reference axis 535 and may be disposed so as to intersect reference axis 535 at a point where barrier 24 meets reference axis 535. Barrier nutation axis 541 may also be referred to as barrier nutation axis 541. Barrier nutation axis 541 may form angle β the barrier 24. The torque transmitted from first barrier interfacing part 503 to second barrier interfacing 504 may cause at least a portion of barrier sides 24A, 24B to nutate about barrier nutation axis 541 according to second nutation path 536. Dotted outline 501A shows the position of barrier 24 after about 180° of rotation of drive element 60 and driven element 62 about reference axis 535. As barrier 24 displaces while torque is transmitted, angle β may remain substantially constant.

Referring now to FIGS. 64C-64F, barrier 24 is displaced as rotation of drive element 60 (FIG. 64B) and driven element 62 (FIG. 64B) about reference axis 535 occurs. Specifically, the progression of FIGS. 64C-64F illustrates a nutational "wobble" of barrier 24 as torque is transmitted from first barrier side 24A to second barrier side 24B. The nutational "wobble" of barrier 24 can be of any magnitude and is not limited by any illustrated configuration herein. In some configurations only a small segment of the barrier 24 at and around the engagement site may be displaced. The displacement of drive rotation indicators A, B, C and D which correspond to respective driven rotation indicators A', B', C' and D' represent rotation of drive element 60 and driven element 62. In FIG. 64C, torque transmission arrangement 520 is in an initial position. Drive element 60 (FIG. 64B) and driven element 62 (FIG. 64B) in each of FIGS. 64C-64F have been rotationally displaced about 90° from their position in each of the preceding figures. Torque can be transmitted across barrier 24 by rotational displacement of drive element 60 (FIG. 64B). Reference marking 674 on barrier 24 indicates that torque is transmitted without the need for barrier 24 to rotate and without the need for a rotating seal in barrier 24. Additionally, the nutational displacement of barrier 24 may facilitate torque transmission without any distortion or effect on the integrity of barrier 24.

Figure 65A:
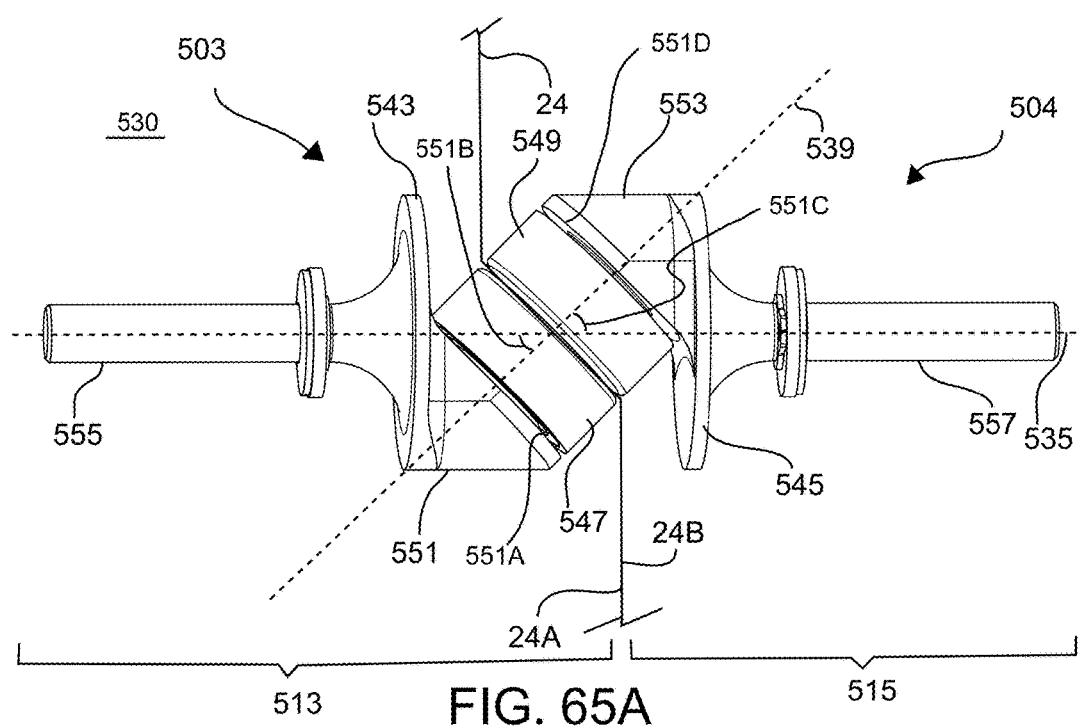
FIG. 65A is a schematic diagram of an example torque transmission arrangement of the present teachings.

Referring now to FIGS. 65A-65D, torque transmission arrangement 530 can transmit torque from non-sterile side 513 to sterile side 515 of barrier 24 in a contact mode. Referring specifically to FIG. 65A, torque transmission arrangement 530 may include a plurality of components on non-sterile side 513 which cooperate with a plurality of allied components on sterile side 515. Components on non-sterile side 513 may be included in first barrier interfacing element 503. The allied components on sterile side 515 may be included in second barrier interfacing element 504. First barrier interfacing element 503 may include for example, but not limited to, first force carrier 555, first planar body 543, first cap-base 551, and first engaging cap 547. Second barrier interfacing element 504 may include second engaging cap 549, second cap base 553, second planar body 545, and second force carrier 557. In some configurations, first and second force carriers 555, 557 may be torque transmitting agents (e.g. drive shafts). First and second force carriers 555, 557 may be coupled to planar bodies 543, 545 such that force carriers 555, 557 and planar bodies 543, 545 may not rotate relative to one another. Any suitable coupling method may be used, for example, but not limited to, threaded couplings, fasteners (e.g. set screws), interference fit, snap fit, adhesive/glue/epoxy, a welding procedure such as ultrasonic or laser welding, solvent bonding, spring loaded bayonet mount, and others. Alternatively, each set of force carriers 555, 557, planar bodies 543, 545, and cap-bases 551, 553 may be a formed as a single part which may, for example, be machined or molded depending on the configuration.

Continuing to refer primarily to FIG. 65A, at least a portion of barrier 24 segregating non-sterile side 513 from sterile side 515 may be captured between caps 547, 549. First barrier interfacing cap 547 and second barrier interfacing cap 549 may contact barrier 24 when assembled and engage or interlock with one another through barrier 24. Rotation of barrier interfacing parts 503, 504 about reference axis 535 can cause displacement of barrier 24. Barrier 24 may displace in a manner which can cause tilt axis 539 to nutate about reference axis 535. Tilt axis 539 may form an angle Ø (FIG. 64A) with reference axis 535 and this angle may be maintained as tilt axis 539 nutates. Additionally, first barrier interfacing cap 547 and second barrier interfacing cap 549 may trap barrier 24 such that the trapped portion of barrier 24 is at and maintains an angle α (FIG. 64A) with respect to reference axis 535 while rotation of barrier interfacing parts 503, 504 about reference axis 535 takes place. First force carrier 555 may be configured to receive torque from a torque generator (e.g. a motor) and transmit the torque to first planar body 543. First planar body 543 may further include base 551 that may extend from first planar body 543 and have a face 551A which is at angle 551B with respect to reference axis 535. Face 551A may serve as a mounting platform or bed for first bearing assembly 565 (FIG. 65C) housed in end cap 547. First bearing assembly 565 (FIG. 65C) may allow for rotational displacement of end cap 547 relative to base 551. In some configurations, end cap 547 may provide the outer race of bearing assembly 565 (FIG. 65C).

Continuing to refer primarily to FIG. 65A, sterile side 515 may provide cooperating components which may be configured to receive the torque transmitted from non-sterile side 513. These components may be collectively referred to as barrier interfacing part 504 and may be included in driven element 62 (FIG. 64B). These components may be similar to or identical to those on non-sterile side 513 of barrier 24. For example, driven barrier interfacing part 504 may include second bearing assembly 567 (FIG. 65C) that may be enclosed in second cap 549 which may be referred to as second barrier interfacing cap 549. Second bearing assembly 567 (FIG. 65C) may allow for rotational displacement of second end cap 549 relative to second base 553. Second barrier interfacing cap 549 and housed bearing 567 (FIG. 65C) may be mounted on second base 553. Second base 553 may include face 551D which is oriented at angle 551C with respect to reference axis 535 and may extend from second planar body 545. Second planar body 545 may be attached to second force carrier 557 such as, for example, but not limited to, a drive shaft. Second force carrier 557 may be configured to receive the transmitted torque and advance it to an actuated component such as end effecter 52 (FIG. 16). Additionally, barrier interfacing caps 547, 549 may be disposed on respective bases 551, 553 such that the faces of each of end caps 547, 549 may be perpendicular to tilt axis 539. During transmission of torque, torque transmission arrangement 530 may be configured to rotate about reference axis 535. Operation of torque transmission arrangement 530 may cause, for example, but limited to, a response nutating movement of barrier 24. Torque may be transmitted without the need for rotation of barrier 24, a rotating seal in barrier 24, or a discontinuity (e.g. hole) in barrier 24. Torque transmission arrangement 530 may allow the faces of end caps 547, 549 to remain perpendicular to tilt axis 539 during transmission of torque from non-sterile side 513 to sterile side 515.

Figure 65B:
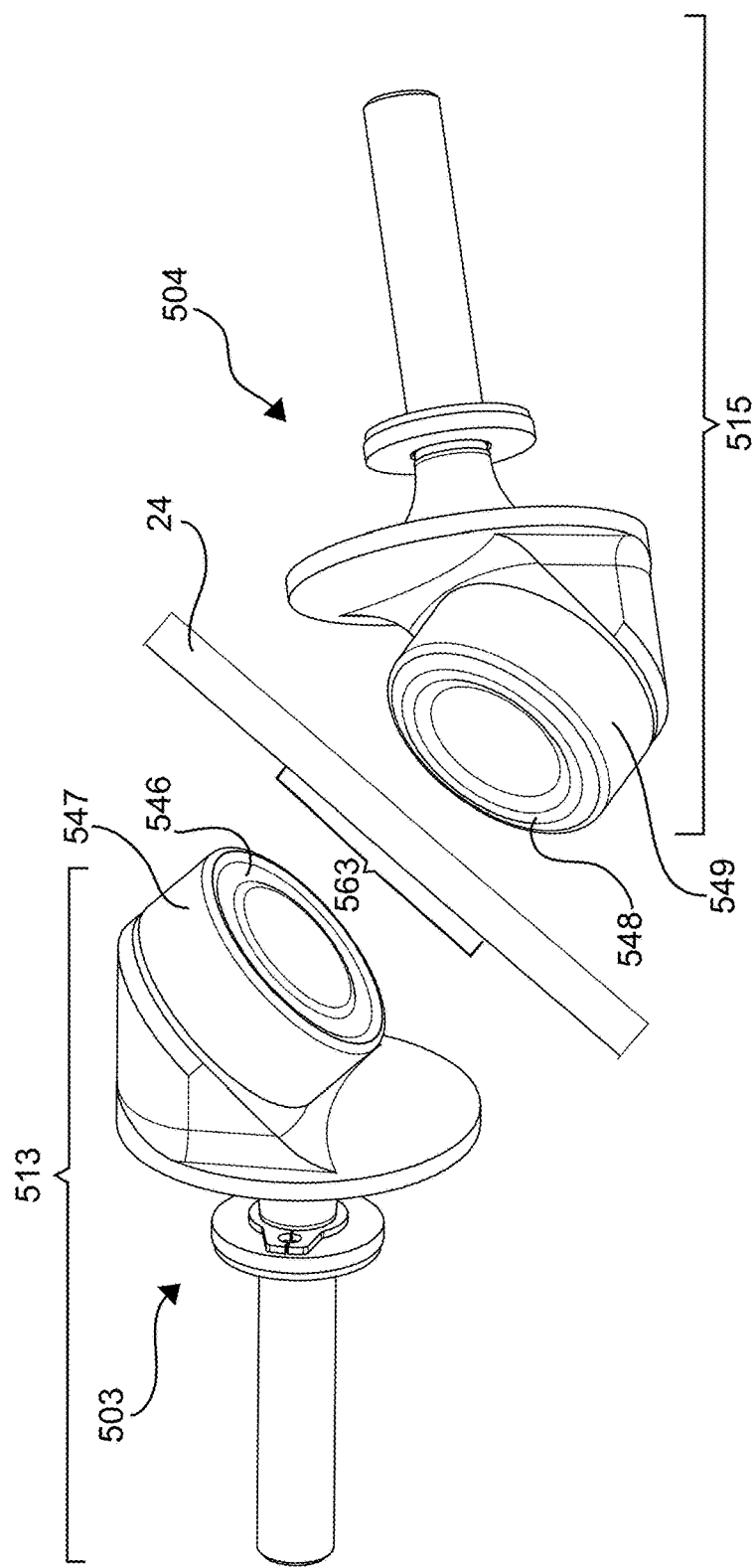
FIG. 65B is a schematic diagram of an exploded view of the torque transmitting arrangement of FIG. 65A.

Referring now to FIG. 65B, end caps 547, 549 may include cooperating engagement or interlocking features. For example, one of end caps 547, 549 may include grooved recess or depression 546. Another of end caps 547, 549 may include raised feature 548 which can mate into grooved recess 546. Such mating of 547, 549 may help to maintain engagement of end caps 547, 549 during transmission of torque through torque transmission arrangement 530. In some configurations, grooved recessed 546 can be included in face 580, and raised feature 548 can be included in face 581 (FIG. 65D). Faces 580, 581 (FIG. 65D) can engage with barrier 24 during operation. Grooved feature 546 may partially or completely occupy the surface of end cap 547, 549. In some configurations, grooved feature 546 can be an annular feature which may be, though is not limited to being disposed near the periphery of end cap 547, 549. Raised feature 548 may partially or completely occupy the surface of end cap 547, 549. In some configurations, raised feature 548 can be an annular feature which may be, though is not limited to being located near the periphery of end cap 547, 549. Grooved recess 546 and raised feature 548, as well as the end caps 547, 549, may be smooth and rounded or have rounded edges. In some configurations, grooved recess 546 and raised feature 548 as well as end caps 547, 549 may be made from or may be covered in a soft, compliant material or a material with a low friction coefficient. In other configurations, the cooperating engagement or interlocking features may differ. Barrier 24 may be trapped between end caps 547, 549 when torque transmission arrangement 530 is engaged with barrier 24. The site at which barrier 24 may be trapped can be referred to as engagement site 563. Any engagement members in addition to end caps 547, 549 may instead be included on barrier interfacing parts 503, 504. An alternative engagement member may be smooth and have rounded edges. An engagement member may also be made from or may be covered in a soft, compliant material or a material with a low friction coefficient.

Figure 65C:
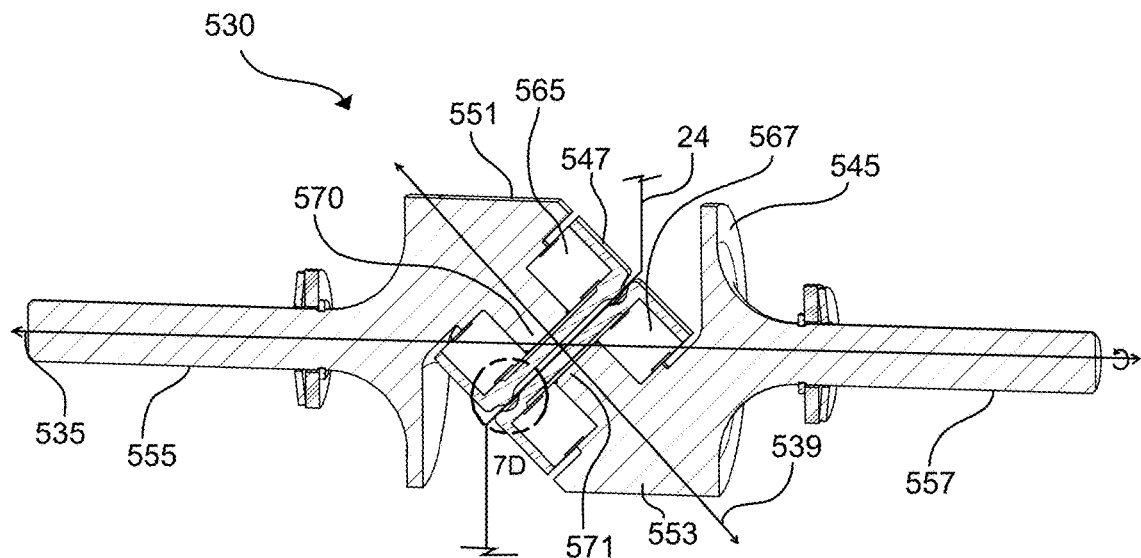
FIG. 65C is a schematic diagram of a cross-sectional view of the torque transmission arrangement shown in FIG. 65A.
Figure 65D:
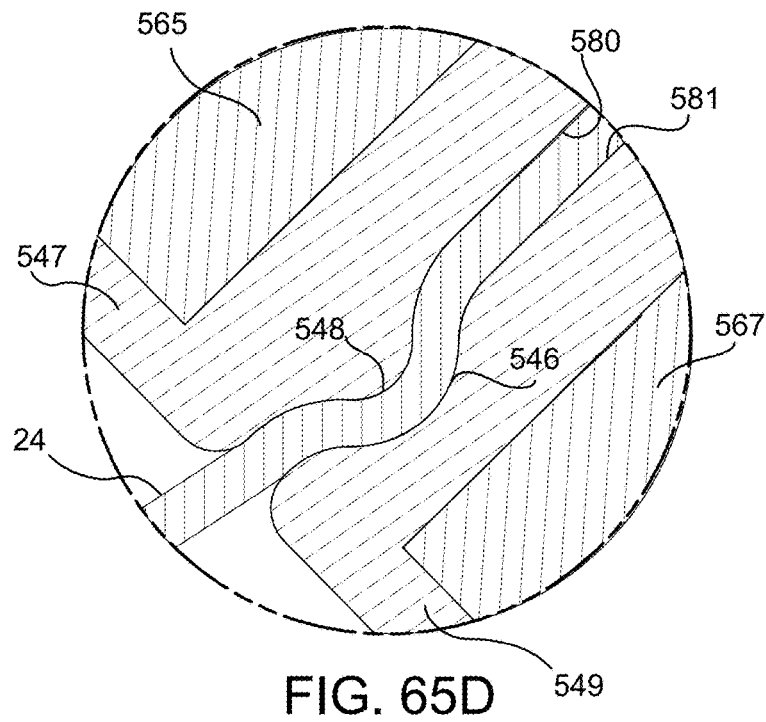
FIG. 65D is a schematic diagram of an enlarged view of a region depicted in FIG. 65C.

Referring now to FIG. 65C, a cross-sectional view of the torque transmission arrangement 530 shown in FIG. 65A is depicted. Barrier 24 can be trapped or held between end cap 547 on non-sterile side 513 and end cap 549 on sterile side 515. First bearing assembly 565 may be provided on non-sterile side 513 and second bearing assembly 567 may be provided on sterile side 515. First cap base 551 and second cap base 553 may provide first support pole 570 and second support pole 571. Support poles 570, 571 may project from the surface of cap bases 551, 553. First support pole 570 may abut an inner race of first bearing assembly 565. Second support pole 571 may abut an inner race of second bearing assembly 567. First bearing assembly 565 may facilitate a low friction displacement of end cap 547 relative to cap base 551 and support pole 570. Similarly, second bearing assembly 567 may facilitate a low friction displacement of end cap 549 relative to cap base 553 and support pole 571. Bearing assemblies 565, 547 may be selected to support pre-determined axial and moment loads on non-sterile side 513 and sterile side 515, respectively. In some configurations, bearing assemblies 565, 567 may be, but are not limited to being, roll element bearing assemblies such as ball bearing assemblies or needle bearing assemblies. In some configurations, angular contact bearings may be used.

Referring now to FIG. 65D, barrier 24 can be trapped between first barrier interface cap 547 and second barrier interface cap 549. As first barrier interfacing part 503 and second barrier interfacing part 504 approach barrier 24, grooved recess 546 and raised feature 548 may interlock and hold barrier 24 between them. During transmission of torque, end caps 547, 549 may remain engaged and barrier 24 may remain be trapped between end caps 547, 549.

Figure 65E:
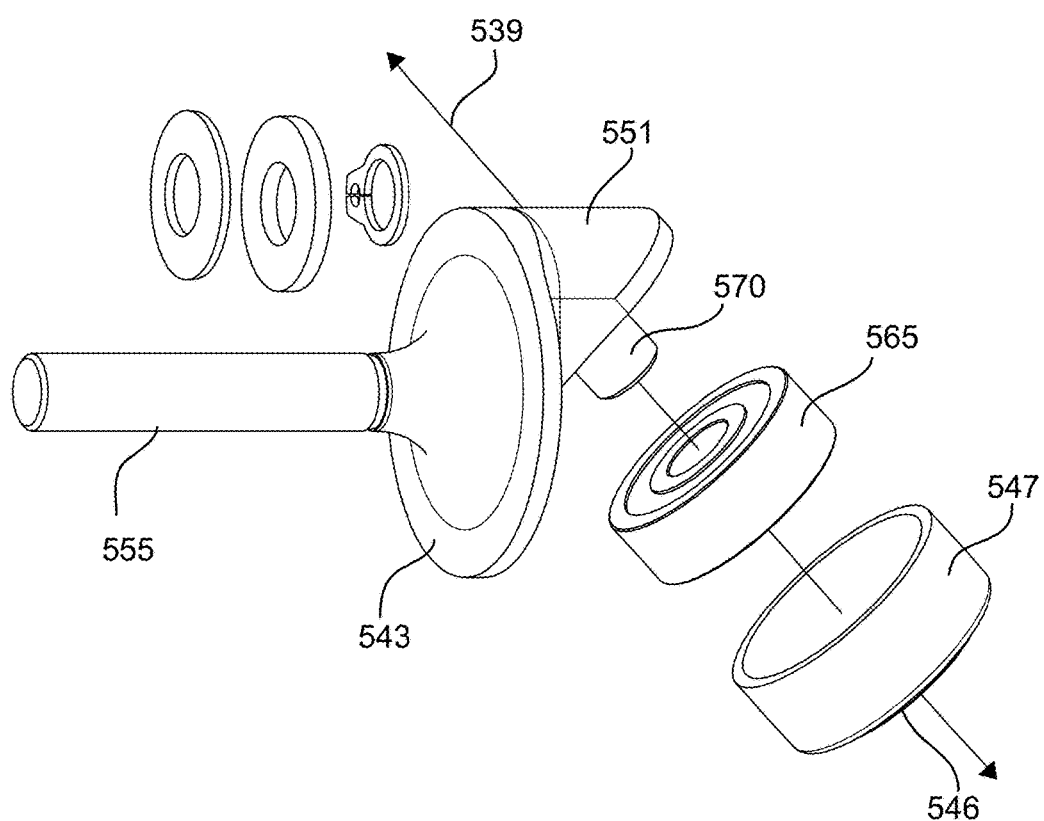
FIG. 65E is a schematic diagram of an exploded view of a first barrier interfacing part of a torque transmission arrangement described in FIGS. 65A-65D.

Referring now to FIG. 65E, first barrier interfacing part 503 (FIG. 65C) of torque transmission arrangement 530 (FIG. 65C) can include planar body 543 and base 551 that may be a single continuous structure that may be machined or molded together as a single part. Components of second barrier interfacing part 504 (FIG. 65C) may be similar or identical to or may differ from those of the first barrier interfacing part 503 (FIG. 65C).

Figure 65F:
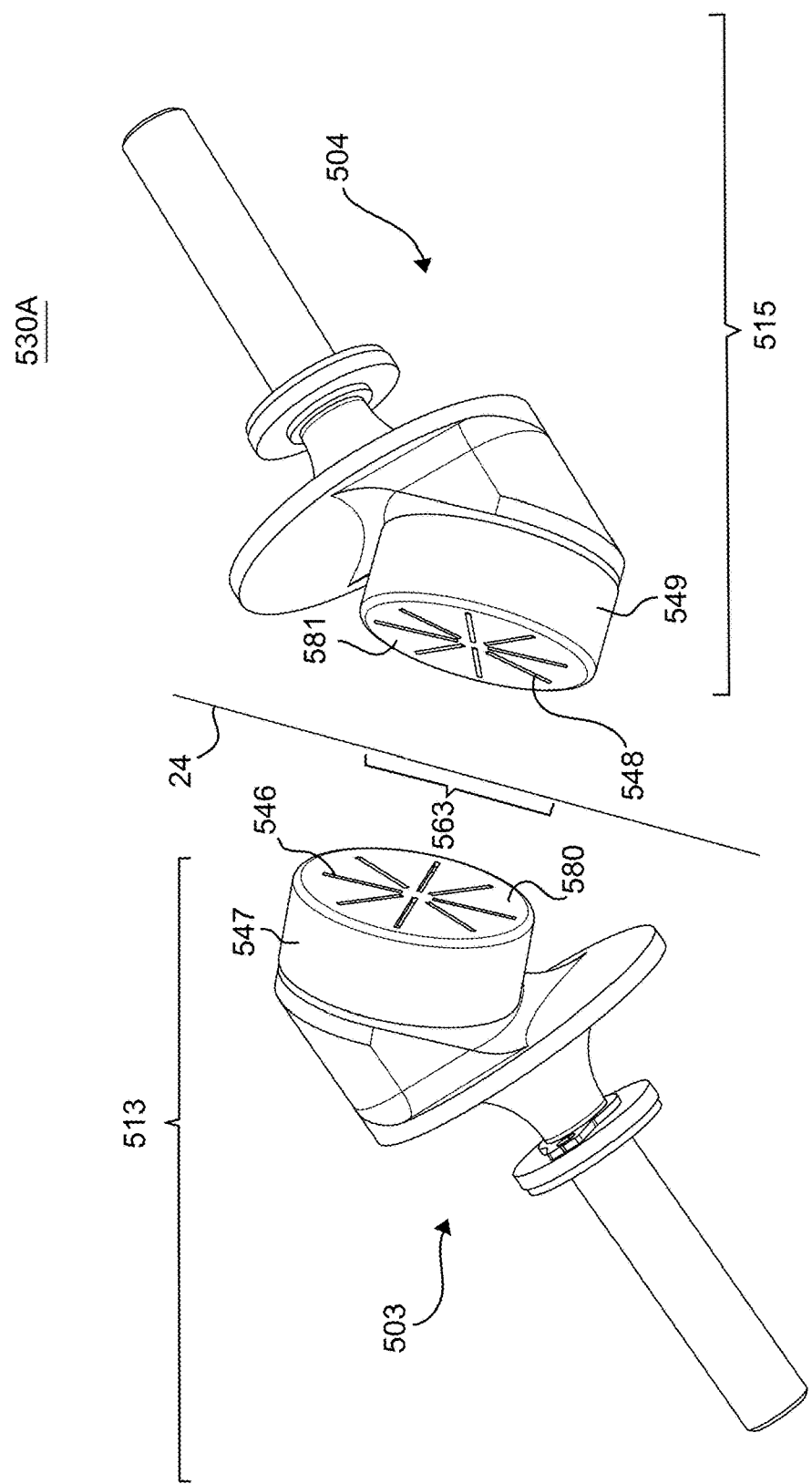
FIG. 65F is a schematic diagram an exploded view of another configuration of the torque transmitting arrangement of FIG. 65A.
Figure 65G:
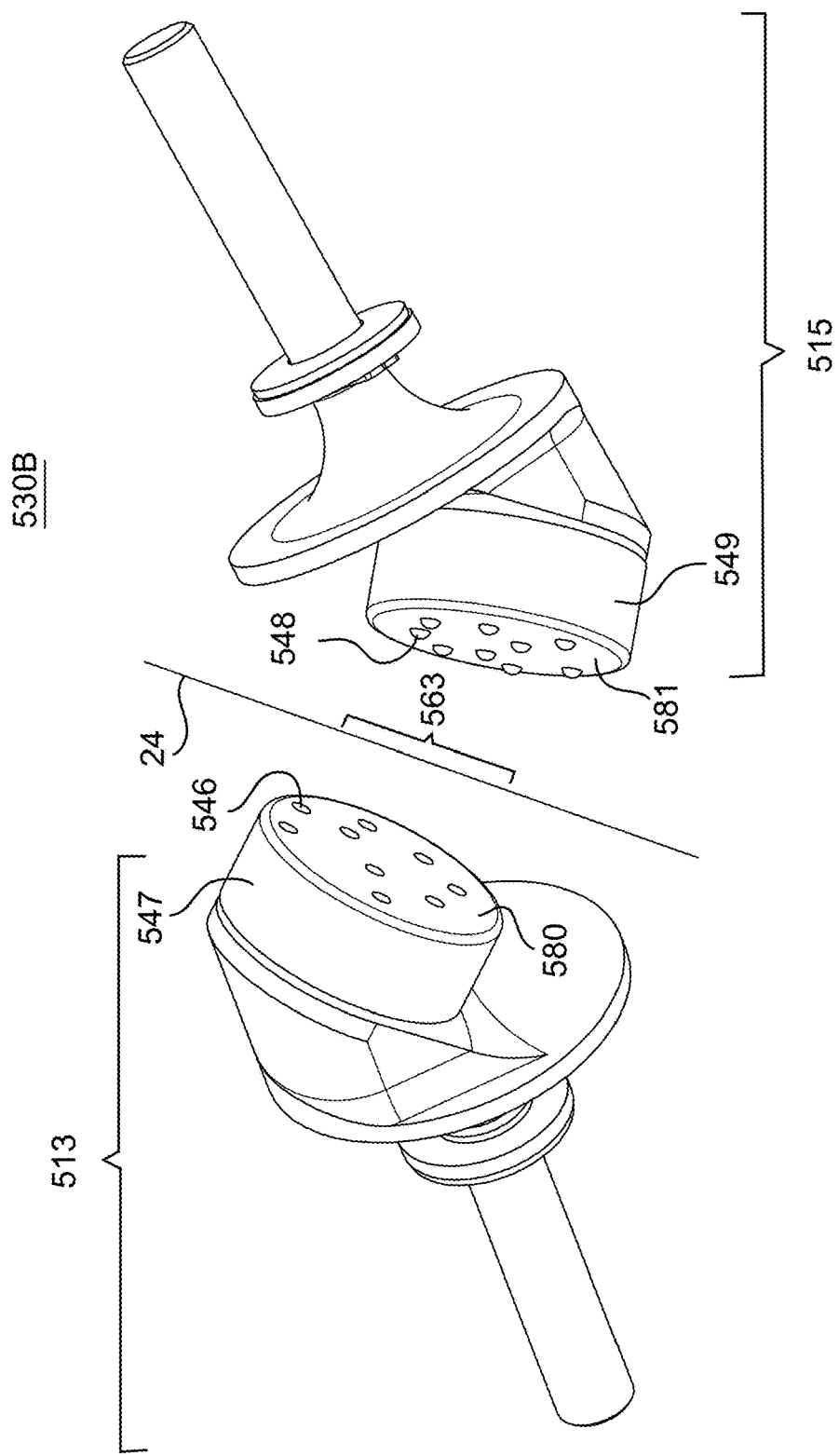
FIG. 65G is a schematic diagram an exploded view of yet another configuration of the torque transmitting arrangement of FIG. 65A.

Referring now to FIG. 65F and FIG. 65G additional configurations related to interlocking features of the end caps 547, 549 are shown. FIG. 65F depicts radially arranged grooved features 546 on the face 580 of end cap 547. A co-operating radial arrangement of raised features 548 on the face 581 of the opposing end cap 549 are also included. It should be noted that the grooved features 546 and the raised features 548 can be interchangeably arranged on the faces 580, 581 of the end caps 547, 549. In operation, the end caps 547, 549 of the torque transmission arrangement 530A may contact the barrier 24. The radial groove features 546 and radially arranged raised features 548 may lock together through the barrier 24. This may aid in prevent of rotation of one of the end caps 547, 549 relative to the other. As in other configurations, the radially arranged grooved and raised features 546, 548 may have rounded edges, may be coated in a complaint and/or low friction coefficient material, etc. The radially arranged grooved and raised features 546, 548 may be, but are not limited to being, spaced apart at even angular intervals.

Referring now to FIG. 65G another configuration of interlocking features between the faces 580 and 581 of end caps 547, 549 is shown. FIG. 65G shows an asymmetric distribution of grooved features 546 and raised features 548 on the end cap 547, 549 faces. Dimples or receptacles form the grooved features 546 on face 580 of the end cap 547. A co-operating asymmetric distribution of raised features 548 on face 580 of end cap 549. The raised features 548 may be protrusions or prominences which project proud of face 581. It should be noted that the grooved features 546 and the raised features 548 can be interchangeably arranged on the faces 580, 581 of the end caps 547, 549. In operation, the end caps 547, 549 of the torque transmission arrangement 530B may contact the barrier 24. The raised features 548 may seat in the groove features 546 locking the end caps 547, 549 together through the barrier 24. This may aid in prevent of rotation of one of the end caps 547, 549 relative to the other. As in other configurations, the grooved and raised features 546, 548 may have rounded edges, may be coated in a compliant and/or low friction coefficient material, etc. Though the grooved and raised features 546, 548 are shown as asymmetrically disposed about the cap faces 580, 581 in other configurations, they may be, but are not limited to being, spaced apart symmetrically, e.g. at even angular intervals. In some configurations, such as any of those shown in FIG. 65A-G, the end caps 547 and 549 may be or include a magnet. In addition to the mechanical interlock provided by the grooved and raised features 546, 548 a magnetic coupling may also be formed. This may further aid in preventing relative rotation of one of the end caps 547,549 relative to the other. Additionally a magnetic coupling may help in locating the end caps together when setting up the torque transmitting arrangement 530B. The magnetic coupling between the two end caps 546, 548 may also help to trap the barrier 24 between the two end caps 546, 548.

Figure 66A:
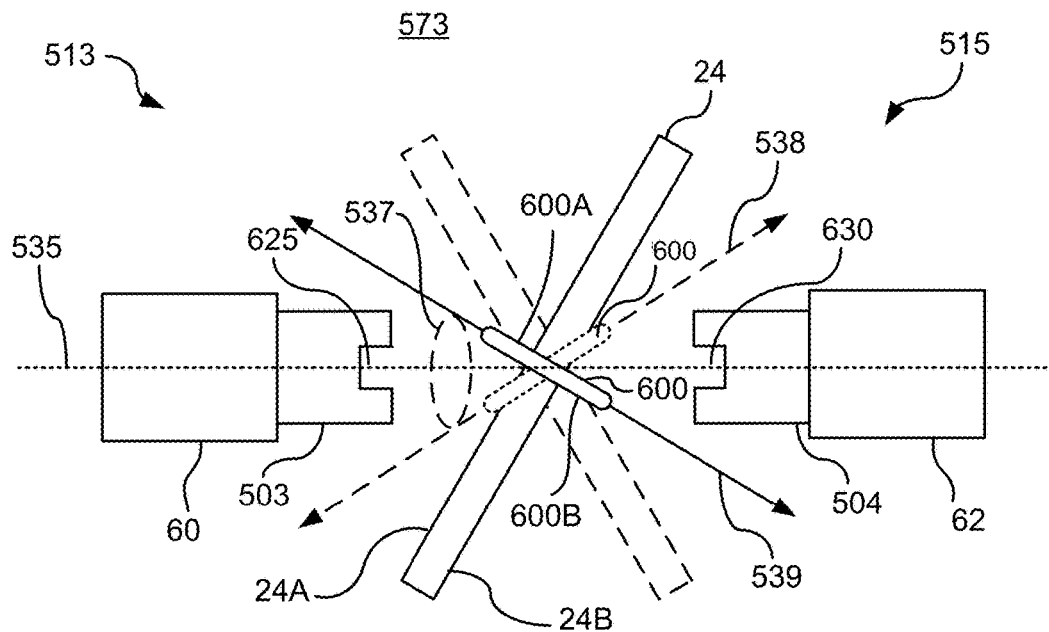
FIGS. 66A and 66B are pictorial representations of a bridging element and a flexible diaphragm of the present teachings.

Referring now to FIG. 66A, barrier 24 may include at least one element, for example, but not limited to, bridging element 600, which may interact with a portion of drive element 60 and driven element 62. Bridging element 600 can be configured to link components on non-sterile side 513 of torque transmission arrangement 573 with those on sterile side 515. Torque transmission arrangement 573 may be segregated using barrier 24 into non-sterile side 513 and sterile side 515. Drive element 60 can be positioned on non-sterile side 513, and driven element 62 can be positioned on sterile side 515. Drive element 60 may further include, but is not limited to including, first barrier interfacing part 503, and driven element 62 may include, but is not limited to including, second barrier interfacing part 504. Bridging element 600 may be partially or completely secured on barrier 24 such that bridging element part 600A may be accessible on non-sterile side 513 and bridging element part 600B may be accessible on sterile side 515. In some configurations, bridging element 600 may be a rod or pin-like member and the accessible portions of bridging element 600 on each side of barrier 24 may be coaxial. In some configurations, first barrier interfacing part 503 may provide first receiver 625, for example, but not limited to, a pocket or port, configured to receive an accessible part of bridging element 600 on non-sterile side 513. Similarly, second barrier interfacing part 504 on sterile side 515 may also provide second receiver 630, for example, but not limited to, a pocket or port, for receiving an accessible portion of bridging element 600 on sterile side 515. In other configurations, bridging element 600 may be coupled on either side using alternative means that may include, but may not be limited to including, clasping structures, permanent fasteners, and threaded coupling. If bridging element 600 is configured to be metallic, for example, but not limited to, a metal pin, then magnetic components on either one or both sides of barrier 24 may be included as part of first and second receiver 625, 630.

Continuing to refer to FIG. 66A, in some configurations, a plurality of bridging elements 600 may be provided on barrier 24. The plurality of bridging elements 600 may allow for multiple pairs of barrier interfacing elements 503, 504 to be engaged in force transmission across barrier 24. In some configurations, bridging element 600 may be branched or split. Such an arrangement may, for example, allow one of drive element 60 to drive a plurality of driven elements 62. Bridging element 600 may facilitate torque transmission across barrier 24. Bridging element 600 may be secured in barrier 24 such that it may not undergo rotational motion relative to barrier 24. Tilt axis 539 may be disposed perpendicular to barrier sides 24A, 24B of barrier 24. In some configurations, a longitudinal axis of bridging element 600 can be coaxial with tilt axis 539. In some configurations, bridging element 600 can be disposed perpendicular to barrier 24. A nutational movement may occur as torque is transmitted. For example, the bridging element axis may nutate about reference axis 535 as barrier interfacing parts 503, 504 rotate about reference axis 535. The angle between bridging element 600 and barrier 24 with respect to reference axis 535 may remain constant as torque is transmitted through torque transmission assembly 573.

Continuing to refer FIG. 66A, bridging element 600 may be secured in barrier 24 using any of a variety of processes. Bridging element 600 may, for example, but not limited to, be attached to barrier 24 with adhesive, and may be molded as part of barrier 24. In some configurations, bridging element 600 may be ultrasonically welded, laser welded, heat bonded, or solvent bonded to barrier 24. Bridging element 600 may be made of a variety of materials. For example, bridging element 600 may be made from a metallic material. Alternatively, bridging element 600 may be made from a plastic material or a fiber reinforced plastic, for example, but not limited to, glass fiber. The material choice for bridging element 600 may depend on the amount of force which is expected to be transferred through bridging element 600. In some configurations, bridging element 600 may be constructed from or coated with a material with a low friction coefficient.

Figure 66B:
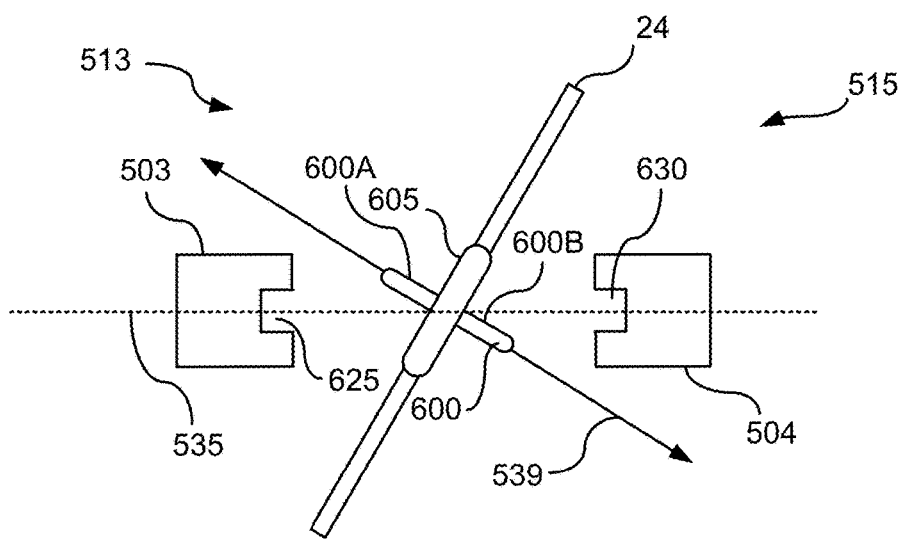

Referring now to FIG. 66B, in some configurations, bridging element 600 may optionally include or be attached to flexible diaphragm 605. Flexible diaphragm 605 may include an orifice of pre-determined dimensions. The orifice may be configured to receive bridging element 600 such that first branch or portion 600A of bridging element 600 may be accessible on non-sterile side 513, and second branch or portion 600B may be accessible on sterile side 515. Flexible diaphragm 605 may be configured to be formed integrally with barrier 24 and bridging element 600 may later be attached to flexible diaphragm 605 after location in the orifice. Alternatively, flexible diaphragm 605 may be attached to, for example, but not limited to, over molded onto, bridging element 600. In some configurations, flexible diaphragm 605 may aid in attachment of bridging element 600 to barrier 24. When attached to barrier 24, flexible diaphragm 605 and barrier 24 may form a seal which can isolate the environments on each side of barrier 24 from each other. The material used for flexible diaphragm 605 may include, but is not limited to including, polyurethane or any other suitable material which may be flexible, durable, and inert towards metal. Flexible diaphragm 605 may be made of a material with properties that facilitate, for example, but not limited to, ultrasonic welding, laser welding, and solvent bonding, to barrier 24. For example, in configurations where barrier 24 is a polyurethane material, flexible diaphragm 605 may also be constructed from polyurethane to facilitate ultrasonically welding flexible diaphragm 605 to barrier 24.

Figure 67A:
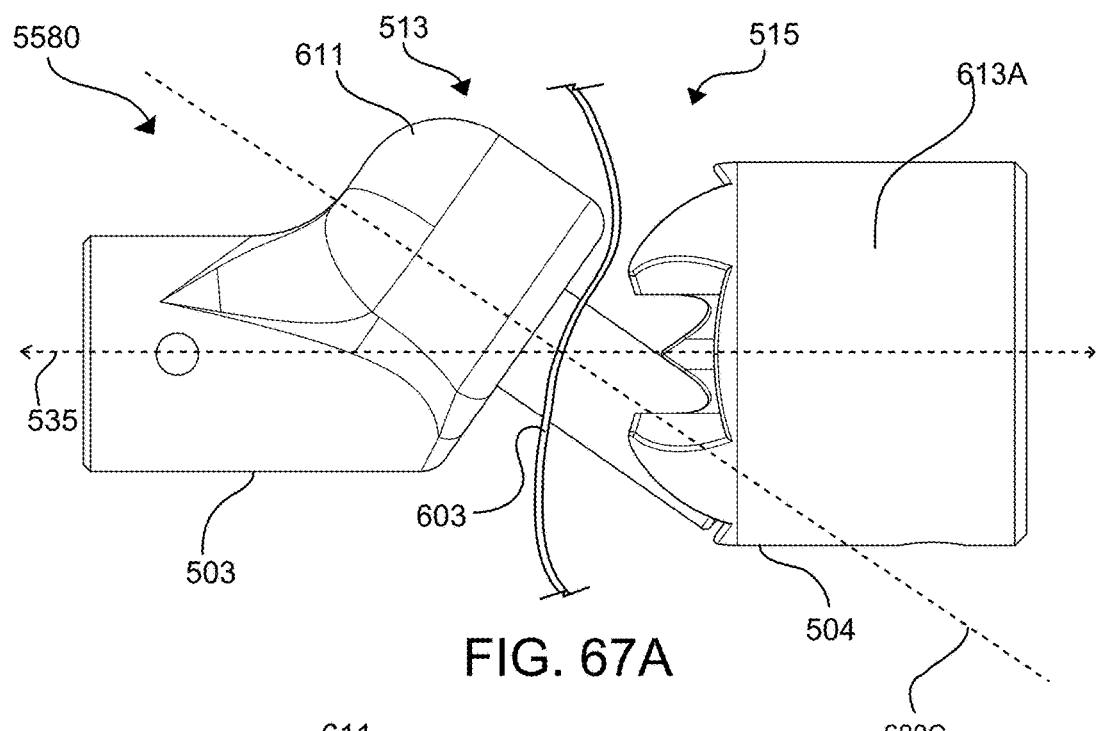
FIG. 67A is a schematic diagram of a side view of a torque transmission assembly of the present teachings.

Referring now primarily to FIG. 67A, torque transmission assembly 5580 can include barrier 24 with bridging element 600. Bridging element 600 may be partially or completely secured to barrier 24. In some configurations, bridging element 600 can be secured to barrier 24 at attachment site 603. The manner of attachment at attachment site 603 may prevent rotational displacement of bridging element 600 relative to barrier 24. First part or portion 600A of bridging element 600 may be accessible on non-sterile side 513, and second part or portion 600B of bridging element 600 may be accessible on sterile side 515. First portion 600A of bridging element 600 may be received by receiving structure 611 that may be part of barrier interfacing element 503 which can be included in drive element 60 (FIG. 66A). Receiving structure 611 may be disposed on non-sterile side 513 of barrier 24 and may be configured to interface barrier 24 via first portion 600A of bridging element 600. Second portion 600B of bridging element 600 may be accepted by second receiving structure 613. Second receiving structure 613 may be disposed on sterile side 515 of torque transmission arrangement 5580. In some configurations, second receiving structure 613 may be configured to serve as barrier interfacing part 504 on sterile side 515 and may be included as part of driven element 62 (FIG. 66A). To facilitate transmission of torque, first receiving structure 611 and second receiving structure 613 may rotate about reference axis 535. Transmitted torque across barrier 24 may be received by multi-pocket receiver 613A via bridging element 600. Torque supplied to second receiving structure 613 may cause rotation of end tool 52 (FIG. 16) for example. As first receiving structure 611 rotates about reference axis 535 and transmits torque to second receiving structure 613, the long axis 600C of bridging element 600 can nutate about reference axis 535.

Figure 67B:
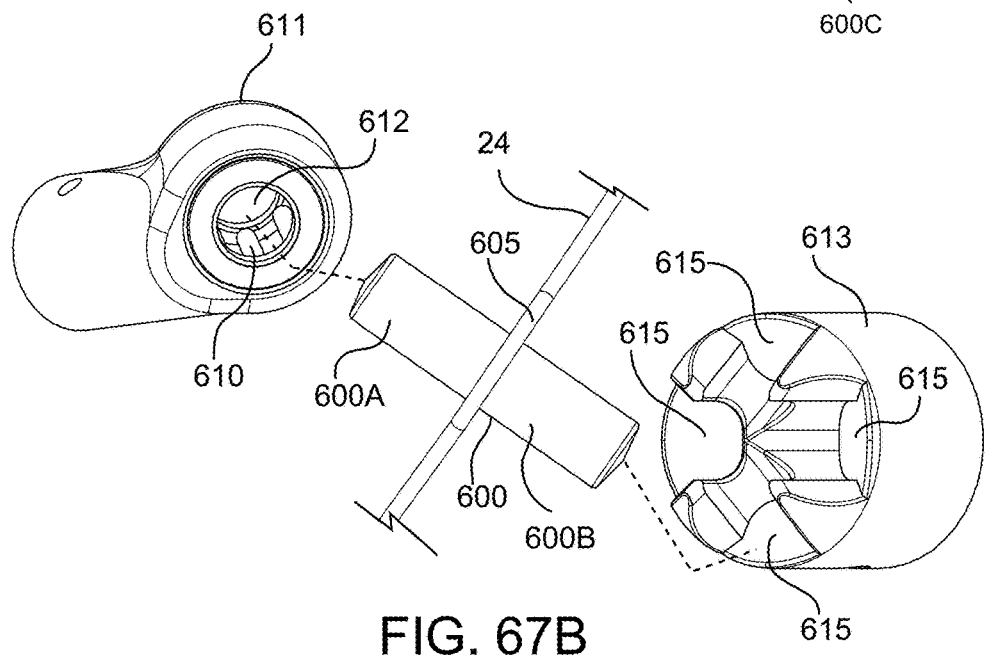
FIG. 67B is a schematic diagram of an exploded view of the torque transmission arrangement in FIG. 67A.

Referring now to FIG. 67B, barrier 24 can include flexible diaphragm 605. First receiving structure 611 may include receiving pocket 612 which may be configured to receive first portion 600A of bridging element 600. In some configurations, receiving pocket 612 can be defined by the inner race of bearing assembly 610. The presence of bearing assembly 610 can allow for low friction rotation of first receiving structure 611 relative to first portion 600A of bridging element 600 during operation. In some configurations, bearing assembly 610 can be, for example, but not limited to, a needle bearing assembly. Roller bearings such as ball bearings may also be used. Alternatively, first receiving structure 611 may include receiving pocket 612 with no rolling bearing element. In some configurations, bridging element 600 and/or the walls of pocket 612 may be made of or coated in a material with a low friction coefficient. In some configurations, first receiving structure 611 may be made from a strong and durable material such as a metallic material.

Still referring to FIG. 67B, second receiving structure 613 may be a multi-pocketed receiver which can include a number of individual receiving pockets 615. Second receiving structure 613 may be made of materials including, but not limited to, various types of rigid plastics. A plastic which has a low friction coefficient when interfacing with bridging element 600 material may be chosen. In some configurations, second receiving structure 613 may be made from, for example, but not limited to, a material such as surgical grade stainless steel which is resistant to degradation after repeated sterilization. Each of pockets 615 of second receiving structure 613 may be sized and shaped so as to receive second portion 600B of bridging element 600. Pockets 615 may also be contoured so as to guide second portion 600B of bridging element 600 into pocket 615. Including multiple pockets 615 in second receiving structure 613 may allow for increased ease of setup as second receiving structure 613 need not be precisely oriented in a specific position. Instead, second receiving structure 613 may be positioned in a variety of rotational orientations and may be able to mate easily with second portion 600B of bridging element 600. First receiving structure 611 may, in some configurations, include a plurality of receiving pockets 615 to reduce any set up burden. Bearing assembly 610 may also be included in second receiving structure 613 in some configurations.

Figure 67C:
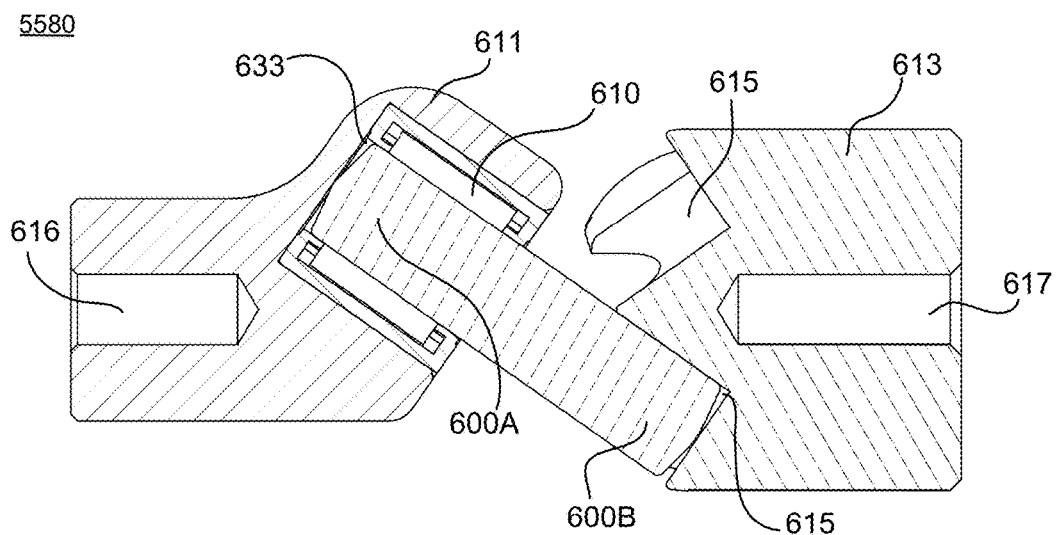
FIG. 67C is a cross-sectional perspective view of a first receiving structure engaging a part of a bridging element of the present teachings.
Figure 67D:
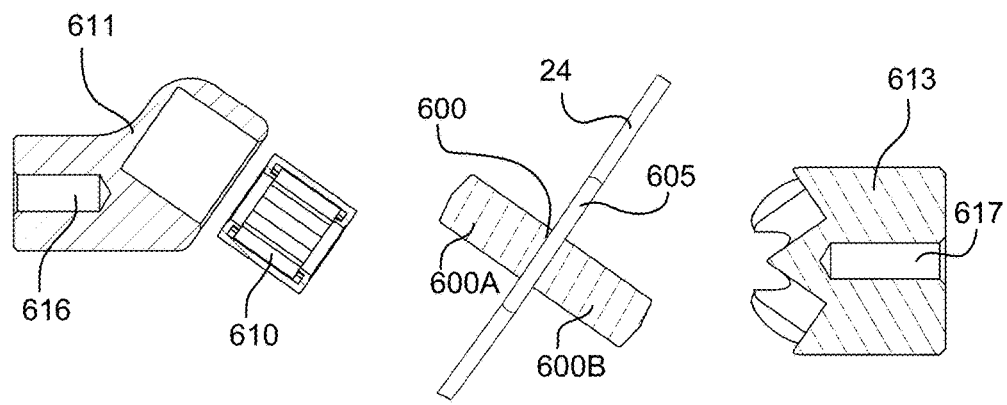
FIG. 67D is a schematic diagram of an exploded view of the cross-sectional view FIG. 67C.

Referring now to FIGS. 67C and 67D, two cross sectional views of the torque transmission arrangement 5580 are shown. FIG. 67C is an assembled view while FIG. 67D is an exploded view.

Referring now to FIG. 67C, first receiving structure 611 can engage first part 600A of bridging element 600, and second receiving structure 613 can engage second part 600B of bridging element 600, in one of its plurality of receiving pockets 615. First receiving structure 611 may be configured to engage with drive element 60 (FIG. 56A). Torque may be supplied to drive element 60 (FIG. 66A) and transmitted to first receiving structure 611. Engagement between drive element 60 (FIG. 66A) and first receiving structure 611 may be established using, for example, but not limited to using, a keyed shaft such as a splined shaft that may be received in first receptacle 616. First receiving structure 611 may further provide bearing assembly 610 configured to be disposed in recess or cavity 633 in first receiving structure 611. In some configurations, bearing assembly 610 may be, but is not limited to being, a needle bearing or an angular contact needle bearing. The torque supplied to first receiving structure 611 may be advanced to second receiving structure 613 (having second receptacle 617) by means of bridging element 600. Second receiving structure 613 may pass the received torque through driven element 62 (FIG. 56A) to an actuated feature such as surgical tool 52 (FIG. 16).

Figure 67E:
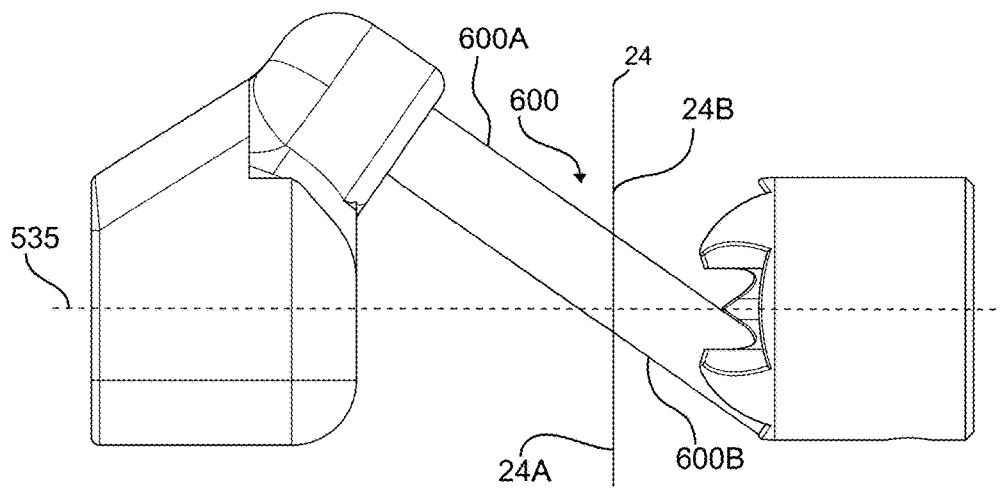
FIG. 67E is a schematic diagram of a configuration of the rotational element of the present teachings.

Referring now to FIG. 67E, the length ratio of first portion 600A of bridging element 600 to second portion 600B of bridging element 600 may be modified to alter the amount of torque transferred. By increasing the length of first portion 600A with respect to second portion 600B, a greater amount of torque may be transferred from first side 24A to second side 24B. Shortening first portion 600A of bridging element 600 with respect to second portion 600B may have the opposite effect. In some configurations, first portion 600A can be longer than second portion 600B, and can have a length ratio of about 2:1, for example.

Figure 67F:
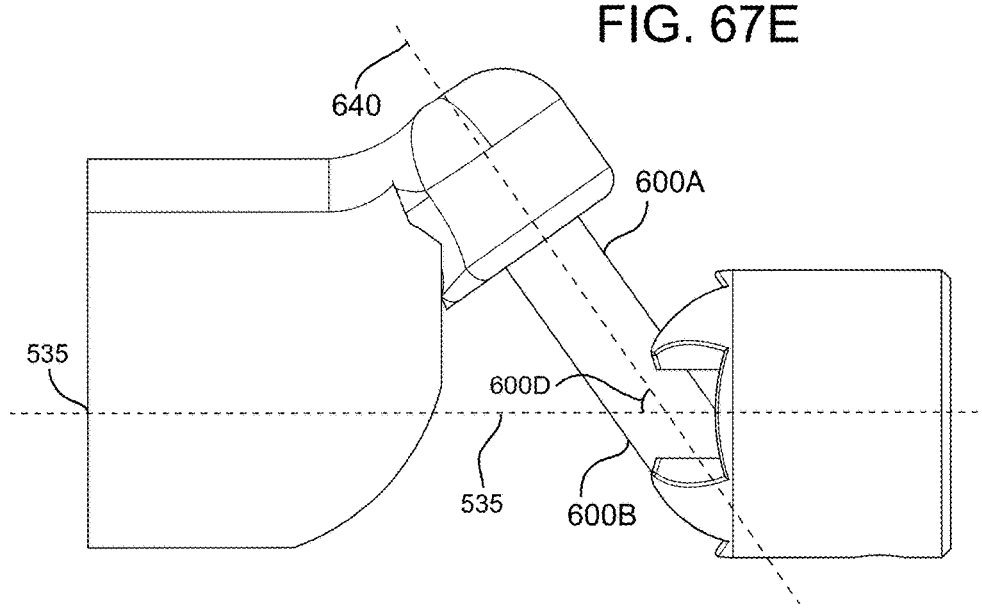
FIG. 67F is a schematic diagram of another configuration of the rotational element of the present teachings.

Referring now to FIG. 67F, modifying the angle 600D of long axis 640 of bridging element 600 with respect to reference axis 535 may alter the amount of torque transmitted. Keeping the lengths of first portion 600A and second portion 600B of bridging element 600 constant, the amount of torque transmitted may increase as angle 600D of long axis 640 with respect to reference axis 535 increases. In some configurations, angle 600D can be about 55-60° for example.

Figure 67G:
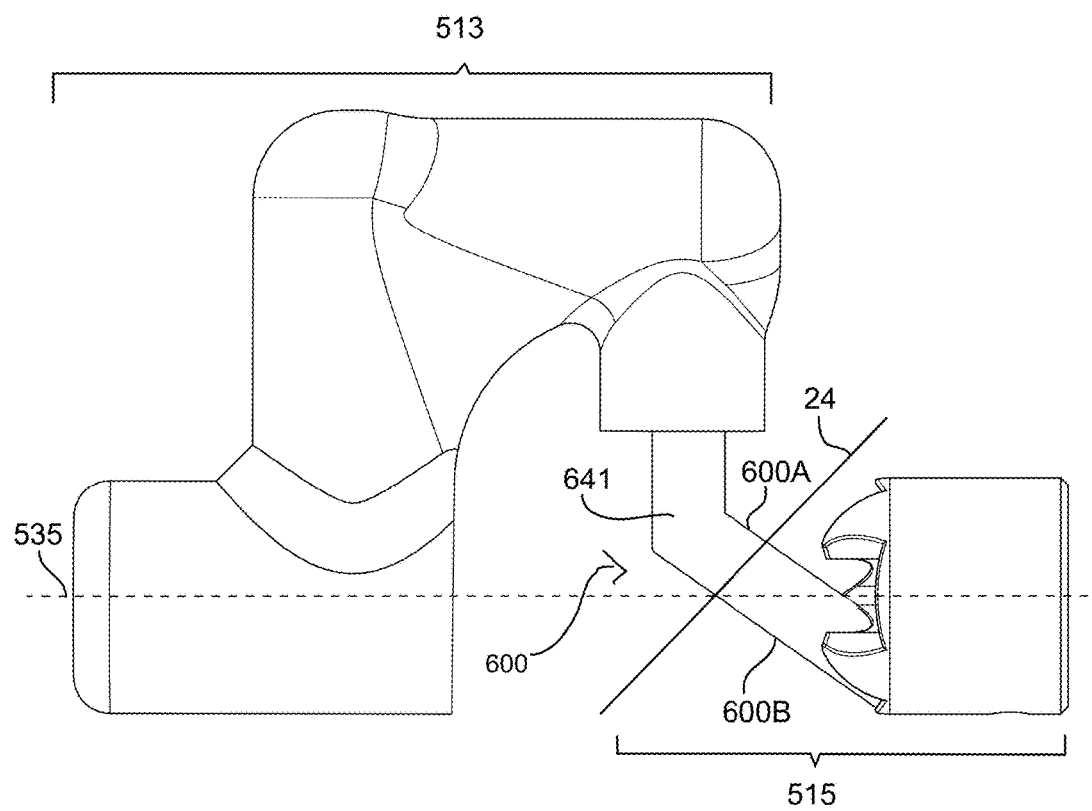
FIG. 67G is a schematic diagram of yet another configuration of the rotational element of the present teachings.

Referring now to FIG. 67G, other modifications may also be made to alter the amount of torque transferred. For example, in some configurations, one of first portion 600A or second portion 600B of bridging element 600 may include extension arm 641. Extension arm 641 may be attached to an end of bridging element 600. Extension arm 641 may extend from bridging element 600 at an angle which can cause extension arm 641 to extend away from and be substantially perpendicular to reference axis 535. Placing extension arm 641 on the drive side, for example, non-sterile side 513, of bridging element 600 may increase the amount of torque transferred. Placing extension arm 641 on the driven side, for example, sterile side 515, may decrease the amount of torque transferred.

Figure 68:
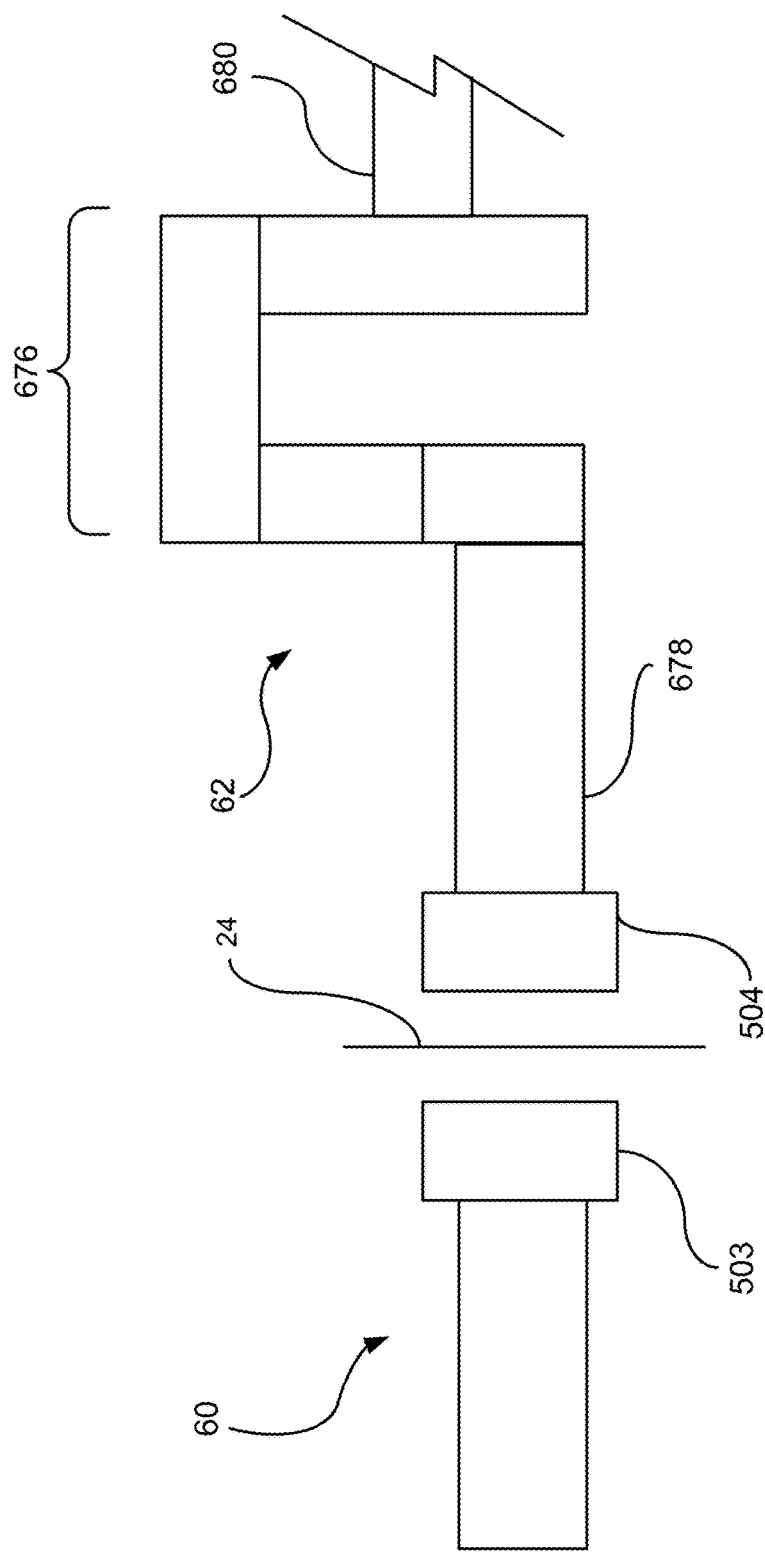

Referring now to FIG. 68, in some configurations gear train 676 may be included as part of driven element 62. Gear train 676 may couple force carrier 678 attached to second barrier interfacing part 504 to drive shaft 680. Drive shaft 680 may either directly or indirectly control an actuated feature such as end tool 52 (FIG. 16). Gear train 676 may be employed to reduce perceived backlash during operation. Without gear train 676, drive element 60 may rotate at a first rate. The rotation rate of drive element 60 may be increased in kind with a gear reduction for gear train 676 to reduce perceived backlash. The gears of gear train 676 may be anti-backlash gears. In some configurations, gear train 676 may be included with a 10:1 gear reduction. If drive element 60 is driven at ten times the first rate, the perceived backlash can be reduced by about 90% (factoring out any backlash in gear train 676). Instead of a gear reduction, gear train 676 may instead be used a mechanical amplifier and which amplifier to increase torque. Any suitable gear ratio may be chosen to amplify the torque by the desired amount.

Referring now to FIG. 69, manipulator 36E may be seated on interface plate 290. Drive component 34A may be operated to cause displacement of driven elements 62 (FIG. 68) in manipulator 36E. This may in turn actuate a feature of manipulated components 38A, 38B and/or end tool 52 on one of manipulated components 38A, 38B. Top portion 78A of manipulator housing 78 has been exploded away to depict components inside of the manipulator 38E. Rotational drive component 34C may transmit torque to a component in manipulator 36E, manipulated component 38A, 38B or to end tool 52. For example, rotation of barrier interfacing part 503 of rotational drive component 34C may cause end tool 52 to rotate. Barrier interfacing part 503 may be, though is not limited to being, any of those described herein. Barrier interfacing part 503 may be adjacent to end 78V of the manipulator 36E. Barrier interfacing part 503 may be positioned to transmit torque to second barrier interfacing part 504 in manipulator 36E at or near the end 78V of manipulator 38E. Barrier interfacing part 504 may be, though is not limited to being, any of those described herein.

Continuing to refer to FIG. 69, in some configurations, rotational drive component 34C may be covered by a rotational drive component cover or housing 290A. Rotational drive component housing 290A may in some configurations be a portion of an interface plate 290 which is proud of the plane of interface plate 290. Rotational drive component housing 290A may allow for drive components 34A and rotational drive components 34C associated with manipulator 36E to be under interface plate 290. In some configurations, all rotational drive components 34C for manipulator 36E may be covered by a rotational drive component housing 290A. In some configurations, manipulator 36E can have a "V" shaped housing 78. In such configurations, rotational motion transmitted to second barrier interfacing part 504 from rotational drive component 34C may need be passed around bend 78U. To facilitate this transmission of rotational motion around the bend, a universal joint (not shown) may be included in the rotating part (e.g. a force carrier such as force carrier 527 (FIG. 56B)). Manipulator 36E need not be "V" shaped and instead may be constructed to avoid needing to transmit any rotational motion around a bend 78U.

Figure 70:
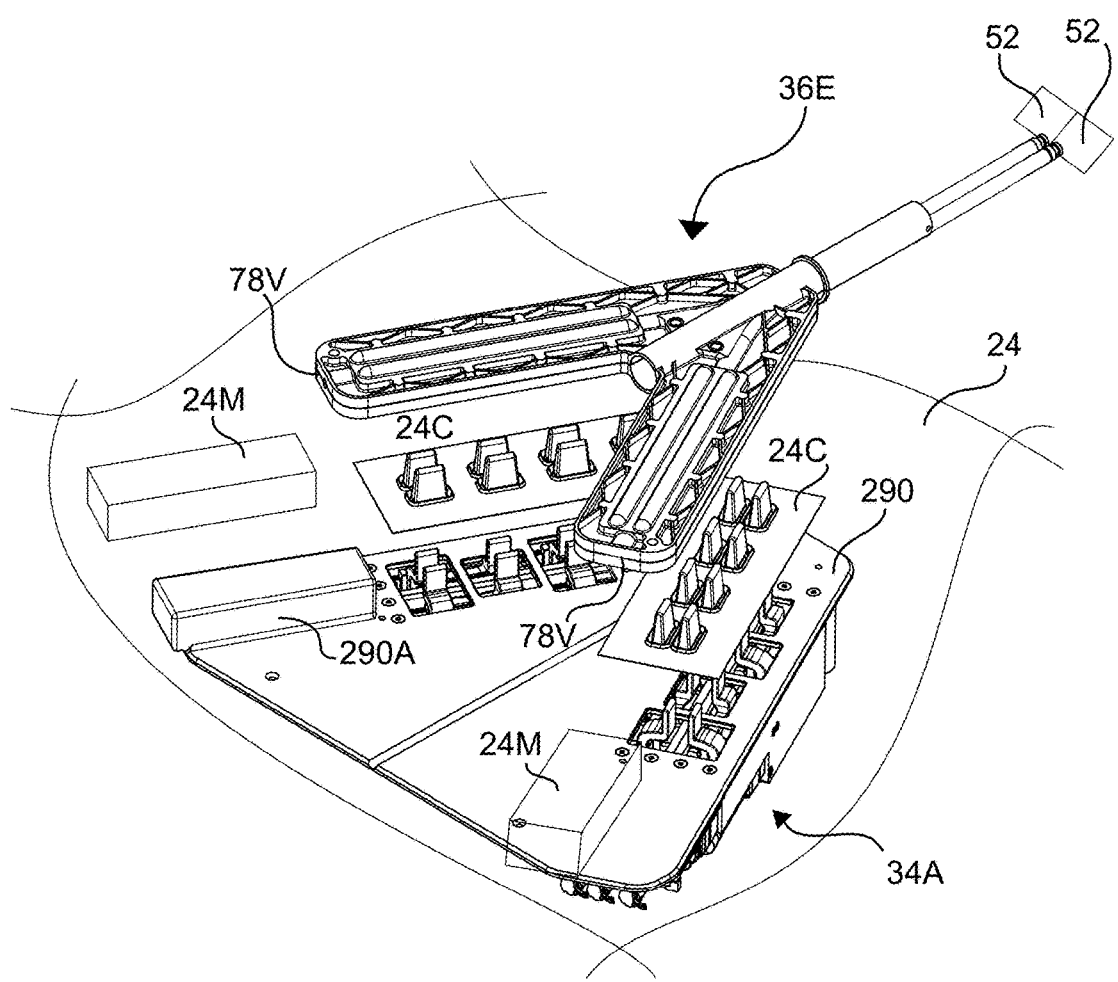

Referring now to FIG. 70, manipulator 36E, which is positioned for docking onto interface plate 290, can include barrier 24. Barrier 24 can include rotational drive component covers or shrouds 24M in addition to pocketed regions 24C. Rotational drive component covers 24M of barrier 24 may be sized to surround rotational drive component housings 290A or rotational drive components 34C. Additionally, when manipulator 36E is docked on interface plate 290, shrouds 24M may extend between rotational drive component housing 290A and end 78V of manipulator housing 78. First barrier interfacing part 503 (FIG. 69) and second barrier interfacing part 504 (FIG. 69) may transmit torque through the portion of barrier 24 between rotational drive component housing 290 and the end of manipulator housing 78. Barrier 24 may maintain segregation of manipulator 36E from drive components 34A, 34C. In some configurations, an element in barrier 24, such as bridging element 600 (FIG. 66A) may extend into rotational drive component housing 290A and/or end 78V of manipulator 36E. Likewise, in some configurations a portion of first barrier interfacing part 503 (FIG. 69) or second barrier interfacing part 504 (FIG. 69) may extend out of the rotational drive component housing 290A or out of end 78V of manipulator 36E respectively.

Figure 71:
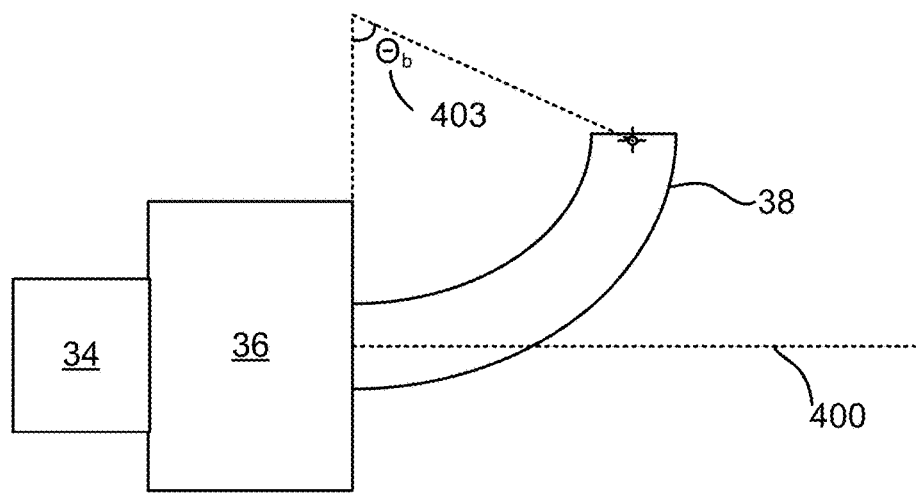

Referring primarily to FIG. 71, at least a part of manipulated component 38 may be articulated to facilitate use of manipulated component 38 to perform a surgery on patient 18 (FIG. 1). The articulation may involve moving or displacing manipulated component 38 or a portion of manipulated component 38 in any of a number of degrees of freedom. Moving or displacing manipulated component 38 may be accomplished by displacing actuators 54A (FIG. 4B) connected to articulated segment 40 (FIG. 4B) of manipulated component 38. Manipulated component 38 can extend from manipulator 36, and can, for example, bend away from neutral axis 400. Neutral axis 400 can align with the longitudinal axis of manipulated component 38 when manipulated component 38 is unactuated or in a "home" position. The degree to which manipulated component 38 is bent away from neutral axis 400 can be referred to as bend angle, $\Theta_b$ 403.

Figure 72:
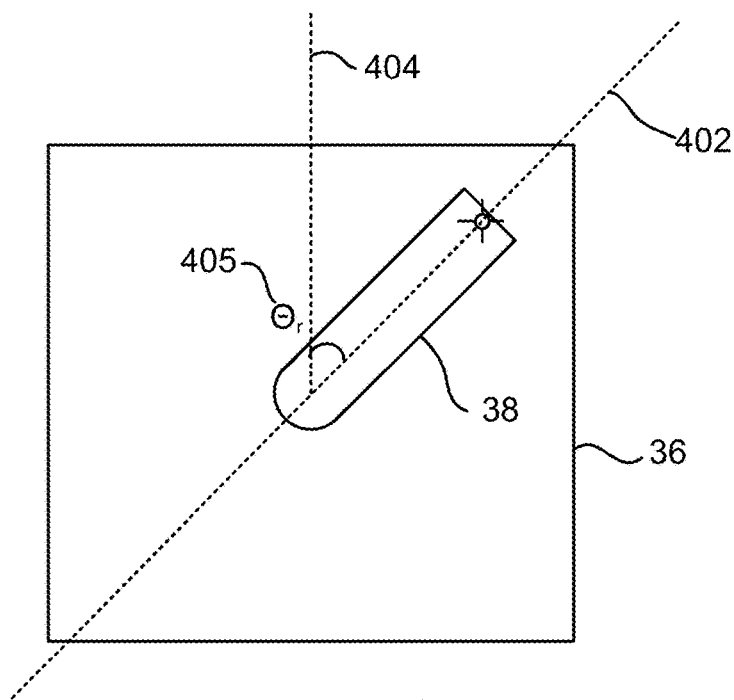

Referring now to FIG. 72, bend plane 402, or the plane in which manipulated component 38 can be bent, may be altered. Bend plane 402 may rotate about neutral axis 400. The amount which bend plane 402 has been rotated from reference plane 404 can be described as rotation angle, $\Theta_r$ 405. In configurations in which articulated segment(s) 40 (FIG. 4B) are controlled by actuators 54A (FIG. 4B), articulated segment(s) 40 (FIG. 4B) can be actuated to a desired position by displacing actuators 54A (FIG. 4B) in a controlled manner. For any combination of rotation angle $\Theta_r$ 405 and bend angle $\Theta_b$ 403 (FIG. 71), an amount of displacement of actuators 54A (FIG. 4B) can be determined. Drive component 34 (FIG. 71) can be commanded to displace actuators 54A (FIG. 4B) the determined amount needed to achieve commanded rotation angle $\Theta_r$ 405 and bend angle $\Theta_b$ 403 (FIG. 71). Thus, manipulated component 38 may be articulated into a desired orientation or configuration. Rotation angle $\Theta_r$ 405 and/or bend angle $\Theta_b$ 403 (FIG. 71) may be specified manually or automatically. For example, a user could enter rotation angle $\Theta_r$ 405 and/or bend angle $\Theta_b$ 403 (FIG. 71) using any suitable user interface or input structure such as, but not limited to a joystick, rollerball, jogwheel, knob, touch screen, or other user input device 14 (FIG. 1) described herein.

Figure 73:
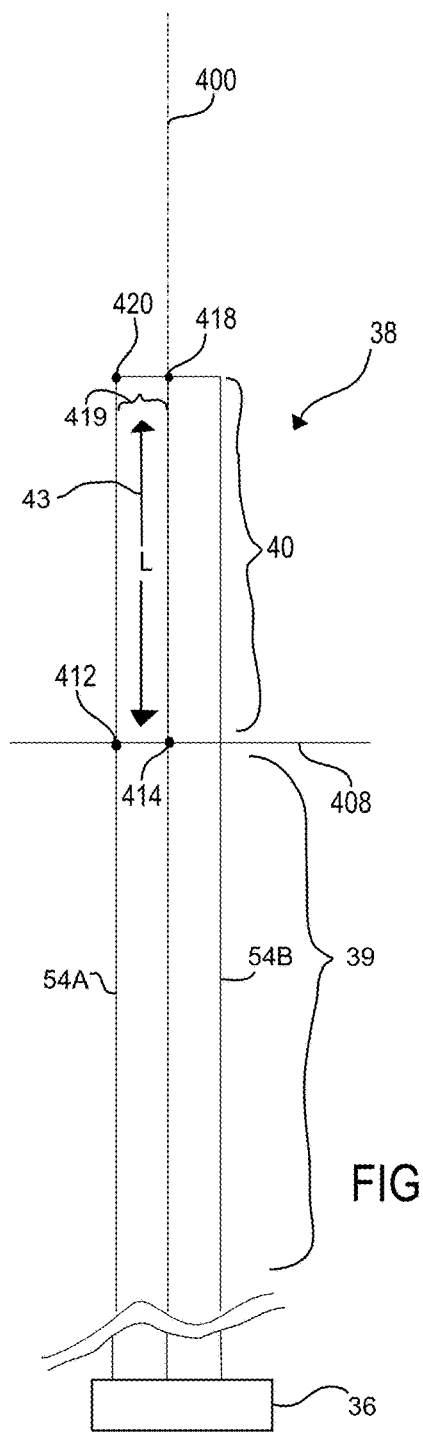
Figure 74:
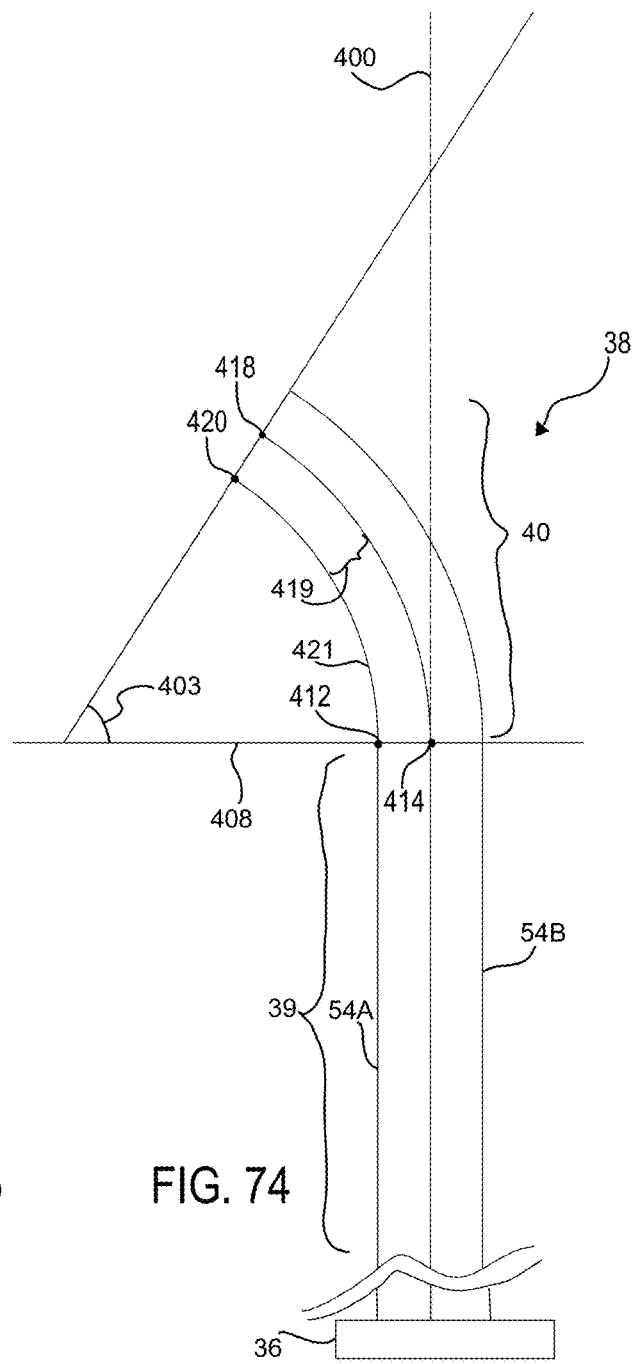

Referring primarily to FIG. 73, manipulated component 38 can include articulated segment 40. Control of a configuration having three actuators 54A (FIG. 8), described herein, can be expanded to include any number of actuators 54A (FIG. 8). Manipulated component 38 can include variable portion 39 and articulated segment or portion 40. Variable portion 39 can telescope and articulate. Manipulated component 38 can be entirely articulated, or can include variable articulation. Variable portion 39 can be located proximal to manipulator 36, and articulated segment 40 can be located distal to manipulator 36. Variable portion 39 can be, for example, but not limited to, rigid or unjointed. Articulated segment 40 can have a neutral or home position and can be bent at a bend angle, $\Theta_b$ 403 (FIG. 74). Articulated segment 40 can begin at start plane 408. For reference, two points 412, 414 on manipulated component 38 which lie on start plane 408 are shown. Nominal length 43, denoted by "L", is the length of articulated segment 40 when articulated segment 40 is aligned in a home or neutral position along neutral axis 400.

Referring primarily to FIG. 74, during articulation of articulated segment 40, points 412, 414 may remain stationary. Points on articulated segment 40 distal to start plane 408 may move during articulation. First moveable point 420 and second moveable point 418 at the distal end of articulated section 40 are also shown for reference. In some configurations, plane 408, first stationary point 412, and second stationary point 414 may move in response to user interaction with robot 16 (FIG. 1) of surgical system (FIG. 1). In some configurations, first stationary point 412 and second stationary point 414 may translationally displace as manipulated component 38 is moved in a fore/aft direction (e.g. telescoped in or out). In some configurations there may be more than one articulatable segment 40 in manipulated component 38. In such configurations, start plane 408 for one of articulated segments 40 may move as other of articulated segments 40 are articulated. As plane 408 moves, all points on manipulated component 38 distal to plane 408 may also move in kind. When articulated segment 40 is not in a neutral or home position (shown in FIG. 73), nominal length 43 may be an arc length in some configurations. In some configurations, when not in the home position, nominal length 43 can be equal to the length of a circular arc between second stationary point 414 and second movable point 418 for a given bend angle $\Theta_b$ 403. Nominal length 43 may be substantially constant regardless of bend angle $\Theta_b$ 403.

Continuing to refer primarily to FIG. 74, desired length, $L_{des}$, of actuator 54A, 54B (e.g. a cable or wire), for a bend angle $\Theta_b$ 403 can be determined. The desired length, $L_{des}$, can correspond to the length of actuator 54A which lies in bend plane 402 (FIG. 72) (when the rotational angle $\Theta_r$ 405 (FIG. 72), is 0°). The term "cable length" is used herein to refer to a length of the portion of actuator 54A, 54B in articulated segment 40. When articulated section 40 is displaced from its home or neutral position (FIG. 73), the cable length is generally an arc length. Arc 421 between first movable point 420 and first stationary point 412 is representative of an actuator 54A with a length of $L_{des}$ for the example bend angle 403 shown. The total actuator length may be substantially longer than the cable length of actuators 54A, B within articulated portion 40. For example, actuators 54A, 54B in many configurations can extend not only along articulated section 40, but also along variable portion 39. Actuators 54A, 54B can also exit manipulated component 38 such that they may be anchored to driven element 62 (FIG. 16).

Continuing to refer primarily to FIG. 74, to find $L_{des}$, offset 419 of actuator 54A, 54B from neutral axis 400 can be used. Offset 419 is denoted by "Ω" herein. For example, given bend angle $\Theta_b$ 403, $L_{des}$ can be equal to the length of arc 421 between first movable point 420 and first stationary point 412 for actuator 54A spanning between points 420, 412. $L_{des}$, can be determined using the following relationship:

$$r-\Omega=L_{des}/\Theta_b$$

where r is equal to $L/\Theta_b$ or the radius defining nominal length L 43 for the given bend angle $\Theta_b$ 402 in radians. $L/\Theta_b$ can be substituted for r and the relationship can be rearranged as follows:

$$L-L_{des}=\Omega*\Theta_b=\Delta_{length}$$

Since nominal length L 43, offset Ω 419, and bend angle $\Theta_b$ 403 can be known, $L_{des}$ may be calculated. $\Delta_{length}$ is the difference between L and $L_{des}$. The $\Delta_{length}$ value may be used to calculate the desired lengths of any number of actuators 54A, 54B which may be present in articulated segment 40 in order to achieve bend angle $\Theta_b$ 403 and rotational angle $\Theta_r$ 405. A configuration of one method for doing so is described herein.

Figure 75:
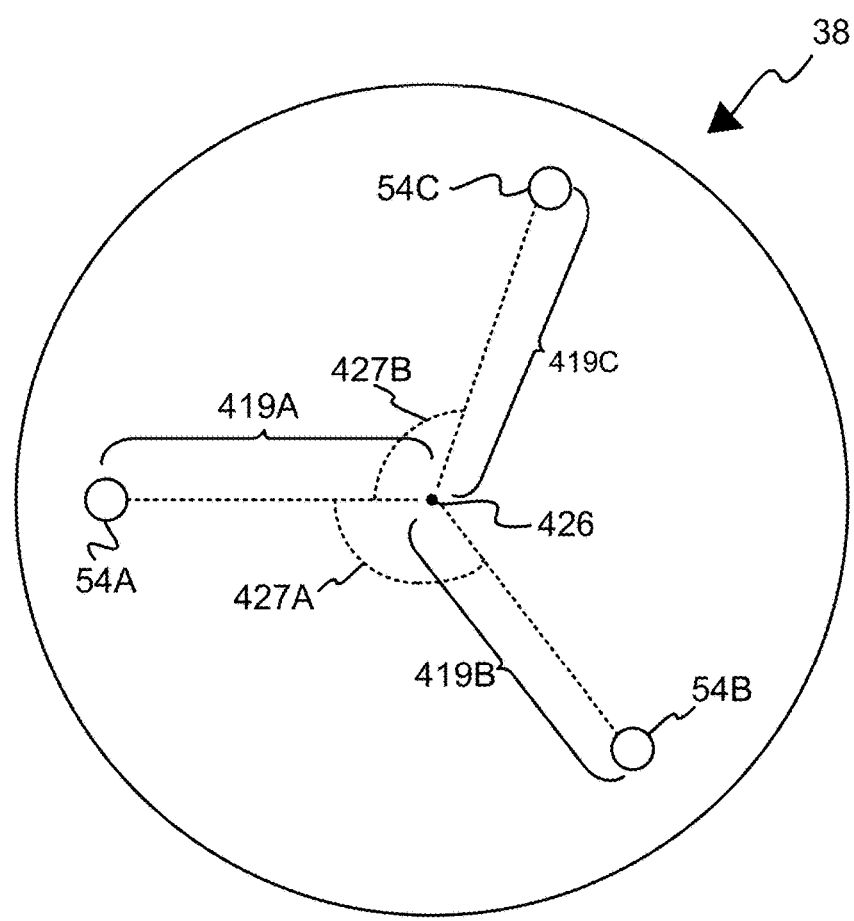

Referring primarily to FIG. 75, manipulated component 38 can, for example, include first actuator 54A, second actuator 54B, and third actuator 54C. The desired lengths for each of first actuator 54A, second actuator 54B, and third actuator 54C can respectively be identified as $L_{des1}$, $L_{des2}$, and $L_{des3}$. The distance between point 426 on neutral axis 400 (FIG. 74) and actuators 54A, 54B, 54C can be referred to as cable offsets 419A, 419B, 419C respectively. In configurations in which bend plane 402 (FIG. 72) is fixed or rotation angle $\Theta_r$ 405 is zero, $L_{des1}$ can be calculated as:

$$\Delta_{length}*\cos 0$$

Each of first actuator 54A, second actuator 54B, and third actuator 54C can be angularly offset from one another, for example, but not limited to, by 120° each. The angular offsets may all be specified in relation to one of actuators 54A, 54B, 54C, for example actuator 54A. First angular offset 427A, denoted herein as "$\Theta_{offset2}$", is the angle between first actuator 54A and second actuator 54B. Second angular offset 427B, denoted herein as "$\Theta_{offset3}$", is the angle between first actuator 54A and third actuator 54C. Exemplarily, $\Theta_{offset2}$ is 120° and $\Theta_{offset3}$ is -120°. Thus, $L_{des2}=\Delta_{length}*\cos(\Theta_{offset2})$ and $L_{des3}=\Delta_{length}*\cos(\Theta_{offset3})$. If $\Theta_r$ 405 (FIG. 72)≠0, $L_{des1}$ $L_{des1}=\Delta_{length}*\cos(0+\Theta_r)$, $L_{des2}=\Delta_{length}*\cos(\Theta_{offset2}+\Theta_r)$, and $L_{des3}=\Delta_{length}*\cos(\Theta_{offset3}+\Theta_r)$. If articulated segment 40 includes additional actuators (not shown in FIG. 75), desired lengths of the additional actuators can be calculated in the same general manner. These lengths may be used to compute the necessary amount of displacement to move articulated segment 40 to desired bend angle $\Theta_b$ 403 (FIG. 74) and rotation angle $\Theta_r$ 405 (FIG. 72). Desired bend angle $\Theta_b$ 403 and desired rotation angle $\Theta_r$ 405 may be specified either manually (e.g. by a user) or automatically. After the desired lengths of actuators 54A, 54B, 54C are determined, the desired lengths may be compared to the current length of each of actuators 54A, 54B, 54C. The computed difference between the desired actuator lengths and the current actuator lengths may be referred to as a length error. These length errors may be expressed as, for example, $length_{err1}$, $length_{err2}$, and $length_{err3}$, for first actuator 54A, second actuator 54B, and third actuator 54C, respectively. The length error values may be used to command drive component 34 (FIG. 71) to cause displacement of actuators 54A, 54B, 54C. As actuators 54A, 54B, 54C displace, manipulated component 38 can be brought to the position designated by desired bend angle $\Theta_b$ 403 (FIG. 71) and rotation angle $\Theta_r$ 405 (FIG. 72) by displacing actuators 54A, 54B, 54C such that the length error values are brought to zero.

Continuing to refer primarily to FIG. 75, desired bend angle $\Theta_b$ 403 (FIG. 71) can be recorded over time to define a set of motions that can be later played back. For example, a skilled operator's motions can be recorded to provide a program for trainees to use, or an operator's own motions can be recorded to reduce the number of repetitious motions required by that operator during a procedure, or during other procedures.

Referring primarily to FIG. 76, method 450 for controlling the operation of articulated segment 40 (FIG. 74) having, for example, three wires can include, but is not limited to including, receiving 431, by a robotic surgical system, at least one command signal. The at least one command signal may be provided by, for example, but not limited to, user input device(s) 14 (FIG. 2), and may be a representation of a user-directed movement command. In some configurations, a sensor or sensors associated with user input device 14 (FIG. 1) may output a representation of the at least one user-directed movement command. The sensor output may be representative of the amount that a portion of user input device 14 (FIG. 1) was displaced, the location of a user's finger on a touch screen, etc. Method 450 can include filtering 432 the at least one command signal. The command signal may be subjected to filtering including, for example, a dead band in some configurations. A gain may also be applied to the command signal. Method 450 can include determining 433 a desired rotation angle $\Theta_r$ and bend angle $\Theta_b$ based at least in part on the command signal. Method 450 can also include determining 435 the $\Delta_{length}$ value, for example, but not limited to, as described herein. Method 450 can include calculating 437 $length_{des}$ values for each of the actuators based on the $\Delta_{length}$ value as, for example, but not limited to, described herein. Method 450 can also include calculating 439 the $length_{err}$ value for each of the actuators based on the $length_{des}$ values, and generating 441 displacement commands based on the $length_{err}$ values. Method 450 can optionally include filtering the $length_{err}$ values and the displacement commands. Method 450 can further include sending 443 the displacement commands to various motor assemblies (e.g. in drive component 34 (FIG. 71)). The commands may be addressed to particular motors in drive component 34 (FIG. 71) which can control the movement of specific actuators. Drive component 34 (FIG. 71) of robot 16 (FIG. 3) may drive the actuators until controller 15 (FIG. 1) determines that the length error value for each of the actuators is equal to zero. Encoder counts, potentiometers, other displacement sensors or a combination of displacement sensors may be used to determine the length of each wire or actuator.

Continuing to refer to FIG. 76, in some configurations, it may be desirable that controller 15 (FIG. 1) be programmed to control articulation of manipulated component 38 (FIG. 75) in a plurality of different modes. These modes may be user selected or may be automatically entered based on data collected from sensors in robot 16 (FIG. 3). For example, controller 15 (FIG. 1) may have a gross movement mode and a fine control mode. The processing of the command signals received in step 431 may be different in each of the plurality of modes. In various configurations, each of the modes can be definable by a number or set of specifiable parameters which can dictate how command signals will be handled by controller 15 (FIG. 1). For instance, the rate at which the length$_{err}$ value for each actuator is brought to zero may depend on the mode selected. The rate may be a parameter which can vary for each of the modes. The rate may be user definable in some configurations. In other configurations, the desired rotation angle $\Theta_r$ and bend angle $\Theta_b$ determined from a given user input may differ depending on the mode selected. The desired rotation angle $\Theta_r$ and bend angle $\Theta_b$ may be subjected to a gain which can scale these values up or down. This gain may be a specifiable parameter for each mode.

Continuing to still further refer to FIG. 76, using the example of gross and fine movement modes, a gross movement mode would allow for quick and/or large displacement movements of the articulated portion of the manipulated component 38 (FIG. 75). This mode may for example be used to move the manipulated component 38 (FIG. 75) within the surgical site and may be useful in getting end effector 52 (FIG. 16) on manipulated component 38 (FIG. 16) into the general location needed for performing the surgery. A fine movement mode would allow for small and precise movement of the articulated portion 40 (FIG. 74) of manipulated component 38 (FIG. 75). This mode may be used in confined spaces or during performance of surgical acts such as cutting, stitching, cauterizing, etc. In some configurations, functionalities associated with some or all surgical acts may be disabled when the system is not in the fine movement mode. For example, actuation of end effectors 52 (FIG. 16) on robot 16 (FIG. 3) may be disabled. Continuing to refer to gross and fine motor movements, the desired rotation angle $\Theta_r$ and bend angle $\Theta_b$ may be scaled up or down depending on the mode controller 15 (FIG. 1) is operating in. Additionally or alternatively, the rate at which the length$_{err}$ value for each actuator is brought to zero may differ. For example, in the gross movement mode, the length$_{err}$ value for each actuator can be brought to zero relatively quickly whereas, this rate could be comparatively slow in the fine movement mode.

Referring now to FIGS. 76A, 76B, and 76C, controller 15 (FIG. 3) can determine the length of each of actuators 76A32 in cable 76A14 from starting position 76A3 to desired position 76A2 by determining neutral length 76A4 for each of actuators 76A32. Controller 15 (FIG. 3) can determine neutral length 76A4 by dividing actuator 76A32 into straight lengths 76C3 (FIG. 76C) and multiplying the number of straight lengths that form the actuator by the size of straight lengths 76C3 (FIG. 76C). Controller 15 (FIG. 3) can determine pitch angle 76B1 (FIG. 76B) as the angle between taut length 76A5 and projection 76B4 (FIG. 76B) onto horizontal axis 76B3 (FIG. 76B). Controller 15 (FIG. 3) can determine yaw angle 76B2 as the angle between horizontal axis 76B3 (FIG. 76B) and projection 76B4 (FIG. 76B). Controller 15 (FIG. 3) can compute rotation angle 76C1 (FIG. 76C) as a tan(sin(pitch angle)/sin(yaw angle)). Controller 15 (FIG. 3) can determine bending arc 76A6 as the angle between intersection 76A8 between a projection from actuator first end 76A3 drawn at rotation angle 76C1 (FIG. 76C) and actuator second end projection 76A10, and bent radius 76A7 as neutral length 76A4/bending arc 76A6. Controller 15 (FIG. 3) can determine cable offset 76A12 as the distance between actuator 76A4 and center 76A13 of cable 76A14 that can house, for example, but not limited to, four of actuators 76A4. Controller 15 (FIG. 3) can determine actuator angle 76A30 as the acute angle between actuator 76A12, for example, and Cartesian axis 76A31 drawn within cable 76A14. In some configurations, controller 15 (FIG. 3) can compute the length of each actuator as neutral length 76A4+bending arc 76A6*cable offset 76A12*sin(rotation angle 76C1+actuator angle 76A30).

Referring now primarily to FIG. 77, method 475 for tensioning actuators for a surgical robot can include, but is not limited to including, commanding 451 a drive component to tension a first actuator until the force in the load path has reached a predetermined threshold value. The force may be determined by sensing the displacement of a compliant member such as, for example, but not limited to mechanical component 150 (FIG. 26) located in the load path. If 453 the force value has not reached the threshold value, method 475 can include repeating monitoring 453 the force value. If 453 the force value has reached a predetermined threshold value, method 475 can include identifying 455 another actuator to tension. In some configuration$_s$, actuators may be tensioned in a cross-tensioning sequence or pattern. In configurations which use cross tensioning, an actuator can be identified in step 455 by finding the actuator which acts on a feature of manipulated component 38 (FIG. 75) that is substantially opposite to the feature controlled by the previously tensioned actuator. The actuators would thus be tensioned in a crisscrossing manner similar to the tightening of lug nuts on a wheel. Consequently, as the actuators are tensioned, the articulated portion of the manipulated component can substantially remain in the same orientation or position throughout the process. If the actuators are arranged in a non-circular pattern, a spiral sequence may be also be used. In alternative configurations, the tensioning can be preprogrammed in the desired sequence and no determination of actuators by the processor is necessary.

Still referring to FIG. 77, method 475 can further include tensioning 457 the identified actuator until the force in the identified actuator load path is above a pre-determined threshold. If 459 the force in the load path has not reached the pre-determined threshold, method 475 can include repeating monitoring 459 the force. If 459 the force in the load path has reached the pre-determined threshold and if 461 there are additional actuators to tension, method 475 can include identifying 455 another actuator to tension. When all of the actuators have been tightened to their respective thresholds, additional rounds of tensioning may be preformed. In such configurations, the actuators may be stepped up to a desired final tension value in one or more increment(s). If 459 the force in the load path has reached the pre-determined threshold value, and if 461 there are no additional actuators to tension, and if 463 there are additional tensioning rounds, method 475 can include possibly adjusting 465 the pre-determined threshold value to a next predetermined threshold value and repeating 451 tensioning of the first actuator by sending a command to a motor, for example. If 463 there are no additional tensioning rounds, method 475 can terminate.

Continuing to refer to FIG. 77, for example, a first round of tensioning may tension the actuators to a quarter of the desired final tension value, a second round may tension the actuators to a half of the desired end tension value, and so on. The number of rounds of tensioning may differ depending on the configuration. Additionally, the increments for each step may differ depending on the configuration. All of the actuators may be tensioned in equal increments in each round of tensioning or the actuators may be assigned individual tensioning increments for each round. Since the tension on each of the actuators can be controllable to a desired amount, the stiffness of manipulated component 38 (FIG. 75) can be varied to best suit the needs of a surgery. The variable stiffness could allow for some tools 52 (FIG. 16) (e.g. retractors) or groups of tools to be more rigid, while other tools (e.g. shavers or cauterizers) can be more compliant. Variable stiffness may be useful in controlling the amount of spring back which occurs for a given tool if a force transverse to the axis of manipulated component 38 (FIG. 75) is suddenly removed. The force transverse to the axis may occur if an obstacle is encountered and overcome. When cutting through a target tissue for example, the force transverse to the axis will no longer be present when the cut is complete. By lowering the actuator tension (making the manipulated component 38 (FIG. 75) more compliant), the resulting spring back can be dampened. In some configurations, the cable tension on the actuator can be up to, for example, but not limited to, 80 pounds.

Continuing to still further refer to FIG. 77, the ability to vary stiffness may allow for dynamic stiffness control. The stiffness of manipulated component 38 (FIG. 75) may be altered in situ as is appropriate for a given situation. In some configurations, manipulated component 38 (FIG. 75) can have a default stiffness setting which is active when manipulated component 38 (FIG. 75) is introduced into patient 18 (FIG. 1). The default setting may specify a tension which can allow the tool to be substantially compliant. The default setting may be a generic setting or tool specific. If suitable, the stiffness may be altered to change the compliance of manipulated component 38 (FIG. 75) when a tool is performing a surgical duty such as cutting, separating, or holding tissue in place. The stiffness of manipulated component 38 (FIG. 75) may be set or changed in a variety of manners. In some configurations, controller 15 (FIG. 1) can be configured to control manipulated component 38 (FIG. 75) in a plurality of modes. Stiffness may be a definable parameter for each of the plurality of modes. A mode can be automatically or manually selected with the desired stiffness for manipulated component 38 (FIG. 75). In configurations which include gross and fine movement modes, the stiffness setting for each mode may differ. The gross movement mode may, for example, be assigned the default stiffness while the fine movement mode may be more or less rigid. Alternatively, stiffness can be prescribed for each end effector or surgical tool 52 (FIG. 16) which can be used with the manipulated component 38 (FIG. 16). In configurations with different operational modes, a stiffness for each mode may be defined. Installation of tool or end effector 52 (FIG. 16) on manipulated component 38 (FIG. 75) may automatically activate a set of parameters which can be associated with tool 52 (FIG. 16). To facilitate automatic parameter set activation, tool 52 (FIG. 16) may include a unique identifier which can be recognizable by the robot. The unique identifier may be any of a variety of suitable unique identifiers. Suitable unique identifiers can include, but are not limited to including, mechanical identifiers (e.g. key features or unique series of projections), RFID or other type of smart label, barcode, data matrix, and other printed labels. During installation of tool 52 (FIG. 16), part of robotic surgery system 10 (FIG. 1) can read the unique identifier and the associated parameter set can be consequentially activated for manipulated component 38 (FIG. 75).

Referring now to FIG. 78, method 1350 for sensing the status of a load sensor can include, but is not limited to including, substantially simultaneously sampling and time-stamping 1301 load sensor data and motor current data. Method 1350 may be used with any load sensor such as those described elsewhere herein. Method 1350 may further include computing 1303 torque/force based on the load sensor data and the motor current data. The following relationships may be employed to make the computation:

$$\text{Force} = t * K_d$$

$$t = \text{Motor constant} * I_m$$

where force is the force exerted on the load sensor, t is the torque generated by the motor, $K_d$ is a drive screw gain (which may, for example, be empirically determined), the motor constant is a constant specific to the motor (which may, for example, be empirically determined), and $I_m$ is the motor current.

Still referring to FIG. 78, if 1305 the load sensor data is in a pre-determined relationship with the motor current data as determined by comparing the computed torque/force, method 1350 can include taking 1301 another sample of load sensor and motor current data and the process may repeat. If 1305 the load sensor data is not in a pre-determined relationship with the motor current data, method 1350 can include entering 1307 a failsafe mode, and generating 1309 a notification on, for example, the user interface.

Referring now primarily to FIG. 79A, the tension and displacement of actuator 54A (FIG. 4B), and therefore stiffness and movement of an articulated section 40 (FIG. 4C) and surgical tool 52 (FIG. 4C) can be controlled, for example, but not limited to, by a pre-selected and/or dynamically-controlled tension and a drive element position command. These may be provided manually and/or automatically. The pre-selected or dynamically-controlled tension can reflect, for example, but not limited to, the type of tool being controlled, the patient, the type of procedure being executed, and the preferences of the user. The tension setting can be referred to as tension set point 805, which can be provided by, for example, but not limited to, user interface 12A, computer memory, and surgical tool 52 (FIG. 4C) or function identification. The tension set point 805 may at least in part control the stiffness of an articulated section 40 (FIG. 4C).

Still referring to FIG. 79A, the user can begin the process of positioning drive element 60 by manipulating user interface 12A. User interface 12A can include a number of sensors which can provide data 802 representative of user interactions with user interface 12A. Data 802 may be processed by user input processor 792 to determine drive element position command 807 associated with the user manipulations.

Still referring to FIG. 79A, motor position feedback 811 can be based on information collected by at least one motor feedback sensor 799 which can sense, for example, position, velocity, and amount of rotation of motor 70A. Load sensor feedback 815 may be based on a sensed load in the load path of drive element 60 sensed by at least one load sensor 98. Tension controller 801 can provide tension controller command 817 based on tension set point 805, drive element position command 807, motor position feedback 811, and load sensor feedback 815. Motor position controller 797 can determine and provide a desired motor position command 796 to motor 70A based on motor position feedback 811, position command 807, and tension controller command 817. Motor 70A can provide force to drive element 60 based on motor command 796 provided by motor position controller 797. By controlling movement of surgical tool 52 (FIG. 4B) in this manner, displacement of surgical tool 52 (FIG. 4B) can be governed by a tension limit based at least in part on tension set point 805. The tension on actuator 54A (FIG. 4B) may be maintained while surgical tool 52 (FIG. 4B) is moved about the surgical site or while performing a surgical act. Based at least in part on tension set point 805, the position command for motor 70A may be adjusted to maintain the tension on actuator 54A (FIG. 4B).

Still referring to FIG. 79A, if load sensor 98 provides load sensor feedback indicating the load has exceeded a maximum value, a processor 792 may determine a threshold has been exceeded. Processor 792 may determine if feedback should be generated by the user interface for the user. If threshold indicator 815 indicates that the load is above a predetermined amount, processor 832 may generate feedback signal 831 which can cause a warning or the like to be generated and conveyed to the user via a display of user interface 12A. Alternatively, processor 832 may generate haptic feedback for the user and may inhibit a user input structure included in user interface 12A from movement until threshold indicator 815 indicates the load is below the threshold.

Referring now primarily to FIG. 79B, the tension setting can be referred to as tension set point 805, which can be provided by, for example, but not limited to, user interface 12A, computer memory, and surgical tool 52 (FIG. 4C) or function identification. The user can begin the process of positioning drive element 60 by manipulating user interface 12A. User interface 12A can include a number of sensors which can provide data representative of user interactions with user interface 12A. The data may be processed by a processor to determine drive element position command 807 associated with the user manipulations. Gain processor 791 can determine position gain 813 based on drive element position command 807 and motor position feedback 811. Motor position feedback 811 can be based on information collected by at least one motor feedback sensor 799 which can sense, for example, position, velocity, and amount of rotation of motor 70A. Tension controller 801 can provide tension controller command 817 based on tension set point 805, position gain 813, and load sensor feedback 815. In some configurations, tension set point 805 can be added to position gain 813, and load sensor feedback 815 can be subtracted from that sum (see summer 794). Load sensor feedback 815 may be based on a sensed load in the load path of drive element 60 sensed by at least one load sensor 98. In some configurations, load sensor feedback 815 may be processed to determine actuator tension and actuator tension may be provided to summer 794. Motor position controller 797 can determine and provide a desired motor position to motor 70A based on motor position feedback 811, position command 807, and tension controller command 817. In some configurations, tension controller command 817 can be added to position command 807 (see summer 793), from which motor position feedback 811 can be subtracted (see summer 795). Motor 70A can provide force to drive element 60 based on motor command 796 provided by motor position controller 797. By controlling movement of surgical tool 52 (FIG. 4B) in this manner, displacement of surgical tool 52 (FIG. 4B) can be governed by a tension limit based at least in part on tension set point 805. The tension on actuator 54A (FIG. 4B) may be maintained while surgical tool 52 (FIG. 4B) is moved about the surgical site or while performing a surgical act. Based at least in part on tension set point 805, the position command for motor 70A may be adjusted to maintain the tension on actuator 54A (FIG. 4B).

Still referring to FIG. 79B, if load sensor 98 detects that the load has exceeded a maximum value, load sensor 98 can send threshold indicator 815 to user interface 12A or a processor within the user interface 12A. Threshold indicator 815 may be used to determine feedback which will be generated by the user interface for the user. If threshold indicator 815 indicates that the load is above a predetermined amount, a processor may generate a feedback signal which may be displayed or otherwise provided through the user interface 12A. For example, a processor may generate a warning or the like to be conveyed to the user via a display of user interface 12A. Alternatively, the processor may generate haptic feedback for the user and may inhibit a user input structure included in user interface 12A from movement until threshold indicator 815 indicates load is below the threshold.

Referring now to FIG. 79C, system 79C1 for positioning drive element 60 can include, but is not limited to including, UI 12A, controller 15, and sensors 79C2 communicating over communications network 21 with drive state cable position system 79C3 and series compliant cable position system 79C4. Drive state cable position system 79C3 can include, but is not limited to including, motors 79C5 such as, for example, but not limited to, 3-phase brushless motors, driving linear actuators 79C6 and receiving feedback from position sensors 79C6. Series compliance cable position system 79C10 can include redundant series compliance sensors 79C8 and absolute position sensors 79C9. Desired location 76A2 (FIG. 76A) can be achieved compliantly or rigidly depending on the goal of the movement. For example, if actuator 76A32 (FIG. 76A) is to be associated with an activity that requires force to achieve the activity, desired location 76A2 (FIG. 76A) could be achieved by rigidly encountering obstacles, whereas if actuator 76A32 (FIG. 76A) is to be associated with simply relocating cable 76A14 (FIG. 76A), desired location 76A2 (FIG. 76A) could be achieved by compliantly navigating obstacles. Drive state cable position system 79C3 can be used to perform an activity that requires force, whereas series compliance cable position system 79C10 can be used to simply relocate cable 76A14 (FIG. 76A). Series compliance can add a compliant element of known stiffness to the load path that can allow the control of force when encountering surface. The stiffness of the system can be varied by, for example, but not limited to, changing the force displacement characteristics in controller 15 (FIG. 3). Tension control during motion can limit the peak force at the edge of a work envelop, and can, under some conditions, ensure no lag when reversing direction.

Referring primarily to FIG. 80A, equipment carrier 1440 can be formed by a combination of inner lumen 1440A and outer lumen 1440B. Such a combination can be collectively referred to as equipment carrier 1440. Outer lumen 1440B can comprise first lumen space 1443 that can accommodate inner lumen 1440A. Inner lumen 1440A can further comprise second lumen space 1442 configured to receive and accommodate at least one surgical tool that can be inserted and can travel along a length of equipment carrier 1440. Inner lumen 1440A can further comprise one or more cable compartments 1444 configured to accommodate at least one cable (not shown) in a matching cable compartment 1444. Cable compartments 1444 can be further configured to run along an outer surface (shown) of inner lumen 1440A. The received cables can remain trapped between the outer surface of inner lumen 1440A and inner surface (not shown) of outer lumen 1440B. Trapping the cables can enable the cables to perform a linear and/or rotational motion. Outer lumen 1440B can further include access windows 1441 that can correspond to cable compartments 1444 thus providing access to cables from outside of equipment carrier 1440. Additionally, inner lumen 1440A and outer lumen 1440B can remain operably coupled during operation of equipment carrier 1440.

Referring now primarily to FIG. 80B, equipment carrier 1440 can be operably coupled with at least one driven component 1480. Such an arrangement can be achieved by partially or completely retaining equipment carrier 1440 within a retaining passage 1481. Driven component 1480 can be further configured to access actuation cables through access windows 1441 of equipment carrier 1440. In some configurations, driven component 1480 can engage actuation cables such that motion of driven component 1480 can influence the position of the actuation cables as discussed further herein. Force or motion can be transferred to driven component 1480 through transfer junction(s) 1482 that can partially or completely occupy a surface of driven component 1480. Transfer junction(s) 1482 can be further configured to receive force and/or motion through an external device or body. The received force and/or motion can then be advanced to the actuation cables of equipment carrier 1440.

Referring primarily to FIGS. 81A-81C. Assembly 1399 can comprise housing 1400 and actuation setup 1398. Housing 1400 can further comprise a first surface 1401 with first set of operative members of actuation setup 1398 engaged therewith and a second surface with a second set of operative members of actuation setup 1398 engaged. Actuation setup 1398 can further comprise equipment carrier 1440 that can be operably coupled with one or more driven components 1480 such that driven component 1480 can influence the motion of actuation cables disposed within cable compartments 1444 (FIG. 80A). Driven component 1480 can completely or partially accommodate equipment carrier 1440 within retaining passage 1481. Retention of equipment carrier 1440 can further allow driven component 1480 to access actuation cables through access windows 1441 (FIG. 81B). Engagement between actuation cables and driven component 1480 can be achieved by providing cable anchors 1483 configured to enter cable compartment 1444 (FIG. 80A) through access windows 1441 (FIG. 81B). Interaction between cable anchors 1483 and actuation cables can be achieved by aligning driven component(s) 1480 such that corresponding cable anchors 1483 can coincide with a matching access window 1441 (FIG. 81B) along equipment carrier 1440. In some configurations, actuation cables can be partially released from access window 1441 (FIG. 81B) and can be secured around driven component 1480 to obtain influence from driven component 1480. In some configurations, driven component 1480 can be a multi-part component. Most parts of driven component 1480 can come together to provide retain passage 1481 (FIG. 81A) that can in turn accommodate equipment carrier 1440.

Continuing to refer to FIGS. 81A-81C, transfer junction 1482 can partially or completely occupy a surface area of driven component 1480 and can be configured to receive force and/or motion from an external body. This received force/motion can be advanced to actuation cables of equipment carrier 1440. In some configurations, driven component(s) 1480 can navigate actuation cables of the manipulated component 1440. Actuation set up 1398 can further include a plurality of driving components 1490 that can correspond to one or more driven components 1480. Driving component 1490 can be composed of stem portion 1491 and operative portion 1493 substantially surrounding stem portion 1491. Stem portion 1491 can be configured to engage with housing 1400 such that driving component 1490 can retain its rotational freedom during operation of actuation setup 1398. Operative portion 1493 can interact with transfer junction 1482 of driven component 1480 for advancing force and/or motion from driving component 1490 to driven component 1480.

Referring now primarily to FIG. 81B, housing 1400 can include linear track 1420 with first station 1420A and second station 1420B. Driven component/s 1480 can be configured to operatively rest over linear track 1420 and can perform, but is not limited to performing, a linear motion in first linear direction 1522 or second linear direction 1523. Linear motion of driven component(s) 1480 can be limited between first station 1420A and second station 1420B of linear track 1420. Linear track 1420 can include cavities 1421 that can be disposed at first station 1420A and second station 1420B. Cavities 1421 can be configured to accommodate equipment carrier 1440. In some configurations, a plurality of cavities 1421 can be provided along the length of linear track 1420 for maintaining equipment carrier 1440 in its operative position. Various sections of equipment carrier 1440 can be jointly retained by cavities 1421 and retaining passage 1481 (FIG. 81A) provided by driven component 1480. Housing 1400 can include receptors 1424 configured to receive corresponding stem portion 1491 of driving component 1490, therein. Such an arrangement can allow engagement between housing 1400 and driving component 1490.

Continuing to refer to FIGS. 81A-81C, driving component 1490 can be configured to perform rotary motion in a first rotary direction 1532 and second rotary direction 1533. In some configurations of assembly, rotary motion can be generated by an external rotary device such as, but not limited to, a harmonic gear motor and/or a planetary gear motor. The external rotary device can be engaged with driving component 1490 through second surface (not shown) of housing 1400. This engagement can be achieved by receiving stem portion 1491 of driving component 1490 into receptor 1424 such that at least a part of stem portion 1491 can protrude through second surface. This protruded part (not shown) can be engaged with external rotary device such as harmonic gear motor 1555 (FIG. 81C) or planetary gear motor 1550 (FIG. 81C). Rotational motion generated by motors 1550, 1555 can be advanced to operative portion 1493 through stem portion 1491 of driving component 1490. In some configurations, operative portion 1493 can be, but is not limited to being, a cylindrical body with a first set of geared teeth that can interact with a matching second set of geared teeth that can be provided on transfer junction 1482 of driven component 1480. The number of geared teeth can be variable in nature depending on the amount or degree of force required.

Referring now to FIG. 81C, second configuration of driving component 1600 can include a higher number of geared teeth and hence a larger diameter than the first configuration. Second configuration of driving component 1600 can engage with housing 1400 through stem portion 1610 and interact with transfer junction 1482 through operative portion 1620.

Various alternatives and modifications can be devised by those skilled in the art without departing from the disclosure. Accordingly, the present disclosure is intended to embrace all such alternatives, modifications and variances. Additionally, while several configurations of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular configurations. And, those skilled in the art will envision other modifications within the scope and spirit of the claims appended hereto. The present configuration is also directed to a system and methods that can be executed in hardware, firmware, and/or software for accomplishing the methods discussed herein, and, possibly, computer readable media storing software for accomplishing these methods and system. The various modules described herein can be provided in conjunction with a single CPU, or on an arbitrary number of different CPUs. Other alternative computer platforms can be used. The operating system can be, for example, but is not limited to, WINDOWS®, LINUX®, and VMS. Communications links can be wired or wireless, for example, using cellular communication systems, military communications systems, and satellite communications systems. Any data and results can be stored for future retrieval and processing, printed, displayed, transferred to another computer, and/or transferred elsewhere.

In compliance with the statute, the present configuration has been described in language more or less specific as to structural and methodical features. It is to be understood, however, that the present configuration is not limited to the specific features shown.

Referring again to FIGS. 76, 77, and 78, methods 450 (FIG. 76), 475 (FIG. 77), and 1350 (FIG. 78) can be, in whole or in part, implemented electronically. Signals representing actions taken by elements of systems that implement the methods of the present teachings, and other disclosed configurations can travel over at least one live communications network 21 (FIG. 2). Control and data information can be electronically executed and stored on at least one computer-readable medium. The system can be implemented to execute on at least one computer node in at least one live communications network 21 (FIG. 2). Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form including, but not limited to, Graphic Interchange Format (GIF), Joint Photographic Experts Group (JPEG), Portable Network Graphics (PNG), Scalable Vector Graphics (SVG), and Tagged Image File Format (TIFF).

The configurations shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the terms such as, for example, "comprising", "including", and "having" are used in the present description and claims, they does not exclude other elements or steps. Where an indefinite or definite article is used when referring to a singular noun, such as, for example, "a" "an" or "the", this includes a plural of that noun unless something otherwise is specifically stated. Hence, the terms "comprising", "including", and "having" should not be interpreted as being restricted to the items listed thereafter; they do not exclude other elements or steps, and so the scope of the expression, for example, "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the configurations of the disclosure described herein are capable of operation in other sequences and/or arrangements than are described or illustrated herein.

What is claimed is:

1. An apparatus for performing robotic surgery comprising:
   a drive component having at least one motor and an associated drive element for each of the at least one motor, the associated drive element having a drive screw, a nut translationally displacing about a longitudinal axis of the drive screw in response to rotation of the drive screw about the longitudinal axis, and a projection oriented at an angle transverse to the longitudinal axis;
   a manipulator including at least one driven element, the at least one driven element having a receiving feature engaging the projection, the at least one driven element achieving translational displacement with the projection when the projection is engaged in the receiving feature;
   a continuous barrier separating at least the projection and the receiving feature, at least a portion of the continuous barrier covering the projection, the projection engaging the receiving feature through the continuous barrier, the continuous barrier maintaining sterility of the drive component, the continuous barrier accommodating the translational displacement; and
   at least one actuator having a first end coupled to the driven element and a second end coupled to an end effector,
   wherein the at least one actuator being driven by the drive component to perform the robotic surgery using the end effector.

2. The apparatus as in claim 1 wherein at least a portion of the continuous barrier moves with the projection and driven element.

3. The apparatus as in claim 1 wherein the load sensor for measuring a load comprises:
   a compliant body, the compliant body deforming in proportion to a magnitude of the load, the compliant body having a compliant body first face and a compliant body second face, the compliant body first face being disposed opposite to the compliant body second face;
   an insert extending through the compliant body, the insert having an insert first face spaced from the compliant body first face by a first gap, the insert having an adjustable spacer, the adjustable spacer having an adjustable insert face spaced from the compliant body second face by a second gap;
   a load sensor projection attached to the compliant body, the load sensor projection displacing based on the deforming of the compliant body, the compliant body, the insert, and the load sensor projection forming a mechanical component; and an electrical component, the electrical component including at least one sensor monitoring a displacement of the load sensor projection, the displacement associated with the load.

4. The apparatus as in claim 3 wherein the electrical component comprises a physically separate component from the mechanical component.

5. The apparatus as in claim 3 wherein the insert comprises a threaded insert.

6. The apparatus as in claim 3 wherein the load sensor projection comprises a bend dividing the load sensor projection into a pre-bend portion and a post-bend portion, the pre-bend portion attaching to the complaint body, the post-bend portion having a face, the face being substantially perpendicular to the complaint body first face.

7. The apparatus as in claim 1 further comprising:
a sterile component for a robotic surgery system comprising:
  a manipulated component having a first proximal portion, the first proximal portion having a proximal end, the manipulated component having an articulated distal portion, the articulated distal portion having a distal end, the articulated distal portion having at least one articulation, the manipulated component having a guide;
  wherein the at least one actuator having a first actuator end and a second actuator end, the first actuator end being anchored to the articulated distal portion;
  a surgical tool disposed at the distal end of the manipulated component; and
  wherein the manipulator having at least one bearing surface, the driven element having an anchor point anchoring the second actuator end, the driven element being configured to displace translationally along the at least one bearing surface, the driven element having a receiving feature engaging at least a portion of the drive element through the continuous barrier,
  wherein the manipulator engages the surgical tool and the manipulated component to perform the robotic surgery.

8. The apparatus as in claim 7 wherein the at least one articulation comprises a living hinge.

9. The apparatus as in claim 7 wherein the at least one articulation comprises a kinematic pair of bodies.

10. The apparatus as in claim 7 wherein the at least one displaceable actuator comprises a wire.

11. The apparatus as in claim 7 wherein the manipulator comprises a housing, the housing having at least one slot, the at least one slot being aligned with a receiving feature of the at least one driven element.

12. The apparatus as in claim 7 wherein the manipulator comprises at least one rotary driven element interacting with a rotary drive element through a barrier.

13. The apparatus as in claim 7 wherein the at least one rotary driven element comprises a magnet.

14. The apparatus as in claim 1 further comprising:
a non-sterile section and a sterile section separated by the continuous barrier, the continuous barrier having a first surface facing the non-sterile section and an opposing second surface facing the sterile section, the at least one drive element located in the non-sterile section, the at least one drive element generating and transmitting a pre-determined force; and
one or more barrier interfacing members configured to communicate with the first surface,
wherein the at least one driven element located in the sterile section, the at least one driven element including at least one co-operating barrier interfacing member configured to communicate with the opposing second face, the at least one driven element receiving the pre-determined force from the at least one drive element across the barrier, the barrier maintaining integrity during the transmission of the pre-determined force.

15. The apparatus as in claim 1 further comprising:
a non-sterile section and a sterile section separated by the continuous barrier, the continuous barrier having a first face and an opposing second face, the at least one drive element disposed in the non-sterile section, the at least one drive element generating and transmitting torque along a reference axis, the reference axis being transverse to a parallel axis, the parallel axis being parallel to the first surface and the second opposing surface, the reference axis originating in the non-sterile section and terminating in the sterile section, the at least one drive element having at least one barrier interfacing member, the barrier interfacing member configured to communicate with the first face,
wherein the at least one driven element disposed in the sterile section, the at least one driven element having at least one cooperating barrier interfacing member configured to communicate with the continuous barrier on the opposing second surface, the at least one driven element receiving the pre-determined torque from the drive element along the reference axis, and
at least one bridging element in the continuous barrier, the at least one bridging element linking the at least one drive element and the at least one driven element, the at least one bridging element including a first set of parts on the non-sterile section and a second set of parts on the sterile section, the first set of parts and the second set of parts mating with the at least one barrier interfacing member in the non-sterile section and the at least one co-operating barrier interfacing member in the sterile section.

16. A method for performing robotic surgery using a robotic surgery apparatus, the robotic surgery apparatus including a drive component having at least one motor and an associated at least one drive element for each of the at least one motor, the at least one motor being associated with a load sensor, the associated at least one drive element having a drive screw, a nut translationally displacing about a longitudinal axis of the drive screw in response to rotation of the drive screw about the longitudinal axis, and a projection oriented at an angle transverse to the longitudinal axis, the robotic surgery apparatus having a manipulator including at least one driven element, the at least one driven element having a receiving feature engaging the projection, the method comprising:
translationally displacing the at least one driven element with the projection when the projection is engaged in the receiving feature;
engaging the receiving feature through a continuous barrier, the continuous barrier separating the projection and the receiving feature, at least a portion of the continuous barrier covering the projection, the continuous barrier maintaining sterility of the drive component, the continuous barrier accommodating the translationally displacing; and performing the robotic surgery by driving, by the drive component, at least one actuator coupled with an end effector, the at least one actuator having a first end coupled to the at least one driven element and a second end coupled to the end effector.

17. The method as in claim 16 further comprising:
controlling the operation of the articulated segment in the robotic surgical apparatus, the controlling including:
  receiving, by the robotic surgical apparatus, at least one command signal, the at least one command signal based on a user-directed movement command;
  determining a desired rotation angle and a desired bend angle of the articulated segment based at least in part on the at least one command signal;
  determining a change of length value of the articulated segment based on the desired rotation angle and the desired bend angle;
  calculating desired length values for the at least one actuator based on the change of length value;
  calculating a length error value for the at least one actuator based on the desired length value; and
  generating at least one displacement command for the articulated segment based on the length error value.

18. The method as in claim 17 further comprising:
sending the displacement commands to the at least one motor to control the movement of at least one actuator.

19. The method as in claim 16 further comprising:
controlling the movement of the at least one actuator based on a mode of the robotic surgical apparatus.

20. The method as in claim 16 further comprising:
positioning a continuous barrier between a non-sterile section and a sterile section of the robotic surgery apparatus, the sterile section and the non-sterile section being separated by the continuous barrier, the continuous barrier having a first surface facing the non-sterile section and an opposing second surface facing the sterile section, the at least one drive element located in the non-sterile section, the at least one drive element generating and transmitting a pre-determined force, one or more barrier interfacing members configured to communicate with the first surface; and
receiving, by the at least one driven element, the pre-determined force from the at least one drive element across the barrier, the at least one driven element located in the sterile section, the at least one driven element including at least one co-operating barrier interfacing member configured to communicate with the opposing second face, the barrier maintaining integrity during the transmission of the pre-determined force.

* * * * *